United States Patent
Kawakami et al.

(10) Patent No.: US 8,940,862 B2
(45) Date of Patent: Jan. 27, 2015

(54) SELECTIVE ANTICANCER CHIMERIC PEPTIDES WHICH BIND TRANSFERRIN RECEPTOR

(71) Applicants: Koji Kawakami, Kyoto (JP); Stella Pharma Corporation, Osaka-shi (JP)

(72) Inventors: Koji Kawakami, Kyoto (JP); Masayuki Kohno, Kyoto (JP); Tomohisa Horibe, Kyoto (JP); Oumi Nakajima, Kyoto (JP); Mari Haramoto, Kyoto (JP); Liying Yang, Kyoto (JP)

(73) Assignees: Koji Kawakami, Kyoto (JP); Stella Pharma Corporation, Osaka (JP)

( * ) Notice: Subject to any disclaimer, the term of this patent is extended or adjusted under 35 U.S.C. 154(b) by 0 days.

(21) Appl. No.: 13/857,752

(22) Filed: Apr. 5, 2013

(65) Prior Publication Data

US 2013/0274200 A1 Oct. 17, 2013

Related U.S. Application Data

(62) Division of application No. 13/132,580, filed as application No. PCT/IB2009/055476 on Dec. 3, 2009, now Pat. No. 8,436,137.

(30) Foreign Application Priority Data

Dec. 3, 2008 (JP) ................................. 2008-309176
Jun. 9, 2009 (JP) ................................. 2009-138729

(51) Int. Cl.
| | | |
|---|---|---|
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C12P 21/06 | (2006.01) |
| C12N 1/20 | (2006.01) |
| C12N 15/00 | (2006.01) |
| C12N 5/00 | (2006.01) |
| C12N 5/02 | (2006.01) |
| C12N 15/74 | (2006.01) |
| A61P 35/00 | (2006.01) |
| C07H 21/04 | (2006.01) |
| C07K 7/08 | (2006.01) |
| A61K 47/48 | (2006.01) |
| C07K 14/475 | (2006.01) |
| C07K 14/485 | (2006.01) |
| C07K 14/54 | (2006.01) |
| C07K 7/06 | (2006.01) |
| C07K 14/00 | (2006.01) |

(52) U.S. Cl.
CPC .............. *C07K 7/08* (2013.01); *A61K 47/48276* (2013.01); *C07K 14/475* (2013.01); *C07K 14/485* (2013.01); *C07K 14/54* (2013.01); *C07K 7/06* (2013.01); *C07K 14/001* (2013.01); *C07K 2319/33* (2013.01); *C07K 2310/55* (2013.01)

USPC ...... 530/324; 435/69.1; 435/252.3; 435/320.1; 435/325; 435/471; 514/1.1; 514/19.3; 530/300; 536/23.4

(58) Field of Classification Search
None
See application file for complete search history.

(56) References Cited

U.S. PATENT DOCUMENTS 6,531,446 B1 * 3/2003 Kim et al. ..................... 514/2.4

FOREIGN PATENT DOCUMENTS

| | | |
|---|---|---|
| JP | 2002-253245 A | 9/2002 |
| WO | 92/01462 A1 | 2/1992 |
| WO | 97/46259 A2 | 12/1997 |
| WO | 2005/094383 A2 | 10/2005 |
| WO | 2008/079973 A2 | 7/2008 |
| WO | 2010/064207 A2 | 6/2010 |

OTHER PUBLICATIONS

Lee JH, et al. Eur. J. Biochem. 268:2004-2012, 2001.*
Marianski JL, et al. Cell. 60(1):63-72, Jan. 12, 1990. available online at—DOI: 10.1016/0092-8674(90)90716-R.*
Nicolaides NC, et al. Expert Opin. Drug Discov. 5(11):1123-1140, 2010.*
Frankel AE, et al. Clinical Cancer Research. 6:326-334, Feb. 2000.*
Kim et al., "In vitro activities of native and designed peptide antibiotics against drug sensitive and resistant tumor cell lines," *Peptides* 24:945-953, 2003.
Lee et al. "Mechanism of anticancer activity of buforin IIb, a histone H2A-derived peptide," *Cancer Letters* 271:47-55, 2008.
Shaw et al., "Cytotoxic Properties of $DAB_{486}EGF$ and $DAB_{389}EGF$, Epidermal Growth Factor (EGF) Receptor-targeted Fusion Toxins," *The Journal of Biological Chemistry* 266(31):21118-21124, 1991.

(Continued)

*Primary Examiner* — Robert Landsman
(74) *Attorney, Agent, or Firm* — Seed IP Law Group PLLC

(57) ABSTRACT

It is an object of the present invention to provide a substance usable as an anticancer agent or DDS, which has intracellular stability, which is capable of evading side effects from functional disorder with respect to normal cells, or which has instantaneous effect. The inventors developed a novel chimeric peptide targeting cancer cells which overexpress EGFR or the like using a binding peptide such as a peptide sequence binding to EGFR, and a lytic peptide sequence, thereby solving such an object. Particularly, by using a chimeric peptide including an EGF receptor-binding peptide or the like and a cytotoxic peptide, this object was solved.

13 Claims, 67 Drawing Sheets

(56) References Cited

OTHER PUBLICATIONS

Chromek et al., "The antimicrobial peptide cathelicidin protects the urinary tract against invasive bacterial infection," *Nature Medicine* 12(6):636-641, Jun. 2006.

Ellerby et al., "Anti-cancer activity of targeted pro-apoptotic peptides," *Nature Medicine* 5(9):1032-1038, Sep. 1999.

Frankel et al., "Targeted Toxins," *Clinical Cancer Research* 6:326-334, Feb. 2000.

Fuessel et al., "Vaccination of Hormone-Refractory Prostate Cancer Patients with Peptide Cocktail-Loaded Dendritic Cells: Results of a Phase I Clinical Trial," *The Prostate* 66:811-821, 2006.

Grünwald et al., "Developing Inhibitors of the Epidermal Growth Factor Receptor for Cancer Treatment," *Journal of the National Cancer Institute* 95(12):851-867, Jun. 18, 2003.

Jänne et al., "Epidermal Growth Factor Receptor Mutations in Non-Small-Cell Lung Cancer: Implications for Treatment and Tumor Biology," *Journal of Clinical Oncology* 23(14):3227-3234, May 10, 2005.

Karapetis et al., "K-ras Mutations and Benefit from Cetuximab in Advanced Colorectal Cancer," *The New England Journal of Medicine* 359(17):1757-1765, Oct. 23, 2008.

Kawakami et al., "Targeted Anticancer Immunotoxins and Cytotoxic Agents with Direct Killing Moieties," *TheScientificWorldJOURNAL* 6:781-790, 2006.

Kreitman, "Immunotoxins for Targeted Cancer Therapy," *The AAPS Journal* 8(3):E532-E551, 2006.

Kumar et al., "Transvascular delivery of small interfering RNA to the central nervous system," *Nature* 448:39-43, Jul. 5, 2007, 7 pages.

Kunwar et al., "Direct Intracerebral Delivery of Cintredekin Besudotox (IL13-PE38QQR) in Recurrent Malignant Glioma: A Report by the Cintredekin Besudotox Intraparenchymal Study Group," *Journal of Clinical Oncology* 25(7):837-844, Mar. 1, 2007.

Li et al., "Identification and characterization of a novel peptide ligand of epidermal growth factor receptor for targeted delivery of therapeutics," *FASEB J* 19: 1978-1985, 2005.

Lien et al., "Therapeutic peptides," *TRENDS in Biotechnology* 21(12):556-562, Dec. 2003.

Papo, N. et al., "New Lytic Peptides Based on the D,L-Amphipathic Helix Motif Preferentially Kill Tumor Cells Compared to Normal Cells," *Biochemistry*, 42:9346-9354 Aug. 12, 2003.

Pastan, "Targeted therapy of cancer with recombinant immunotoxins," *Biochimica et Biophysica Acta* 1333:C1-C6, 1997.

Plescia et al., "Rational design of shepherdin, a novel anticancer agent," *Cell Cancer* 7:457-468, May 2005.

Rand et al., "Intratumoral Administration of Recombinant Circularly Permuted Interleukin-4-Pseudomonas Exotoxin in Patients with High-Grade Glioma," *Clinical Cancer Research* 6:2157-2165, 2000.

Shaw et al., "Cytotoxic Properties of DAB486EGF and DAB389EGF, Epidermal Growth Factor (EGF) Receptor-targeted Fusion Toxins," *J Biol Chem* 266(31):21118-21124, Nov. 6, 1991.

Salomon et al., "Epidermal growth factor-related peptides and their receptors in human malignancies," *Critical Reviews in Oncology/Hematology* 19:183-232, 1995.

Woodburn, "The Epidermal Growth Factor Receptor and Its Inhibition in Cancer Therapy," *Pharmacol. Ther.* 82(2-3):241-250, 1999.

Yao et al., "Identification of core functional region of murine IL-4 using peptide phage display and molecular modeling," *International Immunology* 18(1):19-29, 2005.

\* cited by examiner a  EB + original lytic peptide
YHWYGYTPQNVIGGLKLLLKLLLKLLLKLL-NH2 b  EB + newly designed lytic peptide
YHWYGYTPQNVIGGG KLLLK(L)LK(L)LK(L)LKK

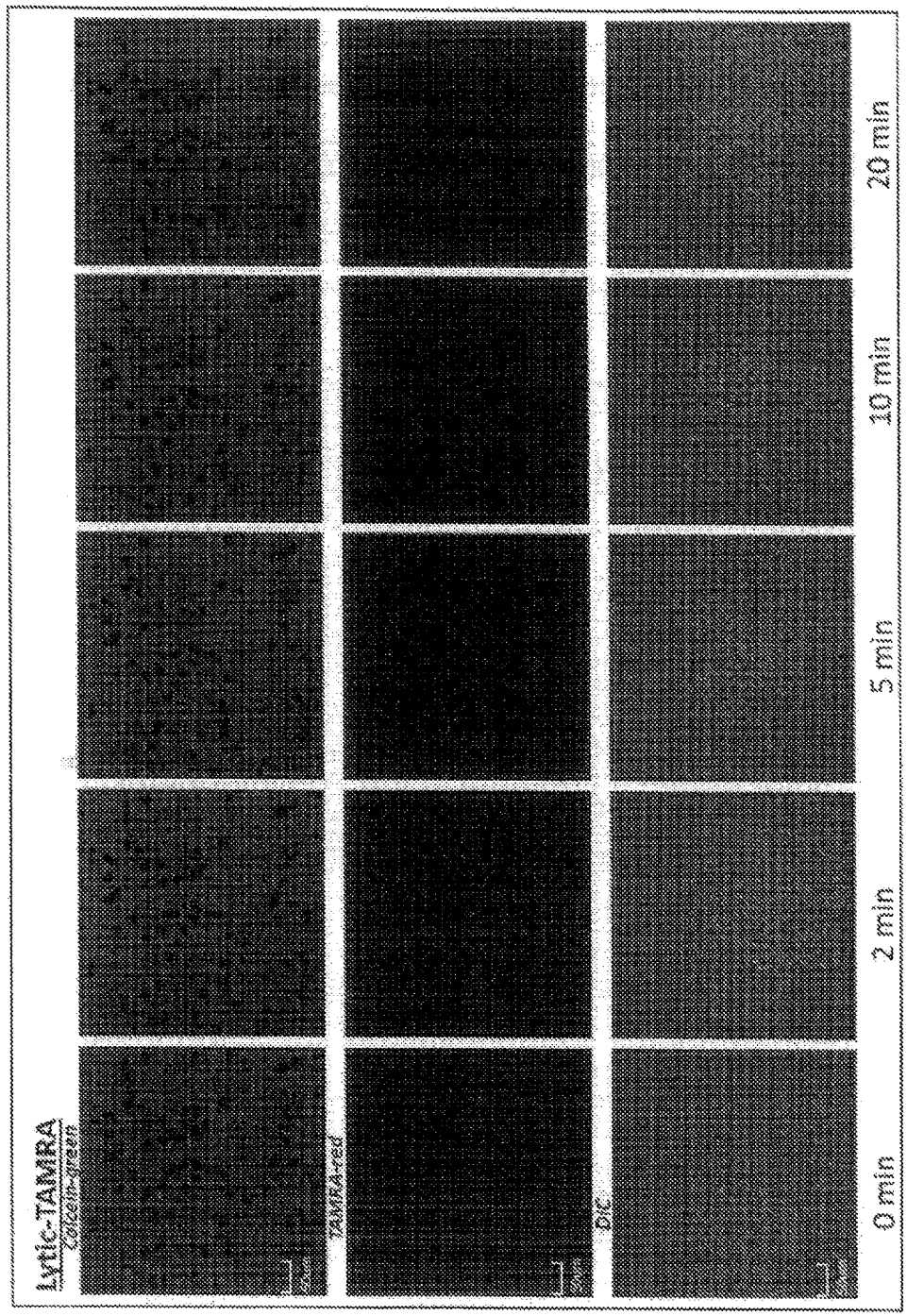

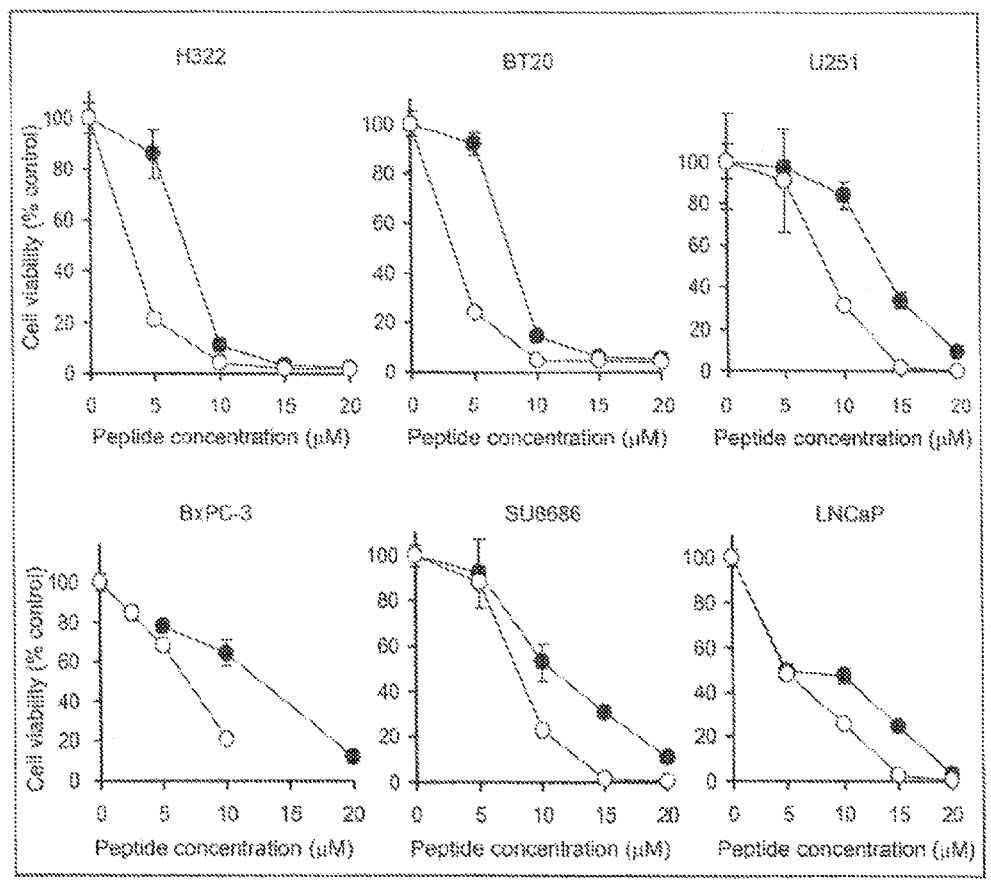

Lytic peptide

EB-Lytic peptide

EB(H2R)-Lytic peptide

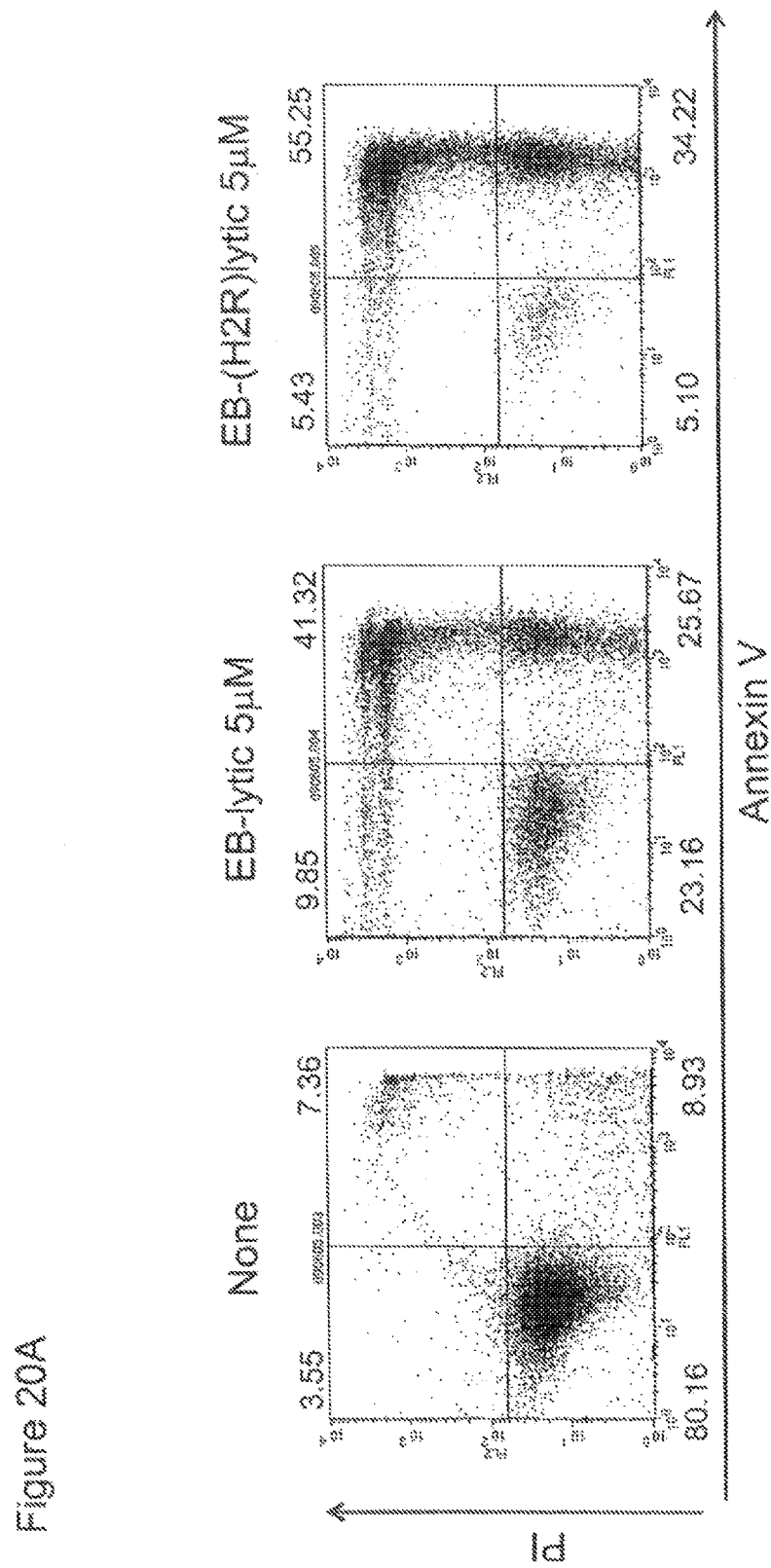

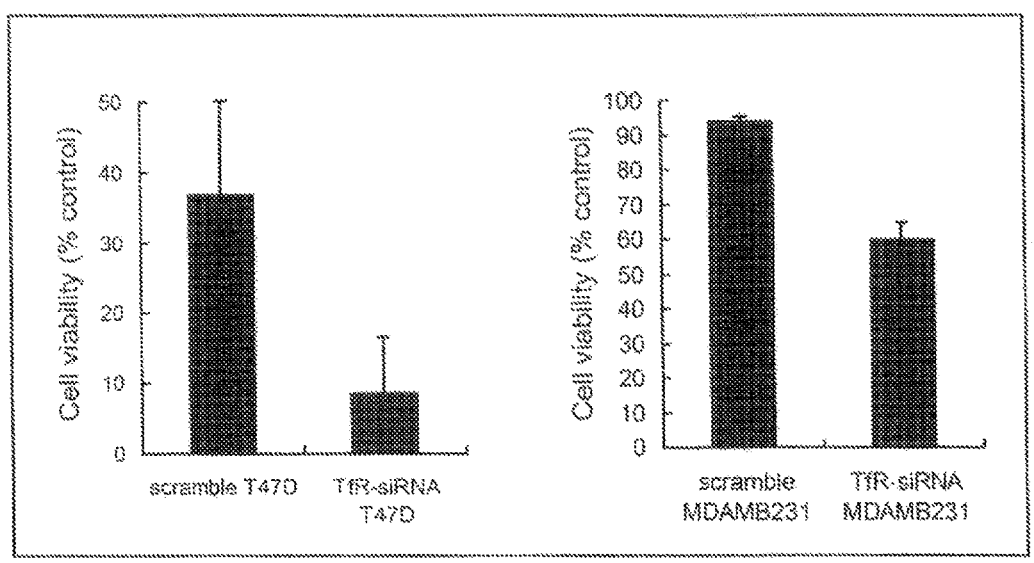

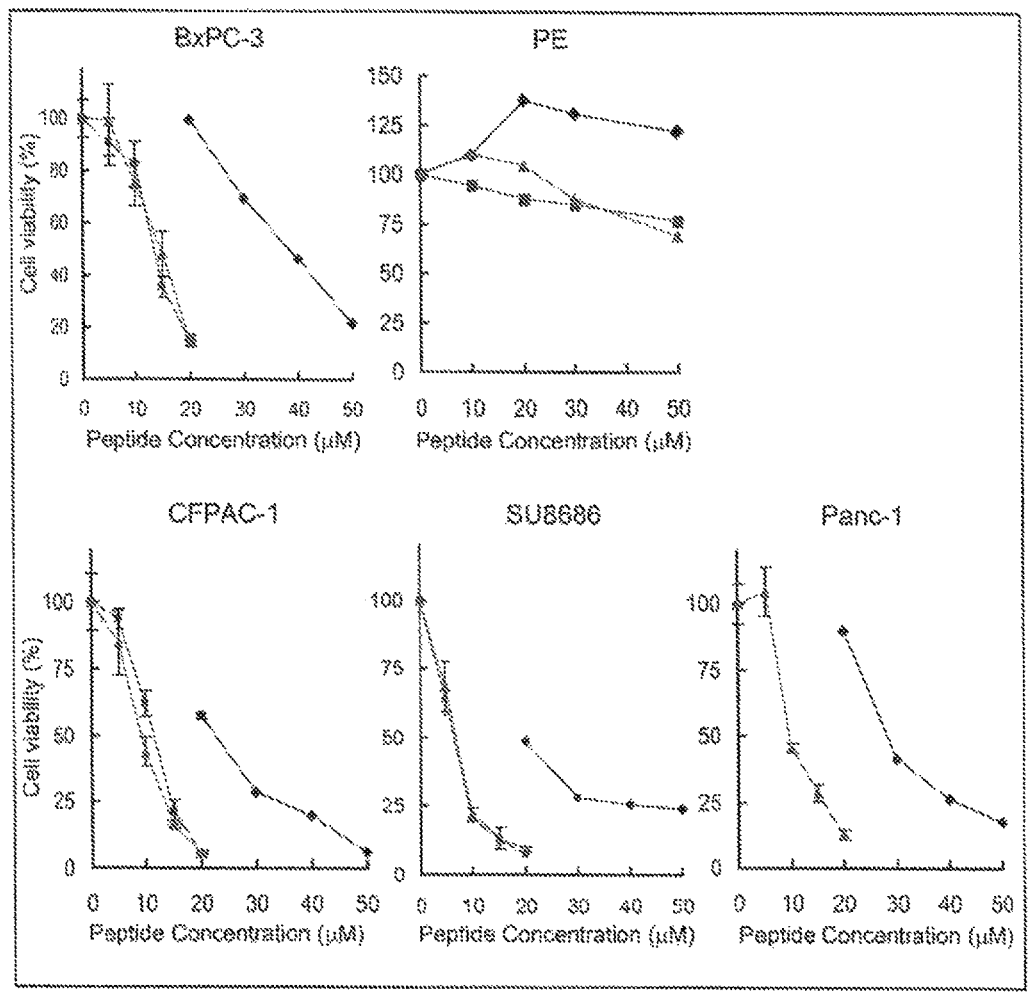

US 8,940,862 B2

SELECTIVE ANTICANCER CHIMERIC PEPTIDES WHICH BIND TRANSFERRIN RECEPTOR

CROSS-REFERENCE TO RELATED APPLICATIONS

This application is a Divisional Patent Application of U.S. application Ser. No. 13/132,580, filed Aug. 15, 2011, now issued as U.S. Pat. No. 8,436,137 on May 7, 2013; which is a U.S. national stage application filed under 35 U.S.C. §371 of International Patent Application No. PCT/IB2009/055476 accorded an international filing date of Dec. 3, 2009, which application claims priority from Japanese Patent Application No. 2009-138729 filed on Jun 9, 2009, now abandoned, and Japanese Patent Application No. 2008-309176 filed on Dec. 3, 2008, now abandoned; which application are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920118_401D1_SEQUENCE_LISTING.txt. The text file is 32 KB, was created on Apr. 4, 2013, and is being submitted electronically via EFS-Web.

TECHNICAL FIELD

The present invention relates to peptidetoxin, a novel targeted therapeutics.

BACKGROUND ART

Immunotoxins in which monoclonal antibodies or ligands against overexpressed proteins on the surface of cancer cells are conjugated to plant or bacterial toxins, have been extensively investigated for their possible use as anticancer agents (Non-Patent Document 1). A number of immunotoxins have been tested in preclinical and clinical trials, and interleukin-2-diphteria toxin (IL2-DT; Ontak™) has been approved for the treatment of chronic T cell lymphocytic leukemia (CLL) (Non-Patent Document 2, Non-Patent Document 3). In addition, *Pseudomonas* extoxin-based immunotoxins including interleukin-4-*Pseudomonas* exotoxin [IL4(38-37)-PE38 KDEL] and interleukin-β-*Pseudomonas* exotoxin (IL13-PE38QQR) have been tested in clinical trials (Non-Patent Document 4, Non-Patent Document 5). Both Diphtheria toxin and *Pseudomonas* exotoxin act by catalytically inactivating the elongation factor 2 protein in the ribosome complex, after uptake into lysosomes, activation and translocation into the cytosol. This mechanism of action allows the immunotoxins to efficiently destroy dormant, non-replicating tumor cells.

Although the targeting approach towards cancer utilizing bacterial toxin-based immunotoxin is fascinating, its limitation of use lies in the liver toxicity due to the bacterial toxin and immunogencity caused by the toxin proteins (Non-Patent Document 2, Non-Patent Document 4, Non-Patent Document 6). In addition, molecular size of immunotoxins is generally larger compared to chemical compounds or fragment antibody drugs, which might prevent drugs from efficiently penetrating into tumor mass in the human body. To overcome these issues, new generation immunotoxins with evolutional approach are critically needed.

Epidermal growth factor receptor (EGFR) has been an important tumor-specific target for many years (Non-Patent Document 7, Non-Patent Document 8). EGFR plays important roles in cellular growth, differentiation, and migration. Its positive signaling was found to cause increased proliferation, decreased apoptosis, and enhanced tumor cell motility and angiogenesis (Non-Patent Document 9). EGFR overexpression has been frequently found in a wide spectrum of human tumors of epithelial origin, including breast, lung, gastric, colorectal, prostate, pancreatic and ovarian cancers (Non-Patent Document 10). All these findings have shown that EGFR is important as a target for receptor-mediated delivery system of drugs. Recently, several studies have reported the successful identification of peptide ligands of EGFR by screening phage display libraries, implicating possible drug delivery targeting EGFR (Non-Patent Document 11, Non-Patent Document 12).

Therapeutic peptides are increasingly gaining popularity in use in a variety of applications (for example, tumor vaccine (Non-Patent Document 13), antimicrobial therapy (Non-Patent Document 14), and nucleic acid delivery (Non-Patent Document 15)) (Non-Patent Document 16). In addition, research and development of new cancer therapy involving peptide-based drug has been undertaken (Non-Patent Document 17, Non-Patent Document 18). It is also known that peptide therapeutics are relatively easily generated using either recombinant or solid-phase chemical synthesis techniques and are generally less expensive when compared to antibody-based therapeutics. In recent years, it has been reported that a new lytic-type peptide composed of a 15-amino acid diastereomeric sequence containing D- and L-forms of leucine and lysine can disrupt the plasma membrane (Non-Patent Document 19). This peptide kills tumor cells better than normal cells, and disintegrates the cell membrane in a detergent-like manner, Cell selectivity is probably determined predominantly by an increase in the level of acidic components or phosphatidylserine on the cancer cell wall (Non-Patent Document 19). The diastereomeric sequence preserves activity in serum and in the presence of proteolytic enzymes (Non-Patent Document 20). It has been suggested that the peptide's selectivity is probably influenced predominantly by an increase in the level of acidic components or phosphatidylserine on the cancer cell wall (Non-Patent Document 19). This lytic peptide has selective cytotoxicity between normal and cancer cells, but still kills normal cells at a lower concentration, and thus is not suitable for the combination with peptides with targeting moiety. Furthermore, the peptides disclosed in Documents 17, 19 and 20 are not suitable for molecular targeting, since enhancement of a cell-killing effect by EGFR targeting is not observed.

Several potential molecular-targeted anticanter marketed drugs inhibit receptor tyrosine kinase and tumor growth. In some cases, mutations of kinase-related signal molecule genes in cancer cells result in the resistance to tyrosine kinase inhibitor (TKI) drugs. Recently, it was revealed that k-ras mutations are significantly associated with a lack of response to epidermal growth factor receptor (EGFR) TKIs and cetuximab in patients with non-small-cell lung cancer and advanced colorectal cancer (Non-Patent Document 21). To overcome this critical issue, development of a novel molecular-targeted anticancer drug directly killing cancer cells, which is superior to a signal pathway blocker is desired.

PRIOR ART DOCUMENTS

Non-Patent Documents

Non-Patent Document 1: Pastan I. Targeted therapy of cancer with recombinant immunotoxins. Biochim Biophys Acta 1997; 1333:C1-6

Non-Patent Document 2: Kawakami K, Nakajima O, Morishita R, Nagai R. Targeted anticancer immunotoxins and cytotoxic agents with direct killing moieties. The Sci World J 2006; 6:781-90

Non-Patent Document 3: Kreitman R J. Immunotoxins for targeted cancer therapy. AAPS J 2006; 8:E532-51

Non-Patent Document 4: Rand R W, Kreitman R J, Patronas N, Varricchio F, Pastan I, Puri R K. Intratumoral administration of recombinant circularly permuted interleukin-4-Pseudomonas exotoxin in patients with high-grade glioma. Clin Cancer Res 2000; 6:2157-65

Non-Patent Document 5: Kunwar S, Prados M D, Chang S M, et al., Cintredekin Besudotox Intraparenchymal Study Group. Direct intracerebral delivery of cintredekin besudotox (IL13-PE38QQR) in recurrent malignant glioma: a report by the Cintredekin Besudotox Intraparenchymal Study Group. J Clin Oncol 2007; 25:837-44

Non-Patent Document 6: Frankel A E, Kreitman R J, Sausville E A. Targeted toxins. Clin Cancer Res 2000; 6:326-34

Non-Patent Document 7: Grunwald V, Hidalgo M. Developing inhibitors of the epidermal growth factor receptor for cancer treatment. J Natl Cancer Inst 2003; 95:851-67

Non-Patent Document 8: Janne P A, Engelman J A, Johnson B E. Epidermal growth factor receptor mutations in non-small-cell lung cancer: implications for treatment and tumor biology. J Olin Oncol 2005; 23:3227-34

Non-Patent Document 9: Woodburn J R. The epidermal growth factor receptor and its inhibition in cancer therapy. Pharmacol Ther 1999; 82:241-50

Non-Patent Document 10: Salomon D S, Brandt R, Ciardiello F, Normanno N. Epidermal growth factor-related peptides and their receptors in human malignancies. Crit Rev Oncol Hematol 1995; 19:183-232

Non-Patent Document 11: Li Z, Zhao R, Wu X, et al., Identification and characterization of a novel peptide ligand of epidermal growth factor receptor for targeted delivery of therapeutics. FASEB J 2005; 19:1978-85

Non-Patent Document 12: Yao G, Chen W, Luo H, et al., Identification of core functional region of murine IL-4 using peptide phage display and molecular modeling. Int Immunol 2005; 18:19-29

Non-Patent Document 13: Fuessel S, Meye A, Schmitz M, et al., Vaccination of hormone-refractory prostate cancer patients with peptide cocktail-loaded dendritic cells: results of a phase I clinical trial. Prostate 2006; 66:811-21

Non-Patent Document 14: Chromek M, Slamova Z, Bergman P, et al., The antimicrobial peptide cathelicidin protects the urinary tract against invasive bacterial infection. Nat Med 2006; 12:636-41

Non-Patent Document 15: Kumar P, Wu H, McBride J L, et al., Transvascular delivery of small interfering RNA to the central nervous system. Nature 2007; 448:39-43

Non-Patent Document 16: Lien S, Lowman H B. Therapeutic peptides. Trends Biotechnol 2003; 21:556-62

Non-Patent Document 17: Ellerby H M, Arap W, Ellerby L M, et al., Anti-cancer activity of targeted pro-apoptotic peptides. Nat Med 1999; 5:1032-8

Non-Patent Document 18: Plescia J, Salz W, Xia F, et al., Rational design of shepherdin, a novel anticancer agent. Cancer Cell 2005; 7:457-68

Non-Patent Document 19: Papo N, Shai Y. New lytic peptides based on the D,L-amphipathic helix motif preferentially kill tumor cells compared to normal cells. Biochemistry 2003; 42:9346-54

Non-Patent Document 20: Papo N, Braunstein A, Eshhar Z, Shai Y. Suppression of human prostate tumor growth in mice by a cytolytic D-, L-amino acid peptide: membrane lysis, increased necrosis, and inhibition of prostate-specific antigen secretion. Cancer Res 2004; 64:5779-86

Non-Patent Document 21: Karapetis, C. S. et al. K-ras mutations and benefit from cetuximab in advanced colorectal cancer. N Engl J Med. 359, 1757-1765 (2008)

DISCLOSURE OF THE INVENTION

Problems to be Solved by the Invention

It is an object of the present invention to provide a novel pharmaceutical (for example, anticancer agent) having a new structure.

Means for Solving the Problems

Using the inventors' recent identification information of peptide sequences binding to an EGFR and lytic-type peptide sequence, the inventors have developed a new chimeric peptide targeting EGFR-overexpressed cancer cells, and have found that a chimeric peptide including a receptor-binding peptide and a cytotoxic peptide can be used as a pharmaceutical such as an anticancer agent. This chimeric peptide, termed herein EGFR-targeted peptidetoxin, is preferably composed of a receptor-binding peptide (for example, EGFR-binding moiety) and a cytotoxic peptide (for example, cell membrane-lytic moiety) with a spacer (for example, three-glycine spacer). This chimeric peptide is characterized in that it is stable when combined with a targeted peptide and has less toxic action on a normal cell line in comparison with the original lytic-type peptide. In the present invention, the inventors demonstrated in vitro cytotoxic activity and selectivity of cell death induced by a chimeric peptide of the present invention (for example, EGFR-targeted peptidetoxin) in seven human cancer cell lines derived from breast cancer, pancreatic cancer, lung cancer, prostate cancer, and brain tumor. The inventors have also investigated the interaction of EGFR-targeted peptidetoxin with cancer cell surface and the mode of action of peptidetoxin-induced cancer cell death. In vivo experiments have also revealed that the chimeric peptide of the present invention exhibited significant antitumor activity. This has allowed enabled the peptide to be applied to fields to which it can be applied other than application as an actual pharmaceutical of anticancer agent, for example, application to screening of a drug or the like, which has not been known so far. This is because an application in the form of screening for finding a peptide sequence binding to a particular protein such as a receptor, in which a number of types of chimeric peptides of candidate sequences and Lytic peptide are synthesized and in which in vitro cell-killing effect is an indicator is possible. For example, it is possible to realize a method of screening a pharmaceutical/anticancer agent using an amino acid sequence which targets both EGFR in a cancer cell with high EGFR expression and a cancer cell membrane of the cancer cell. Lytic-type peptides of conventional arts have selective cytotoxicity between normal cells and cancer cells, as described above, whereas the peptide of the present invention has reduced toxicity for normal cells. Thus, the peptide of the present invention has been revealed to be suitable for the combination with a peptide and a targeting moiety.

This peptidetoxin is a chemically synthesized peptide composed of a target-binding peptide and a cytotoxic lytic peptide moiety. As one example, an epidermal growth factor receptor (EGFR)-binding peptide was conjugated to a lytic-type peptide including a cation-rich amino acid, which disintegrates a cell membrane by positive charge to kill a cancer cell. In an EGFR-overexpressing cancer cell line, the EGFR-targeted peptidetoxin induced improvement of $IC_{50}$ (peptide concentration which induces 50% inhibition of proliferation of a control cell) of about three times in comparison with a lytic peptide alone. On the contrary, a normal cell line had low sensitivity to the EGFR-targeted peptidetoxin or lytic peptide alone. In the normal cells, $IC_{50}$ of four to eight times higher than in the cancer cells was exhibited. Interestingly, expression of EGFR on the cell surface was sufficiently correlated to a degree of enhancement of the cell-killing effect of the peptidetoxin due to EGFR targeting, which suggested specificity. Surprisingly, exposure of the EGFR-targeted peptidetoxin for less than 10 minutes was sufficient for killing over 50% of the cancer cells. Furthermore, the inventors have found that in cancer cells provided with a peptidetoxin, activation of polycaspase and Annexin V-positive expression are induced and that induction of an apoptotic mechanism is suggested. In conclusion, a peptidetoxin targeted for a protein highly expressing in a cancer cell may be a landmark tool for novel targeted therapy of cancer.

Thus, the present invention provides the following.

In a first aspect of the present invention, the present invention provides a chimeric peptide including a receptor-binding peptide and a cytotoxic peptide.

In one embodiment, the receptor-binding peptide may be EGF receptor-binding peptide, interleukin-4 (IL-4) receptor-binding peptide, interleukin-13 (IL-13) receptor-binding peptide, neuropilin receptor-binding peptide, human epidermal growth factor receptor type 2 (HER2)-binding peptide, vascular epithelial growth factor receptor (VEGFR)-binding peptide, Transferrin Receptor (TfR)-binding peptide, ephrin B1 (EphB1)-binding peptide, ephrin B2 (EphB2)-binding peptide, a glucose-regulated protein 78 (GRP78)-binding peptide, prostate-specific membrane antigen (PSMA)-binding peptide or the like.

Discussing from another viewpoint, in the main aspect of the present invention, the present invention provides a peptidetoxin, a chimeric peptide including an anticancer targeting peptide and a cell membrane-lytic peptide moiety.

Specific embodiments in the main aspect of the invention include, for example, peptidetoxins using a peptide which binds a receptor such as epidermal growth factor (EGF), human epidermal growth factor receptor type 2 (HER), vascular epithelial growth factor receptor 1 (VEGFR1), Transferrin Receptor (TfR), interleukin-4 (IL4), inetrleukin-13 (IL13), neuropilin (NRP), neuropilin 1 (NRP1)/vascular endothelial growth factor receptor 2 (VEGFR2), ephrin B1 (EphB1), ephrin B2 (EphB2), glucose-regulated protein (GRP78), prostate-specific membrane antigen (PSMA), or the like. The following are exemplified as chimeric peptides (as used herein, each alphabet indicates one-letter amino acid representation).

```
EB-Lytic:
                                        (SEQ ID NO: 2)
YHWYGYTPQNVIGGGKLLLKLLKKLLKLLKKK EB(H2R)-Lytic:
                                        (SEQ ID NO: 14)
YRWYGYTPQNVIGGGKLLLKLLKKLLKLLKKK HER2-Lytic:
                                        (SEQ ID NO: 15)
YCDGFYACYMDVGGGKLLLKLLKKLLKLLKKK VEGFR1-Lytic:
                                        (SEQ ID NO: 16)
WHSDMEWWYLLGGGGKLLLKLLKKLLKLLKKK TfR-Lytic:
                                        (SEQ ID NO: 17)
THRPPMWSPVWPGGGKLLLKLLKKLLKLLKKK LyticL peptide:
                                        (SEQ ID NO: 27)
KLLLKLLKKLLKLLKKK IL4-LyticL:
                                        (SEQ ID NO: 18)
KQLIRFLKRLDRNGGGKLLLKLLKKLLKLLKKK IL13-LyticL:
                                        (SEQ ID NO: 19)
KDLLLHLKKLFREGQFNGGGKLLLKLLKKLLKLLKKK Sema3A-LyticL <binding to human
neuropilin-1>:
                                        (SEQ ID NO: 20)
NYQWVPYQGRVPYPRGGGKLLLKLLKKLLKLLKKK EGFbuf:
                                        (SEQ ID NO: 21)
YHWYGYTPQNVIGGGGGRLLRRLLRRLLRK
```

In one embodiment, a cell membrane-lytic peptide moiety used in the present invention is composed of an amino acid having a plus charge [K, R or (H)] and a hydrophobic amino acid [L, A, F or the like] and has a 10- to 30-amino acids sequence with an amphipathic helix structure.

In one embodiment, an anticancer targeting peptide used in the present invention has a binding sequence specific for a receptor with high expression in cancer cells, and the lytic peptide moiety has a cancer cell membrane-lytic sequence and has a spacer.

In one embodiment, a lytic peptide moiety used in the present invention is composed of an amino acid having a plus charge [K, R or (H)] and a hydrophobic amino acid [L, A, F or the like] and has a 10- to 30-amino acids sequence with an amphipathic helix structure.

In one embodiment, a spacer used in the present invention is a 0- to 5-amino acids sequence consisting of G and P.

In one aspect, the present invention provides a chimeric peptide including an EGF receptor-binding peptide and a cytotoxic peptide or a cytolytic peptide.

In one embodiment, an EGF receptor-binding peptide used in the present invention has the amino acid sequence YHWYGYTPQNVI (SEQ ID NO: 7) wherein each alphabet indicates one-letter amino acid representation, or a modified sequence thereof.

In one embodiment, an EGF receptor-binding peptide used in the present invention has the amino acid sequence $X_1X_2X_3X_4X_5X_6X_7X_8X_9X_{10}X_{11}X_{12}$ (SEQ ID NO: 8), wherein:

$X_1$ is Y or an amino acid similar thereto;
$X_2$ is H or an amino acid similar thereto;
$X_3$ is W or an amino acid similar thereto;
$X_4$ is Y or an amino acid similar thereto;
$X_5$ is G or an amino acid similar thereto;
$X_6$ is Y or an amino acid similar thereto;
$X_7$ is T or an amino acid similar thereto;
$X_8$ is P or an amino acid similar thereto;
$X_9$ is Q or an amino acid similar thereto;

$X_{10}$ is N or an amino acid similar thereto;
$X_{11}$ is V or an amino acid similar thereto; and
$X_{12}$ is I or an amino acid similar thereto.

In a preferred embodiment, $X_1$ is Y, or an amino acid similar thereto having an OH group or an aromatic group;
$X_2$ is H, or an amino acid similar thereto having a plus charge;
$X_3$ is W, or an amino acid similar thereto having an aromatic group;
$X_4$ is Y, or an amino acid similar thereto having an OH group;
$X_5$ is G, or an amino acid similar thereto having an aliphatic side chain;
$X_6$ is Y, or an amino acid similar thereto having an OH group;
$X_7$ is T, or an amino acid similar thereto having an OH group;
$X_8$ is P or an imino acid-type amino acid similar thereto;
$X_9$ is Q or an amide-type amino acid similar thereto;
$X_{10}$ is N, or an amino acid similar thereto having an OH group;
$X_{11}$ is V, or an amino acid similar thereto having an aliphatic side chain; and
$X_{12}$ is I, or an amino acid similar thereto having an aliphatic side chain.

In a more preferable example, $X_1$ is Y, or an amino acid similar thereto which is S, H or F;
$X_2$ is H, or an amino acid similar thereto which is R or K;
$X_3$ is W, or an amino acid similar thereto which is Y, F or H;
$X_4$ is Y, or an amino acid similar thereto which is S, H or F;
$X_5$ is G, or an amino acid similar thereto which is A, V, I or L;
$X_6$ is Y, or an amino acid similar thereto which is S, H or F;
$X_7$ is T, or an amino acid similar thereto which is S, H or F;
$X_8$ is P, or an amino acid similar thereto which is hydroxyl proline;
$X_9$ is Q, or an amino acid similar thereto which is N;
$X_{10}$ is N, or an amino acid similar thereto which is S, H or F;
$X_{11}$ is V, or an amino acid similar thereto which is G, A, L or I; and
$X_{12}$ is I, or an amino acid similar thereto which is G, A, V or L.

In a more preferable embodiment, $X_2$ is H, or an amino acid similar thereto which is R or K.

In a more preferable embodiment, a chimeric peptide of the present invention has the sequence YRWYGYTPQNVI (SEQ ID NO: 9) or YKWYGYTPQNVI (SEQ ID NO: 10).

In one embodiment, a cytotoxic peptide used in the present invention is selected from the group consisting of: cell membrane-lytic peptide, cell membrane potential-destabilizing peptide, cell membrane-lytic peptide and mitochondrial membrane-disintegrating peptide.

In a preferred embodiment, a cell membrane-lytic peptide used in the present invention has a 10- to 20-amino acids sequence consisting only of K and L, and the amino acids are L-, D- or D,L-mix amino acids.

In a preferred embodiment, a cell membrane-lytic peptide used in the present invention is KLLLKLLKKLLKLLKKK (SEQ ID NO: 48; specifically SEQ ID NO:1 or 27, or the like), and the amino acids are L-, D- or D,L-mix amino acids.

In a preferred embodiment, a cell membrane potential-destabilizing peptide used in the present invention is FLKLLKKLAAKLF (SEQ ID NO: 11).

In a preferred embodiment, a cell membrane-lytic peptide used in the present invention is RLLRRLLRRLLRRLLR-RLLR (SEQ ID NO: 12) or RLLRRLLRRLLRK (SEQ ID NO: 13).

In a preferred embodiment, a mitochondrial membrane-disintegrating peptide used in the present invention is KLAKLAKKLAKLAK (SEQ ID NO: 4).

In one embodiment, a cytotoxic peptide used in the present invention is composed of an amino acid having a plus charge [K, R or (H)] and a hydrophobic amino acid [L, A, F or the like] and has a 10- to 30-amino acids sequence with an amphipathic helix structure.

In a preferred embodiment, an amino acid having a plus charge used in the present invention is K, R or H.

In a preferred embodiment, a hydrophobic amino acid used in the present invention is I, L, V, A or F.

In a more preferable embodiment, a hydrophobic amino acid used in the present invention is KL<u>L</u>LK<u>L</u>LKK<u>L</u>LK<u>L</u>LKKK (SEQ ID NO: 1), wherein each amino acid is L- or D-amino acid and the underlined letters represent D-amino acids.

In one embodiment, a cytotoxic peptide used in the present invention is composed of an amino acid having a plus charge [K, R or (H)] and a hydrophobic amino acid [L, A, F or the like] and has a 10- to 30-amino acids sequence with an amphipathic helix structure.

In one embodiment, an amino acid having a plus charge used in the present invention is K, R or H.

In one embodiment, a hydrophobic amino acid used in the present invention is I, L, V, A or F.

In one embodiment, a hydrophobic amino acid used in the present invention is KL<u>L</u>LK<u>L</u>LKK<u>L</u>LK<u>L</u>LKKK (SEQ ID NO: 1), wherein each amino acid is L- or D-amino acid and the underlined letters represent D-amino acids.

In one embodiment, a chimeric peptide of the present invention further has a spacer peptide.

In one embodiment, a spacer peptide used in the present invention exhibits a sequence in which 0 to 4 glycine alone, proline alone or glycine and proline mixed are linked, and is preferably GGG.

In one embodiment, a chimeric peptide of the present invention has the sequence of YHWYGYTPQNVIGGGKL<u>L</u>LK<u>L</u>LKK<u>L</u>LK<u>L</u>LKKK (SEQ ID NO: 2)

In one embodiment, a chimeric peptide of the present invention has the sequence of YRWYGYTPQNVIGGGKL<u>L</u>LK<u>L</u>LKK<u>L</u>LK<u>L</u>LKKK (SEQ ID NO: 43), wherein the underlined letters represent D-amino acids.

In one embodiment, a receptor-binding peptide of a chimeric peptide of the present invention is an interleukin-4 (IL-4) receptor-binding peptide and has the amino acid sequence KQLIRFLKRLDRN (SEQ ID NO: 26) or a modified sequence thereof.

In one embodiment, a receptor-binding peptide of a chimeric peptide of the present invention is an interleukin-13 (IL-13) receptor-binding peptide and has the amino acid sequence KDLLLHLKKLFREGQFN (SEQ ID NO: 28) or a modified sequence thereof.

In one embodiment, a receptor-binding peptide of a chimeric peptide of the present invention is a neuropilin receptor-binding peptide and has the amino acid sequence NYQWVPYQGRVPYPR (SEQ ID NO: 29) or a modified sequence thereof.

In one embodiment, a receptor-binding peptide of a chimeric peptide of the present invention is a human epidermal growth factor receptor type 2 (HER2)-binding peptide and has the amino acid sequence YCDGFYACYMDV (SEQ ID NO: 30), LLGPYELWELSH (SEQ ID NO: 52), ALVRYKD- PLFVWGFL (SEQ ID NO: 53), KCCYSL (SEQ ID NO: 54), WTGWCLNPEESTWGFCTGSF (SEQ ID NO: 55), DTDMCWWWSREFGWECAGAG (SEQ ID NO: 56) or a modified sequence thereof.

In one embodiment, a receptor-binding peptide of a chimeric peptide of the present invention is a vascular epithelial growth factor receptor 1 (VEGFR1)-binding peptide and has the amino acid sequence WHSDMEWWYLLG (SEQ ID NO: 31), VEPNCDIHVMWEWECFERL-NH2 (SEQ ID NO: 32) or GGNECDAIRMWEWECFERL (SEQ ID NO: 33), or a modified sequence thereof.

In one embodiment, a receptor-binding peptide of a chimeric peptide of the present invention is a Transferrin Receptor (TfR)-binding peptide and has the amino acid sequence THRPPMWSPVWP (SEQ ID NO: 34) or a modified sequence thereof.

In one embodiment, a receptor-binding peptide of a chimeric peptide of the present invention is: a fibroblast growth factor receptor (FGFR)-binding peptide and is MQLPLAT (SEQ ID NO: 5) or AAVALLPAVLLALLAP (SEQ ID NO: 6); neuropilin 1 (NRP1)/vascular endothelial growth factor receptor 2 (VEGFR2)-binding peptide and is ATWLPPR (SEQ ID NO: 36); ephrin B1 (EphB1)-binding peptide and is EWLS (SEQ ID NO: 37); ephrin B2 (EphB2)-binding peptide and is SNEW (SEQ ID NO: 38); interleukin-11 receptor (IL11R)-binding peptide and is CGRRAGGSC (cyclic) (SEQ ID NO: 22); a glucose-regulated protein 78 (GRP78)-binding peptide and is WDLAWMFRLPVG (SEQ ID NO 39) or CTVALPGGYVRVC (cyclic) (SEQ ID NO: 40); a prostate-specific membrane antigen (PSMA)-binding peptide and is CQKHHNYLC (SEQ ID NO: 35); or a modified sequence thereof.

In one embodiment, a chimeric peptide of the present invention has a sequence selected from the group consisting of: SEQ ID NOS: 2, 14, 21, 42 and 43, or a modified sequence thereof.

In one embodiment, a chimeric peptide of the present invention has the sequence set forth in SEQ ID NO: 15 or a modified sequence thereof.

In one embodiment, a chimeric peptide of the present invention has the sequence set forth in SEQ ID NO: 16 or a modified sequence thereof.

In one embodiment, a chimeric peptide of the present invention has the sequence set forth in SEQ ID NO: 17 or a modified sequence thereof.

In one embodiment, a chimeric peptide of the present invention has the sequence set forth in SEQ ID NO: 18 or 44 or a modified sequence thereof.

In one embodiment, a chimeric peptide of the present invention has the sequence set forth in SEQ ID NO: 19 or a modified sequence thereof.

In one embodiment, a chimeric peptide of the present invention has the sequence set forth in SEQ ID NO: 20, 46 or 47 or a modified sequence thereof.

In one aspect, the present invention provides a nucleic acid encoding the chimeric peptide of the present invention.

In another aspect, the present invention provides a vector including a nucleic acid which encodes the chimeric peptide of the present invention.

In another aspect, the present invention relates to a cell including a nucleic acid which encodes the chimeric peptide of the present invention.

In another aspect, the present invention relates to a pharmaceutical, preferably a pharmaceutical composition, including the chimeric peptide of the present invention.

In another aspect, the present invention relates to an anticancer agent including the chimeric peptide of the present invention.

In another aspect, the present invention relates to a use of the chimeric peptide of the present invention for the manufacture of a pharmaceutical composition.

In another aspect, the present invention relates to a use of the chimeric peptide of the present invention for the manufacture of an anticancer agent.

In another aspect, the present invention relates to a method of treatment including the step of administering the chimeric peptide of the present invention.

In another aspect, the present invention relates to a method of treating cancer including the step of administering the chimeric peptide of the present invention.

In one aspect, the present invention relates to a method of screening a pharmaceutical using an amino acid sequence targeted by an EGF receptor-binding peptide of the present invention.

In one aspect, the present invention relates to a method of screening an anticancer agent using an amino acid sequence targeted by an EGF receptor-binding peptide of the present invention.

Production of various types of chimeric peptides have been attempted. In comparison with the closest prior art (Ellerby H M, Arap W, Ellerby L M, et al., Nat Med 1999; 5:1032-8; Papo N, Shai Y. Biochemistry 2003; 42:9346-54; and Papo N, Braunstein A, Eshhar Z, Shai Y. Cancer Res 2004; 64:5779-86), the present invention can be recognized to attain a significant effect in that it achieved cancer cell targeting and enhancement and immediateness of cell-killing effect with respect to cancer cells as compared to a cancer cell membrane-lytic peptide alone, as a result of chimerization of the present invention. Specifically, although another closest prior art, the targeting approach towards cancer utilizing bacterial toxin-based immunotoxin, is fascinating, its limitation of use lies in the liver toxicity due to the bacterial toxin and immunogencity caused by the toxin proteins (Non-Patent Document 2, 4, 6). In addition, molecular size of immunotoxins is generally larger compared to chemical compounds or fragment antibody drugs, which might prevent drugs from efficiently penetrate into tumor mass in the human body (Non-Patent Document 2, 4, 6). These documents merely present an issue of protein formulations such as immunotoxin, and present no means for solving the issue. To overcome this issue, a new generation immunotoxins with evolutional approach are critically needed.

In all these aspects, it is understood that each embodiment described herein may be applied in other aspect as long as it is applicable.

Effect of the Invention

A substance usable as an anticancer agent or DDS which has intracellular stability, capable of evading side effects from functional disorder with respect to normal cells, or which has instantaneous effects is provided.

BRIEF DESCRIPTION OF THE DRAWINGS

FIG. 4C shows permeabilization of cell membranes by lytic peptide in MDA-MB-231 breast cancer cells. Cells ($3 \times 10^4$ cells/ml) in calcein solution for 0 minute, two minutes, five minutes, 10 minutes and 20 minutes after addition of lytic peptide-TAMRA at a final concentration of 10 μM.

FIG. 17A shows that the newly designed lytic peptide is suitable for chimeric peptides for enhancing cytotoxic activity to cancer cells. Cancer cell lines H322, BT-20, U251, BxPC-3, SU8686 and LNCaP were cultured with various concentrations (0 to 20 µM) of EB-lytic chimeric peptide (black circle) or EB(H2R)-lytic chimeric peptide (white circle), and cytotoxic activity was assessed using WST-8 reagent.

FIG. 20A shows that EB(H2R)-Lytic peptide induces Annexin V-positive expression more strongly than EB-Lytic peptide in cancer cells. Human breast cancer cell line BT20 cells were incubated with EB-Lytic peptide or EB(H2R)-Lytic peptide (5 µM of each) at 37° C. for two hours, and analyzed by dual-color flow cytometry for Annexin V labeling.

FIG. 25B shows cytotoxicity of siRNA or scramble sequence (sc) RNA to cancer cell lines. T47D cells and MDA-MB-231 cells were transfected with siRNA or scRNA. Four days after the transfection, the levels of target gene in the cells were analyzed by flow cytometry analysis (data not shown), and the percentage of inhibition was assessed using WST-8 reagent. The assay was repeated three times, and the results are represented as means of triplicate measurements ±SD (bar).

FIG. 28A shows entire structure of IL4 and IL-4Ra. FIG. 28B shows an enlarged region of the position of interface between IL4 and IL-4Ra. A residue important for binding IL4 to IL-4Ra is represented by a black letter.

FIG. 34A shows cytotoxic activity of Sema3A-nLytic for various cell lines. Pancreas cell line was cultured with various concentrations (0 to 50 μM) of Sema3A-nLytic peptide or nLytic peptide alone for 48 hours, and cytotoxic activity was assessed using WST-8 reagent. Rhomboid, nLytic peptide; quadrangle, Sema3A-nLytic (363-377) peptide; triangle, Sema3A-nLytic (371-377) peptide.

FIG. 35A shows binding of Sema3A wild-type peptide to NRP1 protein. Samples of serially diluted various concentrations (1.6 μM, 13 μM, 26 μM) of Sema3A wild-type peptide were analyzed on parallel sensor surface. FIG. 35B shows binding of wild-type and mutated peptides of Sema3A (R372K and R372K/R377K) to NRP1 protein. Samples of various serially diluted Sema3A peptides (26 μM) were analyzed on parallel sensor surface. FIG. 35C shows outline of binding ability of various Sema3A peptides to NRP1 protein. FIG. 35D shows peptide sequence of wild-type and mutated peptides of Sema3A. The sequence identifiers corresponding to the amino acid sequences shown in FIG. 35D are as follows: Sema3A wild peptide, SEQ ID NO:29; R372K, SEQ ID NO:60; V373A, SEQ ID NO:61; P374T, SEQ ID NO:62; Y375L, SEQ ID NO:63; P376T, SEQ ID NO:64; R377K, SEQ ID NO:65; R372K/R377K, SEQ ID NO:66; and Sema3A short peptide, SEQ ID NO:67.

FIG. 36A shows expression of NRP1 in some pancreatic cancer cell lines (BxPC-3, CFPAC-1, Panc-1 and SU8686) and pancreatic epithelial cells as analyzed by RT-PCR analysis. FIG. 36B shows expression of NRP1 in breast cancer cell lines (BT-20, MDA MB-231, SKBR-3, TD47D and ZR-75-1) as analyzed by RT-PCR analysis. In all RT-PCR analysis, β-actin was used as positive control.

BEST MODE FOR CARRYING OUT THE INVENTION

Figure 1A:
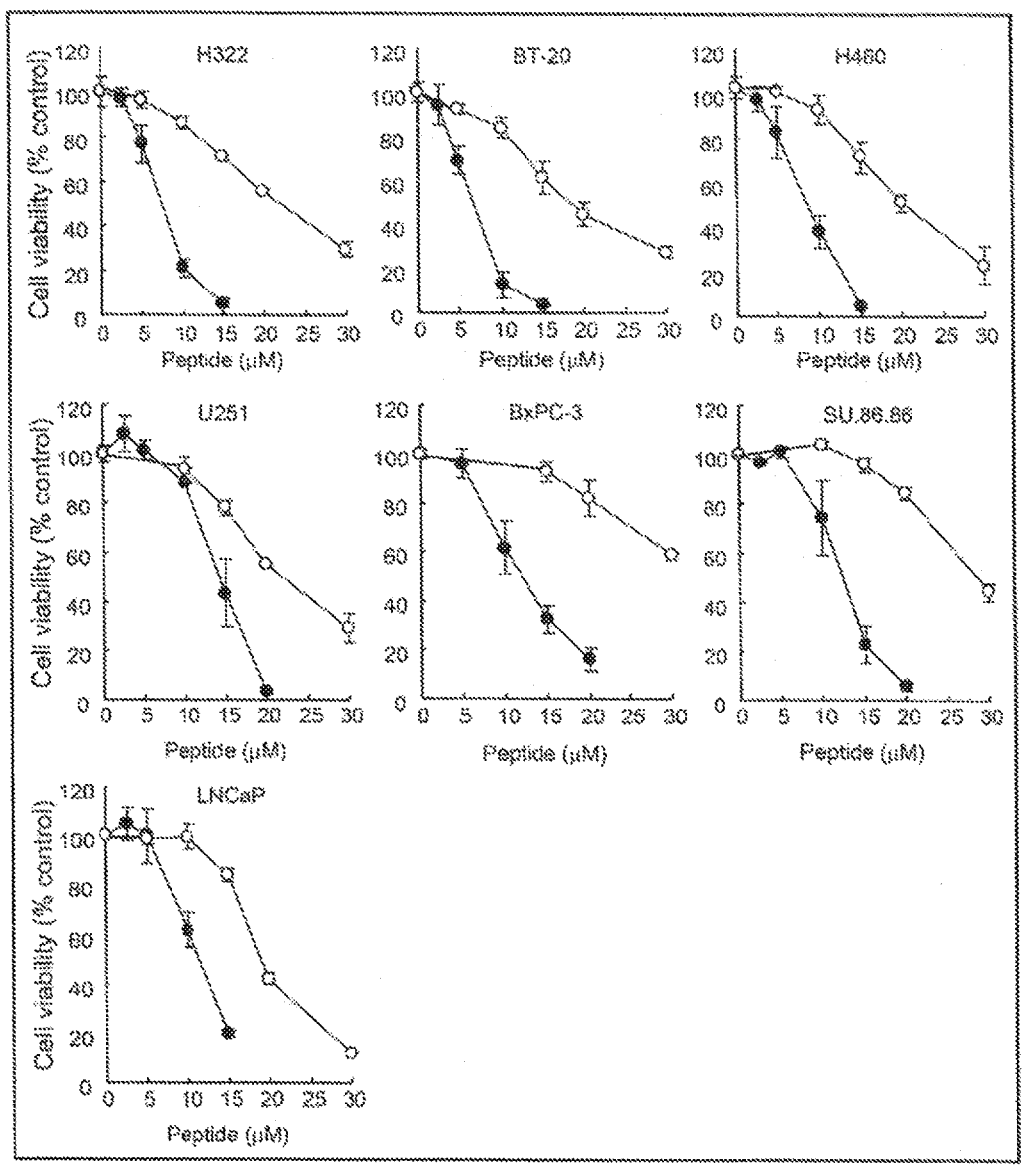
FIG. 1A shows cell-killing effect of EGFR-binding (EB)-lytic chimeric peptide or lytic peptide alone in various human cancer cell lines. Cancer cell line H322, BT-20, H460, U251, BxPC-3, SU.86.86 or LNCaP was cultured with various concentrations (0 to 30 µM) of EB-lytic chimeric peptide or lytic peptide for 72 hours, and cytotoxic activity was assessed using WST-8 reagent. The results are represented as mean of triplicate measurements ±SD (bar). This assay was repeated three times. Black circle, EB-lytic chimeric peptide; white circle, lytic peptide.
Figure 1B:
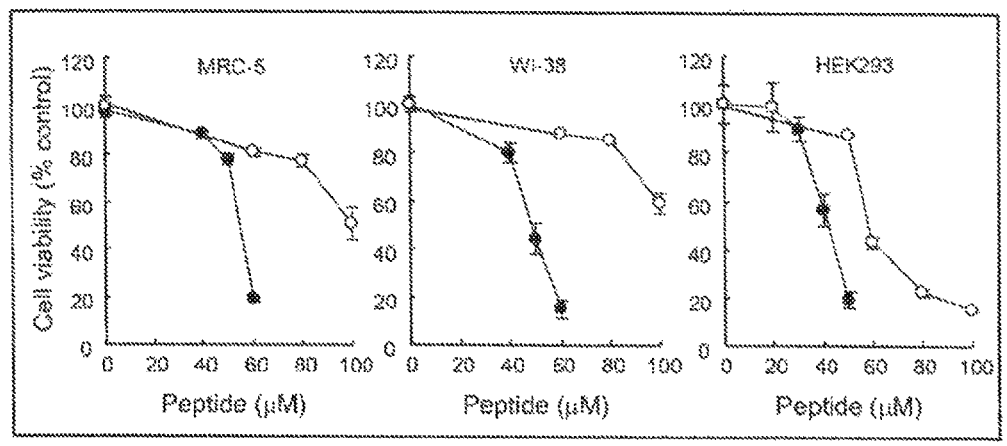
FIG. 1B shows a cell-killing effect of EB-lytic chimeric peptide or lytic peptide alone in various human normal cell lines. Normal cell lines MRC-5, WI-38 or HEK293 was cultured with various concentrations (0 to 100 μM) of the peptides for 72 hours, and cytotoxic activity was assessed. The results are represented as mean of triplicate measurements ±SD (bar). This assay was repeated three times. Black circle, EB-lytic chimeric peptide; white circle, lytic peptide.

Hereinafter, regarding the present invention, embodiments of the invention will be explained. It should be understood that throughout the present specification singular expressions (corresponding articles, adjectives and the like in other languages, such as "a," "an" and "the" in English) also include concepts in plural form, unless particularly mentioned. Further, it should be understood that the terms used herein are used in the meaning normally used in the art, unless particularly mentioned. Thus, unless defined otherwise, all technical terms and scientific technology terms used herein have the same meaning as generally understood by those skilled in the art to which the present invention belongs. In the case of contradiction, the present specification (including definitions) precedes.

(Definitions Of Terms)

Hereinafter, definitions of terms particularly used herein are listed.

As used herein, "epidermal growth factor (EGF)" refers to a growth factor belonging to EGF superfamily. In terms of history, a representative example of EGF is a polypeptide having a molecular weight of about 6,000 and consisting of 53 amino acids, which has been reported as a pharmacologically active substance present in the submandibular gland of a male mouse and which has three disulfide bonds composed of six cysteines in a molecule. For the first time, it was believed to act specifically on the growth of epidermal cells, but it also acts on non-epidermal cells, and exhibits various biological activities. As EGF, genes of the following GenBank accession number or the like can be included as representative examples: GenBank#NM_001963 (human) or Entrez Gene ID 1950.

As used herein, "epidermal growth factor receptor" and "EGF receptor" (EGFR) are interchangeably used, and refer to a receptor, of which a ligand is EGF. EGF receptor was found as v-erbB, one of viral cancer genes present in a genome of avian erythroblastosis virus (AEV). A corresponding gene c-erbB1 present in a human genome is an EGFR gene. The structure thereof is as described below.

Specifically, an EGF receptor is composed of a single polypeptide. The N-terminal side continues to an extracellular region having a ligand-binding site, and forms a single-spanning transmembrane region. The C-terminal side forms an intracellular region having tyrosine kinase activity. The receptor is associated via binding of a ligand, resulting in activation of tyrosine kinase. A human EGF receptor is a transmembrane glycoprotein having a molecular mass of about 170 kDa, among which an extracellular region causing association of a receptor in a ligand-dependent manner is a glycoprotein of about 95 kDa (Ogiso H, et al., 2002, Cell, 110:775-87). Binding of EGF or TGF-α to EGFR activates a signal transduction pathway to cause cellular growth. Dimerization, high-order structural change and internalization of an EGFR molecule function to transduce intracellular signal to cause cellular growth control (G. Carpenter and S. Cohen, 1979, Ann. Rev, Biochem., 48:193-216). Genetic change which influences on control of a growth factor receptor functions to or leads to over-express a receptor and/or a ligand, thereby causing cellular growth (M.-J. Oh et al., 2000, Clin. Cancer Res., 6:4760-4763). GenBank# is NM_005228 (human). As EGFR, in addition, the gene of the following GenBank accession number or the like can be included as a representative example: Entrez Gene ID 1956.

As used herein, "target-binding" peptide or "target-binding" sequence refers to a peptide or sequence which binds to a target (for example, EGF receptor or other target). For example, a binding sequence specific for a receptor with high expression in cancer cells can be included as an example thereof.

As used herein, "a binding sequence specific for a receptor with high expression in cancer cells" refers to a sequence specifically binding to a receptor which expresses highly in cancer cells. A receptor for which high expression is observed in cancer cells as specifically defined below includes peptide sequences which respectively bind specifically to a growth factor receptor involved in cellular growth, a receptor involved in angiogenesis, a cytokine/chemokine receptor, and the like. By phage display technique, three-dimensional structure analysis or the like, specific binding sequences are found.

As used herein, "EGF receptor-binding peptide (EB peptide)" or "EGF receptor-binding sequence (EB sequence)" refers to a peptide or sequence binding to EGF receptor.

Typically, the following can be included as examples of EGF receptor-binding sequences.

1) YHWYGYTPQNVI (SEQ ID NO: 7; wherein H may be substituted with R or K). These modified sequences are sequences screened from a peptide library by phage display technique, and have never been published in mutation analysis or the like conducted so far. They are mutants in which H having a plus charge has been substituted with R or K, while paying attention to an amino acid having a charge believed to be important in receptor-ligand bond, and are expected to have a significant effect in the present invention.

Herein, when not particularly mentioned, "lytic peptide moiety," "cytotoxic peptide" and "cytotoxic sequence" are used interchangeably with "cytolytic peptide (sequence)" or "cell membrane-lytic peptide (sequence)." They have a peptide which may lyse a cell membrane. Typically, examples thereof include those which are composed of an amino acid having a plus charge [K, R or (H)] and a hydrophobic amino acid [L, A, F or the like] and which have a 10- to 30-amino acids sequence with an amphipathic helix structure. Representative peptide sequences as those which act on a cancer cell membrane to exhibit cell-killing effect and which may be particularly used in the present invention are described below: KLLLKLLKKLLKLLKKK (SEQ ID NO: 48; specifically SEQ ID NO: 1, 27 or the like): cell membrane-lytic, FLKLLKKLAAKLF (SEQ ID NO: 11): antibacterial peptide derivative, cell membrane potential-disintegrating, RLLRRLLRRLLRRLLRRLLR (SEQ ID NO: 12) and RLLRRLL-RRLLRK (SEQ ID NO: 13): antibacterial peptide derivative, cell membrane-lytic and nucleic acid-biding, KLAK-LAKKLAKLAK (SEQ ID NO: 4): mitochondrial membrane disintegrating.

Thus, from such information, it can be recognized that representative cytotoxic peptide is a 10- to 30-amino acids sequence composed of an amino acid having a plus charge [K, R or (H)] and a hydrophobic amino acid [L, A, F or the like], and having amphiphatic helix structure.

It revealed that use of KLLLKLLKKLLKLLKKK (SEQ ID NO: 1; the underlined letters represent D-amino acids) attains a significant effect in comparison with LKLLKKL LKKLLKLL-NH$_2$ (SEQ ID NO: 41; the underlined letters represent D-amino acids) known as the original sequence, on the following points: for example, it revealed that combination of an EGFR-binding sequence before the sequence results in synergistic effect in a cell-killing activity in a cancer cell-specific manner. It also revealed that more selectivity with normal cells is achieved. Hybridization with various target proteins is possible. Thus, it is understood that further targeting to cancer cells is possible.

Furthermore, it revealed that a peptide referred to as nLytic (LLKLLKKLLKKLLKL; SEQ ID NO: 45; the underlined letters represent D-amino acids) attains a significant effect on the following points: as it revealed that selectivity with normal cells are achieved, it is believed that the toxicity is low. It also revealed that combination with Sema3A peptide results in synergistic effect in a cell-killing activity in a cancer cell-specific manner. Thus, it is understood that further targeting to cancer cells is possible.

As used herein, "spacer" refers to a portion which forms a chemical bond between molecules of chain macromolecules, like bridging. Representative examples of spacer include a O— to 5-amino acids sequence consisting of G and P. Herein, particularly, a spacer may intervene and may be bound between a lytic peptide and an EGF receptor-binding peptide. Examples of such a spacer include, for example, GGG, GG, G, PP and GPG. A spacer is not essential and may be absent, but in the present invention, such a spacer is preferably included.

As used herein, "peptidetoxin" refers to an anticancer-targeted peptide which has cytotoxicity and cell-killing ability. Peptidetoxin of the present invention can include peptides formed by combining cytotoxic moiety which corresponds to an explosive portion and a moiety assigned for specificity for cancer cells, which corresponds to a warhead portion (for example, a peptide/sequence binding specifically to a receptor which expresses highly in cancer cells). Regarding "explosive portion," in the actual circumstance, a cell membrane-lytic sequence is preferred, and regarding "warhead portion," any sequence that binds specifically to a protein (particularly receptor) which highly expresses in cancer cells is possible. For example, "cancer cell membrane-lytic peptidetoxin" composed of a binding sequence specific for a receptor with high expression in cancer cells, spacer and a cancer cell membrane-lytic sequence can be included as a representative example.

Methods of production and use of "cancer cell membrane-lytic peptidetoxin" composed of a binding sequence specific for a receptor with high expression in cancer cells, spacer and cancer cell membrane-lytic sequence are described below. Herein, any binding sequence specific for a receptor with high expression in cancer cells, any spacer, and any cancer cell membrane-lytic sequence can be combined arbitrarily. Methods of production and use thereof are specifically described below.

(Method of Production)

For peptidetoxins formed of a number of combinations of warhead and explosive sequences, which allow early individuated therapy of cancer, chemical synthesis capable of providing them in a short period is suitable, but a method is also possible in which peptidetoxins are forcibly expressed by genetic recombination and then purified.

(Method of Use)

Regarding a cancer cell to be treated, profile of a protein which highly expresses on cell surface and sensitivity to damage of the cancer cell against the explosive peptide are investigated. Based on the results, the warhead and explosive are selected, and a peptidetoxin optimal for the cancer cell is designed. A tailor-made peptidetoxin obtained by chemical synthesis or the like is combined with DDS such as atelocollagen depending on necessity, and is topically or systemically administered for treatment.

The cell membrane-lytic sequence used by the present inventors, when used alone, contact for a long time is necessary for exhibiting a cell-killing effect on cancer cells, and the cell-killing effect is also mild. However, when the cell membrane-lytic sequence is conjugated with a cancer cell-targeted sequence to be chimerized, the resulting sequence binds preferentially to cancer cells in which the target molecules of the sequence are highly expressed. Thus, contact time can be reduced, and the cell-killing effect is also enhanced. Actually, in chimerization of binding sequence such as IL4 receptor, her2 or the like, enhancement of cell-killing effect and reduction of contact time were confirmed. Accordingly, it can be rationally expected that even other similar chimeric sequences attain similar effects of enhancement of cell-killing effect and reduction in contact time.

Regarding peptidetoxins which allow such individuated therapy at early stage, combination of warhead and explosive can lead to a landmark therapy for patients with cancer. Thus, the new concept of peptidetoxins of the present invention is important in that it provides the maximum advantage for patients with cancer.

A chimeric peptide or peptidetoxin of the present invention should be noted in that it attained cancer cell targeting, enhancement of cell-killing effect and instantaneous cell-killing effect with respect to cancer cells as compared to a cell membrane-lytic peptide alone, as a result of chimerization, even in comparison with the closest prior art in the circumstance where various types of chimeric peptides have been granted a patent.

Sequences of a portion assigned for cell membrane permeability, which can be used herein are as described below. Common feature includes, for example, content of a large amount of amino acids having a charge.

As used herein, "cell-permeable peptide" refers to a peptide capable of passing a cell membrane to invade inside the cell. Whether or not a peptide is "a cell-permeable peptide" can be evaluated by the following test. Specifically, herein, regarding Antp, as described in known methods (see Derossi et al., J. Biol. Chem. 1996, 271, 18188-18193), it is possible to add a biotinized Antp peptide to a cell, subsequently add a compound chemically labeled with streptavidin, and confirm localization in the cell using fluorescence microscope. Alternatively, it is possible to similarly confirm localization of an antibody which has been reacted with a streptavidin-binding antibody and then chemically labeled in the same manner using fluorescence microscope, thereby confirming invasion inside the cell.

Examples of cell-permeable peptides can include, for example, RQIKIQFQNRRMKWKK (Antp; SEQ ID NO: 58) which is Antennapedia homeobox sequence, YGRKKRRQRRR (TAT; SEQ ID NO: 23), RRRRRRRRRRR (SEQ ID NO: 24) and the like. Typically, the structure thereof can include, for example, Gene ID 155871 (TAT protein per se). As cell-permeable peptide, in addition, a gene of the following GenBank accession number or the like can be a representative example: NP_057853; Tat [human immunodeficiency virus 1, amino acid sequence] MEPVDPRLEP WKHPGSQPKT ACTNCYCKKC CFHC-QVCFIT KALGISYGRK KRRQRRRAHQ NSQTHQASLS KQPTSQPRGD PTGPKE 1 (SEQ ID NO: 57).

Examples of a sequence of a portion assigned for specific inhibition of cancer cell growth in the cytoplasm, which can be used herein include KAYARIGNSYFK (TPR; SEQ ID NO: 59) which is HSP90 TPR domain-binding peptide, and the like.

Representatives cytotoxic peptides used herein can include cell membrane-lytic peptide, cell membrane potential-destabilizing peptide, cell membrane-lytic and nucleic acid-binding peptide and mitochondrial membrane-disintegrating peptide.

As used herein, "cell membrane-lytic peptide" refers to a peptide composed of an amino acid having a plus charge [K, R or (H)] and a hydrophobic amino acid [L, A, F or the like] and having a 10- to 30-amino acids sequence with an amphipathic helix structure, which disintegrates a cell membrane from outside to exhibit a cell-killing effect. Representative specific examples include: a peptide having a 10- to 20-amino acids sequence consisting only of K and L, wherein the amino acids are L-, D- or D,L-mix amino acids, such as KLLLKLLKKLLKLLKK (SEQ ID NO: 48; specifically SEQ ID NO: 1, 27 or the like).

As used herein, "cell membrane potential-destabilizing peptide" refers to a peptide composed of an amino acid having a plus charge [K, R or (H)] and a hydrophobic amino acid [L, A, F or the like] and having a 10- to 30-amino acids sequence, which forms a pore on a cell membrane from the outside, destabilizes the cell membrane potential, disintegrate the cell membrane, and exhibits a cell-killing effect. Representative specific examples include FLKLLKKLAAKLF (SEQ ID NO: 11) and the like.

As used herein, "cell membrane-lytic and nucleic acid-binding peptide" refers to a peptide composed of an amino acid having a plus charge [K, R or (H)] and a hydrophobic amino acid [L, A, F or the like] and having a 10- to 30-amino acids sequence with an amphipathic helix structure, which disintegrates a cell membrane from outside, invades inside the cell, binds to a nucleic acid and induces cell death. Representative specific examples include a peptide having a 10- to 20-amino acids sequence consisting only of K and L, wherein the amino acids are L-, D-, or D,L-mix amino acids, such as RLLRRLLRRLLRRLLRRLLR (SEQ ID NO: 12), RLLRRLLRRLLRK (SEQ ID NO: 13) and the like.

As used herein, "mitochondrial membrane-disintegrating peptide" refers to a peptide composed of an amino acid having a plus charge [K, R or (H)] and a hydrophobic amino acid [L, A, F or the like] and having a 10- to 30-amino acids sequence with an amphipathic helix structure, which disintegrates a mitochondrial membrane to induce cell death only upon successful invasion inside the cell. Representative specific examples include KLAKLAKKLAKLAK (SEQ ID NO: 4) and the like.

Preferred examples of cytotoxic peptides include a peptide composed of an amino acid having a plus charge [K, R or (H)] and a hydrophobic amino acid [L, A, F or the like] and having a 10- to 30-amino acids sequence with an amphipathic helix structure. Preferably, the amino acid having a plus charge may be K, R or H, and the hydrophobic amino acid may be I, L, V, A or F.

The hydrophobic amino acid used in the present invention is KLLLKLLKKLLKLLKKK, wherein each amino acid is L- or D-amino acid and the underlined letters represent D-amino acids.

As a matter clarified by the present invention, it revealed that a chimeric peptide in which a receptor-binding peptide, such as EGFR, has been conjugated is advantageous to have an amphipathic helix structure, preferably a-helix structure. Thus, also in a case of constructing a chimeric peptide including other, receptor-binding peptide and cytotoxic peptide, it is advantageous that such a peptide has an amphipathic helix structure, preferably a-helix structure. It is understood that these matters can be also deduced from the results shown in FIG. 1D. Specifically, it has been demonstrated that EB-lytic peptide weakly bound to small unilamellar vesicles (SUVs) composed of phosphatidylcholine (PC), which is the dominant lipid species on the surface of normal cell membranes, and was not well structured with the PC liposome, while this EB-lytic peptide was capable of binding to SUVs containing phosphatidylserine (PS), which is exposed specifically on cancer cell membranes, and conformed to a partial helical structure as characterized by double minima at 209-210 and 222 nm. It has revealed that, EB-original lytic peptide was capable of binding strongly to both PC and PC/PS liposomes, and conformed to helical structures (FIG. 1D(c)). It is indicated that the chimeric peptide newly designed in the present invention has a selectivity to PS-containing membranes and conforms to a helical structure which is supposed to be essential for making a pore on the cell surface (Papo, N. & Shai, Y. New Lytic peptides based on the D,L-amphipathic helix motif preferentially kill tumor cells compared to normal cells. Biochemistry 42, 9346-9354 (2003)). Thus, these data can be a reference and help in designing other forms of the lytic peptide.

Examples of such include a sequence selected from the group consisting of SEQ ID NO: 2, 14, 21, 42 and 43 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 15 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 16 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 17 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 18 or 44 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 19 or a modified sequence thereof. Here, modified sequence includes a sequence which includes one or several amino acid substitutions, additions or deletions, preferably conservative substitutions, of the sequence specifically described here.

In one embodiment, a chimeric peptide of the present invention has the sequence set forth in SEQ ID NO: 20, 46 or 47 or a modified sequence thereof. Here, modified sequence includes a sequence which includes one or several amino acid substitutions, additions or deletions, preferably conservative substitutions, of the sequence specifically described here.

Regarding a modified sequence of them, those skilled in the art can carry out modification such that the sequence has a preferred amphipathic (a) helical structure, based on the description herein. Furthermore, for example, regarding one amino acid substitution, it has been demonstrated that an amphipathic (a) helical structure is retained in a chimeric peptide related to EGF-R. It is understood that other chimeric peptide is also expected to retain the amphipathic (a) helical structure. Furthermore, it is understood that other modifications such as substitution of a plurality of amino acids can be appropriately carried out by those skilled in the art with reference to the descriptions in the Examples, and the like.

In another preferred embodiment, as a cancer cell growth-inhibiting peptide which acts intracellularly, a peptide having the sequence of RQIKIQFQNRRMKWKKKAYARIGN-SYFK (SEQ ID NO: 25) is used. Alternatively, a peptide referred to as TAT (YGRKKRRQRRR) (SEQ ID NO: 23) may also be used. It is known that a sequence in which 11 Rs are linked, RRRRRRRRRRR (SEQ ID NO: 24), permeates cells, and such a sequence can also be used. Furthermore, those skilled in the art can appropriately determine preferred combination of cell-permeable peptide and TPR domain-binding peptide. Preferably, combination with Antp can be used.

As used herein, "chimericpeptide" refers to a peptide formed of two or more moieties (peptides) of different genotypes. It is also referred to as a fusion protein. It is used for studying function of a domain of a protein or detecting expression of a protein of interest.

As used herein, "similar amino acid" refers to an amino acid which is in a relationship of conservative substitution, and the following amino acids correspond:
A: G, I, V, L
C: M (S-containing amino acid)
D: N, Q or E
E: Q, N or D
F: Y, A or the like
G: A
H: W, R, K or the like
I: A, L, V, (G)
K: R, H
L: A, I, V, (G)
M: S or the like
N: D, E or Q
P: HyP
Q: E, N or D
R: K, H
S: T, Y
T: S, Y
V: I, L, A, (G)
W: H
Y: F, S, T.

Substitutions between these amino acids are also referred to as "conservative substitution" herein.

Herein, amino acids which are frequently found in an EGF receptor-binding peptide refer to those which are found frequently in various EGF receptor-binding peptides. Typically, amino acids in a relationship of conservative substitution are included. Or, the following amino acids correspond:
the peptide having an amino acid sequence $X_1X_2X_3X_4X_5X_6X_7X_8X_9X_{10}X_{11}X_{12}$ (SEQ ID NO: 8), wherein:
$X_1$ is Y or an amino acid similar thereto;
$X_2$ is H or an amino acid similar thereto;
$X_3$ is W or an amino acid similar thereto;
$X_4$ is Y or an amino acid similar thereto;
$X_5$ is G or an amino acid similar thereto;
$X_6$ is Y or an amino acid similar thereto;
$X_7$ is T or an amino acid similar thereto;
$X_8$ is P or an amino acid similar thereto;
$X_9$ is Q or an amino acid similar thereto;
$X_{10}$ is N or an amino acid similar thereto;
$X_{11}$ is V or an amino acid similar thereto; and
$X_{12}$ is I or an amino acid similar thereto.

Preferably, $X_1$ is Y, or an amino acid similar thereto having an OH group or an aromatic group;
$X_2$ is H, or an amino acid similar thereto having a plus charge;
$X_3$ is W, or an amino acid similar thereto having an aromatic group;
$X_4$ is Y, or an amino acid similar thereto having an OH group;
$X_5$ is G, or an amino acid similar thereto having an aliphatic side chain;
$X_6$ is Y, or an amino acid similar thereto having an OH group;
$X_7$ is T, or an amino acid similar thereto having an OH group;
$X_8$ is P or an imino acid-type amino acid similar thereto;
$X_9$ is Q or an amide-type amino acid similar thereto;
$X_{10}$ is N, or an amino acid similar thereto having an OH group;
$X_{11}$ is V, or an amino acid similar thereto having an aliphatic side chain; and
$X_{12}$ is I, or an amino acid similar thereto having an aliphatic side chain.

More preferably, $X_1$ is Y, or an amino acid similar thereto which is S, H or F;
$X_2$ is H, or an amino acid similar thereto which is R or K;
$X_3$ is W, or an amino acid similar thereto which is Y, F or H;
$X_4$ is Y, or an amino acid similar thereto which is S, H or F;
$X_5$ is G, or an amino acid similar thereto which is A, V, I or L;
$X_6$ is Y, or an amino acid similar thereto which is S, H or F;
$X_7$ is T, or an amino acid similar thereto which is S, H or F;
$X_8$ is P, or an amino acid similar thereto which is hydroxyl proline;
$X_9$ is Q, or an amino acid similar thereto which is N;
$X_{10}$ is N, or an amino acid similar thereto which is S, H or F;
$X_{11}$ is V, or an amino acid similar thereto which is G, A, L or I; and
$X_{12}$ is I, or an amino acid similar thereto which is G, A, V or L.

A sequence in which $X_2$ is H or an amino acid similar thereto, which is R or K (for example, YRWYGYTPQNVI (SEQ ID NO: 9) or YKWYGYTPQNVI (SEQ ID NO: 10)) is preferred, because enhanced activity was found.

Herein, when a receptor-binding peptide used is interleukin 4 (IL-4) receptor-binding peptide, the amino acid sequence KQLIRFLKRLDRN (SEQ ID NO: 26) or a modified sequence thereof may be used. Here, the modified sequence can be modified in the same manner as the EGFR-binding peptide. In this modification, Thorsten Hage et al., Cell. 1999, vol. 97, No. 2, pp. 271-81 can be referenced. This literature is incorporated herein as a reference.

Herein, when a receptor-binding peptide used is interleukin 13 (IL-13) receptor-binding peptide, the amino acid sequence KDLLLHLKKLFREGQFN (SEQ ID NO: 28) or a modified sequence thereof may be used. Here, the modified sequence can be modified in the same manner as the EGFR-binding peptide. In this modification, Yuichiro Yoshida et al., Biochem Biophys Res Commun. 2007, vol. 358, No. 1, pp. 292-297 can be referenced. This literature is incorporated herein as a reference.

Herein, when a receptor-binding peptide used is neuropilin receptor-binding peptide, the amino acid sequence NYQWVPYQGRVPYPR (SEQ ID NO: 29) or a modified sequence thereof may be used. Here, the modified sequence can be modified in the same manner as the EGFR-binding peptide. In this modification, Alexander Antipenko et al., Neuron. 2003, vol. 39, No. 4, pp. 589-598 can be referenced. This literature is incorporated herein as a reference. These literatures merely present problems in protein formulations such as immunotoxins, and do not provide a chimeric peptide as in the present invention.

Herein, when a receptor-binding peptide used is human epidermal growth factor receptor type 2 (HER2)-binding peptide, the amino acid sequence YCDGFYACYMDV (SEQ ID NO: 30), LLGPYELWELSH(SEQ ID NO: 52), ALVRYKDPLFVWGFL (SEQ ID NO: 53), KCCYSL (SEQ ID NO: 54), WTGWCLNPEESTWGFCTGSF (SEQ ID NO: 55), DTDMCWWWSREFGWECAGAG (SEQ ID NO: 56)

or a modified sequence thereof may be used. Here, the modified sequence can be modified in the same manner as the EGFR-binding peptide. In this modification, Valeria R. Fantin et al., Cancer Res. 2005, vol. 65. No. 15, pp. 6891-6900 can be referenced. This literature is incorporated herein as a reference.

Herein, when a receptor-binding peptide used is vascular epithelial growth factor receptor 1 (VEGFR1)-binding peptide, the amino acid sequence WHSDMEWWYLL (SEQ ID NO: 31) or a modified sequence thereof may be used. Here, the modified sequence can be modified in the same manner as the EGFR-binding peptide. In this modification, Kimberly J. Peterson et al., Analytical Biochemistry 2008, vol. 378, No. 1, pp. 8-14 (regarding VEPNCDIHVMWEWECFERL-NH2 (SEQ ID NO: 32)) and Borlan Pan et al., J. Mol. Biol. 2002, vol. 316, No. 3, pp. 769-787 (regarding GGNECDAIRM-WEWECFERL (SEQ ID NO: 33)) can be referenced. These literatures are incorporated herein as references.

Herein, when a receptor-binding peptide used is Transferrin Receptor (TfR)-binding peptide, the amino acid sequence THRPPMWSPVWP (SEQ ID NO: 34) or a modified sequence thereof may be used. Here, the modified sequence can be modified in the same manner as the EGFR-binding peptide. In this modification, Jae H. Lee et al., Eur. J. Biochem. 2001, vol. 268, pp. 2004-2012 can be referenced. This literature is incorporated herein as a reference.

In addition, a receptor-binding peptide may be a fibroblast growth factor receptor (FGFR)-binding peptide which is MQLPLAT (SEQ ID NO: 5) or AAVALLPAVLLALLAP (SEQ ID NO: 6); neuropilin 1 (NRP1)/vascular endothelial growth factor receptor 2 (VEGFR2)-binding peptide which is ATWLPPR (SEQ ID NO: 36); ephrin B1 (EphB1)-binding peptide which is EWLS (SEQ ID NO: 37); ephrin B2 (EphB2)-binding peptide which is SNEW (SEQ ID NO: 38); interleukin-11 receptor (IL11R)-binding peptide which is CGRRAGGSC (cyclic) (SEQ ID NO: 22); a glucose-regulating protein 78 (GRP78)-binding peptide which is WDLAW-MFRLPVG (SEQ ID NO 39) or CTVALPGGYVRVC (cyclic) (SEQ ID NO: 40); a prostate-specific membrane antigen (PSMA)-binding peptide which is CQKHHNYLC (SEQ ID NO: 35); or a modified sequence thereof. Here, the modified sequence can be modified in the same manner as the EGFR-binding peptide. In this modification, the following literatures can be referenced: for FGFR (MQLPLAT (SEQ ID NO: 5)), Fukuto Maruta et al., Cancer Gene Therapy. 2002, vol. 9, pp. 543-552; for FGFR (AAVALLPAVLLALLAP (SEQ ID NO: 6)), Akiko Komi et al., Exp. Cell Res. 2003, Vol. 283, No. 1, pp. 91-100; for NRP1/VEGFR2 (ATWLPPR (SEQ ID NO: 36)), Loraine Tirand et al., J. Control Release. 2006, vol. 111, pp. 153-164; for EphB1 and EphB2, Mitchell Koolpe et al., J Biol. Chem. 2005, vol. 280, No. 17, pp. 17301-11; for IL11R, Amado J. Zurita et al., Cancer Res. 2004, vol. 64, pp. 435-439; for GRP78 (WDLAWMFRLPVG (SEQ ID NO: 39)), Marco A. Arap et al., Cancer Cell. 2004, vol. 6, pp. 275-284; for GRP78 (CTVALPGGYVRVC (SEQ ID NO: 40) and he like), Ying Liu et al., Mol. Pharmaceutics. 2007, Vol. 4, No. 3, pp. 435-447, Hardy B et al., Therapeutic angiogenesis of mouse hind limb ischemia by novel peptide activating GRP78 receptor on endothelial cells. Biochemical Pharmacology 75, 891-899, 2008; and for PSMA, Kaushal Rege et al., Cancer Res. 2007, vol. 67, No. 13, pp. 6368-6375. These literatures are incorporated herein as references.

These substitutions may be used alone or in combination of more than one. It is understood that any combination of these preferred substitutions may be effective, because enhancement of the effect was found as a result of these substitutions. It is understood that either one or a plurality of these mutations may be introduced. This is because, although not desired to be restricted by a theory, when it is understood that a mutation is permitted, it is understood that the three-dimensional structure and activity in interaction with a biological target and the like of the original active type is retained or enhanced, and thus it is expected that combination of a plurality of them also has a similar effect. In the case of the present invention, regarding change in activity as a result of one amino acid substitution, it is predicted that interaction with a partner protein thereof was influenced, but from a viewpoint of anticancer activity, the final purpose of the present invention, the activity was retained. Thus, it can be expected that a similar effect is obtained even in the case of combination of these amino acid substitutions.

As used herein, "protein", "polypeptide", "oligopeptide" and "peptide" are used in the same meaning in the present specification and refer to an amino acid polymer having any length. This polymer may be straight, branched or cyclic. An amino acid may be a naturally occurring or non-naturally occurring amino acid, and may be a modified amino acid. These terms may encompass those assembled with a complex of a plurality of polypeptide chains. These terms further encompass a naturally occurring or artificially modified amino acid polymer. Examples of such a modification include, for example, formation of a disulfide bond, glycosylation, lipidation, acetylation, phpophorylation, or any other manipulation or modification (for example, conjugation with a label component). The definition also encompasses, for example, a polypeptide including one or more analog(s) of amino acid (including, for example, an unnatural amino acid and the like), peptide-like compounds (for example, peptoid) and other modifications known in the art.

As used herein, "amino acid" may be either naturally occurring or non-naturally occurring amino acid, as long as it satisfies the purpose of the present invention.

As used herein, "nucleic acid" is used interchangeably with gene, cDNA, mRNA, oligonucleotide and polynucleotide. A particular nucleic acid sequence also encompasses "splice variant." Similarly, a particular protein encoded by a nucleic acid implicitly encompasses any protein encoded by a splice variant of the nucleic acid. As suggested by the name, "splice variant" is a product of alternative splicing of a gene. After transcription, the first nucleic acid transcript may be spliced so that a different (other) nucleic acid splice product encodes a different polypeptide. A production mechanism of a splice variant is changed, and alternative splicing of exon is included. Other polypeptide derived from the same nucleic acid by read through transcription is also encompassed in this definition. Any product of splicing reaction (including splice product of recombinant form) is encompassed in this definition. Or, allelic gene mutant is also included within this scope.

As used herein, "polynucleotide," "oligonucleotide" and "nucleic acid" is used in the same meaning and refer to a nucleotide polymer having any length. These terms may encompass "oligonucleotide derivative" or "polynucleotide derivative." "Oligonucleotide derivative" or "polynucleotide derivative" refers to oligonucleotide or polynucleotide which includes a nucleotide derivative or in which a bond between nucleotides is different from usual, and these terms are used interchangeably. Specific examples of such oligonucleotide include, for example, 2'-O-methyl-ribonucleotide, oligonucleotide derivative obtained by converting phosphodiester bond in the oligonucleotide into phosphorothioate bond, oligonucleotide derivative obtained by converting phosphodiester bond in the oligonucleotide into N3'-P5' phosphoroamidate bond, oligonucleotide derivative obtained by converting ribose and phosphodiester bond in the oligonucleotide into peptide nucleic acid bond, oligonucleotide derivative obtained by substituting uracil in the oligonucleotide with C-5 propynyl uracil, oligonucleotide derivative obtained by substituting uracil in the oligonucleotide with C-5 thiazol uracil, oligonucleotide derivative obtained by substituting cytosine in the oligonucleotide with C-5 propynyl cytosine, oligonucleotide derivative obtained by substituting cytosine in the oligonucleotide with phenoxazine-modified cytosine, oligonucleotide derivative obtained by substituting ribose in DNA with 2'-O-propylribose, oligonucleotide derivative obtained by substituting ribose in the oligonucleotide with 2'-methoxyethoxy ribose, and the like. Unless otherwise indicated, it is intended that a particular nucleic acid sequence encompasses an expressly described sequence and a conservatively modified variant thereof (for example, variant with substitution of degeneracy codon) and a complementary sequence. Specifically, a variant with substitution of degeneracy codon may be achieved by producing a sequence in which position 3 of one or more selected (or all) codons has been substituted with mix base and/or deoxyinosine residue (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

As used herein, "nucleotide" may be either naturally occurring or non-naturally occurring nucleotide, as long as the desired function is retained.

As used herein, "search" refers to utilizing a nucleic acid base sequence to find other nucleic acid base sequence having a particular function and/or property by electronic or biological method or other method. Electronic search includes, but is not limited to, BLAST (Altschul et al., J. Mol. Biol. 215:403-410 (1990)), FASTA (Pearson & Lipman, Proc. Natl. Acad. Sc., USA 85:2444-2448 (1988)), Smith and Waterman method (Smith and Waterman, J. Mol. Biol. 147:195-197 (1981)), and Needleman and Wunsch method (Needleman and Wunsch, J. Mol. Biol. 48:443-453 (1970)). Biological search includes, but is not limited to, stringent hybridization, microarray formed by attaching genomic DNA on nylon membrane or the like, microarray formed by attaching genomic DNA to a glass plate (micoarray assay), PCR, in situ hybridization, and the like. Herein, it is intended that a gene used in the present invention (for example, HSP90 or the like) should include corresponding genes identified by such electronic search or biological search.

Herein, a nucleic acid sequence which hybridizes to a particular gene sequence can also be used, as long as it has a function. Here, "stringent conditions" for hybridization refers to conditions under which a complementary strand of a nucleotide chain having similarity or homology to a target sequence preferentially hybridizes to a target sequence and a complementary strand of a nucleotide chain without similarity or homology does not substantially hybridize. "Complementary strand" of a nucleic acid sequence refers to a nucleic acid sequence which pairs based on a hydrogen bond between bases of the nucleic acid (for example, T to A and C to G). Stringent conditions are sequence-dependent, and vary in different situations. A longer sequence hybridizes specifically at a higher temperature. Generally, stringent conditions are selected at about 5° C. lower than thermal melting temperature ($T_m$) for a particular sequence at a defined ionic strength and pH. $T_m$ is a temperature at which 50% of nucleotides complementary to a target sequence hybridize to a target sequence at equilibrium state at a defined ionic strength, pH and nucleic acid concentration. "Stringent conditions" are sequence-dependent, and vary depending on various environmental parameters. General guideline of hybridization of nucleic acid are found in Tijssen (Tijssen (1993), Laboratory Techniques In Biochemistry And Molecular Biology-Hybridization With Nucleic Acid Probes Part I, Chapter 2, "Overview of principles of hybridization and the strategy of nucleic acid probe assay", Elsevier, New York).

Typically, stringent conditions are conditions under which salt concentration is less than about 1.0M $Na^+$. Typically, $Na^+$ concentration (or other salt) is about 0.01 to 1.0M at pH of 7.0 to 8.3, and a temperature is at least about 30° C. for a short nucleotide (for example, 10 to 50 nucleotides) and at least about 60° C. for a long nucleotide (for example, longer than 50 nucleotides). Stringent conditions also may be achieved by addition of a destabilizing agent such as formamide. Example of stringent conditions in the present specification include hybridization in buffer (50% formamide, 1M NaCl, 1% SDS) (37° C.) and washing at 60° C. in 0.1×SSC.

As used herein, "polynucleotide hybridizing under stringent conditions" refers to well-known conditions commonly used in the art. By using a polynucleotide selected from polynucleotides of the present invention as a probe and by using colony hybridization technique, plaque hybridization technique or Southern blot hybridization technique or the like, such a polynucleotide can be obtained. Specifically, the term means a polynucleotide which can be identified by hybridization at 65° C. in the presence of 0.7 to 1.0M NaCl using a filter immobilized with colony- or plaque-derived DNA, followed by washing of the filter at 65° C. conditions using 0.1- to 2-fold concentration of SSC (Saline-sodium citrate) solution (composition of 1-fold concentration of SSC solution is 150 mM sodium chloride and 15 mM sodium citrate). Hybridization can be performed in accordance with a method described in experiment books such as Molecular Cloning 2nd ed., Current Protocols in Molecular Biology, Supplement 1-38, DNA Cloning 1: Core Techniques, A Practical Approach, Second Edition, Oxford University Press (1995). Here, from a sequence hybridizing under stringent conditions, preferably, a sequence including A bases alone or T bases alone is excluded. "Hybridizable polynucleotide" refers to a polynucleotide capable of hybridizing to other polynucleotide under the aforementioned hybridization conditions. Examples of hybridizable polynucleotide specifically include a polynucleotide having at least 60% homology with a base sequence of DNA which encodes a polypeptide having an amino acid sequence specifically described in the present invention, preferably a polynucleotide having 80% or more homology or polynucleotide having 90% or more homology, and more preferably, a polynucleotide having 95% or more homology.

Amino acids may be mentioned herein by either three-letter code thereof as generally known or one-letter code recommended by IUPAC-IUB Biochemical Nomenclature Commission. Nucleotides may also be mentioned by one-letter code as generally recognized.

As used herein, "homology" of a gene refers to a degree of identity to each other among two or more gene sequences. Thus, the higher the homology of two genes is, the higher the identity or similarity of the sequences is. Whether or not two genes have homology can be investigated by direct comparison of the sequences, or in a case of nucleic acid, hybridization under stringent conditions, or the like. In a case of direct comparison of two gene sequences, when DNA sequences have typically at least 50% identity, preferably at least 70% identity, more preferably at least 80%, 90%, 95%, 96%, 97%, 98% or 99% identity, between the gene sequences, the genes have homology.

Herein, comparison of similarity, identity and homology of amino acid sequence and base sequence are calculated using default parameters with BLAST, a tool for sequence analysis. Identity search can be performed by using NCBI BLAST 2.2.9 (published May 12, 2004). Value of identity described herein normally refers to a value in a case of alignment under default conditions using the BLAST. However, when a higher value is given by change of parameter, the highest value is employed as a value of identity. When identity is evaluated in a plurality of regions, the highest value thereof is employed as a value of identity.

As used herein, "corresponding" gene refers to a gene having or predicted to have in a species an action similar to a given gene of a species which is the basis of comparison. When a plurality of genes having such action exist, "corresponding" gene refers to a gene having evolutionarily the same origin. Thus, a gene corresponding to a gene (for example, EGFR) may be ortholog of the gene. Thus, a gene corresponding to a human gene can also be found in other animals (such as mouse, rat, pig, rabbit, guinea pig, bovine and ovine). Such a corresponding gene can be identified using well-known techniques in the art. Accordingly, for example, a corresponding gene in an animal can be found by searching in sequence database of the animal (for example, mouse, rat, pig, rabbit, guinea pig, bovine, ovine or the like) using a sequence of a gene which is the basis of the corresponding gene as a query sequence.

As used herein, "fragment" refers to a polypeptide or polynucleotide having a sequence length up to 1 to n−1 with respect to the full-length polypeptide or polynucleotide (length: n). A length of a fragment can be appropriately changed depending on the purpose. Examples of a lower limit of the length include 3, 4, 5, 6, 7, 8, 9, 10, 15, 20, 25, 30, 40, 50 and more amino acids. A length represented by an integer not specifically listed here (for example, 11) may also be appropriate as a lower limit. Furthermore, in a case of polynucleotide, examples of lower limit include 5, 6, 7, 8, 9, 10, 15, 20, 25, 30, 40, 50, 75, 100 and more nucleotides, and a length represented by an integer not specifically listed here (for example, 11) may also be appropriate as a lower limit. Herein, a length of polypeptide and polynucleotide can be represented by the number of amino acids and nucleic acids, respectively, as described above. The aforementioned numbers are not absolute. It is intended that the aforementioned numbers as an upper limit or lower limit also include numbers some more or less (or, for example, 10% more or less) than the aforementioned numbers, as long as the same function is possessed. In order to express such intention, herein, the numbers may be expressed with "about" attached before the numbers. However, it should be understood that herein the presence or absence of "about" does not influence on interpretation of the numerical value. Herein, a length of useful fragment may be determined depending on whether or not at least one of functions of the full-length protein which is the basis for the fragment is retained.

As used herein, "variant," "modified sequence" or "analog" refers to what includes partial change with respect to an original substance such as polypeptide or polynucleotide, which preferably retains substantially at least one of functions of the original polypeptide or polynucleotide. Examples of such variant include substitution variant, addition variant, deletion variant, truncated variant, allelic mutant and the like. Allele refers to one member of a pair of distinct genetic variants located at the same gene locus. Therefore, "allelic mutant" refers to a variant in a relationship of allele of a certain gene. "Species homolog or homolog" refers to what has homology (preferably 60% or more homology, and more preferably 80% or more, 85% or more, 90% or more, and 95% or more homology) to a given gene in certain species at the amino acid or nucleotide level. A method for obtaining such a species homolog is apparent from the description of the specification.

In the specification, in order to produce a functionally equivalent polypeptide, an amino acid addition, deletion, or modification can be carried out in addition to an amino acid substitution. An amino acid substitution refers to replacement of an amino acid of an original peptide with one or more (for example, 1 to 10, preferably 1 to 5, and more preferably 1 to 3) amino acids. An amino acid addition refers to addition of one or more (for example, 1 to 10, preferably 1 to 5, and more preferably 1 to 3) amino acids to an original peptide. An amino acid deletion refers to deletion of one or more (for example, 1 to 10, preferably 1 to 5, and more preferably 1 to 3) amino acids from an original peptide. An amino acid modification includes, but is not limited to, amidation, carboxylation, sulfation, halogenation, alkylation, phosphorylation, hydroxylation, acylation (for example, acetylation), and the like. An amino acid to be substituted or added may be a naturally occurring amino acid, a non-naturally occurring amino acid, or an amino acid analog. A naturally occurring amino acid is preferable.

Such a nucleic acid can be obtained by well-known PCR technique, and can also be synthesized chemically. For example, site specific mutagenesis technique, hybridization technique or the like may be combined with such a method.

As used herein, "substitution, addition and/or deletion" of a polypeptide or a polynucleotide refers to replacement, addition, or removal of an amino acid or a substitute thereof, or a nucleotide or a substitute thereof, in an original polypeptide or polynucleotide. Such a substitution, addition and/or deletion technique is well known in the art, including, for example, site specific mutagenesis technique. These changes in the nucleic acid molecule or polypeptide which is the basis may be caused at 5' or 3' terminus of the nucleic acid molecule, at amino terminal site or carboxyl terminal site of an amino acid sequence which indicates this polypeptide, or may be caused anywhere between these terminal sites, and separately spread among residues in the sequence as the basis, as long as the desired function (for example, binding to TPR domain) is retained. Any number of substitution, addition or deletion is possible, as long as the number is one or more. Such a number can be increased, as long as the desired function (for example, binding to TPR domain) is retained in a variant having such substitution, addition or deletion. For example, the number may be one or several, and may be preferably 20% or less, 15% or less, 10% or less or 5% or less of a full length, or 150 or less, 100 or less, 50 or less, 25 or less, or the like.

(Production and Analysis of Peptide)

The peptide of the present invention (for example, chimeric peptide) may be obtained or produced by a method well known in the art (for example, chemical synthesis and general industrial technique discussed below). For example, a peptide corresponding to a part of a peptide including a desired region or domain or a peptide which mediates a desired activity in vitro may be synthesized by use of a peptide synthesizer. A peptide may also be analyzed by hydrophilicity analysis which may be used for identification of hydrophobic and hydrophilic regions of a peptide (see, for example, Hopp and Woods, 1981. Proc. Natl. Acad. Sci. USA. 78:3824-3828), and thus is a help in designing a substance for experimental manipulation (for example, binding test or antibody synthesis). Secondary structure analysis may also be performed in order to identify a region of a peptide which establishes a particular structural motif (see, for example, Chou and Fasman, 1974, Biochem. 13:222-223). Manipulation, translation, prediction of secondary structure, hydrophilicity and hydrophobicity profiles, prediction and plotting of open reading frame and determination of sequence homology may be achieved using a computer soft program available in the art. Examples of other method for structural analysis include X-ray crystal analysis (see, for example, Engstrom, 1974. Biochem. Exp. Biol. 11:7-13)); mass spectrometry and gas chromatography (see, for example, METHODS IN PROTEIN SCIENCE, 1997. J. Wiley and Sons, New York, N.Y.). Computer modeling (see, for example, Fletterick and Zoller, ed., 1986. Computer Graphics and Molecular Modeling: CURRENT COMMUNICATION IN MOLECULAR BIOLOGY, Cold Spring Harbor Laboratory Press, Cold Spring Harbor, N.Y.) may also be used.

The present invention further relates to a nucleic acid encoding a peptide of the present invention having an L-amino acid. An appropriate source of a nucleic acid encoding the peptide of the present invention includes a human genome sequence. As other source, rat genome sequence is included. Protein sequences are respectively available from GenBank, and the entirety thereof is incorporated herein as a reference. A nucleic acid encoding a peptide may be obtained by any method known in the art (for example, by PCR amplification using a synthetic primer hybridizable to 3'- and 5'-terminuses of a sequence and/or by cloning from a genome library using an oligonucleotide sequence specific for cDNA or a predetermined gene sequence).

For expression of a recombinant of a peptide, a nucleic acid including all or a part of the nucleic acid sequence which encodes the peptide may be inserted in an appropriate expression vector (i.e., a vector including elements necessary for transcription and translation of the inserted peptide coding sequence). In some embodiments, a regulatory element is heterologous (i.e. not native gene promoter). Or, necessary transcription signal and translation signal may be provided by a promoter native for a gene and/or a region adjacent thereto. Various host vector systems may be used for expression of a sequence encoding a peptide. They include, but are not limited to: (i) mammalian cell system infected with vaccinia virus, adenovirus or the like; (ii) insect cell system infected with baculovirus or the lik; (iii) yeast including yeast vector; or (iv) bacteria transformed with bacteriophage DNA, plasmid DNA or cosmid DNA. Depending on a host cell system to be used, any one of a number of suitable transcription elements and translation elements may be used.

As a promoter/enhancer sequence in an expression vector, plant, animal, insect or mycotic regulatory sequence provided in the present invention may be used. For example, a promoter/enhancer element may be used from yeast and other mycete (for example, GAL4 promoter, alcohol dehydrogenase promoter, phosphoglycerol kinase promoter, alkali phosphatase promoter). Examples of expression vector or derivative thereof include human or animal virus (for example, vaccinia virus or adenovirus); insect virus (for example, baculovirus); yeast vector; bacteriophage vector (for example, λ phage); plasmid vector and cosmid vector.

As a host cell line, expression of a desired sequence inserted may be regulated, or an expressed peptide encoded by the sequence may be modified, treated or selected by a particular desired means. Furthermore, expression from a particular promoter may be enhanced in the presence of a particular inducer in a selected host cell line, thereby facilitating control of expression of a generally designed peptide. Furthermore, a different host cell has a particular characterized mechanism for translation and post-translational processes and modification of the expressed peptide (for example, glycosylation, phosphorylation or the like). Thus, an appropriate cell line or host cell system may be selected for guaranteeing that a desired modification and process of a foreign peptide has been achieved. For example, peptide expression in bacterial system may be used for producing a non-glycosylated core peptide. On the other hand, expression in mammalian cell guarantees "native" glycosylation of a heterologous peptide.

Derivatives, fragments, homologs, analogs and mutants of a peptide, and nucleic acids encoding these peptides are included. Regarding nucleic acids, the derivatives, fragments and analogs provided herein are defined as a nucleic acid sequence of at least six (contiguous), and have a length sufficient for specific hybridization. Regarding amino acids, the derivatives, fragments and analogs provided herein are defined as an amino acid sequence of at least four (contiguous) and have a length sufficient for specific recognition.

In designing a variant, based on sequential information of other receptor and the like described in the following documents, a similar receptor-binding peptide can be designed: for IL-13, Yuichiro Yoshida et al., Biochem Biophys Res Commun. 2007, vol. 358, No. 1, pp. 292-7; for IL-4, Thorsten Hage et al., Cell. 1999, vol. 97, No. 2, pp. 271-81; for neuropilin-1, Alexander Antipenko et al., Neuron. 2003, vol. 39, No. 4, pp. 589-98; for Transferrin R, Jae H. Lee et al., Eur. J. Biochem. 2001, vol. 268, pp. 2004-2012; for VEGFR1 (WHSDMEWWYLLG (SEQ ID NO: 31)), Ping A N et al., 2004, Int. J. Cancer. Vol. 111, pp. 165-173; for HER-2, Valeria R. Fantin et al., Cancer Res. 2005, vol. 65, No. 15, pp. 6891-6900, Stephanie C. Pero et al., Int J Cancer. 2004, vol. 111, pp. 951-960, Beihai Jiang et al., J Biol Chem. 2006, vol. 280, No. 6, pp. 4656-4662; for VEGFR1 (VEPNCDIHVM-WEWECFERL-NH2 (SEQ ID NO: 32)), Kimberly J. Peterson et al., AnaLytical Biochemistry 2008, vol. 378, No. 1, pp. 8-14; for VEGFR1 (GGNECDAIRMWEWECFERL (SEQ ID NO: 33)), Borlan Pan et al., J. Mol. Biol. 2002, vol. 316, No. 3, pp. 769-87; for Buforin, Hyun Soo Lee et al., Cancer Lett. 2008, vol. 271, No. 1, pp. 47-55; for FGFR (MQLPLAT (SEQ ID NO: 5)), Fukuto Maruta et al., Cancer Gene Therapy. 2002, vol. 9, pp. 543-552; for FGFR (AAVALLPAV-LLALLAP (SEQ ID NO: 6)), Akiko Komi et al., Exp. Cell Res. 2003, Vol. 283, No. 1, pp. 91-100; for NRP1/VEGFR2 (ATWLPPR(SEQ ID NO: 36)), Loraine Tirand et al., J. Control Release. 2006, vol. 111, pp. 153-164; for EphB1 and EphB2, Mitchell Koolpe et al., J. Biol. Chem. 2005, vol. 280, No. 17, pp. 17301-11; for IL11R, Amado J. Zurita et al., Cancer Res. 2004, vol. 64, pp. 435-439; for GRP78 (WD-LAWMFRLPVG (SEQ ID NO: 39)), Marco A. Arap et al., Cancer Cell. 2004, vol. 6, pp. 275-284; for GRP78 (CTVALPGGYVRVC (SEQ ID NO: 40)), Ying Liu et al., Mol. Pharmaceutics. 2007, Vol. 4, No. 3, pp. 435-447; for PSMA, Kaushal Rege et al., Cancer Res. 2007, vol. 67, No. 13, pp. 6368-6375 (these documents are incorporated herein as a reference). Such modification includes, but is not limited to, conservative substitution. Here, IL4-, IL13- and neuropilin-1-binding sequence were designed based on results of three-dimensional structure analysis. In the specification, for HER2, VEGFR and TfR, activity was found in those which used the binding sequence information per se described in the aforementioned documents, as well as in EGFR.

Furthermore, regarding modification of a cell-permeable peptide, modification can be carried out with reference to conventional knowledge and based on the description herein. For example, Daniele Derossi et al., THE JOURNAL OF BIOLOGICAL CHEMISTRY Vol. 271, No. 30, Issue of July 26, pp. 18188-18193, 1996 provides knowledge related to a mechanism of Antp and a variant thereof obtained by adding a partial mutation. It describes a site important for cell permeation, and can be referenced in production of a variant or analog of the present invention. This document is incorporated herein as a reference in entirety thereof.

As other document, GenevieAve Dom et al., Nucleic Acids Research, 2003, Vol. 31, No. 2 556-561; Wenyi Zhang and Steven O. Smith, Biochemistry 2005, 44, 10110-10118; and ISABELLE LE Roux, et al., Proc. Natl. Acad. Sci. USA Vol. 90, pp. 9120-9124, October 1993 provide information related to transmambrane mechanism and mutation. These documents can also be referenced in production of a variant or analog of the present invention. These documents are incorporated herein as a reference in entirety thereof.

(Drug)

A compound of the present invention or a pharmaceutically acceptable salt thereof can be administered alone, but is preferably provided normally as various pharmaceutical preparations. Furthermore, such pharmaceutical preparations are used for animals and human.

It is preferred to use the administration route most effective in therapy. Examples of administration route include oral route or parenteral route such as intrarectal route, buccal route, subcutaneous route, intramuscular route, intravenous route and the like. Examples of administration form include capsule, tablet, granule, powder, syrup, emulsion, suppository, injection and the like. Liquid preparations suitable for oral administration, such as emulsion and syrup, can be produced using water, saccharides such as sucrose, sorbitol, fruit sugar and the like; glycols such as polyethylene glycol, propylene glycol and the like; oils such as sesame oil, olive oil, soybean oil and the like; a preservative such as p-hydroxybenzoic acid esters; flavors such as strawberry flavor, peppermint and the like. Furthermore, capsules, tablets, powders, granules and the like can be produced using an excipient such as lactose, glucose, sucrose, mannitol and the like; a disintegrator such as starch, soda alginate and the like; a lubricant such as magnesium stearate, talc and the like; a binding agent such as polyvinyl alcohol, hydroxypropyl cellulose, gelatin and the like; a detergent such as fatty acid ester and the like; and a plasticizer such as glycerin and the like.

Preparations suitable for parenteral administration are preferably composed of sterilized aqueous preparation containing an active compound which is isotonic to the blood of an acceptor. For example, in a case of injection, a solution for injection is prepared using a carrier formed of salt solution, glucose solution or a mixture of salt water and glucose solution.

A topical preparation is prepared by dissolving or suspending an active compound in one or more solvent (for example, mineral oil, petroleum, polyvalent alcohols, or other base used in topical pharmaceutical preparation. A preparation for intestinal administration is prepared using a normal carrier, for example, cacao butter, hydrogenated fat, hydrogenated fatty carboxylic acid, and the like, and is provided as a suppository.

In the present invention, also in a parenteral preparation, one or more auxiliary components selected from glycols, oils, flavors, preservatives (including antioxidant), excipients, disintegrators, lubricants, binding agents, detergents, plasticizer and the like exemplified in relation to an oral preparation.

An effective dose and the number of administrations of the compound of the present invention or a pharmaceutically acceptable salt thereof vary depending on administration form, age and weight of a patient, nature and severity of a symptom to be treated, and the like. Normally, a dose is 0.01 to 1000 mg/person per day, preferably 5 to 500 mg/person. Regarding the number of administrations, it is preferred to administer one time per day or administer separately.

The present invention also relates to a system, device and kit for producing a pharmaceutical composition of the present invention. It is understood that elements known in the art can be used as elements of such a system, device and kit, which can be appropriately designed by those skilled in the art.

The present invention also relates to a system, device and kit using a compound of the present invention, a pharmaceutically acceptable salt thereof, or a prodrug such as a hydrate thereof. It is understood that elements known in the art can be used as elements of such a system, device and kit, which can be appropriately designed by those skilled in the art.

(DDS)

As used herein, "delivery agent" or "delivery medium" refers to a carrier (vehicle) which mediates delivery of a substance of interest. If a substance to be delivered is a drug, it is referred to as "drug delivery medium." Drug Delivery System (DDS) may be classified to absorption-controlling DDS, release-controlling DDS, and targeting DDS. An ideal DDS is a system which delivers "a necessary amount" of a drug "to a necessary site of a body" "for a necessary time." Targeting DDS is classified to passive targeting DDS and active targeting DDS. The former is a method of controlling behavior in a body utilizing physicochemical properties such as a particle size and hydrophilicity of the carrier (drug carrier or drug vehicle). The latter is a method in which a special mechanism is added to them to actively control directivity to a targeted tissue. For example, there is a method using a carrier conjugated with an antibody having a function of specific molecule recognition for a target molecule of a particular cell composing the target tissue (for example, TPR-binding peptide of the present invention), which may be also referred to as "missile drug."

As used herein, "drug delivery medium" refers to a vehicle for delivering a desired drug.

As used herein, "a substance of interest" particularly refers to a substance desired to be delivered into a cell.

As used herein, "liposome" normally refers to a closed vesicle composed of a lipid layer gathering in a membrane shape and a water layer inside. In addition to phospholipids typically used, it is also possible to incorporate cholesterol, glycolipids and the like. Since liposome is a close vesicle containing water inside, it is also possible to retain a water-soluble drug or the like in the vesicle. Accordingly, such a liposome is used for delivering a drug or gene which cannot pass the cell membrane into a cell. Furthermore, due to good biocompatibility, liposome is significantly expected as a nano particle carrier material for DDS. In the present invention, in order to add a modification group, by optionally using a linker, a crosslinking agent or the like, liposome can be possessed as a constitutional unit having a functional group to give an ester bond (for example, glycolipids, ganglioside, phosphatidyl glycerol or the like) or a constitutional unit having a functional group to give a peptide bond (for example, phosphatidyl ethanolamine).

Liposome can be prepared by any method known in the art. For example, among known methods, a method by cholic acid dialysis is included. In cholic acid dialysis, production is performed by a) preparation of mixed micelle of lipids and detergent and b) dialysis of the mixed micelle. Next, regarding a sugar chain liposome used in the present invention, in a preferred embodiment, a protein is preferably used as a linker, and coupling of glycoprotein in which sugar chain has been bound to a protein to a liposome can be performed by the following two-step reaction: a) periodate oxidation of ganglioside portion on liposomal membrane and b) coupling of glycoprotein to oxidized liposome by a reducing amination reaction. By such a method, it is possible to bind a glycoprotein including a desired sugar chain to a liposome, thereby obtaining various glycoprotein-liposome conjugates having a desired sugar chain. For observing purity and stability of liposome, it is very important to investigate particle size distribution. As a method therefor, gel permeation chromatography (GPC), scanning electronic microscope (SEM), dynamic light scattering (DLS) and the like can be used.

As used herein, "linker" refers to a molecule which mediates binding of a surface-binding molecule (for example, TRP-binding peptide) and other molecule (for example, liposome surface). In a sugar chain-modified liposome used in the present invention, a peptide may be bound to a liposome surface via a linker. A linker can be appropriately selected by those skilled in the art, but is preferably biocompatible, and more preferably, pharmaceutically acceptable. As used herein, "linker protein" refers to protein, peptide, amino acid polymer among linker molecules.

As used herein, "linker (protein) group" is a name given when a linker (protein) has bound to other group. A linker (protein) group refers to monovalent or bivalent group, depending on the case. Examples thereof include mammal-derived protein group, human-derived protein group, human serum protein group and serum albumin group. A linker (protein) group is preferably derived from "human" because it is believed to have high biocompatibility in administration to human. Furthermore, a protein without immunogenicity is preferred.

As used herein, "crosslinking group" refers to a group which forms chemical bond between molecules of chain macromolecules like a bridge. Thus, this term partly overlaps with "linker" as a concept. Typically, this term refers to a group which acts between a macromolecule such as lipids, proteins, peptides, sugar chains and the like and other molecule (such as lipids, proteins, peptides and sugar chains) to form covalent bond linking a portion which lacked covalent bond in the molecule or between molecules. In the present specification, a crosslinking group varies depending on a target to be crosslinked, and examples thereof include, but are not limited to, aldehydes (such as glutaraldehyde), carbodiimides, imido esters and the like. When a substance containing an amino group is crosslinked, an aldehyde-containing group, for example, glutaraldehyde can be used.

As used herein, "biocompatibility" refers to a property of being compatible to an organism tissue or organ without causing toxicity, immune response, damage and the like. Examples of biocompatible buffer include, but are not limited to, phosphate buffered saline (PBS), saline, Tris buffer, carbonate buffer (CBS), Tris(hydroxymethyl)methylaminopropane sulfonate buffer (TAPS), 2-[4-(2-hydroxyethyl)-1-piperazinyl]ethanesulfonate (HEPES), other Good's buffer (for example, 2-morpholinoethanesulfonic acid, monohydrate (MES), bis(2-hydroxyethyl)iminotris(hydroxymethyl)methane (Bis-tris), N-(2-acetamide)iminodiacetic acid (ADA), 1,3-bis[tris(hydroxymethyl)methylamino]propane (Bis-tris propane), piperazine-1,4-bis(2-ethanesulfonic acid) (PIPES), N-(2-acetamide)-2-aminoethanesulfonic acid (ACES), coramine chloride, N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), N-(2-hydroxyethyl)piperazine-N'-3-propanesulfonic acid (HEPPS), N-[tris(hydroxymethyl)methyl]glycine (Tricine), amino acetamide (glycine amide), N,N-bis(2-hydroxyethyl) glycine (Bicine), N-cyclohexyl-2-aminoethanesulfonic acid (CHES), N-cyclohexyl-3-aminopropanesulfonic acid (CAPS)) and the like.

As described above, the present invention provides a delivering agent for delivering a substance of interest to a cancer cell, which contains a receptor-binding peptide such as EGFR domain-binding peptide. A substance of interest may or may not be conjugated with a receptor-binding peptide such as EGFR domain-binding peptide. When conjugated, the substance becomes a fusion substance, and in a case of peptide, such a peptide is referred to as chimeric peptide. A chimeric peptide of the present invention can be also regarded as this embodiment. Regarding such a substance, a conjugate agent may be formed using a medium (vehicle). As such a medium, liposome can be used, and a substance of interest may be either outside of the liposome or included inside.

(Screening)

As used herein, "screening" refers to selecting a target such as an organism or substance having a particular property of interest from a population including a mass by a particular manipulation/evaluation method. For screening, a specific moiety of the present invention can be used.

As used herein, for example, performing screening using immune response is also referred to as "immunophenotyping". In this case, a peptide of the present invention may be used for classification of cell lines and biological samples. The present invention is useful as a cell-specific marker, or more particularly, as a cell marker which is distinctively expressed at various stages of differentiation and/or maturation of a particular cell type. A monoclonal antibody directed to specific epitope or a combination of epitope allows screening of cell population which expresses a marker. Various techniques may be used for screening a cell population which expresses the marker, by using a monoclonal antibody. Examples of such a technique include magnetic separation using magnetic beads coated with antibody, "panning" using antibody attached to a solid matrix (i.e. plate) and flow cytometry (see, for example, U.S. Pat. No. 5,985,660 and Morrison et al., Cell, 96: 737-49 (1999)).

For example, it can be utilized for screening a cell population including undifferentiated cells (for example, embryonic stem cells, tissue stem cells and the like), such as a cell population which may occur cellular growth and/or differentiation as may be found in human umbilical cord blood, or cell population in which modification treatment to untreated state has been performed.

The references quoted herein, such as scientific articles, patents, patent applications or the like are incorporated herein as a reference in entirety thereof, to the same extent as respectively described in a specific manner.

Hereinafter, the present invention will be described based on Examples. The Examples described below are provided only for the purpose of illustration. Thus, the scope of the present invention is limited neither by the aforementioned embodiments nor the Examples below but is limited only by the claims attached hereto.

EXAMPLES

Hereinafter, the present invention will be described in further detail by way of Examples, but the technical scope of the invention is not limited by such Examples. Reagents used in the Examples described below can be obtained from Nakalai Tesque, Sigma-Aldrich, Wako Pure Chemical Industries, Ltd. or the like, unless particularly indicated. Animal experiments were conducted based on the standard determined by Kyoto University and in accordance with the spirit of animal protection.

Example 1

EGFR-targeted Chimeric Peptide

[Materials and Methods]
(Cell Lines)
Human breast cancer (BT-20 and T47D), lung cancer (H322 and H460), pancreatic cancer (SU.86.86), prostate cancer (LNCaP), brain tumor (U251), and lung fibroblast (MRC-5 and WI-38) cell lines were purchased from the American Type Culture Collection (Manassas, Va.). Human pancreatic cancer cell line (BxPC-3) and colon cancer cell line (HCT116 and DLD-1) were purchased from the European Collection of Cell Cultures (ECACC; Salisbury, Wiltshire, UK). Human embryonic kidney cell line (HEK293) was purchased from RIKEN Cell Bank (Tsukuba, Japan). Cells were cultured in RPMI1640 (BT-20, T47D, H322, H460, SU.86.86, LNCaP, U251, BxPC-3, DLD-1 and SW837), MEM (MRC-5 and WI-38), McCoy's 5a (HCT116) or D-MEM (HEK293) containing 10% FBS (BioWest, Miami, Fla.), 100 μg/ml penicillin and 104 μg/ml streptomycin (Nakalai Tesque, Kyoto, Japan).

(Peptides)

The following peptides were purchased from Invitrogen, Carlsbad, Calif.:
1. cancer cell membrane-lytic peptide: KLLLKLLKKLLK LLKKK (SEQ ID NO: 1; the underlined letters represent D-amino acids);
2. EGFR binding (EB)-cancer cell membrane-lytic chimeric peptide: YHWYGYTPQNVIGGGKLLLKLLKKLLK LLKKK (SEQ ID NO: 2);
3. original lytic peptide: LKLLKKLLKKLLKLL-NH$_2$ (SEQ ID NO: 41); and
4. EB-original lytic chimeric peptide: YHWYGYTPQN-VIGGGLKLLKKLLKKLLKLL-NH$_2$ (SEQ ID NO: 42).

The peptides were chemically synthesized using solid phase chemistry, purified by high performance liquid chromatography until they became homogeneous (i.e. purity higher than 90%), and evaluated by mass spectrometry. The peptides were dissolved in water, and buffered to pH 7.4. The peptide solutions were newly prepared for each time just before use so as to prevent reuse.

(Drugs)

Gefinitib and Erlotinib were purchased from Toronto Research Chemicals (Ontario, Canada). Anti-EGFR mouse monoclonal antibody (clone 225) and PD153035 were purchased from Calbiochem (La Jolla, Calif.).

(Preparation of Small Unilamilar Vesicles (SUVs))

Small unilamilar vesicles (SUVs) were prepared as described previously (Matsuzaki, K. & Horikiri, C. Interactions of Amiloid β-peptide (1-40) with Ganglioside-containing membranes. Biochemistry 38, 4137-4142 (1999)). Briefly, a lipid film of the desired composition was dispersed in water or Tris buffer (10 mM Tris/150 mM NaCl/1 mM EDTA, pH7.4). The resulting MLVs were subjected to five freeze-thaw cycles, and then subjected to ultrasonic treatment in ice-cold water under a nitrogen atmosphere for 15 minutes using a probe-type sonicator (Tomy UD-201). Metal debris from the titanium tip of the probe was removed by centrifuge. The lipid concentration was determined in triplicate by phosphorous analysis (Bartlett, G. R. Phosphorus assay in column chromatography. J. Biol. Chem. 234, 466-468 (1959)).

(CD Spectra)

CD spectra were measured in Jasco J-820 using 1 mm path-length quartz cell to minimize the absorbance due to buffer components. For each sample, an average of eight scannings was determined. The averaged blank spectra (small vesicle suspension or solvent) were subtracted. The peptide and lipid concentrations were 50 μM and 4 mM, respectively.

Visualization of membrane permeabilization (Imura Y., Choda, N., & Matsuzaki, K. Magainin 2 in action: distinct modes of membrane permeabilization in living bacterial and mammalian cells. Biophys. J. 95, 5757-5765 (2008)) Calcein, a soluble fluorescence molecule, was added to MDA-MB-231 cell in a glass-bottomed dish at a final concentration of 2 μM. Small aliquots of labeled peptide, EB-Lytic-TAMRA-OH or Lytic-TAMRA-OH (Invitrogen) (15 μl) were directly added to the dish at a final concentration of 10 μM. Using Olympus FV1000 confocal laser scanning microscope (Olympus), confocal images were taken.

(Cell Viability Assay)

A total of $3 \times 10^3$ cells per well were seeded in 96-well plates, cultured for 24 hours in a medium containing 10% FBS, and incubated with increasing concentrations of peptide in 100 μl for 48 to 72 hours at 37° C. Cell viability was measured with WST-8 solution (Cell Count Reagent SF; Nakalai Tesque)

(Immunofluorescence Staining)

EGFR expression by flow cytometry was determined by incubation of $1 \times 10^5$ cells with the human monoclonal antibody to EGFR conjugated with FITC (Santa Cruz). All stainings were performed at room temperature for 40 minutes. The cell fluorescence was measured by flow cytometry (FACS-Calibur, Becton Dickinson, San Jose, Calif.). The mean fluorescence intensity (MFI) of EGFR-positive cells was determined using the CellQuest software (Becton Dickinson)

(Annexin V Assay and Caspase Assay)

BT-20 cells were treated for 2 hours at 37° C. with or without EB-lytic chimeric peptide at 5 μM. For determination of caspase activation or Annexin V-positive expression, peptide-treated cultures were simultaneously analyzed for caspase activity and propidium iodide (PI) staining using a carboxyfluorescein FLICA caspase-3&7 assay (Immunochemistry Technologies, Bloomington, Minn.), or, alternatively, for Annexin V labeling and PI staining by multiparametric flow cytometry. Furthermore, in accordance with the manufacturer's instructions, using a confocal laser scanning microscope, terminal deoxynucleotidyl transferase-dUTP nick end labeling (TUNEL) assay was conducted by MEB-STAIN Apoptosis Kit Direct (MEL)

(Biomolecular Interaction)

Surface plasmon resonance (SPR) experiments were performed with a BIACORE biosensor system 3000 (BIACORE Inc., Uppsala, Sweden). About 5000 RU of streptavidin (Sigma) was immobilized on the surface of CM5 sensor chips via N-hydroxysuccinimide and N-ethyl-N' (dimethylaminopropyl) carbodiimide activation chemistry, and then 2000-3000 RU of peptide conjugated with biotin were injected over the streptavidin-immobilized sensor chip. As a control of nonspecific binding, the unreacted carboxymethyl groups of a sensor chip without immobilized streptavidin were blocked with ethanolamine. As an analyte, cell surface proteins which were prepared using the Mem-PER eukaryotic membrane protein extraction reagent kit (Pierce) were injected over the flow-cell in the flow rate of 20 μl/min. at 25° C. In order to prevent nonspecific binding during the assay, HBS buffer (0.01 M HEPES, 0.15 M NaCl, 0.005% Tween 20, 3 mM EDTA [pH 7.4]) was used as running buffer. Interaction analysis of recombinant human EGF receptor (rhEGFR) with EB-lytic chimeric peptide was carried out as following: about 5000RU of rhEGFR (SEQ ID NO: 3) was immobilized on the sensor chip of CM5 as described above, and then several concentrations of peptides were injected over this sensor chip. All protein concentrations used in these experiments were determined by the Bradford method (Bradford MM. A rapid and sensitive method for the quantitation of microgram quantities of protein utilizing the principle of protein-dye binding. Anal Biochem 1976; 72:248-54). Data analysis was performed using BIA evaluation ver.3.2 software (BIACORE).

(Colony-forming Assay)

The in vitro cytotoxic activity of the lytic peptide or the chimeric peptide against H322 cells was determined by a colony-forming assay. The cells were seeded in 6 cm dishes with 3 ml of RPMI 1640 containing 10% FBS and were allowed to attach. The number of cells/dishes was set so that >100 colonies were obtained in the control group. Twenty four hours after seeding the cells, the cells were exposed to different concentrations of lytic peptide or EB-lytic chimeric peptide (0 to 22.5 µM) and cultured for 10 days. The dishes were washed with phosphate buffer, and stained with crystal violet (0.25% in 25% alcohol). The percentage of colony survival was determined from the number of colonies formed in the control and treated groups.

[Results]

(Designing of a Novel Chimeric Peptide Based on a Secondary Structure)

Figure 1C:
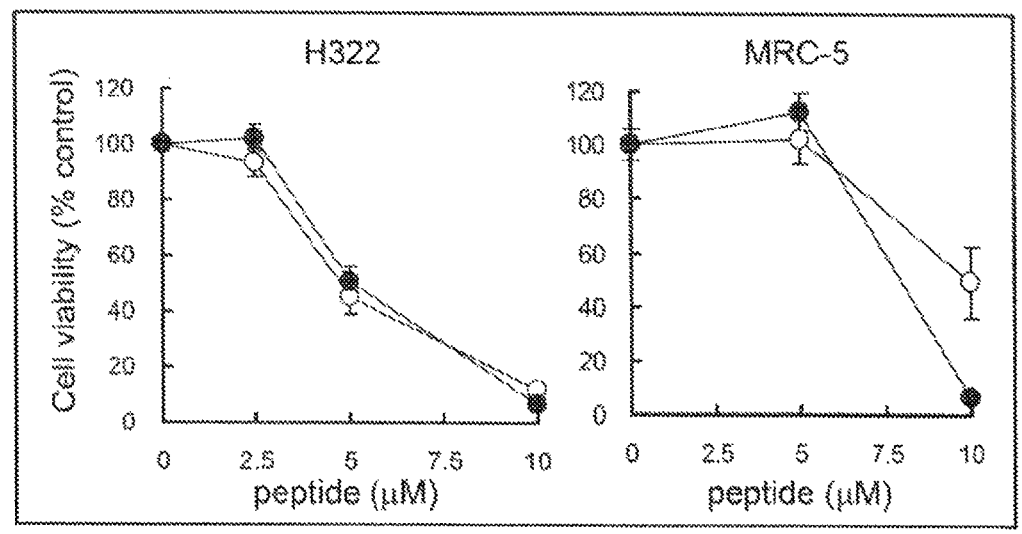
FIG. 1C shows a cell-killing effect of EB-original lytic chimeric peptide or original lytic peptide alone in various human cancer cells and normal cells. Cancer cell line H322 and normal cell line MRC-5 were cultured with various concentrations (0 to 30 μM) of EB-original lytic chimeric peptide or original lytic peptide alone, and cytotoxicity assay was performed as described above. Black circle, EB-original lytic chimeric peptide; white circle, original lytic peptide.
Figure 1D:
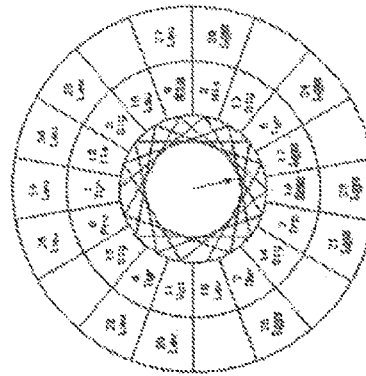
FIG. 1D shows designing and secondary structure analysis of a novel chimeric peptide using CD spectrum. The upper shows wheel projection of Schiffer Edmundson for EGFR-binding (EB) peptide conjugated to a lytic peptide (a) reported by Papo and Shai (original lytic peptide) or to a newly designed lytic peptide (b). In the peptide sequences, underlined italic letters represent D-amino acids. Bold letters in the wheel diagrams represent hydrophilic amino acids (mainly Lys). Arrows represent a direction of a hydrophilic surface of these peptides. CD spectra of EB-original lytic peptide (c) and EB-lytic peptide (d) in the presence of PC SUV or PC/PS (4:1) SUV are shown. Concentrations of peptide and lipid were respectively 50 μM and 4 mM. The amino acid sequence shown in FIG. 1D, part a, is SEQ ID NO:42, and the amino acid sequence shown in FIG. 1D, part b, is SEQ ID NO: 2.
Figure 1D:
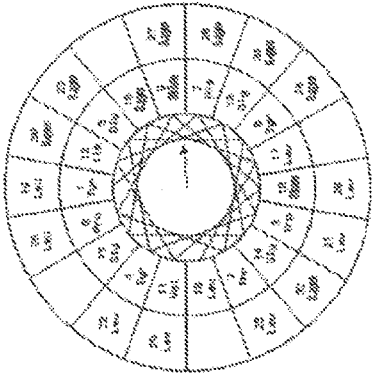
Figure 1D:
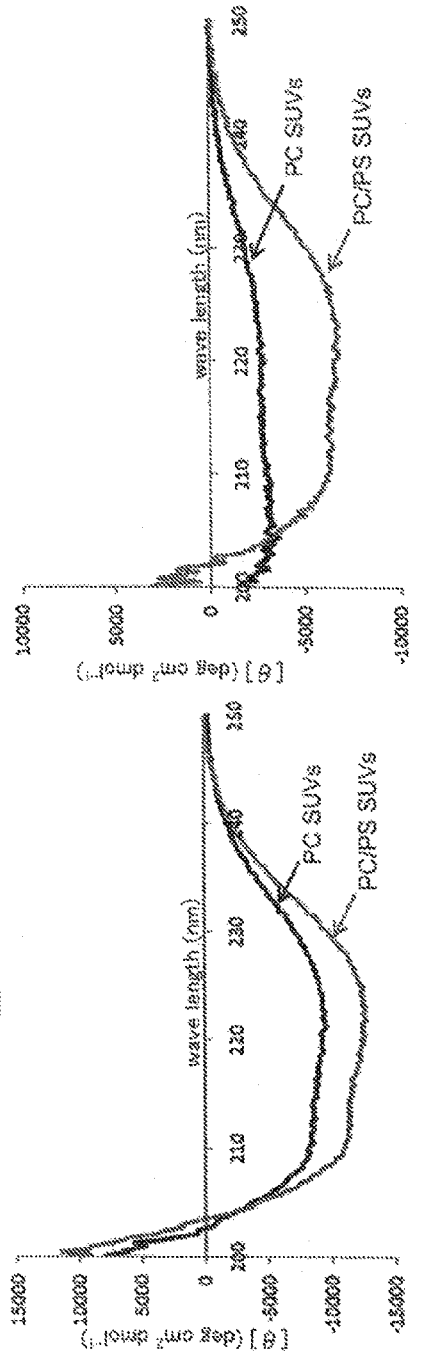

Previously, Papo and Shai have reported a new lytic peptide composed of a 15-amino acid diastereomeric sequence containing D- and L-leucine and lysine (Papo, N. & Shai, Y. New Lytic peptides based on the D,L-amphipathic helix motif preferentially kill tumor cells compared to normal cells. Biochemistry 42, 9346-9354 (2003)). In this study, the inventors designed a novel lytic peptide which is suitable for combination with EGFR-binding (EB) peptide, based on amphipathicity in a secondary structure. As shown in FIG. 1D, the location of cluster of positively charged amino acids (Lys) in the newly designed lytic peptide was still retained after the combination with EB peptide in comparison with that of EB-lytic peptide (FIG. 1D a and b). CD spectra analysis demonstrated that EB-lytic peptide weakly bound to small unilamellar vesicles (SUVs) composed of phosphatidylcholine (PC), which is the dominant lipid species on the surface of normal cell membranes, and was not well structured with the PC liposome, while this EB-lytic peptide was capable of binding to SUVs containing phosphatidylserine (PS), which is exposed specifically on cancer cell membranes, and conformed to a partial helical structure as characterized by double minima at 209-210 and 222 nm (FIG. 1D (d)). On the other hand, EB-original lytic peptide was capable of strongly binding to both PC and PC/PS liposomes, and conformed to helical structures (FIG. 1D(c)). These results indicate that the chimeric peptide newly designed in this study has a selectivity to PS-containing membranes and conforms to a helical structure which is supposed to be essential for making a pore on the cell surface (Papo, N. & Shai, Y. New Lytic peptides based on the D,L-amphipathic helix motif preferentially kill tumor cells compared to normal cells. Biochemistry 42, 9346-9354 (2003)).

(EGFR Targeting Enhances the Cytotoxic Action of the Lytic Peptide in EGFR-expressing Cancer Cells)

Figure 13:
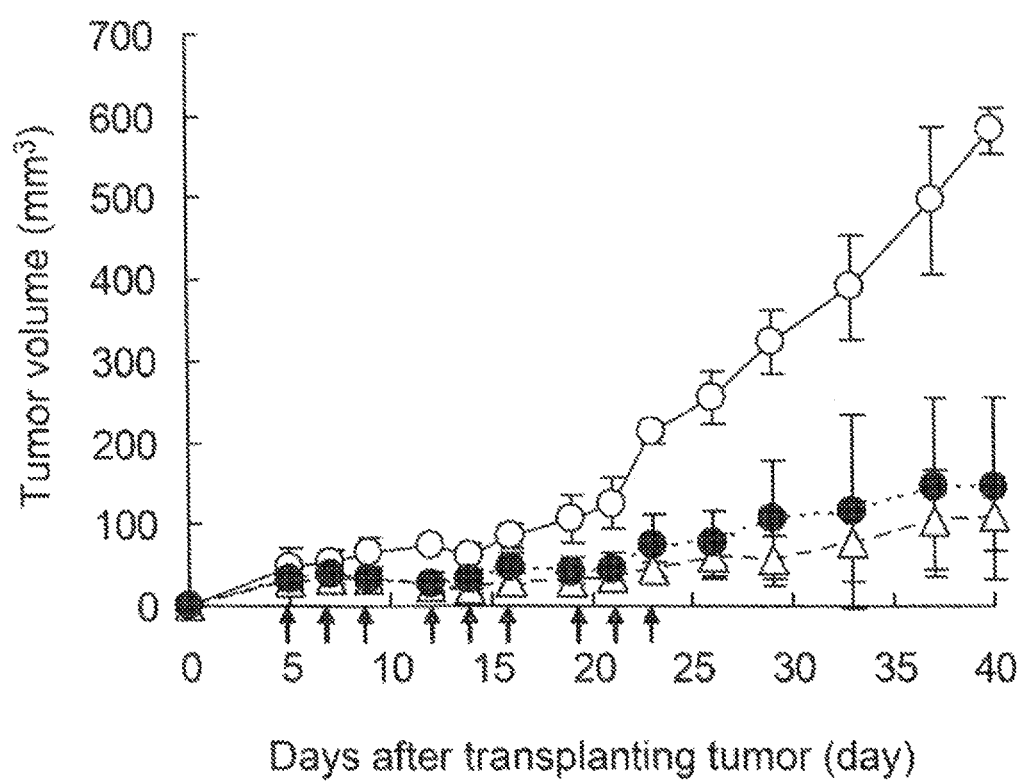
FIG. 13 shows antitumor effect of the same EB-lytic chimeric peptide as in Example 1 in mouse models bearing human pancreatic cancer cell line BxPC-3. Human pancreatic cancer cell line BxPC-3 was subcutaneously transplanted to nude mice. From day 5 after the transplantation, the peptide was intratumorally administered three times per week for three weeks. The results are represented as mean of four mice of each group ±SD (bar). White circle is a group administered with a solvent, white triangle is a group administered with 0.3 mg/kg of the EB-lytic chimeric peptide, and black circle is a group administered with 1 mg/kg of the EB-lytic chimeric peptide.

The cytotoxicity of the lytic peptide was compared with the EGFR-targeted peptidetoxin, an EGFR-binding binding-lytic chimeric peptide, against seven EGFR expressing cancer cell lines. As shown in FIG. 1A, treatment with the lytic peptide or chimeric peptide resulted in a concentration-dependent cytotoxicity in all cancer cell lines tested. The chimeric peptide demonstrated considerable enhancement in cytotoxic activity to cancer cells, when compared with the lytic peptide alone. A 15 to 2 µM concentration of the chimeric peptide was sufficient to induce more than 80% of cell death in all the cell lines. In contrast, the same concentration of the lytic peptide alone could not induce sufficient cell killing of cancer cells. As shown in Table 1, the lytic peptide upon EGFR targeting enhanced the $IC_{50}$ (the peptide concentration inducing 50% inhibition of control cell growth) for cancer cells by 1.6- to 3.1-fold, suggesting that the EGFR targeting enhanced susceptibility of cancer cells to the EB-lytic chimeric peptide in comparison with the lytic peptide alone. The inventors then assessed the cytotoxicity of the EB-lytic chimeric peptide and the lytic peptide alone in three normal cell lines. As shown in FIG. 13, three normal cell lines including MRC-5, WI-38 and HEK293 were less susceptible to the lytic peptide, demonstrating less cytotoxicity compared to cancer cell lines. The $IC_{50}$ of the chimeric peptide in normal cell lines was 3.6- to 8-fold higher for normal cells than for cancer cells (Table 1). The EB-lytic chimeric peptide also enhanced the cytotoxicity to normal cells, which is similar to the phenomena in cancer cells. These findings suggest that the lytic peptide has stronger cytotoxic activity in cancer cells than in normal cells and that the EGFR-targeted peptidetoxin has superior cytotoxic activity to cancer cells with high EGFR expression. Interestingly, EB peptide combined with the original lytic peptide did not show enhancement of cytotoxic activity, and moreover, the EB-original lytic peptide killed even normal cell line (MRC-5) at lower concentration of the peptide, suggesting that the original lytic peptide is not suitable for chimerization with EB peptide (FIG. 1C).

(Treatment with the EB-lytic Chimeric Peptide Results in Sufficient Cytotoxicity to Cancer Cells Resistant to Tyrosine Kinase Inhibitor (TKI))

In cancer cells with or without k-ras mutation, cytotoxic activity of the EB-lytic peptide and TKI were compared.

(Evaluation of Sensitivity of k-ras Mutated Cancer Cells to TKI)

Sensitivity of various cancer cells to erlotinib or anti-EGFR antibody in the presence and absence of k-ras mutation was studied.

A total of $3 \times 10^3$ cells per well of k-ras wild-type (WT) cancer cell lines (H322 and BT-20) and k-ras mutated cancer cell lines (MDA-MB-231, HCT116, SW837 and DLD-1) were seeded in 96-well plates, and incubated for 24 hours in a medium containing 10% FBS. These cells were cultured with various concentrations of erlotinib (0 to 80 µM) or anti-EGFR antibody (right: 0 to 20 µg/ml) for 72 hours, and cytotoxic activity was assessed using WST-8 reagent (Cell Count Reagent SF; Nakalai Tesque).

Figure 1E:
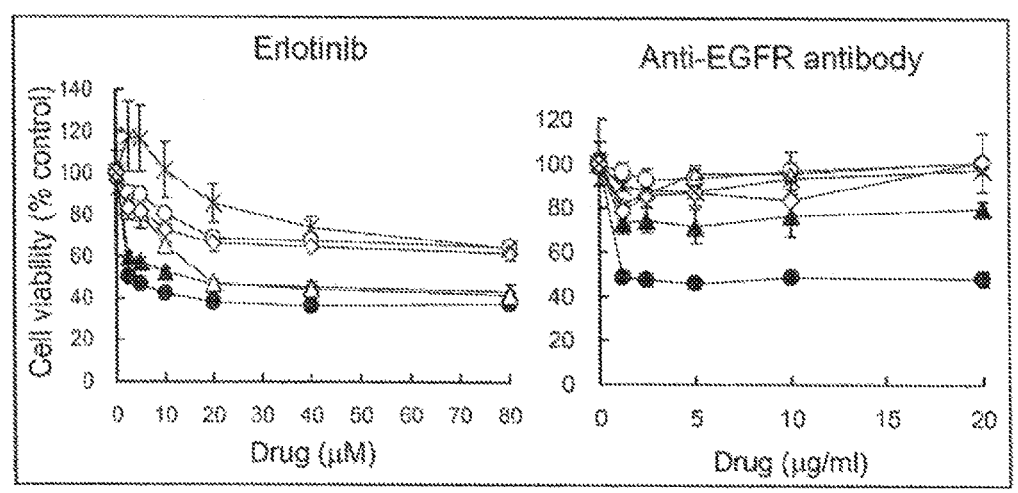
FIG. 1E shows resistance to tyrosine kinase inhibitor (TKI) of k-ras mutated cancer cell line. Wild-type k-ras cancer cell lines (H322 (black circle) and BT-20 (black triangle) and mutated k-ras cancer cell lines (MDA-MB-231 (white circle), HCT116 (white triangle), SW837 (white rhomboid) and DLD-1 (x)) were cultured with various concentrations of erlotinib (left; 0 to 80 μM) or anti-EGFR antibody (right; 0 to 20 μM) for 72 hours, and cytotoxic activity was assessed using WST-8 reagent. The vertical axis shows cell viability (%) with respect to control, and the horizontal axis shows concentration of erlotinib (left) and anti-EGFR antibody (right). The assay was repeated three times, and the results are represented as mean of the triplicate measurements ±SD (bar).

The k-ras WT cancer cell lines (H322 and BT-20) were sensitive to erlotinib and anti-EGFR antibody, but the k-ras mutated cancer cell lines (MDA-MB-231, HCT116, SW837 and DLD-1) were resistant to both erlotinib and anti-EGFR antibody (FIG. 1E).

(Cytotoxicity of TKI or EB-lytic in k-Ras Wild-type Cells)

Cytotoxicity of TKI or EB-lytic chimeric peptide to cancer cells without k-ras mutation and normal cells was studied.

A total of $3 \times 10^3$ cells per well of three k-ras wild-type (WT) cancer cell lines (H322, BT-20 and BxPC-3) and lung normal cell line (MRC-5) were seeded in 96-well plates, and incubated for 24 hours in a medium containing 10% FBS. These cells were cultured with various concentrations of TKI (erlotinib, gefitinib and PD153035; 0 to 20 µM) or the EB-lytic chimeric peptide (0 to 20 µM) for 72 hours, and cytotoxic activity was assessed using WST-8 reagent (Cell Count Reagent SF; Nakalai Tesque).

Figure 1F:
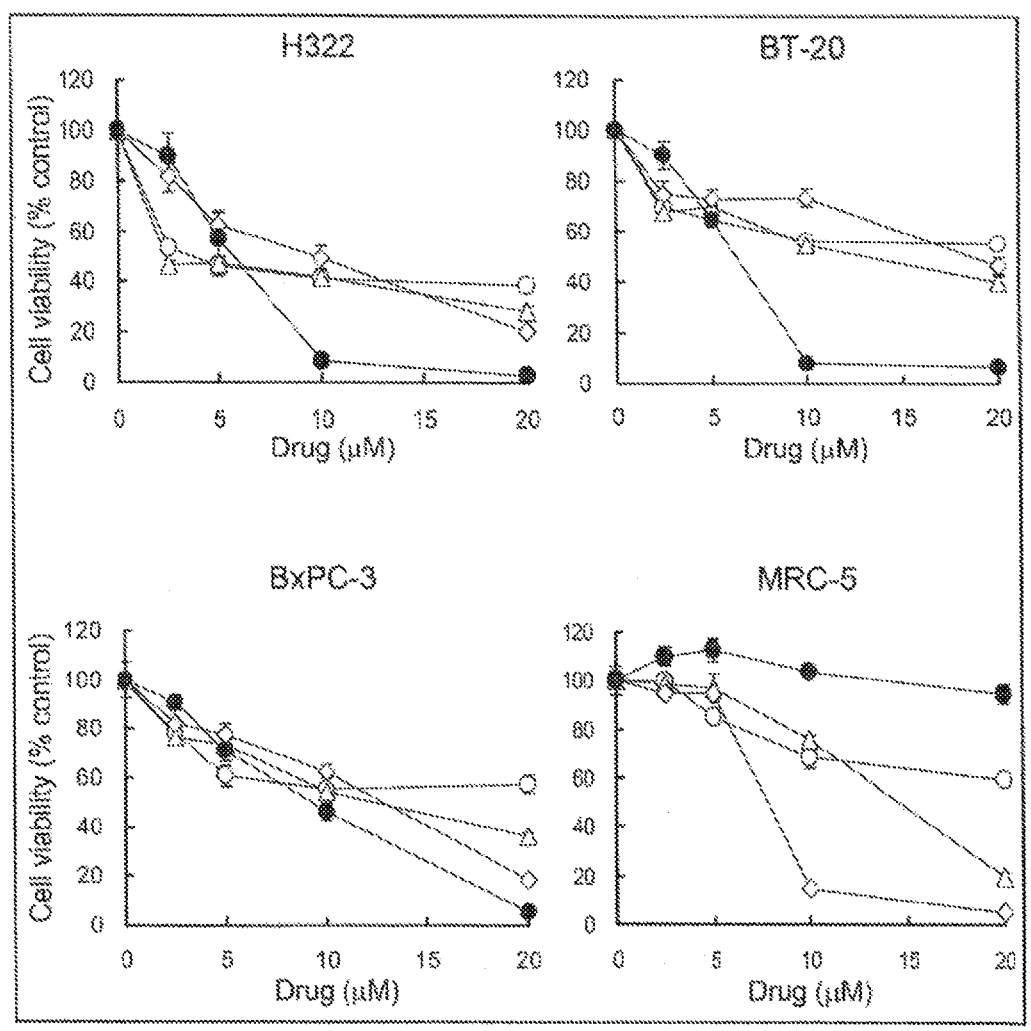
FIG. 1F shows comparison of cytotoxicity between TKI and EB-lytic chimeric peptide in wild-type k-ras cell line. Cancer cell lines (H322, BT-20 and BxPC-3) and lung normal cell line (MRC-5) were cultured with various concentrations of TKI (erlotinib (white circle), gefitinib (white triangle) and PD153035 (white rhomboid); 0 to 20 μM) or EB-lytic chimeric peptide (black circle; 0 to 20 μM) for 72 hours, and cytotoxic activity was assessed using WST-8 reagent. The vertical axis shows cell viability (%) with respect to control, and the horizontal axis shows concentration (μM) of TKI and EB-lytic. The assay was repeated three times, and the results are represented as mean of the triplicate measurements ±SD (bar).

The treatment with the three TKIs (erlotinib, gefinitib and PD153035) resulted in concentration-dependent growth inhibition in the k-ras WT cancer cell lines (H322, BT-20 and BxPC-3), but the cytotoxic activity was insufficient. On the other hand, treatment with EB-lytic peptide exhibited sufficient cytotoxic activity to these cancer cell lines, but did not exhibit cytotoxic activity to the lung normal cell line MRC-5 (FIG. 1F).

(Cytotoxic Activity of the EB-lytic to TKI-resistant Cancer Cell Line with k-Ras Mutation)

Cytotoxicity of the EB-lytic chimeric peptide to TKI-resistant cancer cells with k-ras mutation was studied.

A total of $3\times10^3$ cells per well of four k-ras mutated cancer cell lines (MDA-MB-231, HCT116, SW837 and DLD-1) were seeded in 96-well plates, and incubated for 24 hours in a medium containing 10% FBS. These cells were cultured with various concentrations of TKI (erlotinib, gefitinib and PD153035; 0 to 20 μM) or the EB-lytic chimeric peptide (0 to 20 μM) for 72 hours, and cytotoxic activity was assessed using WST-8 reagent.

Figure 1G:
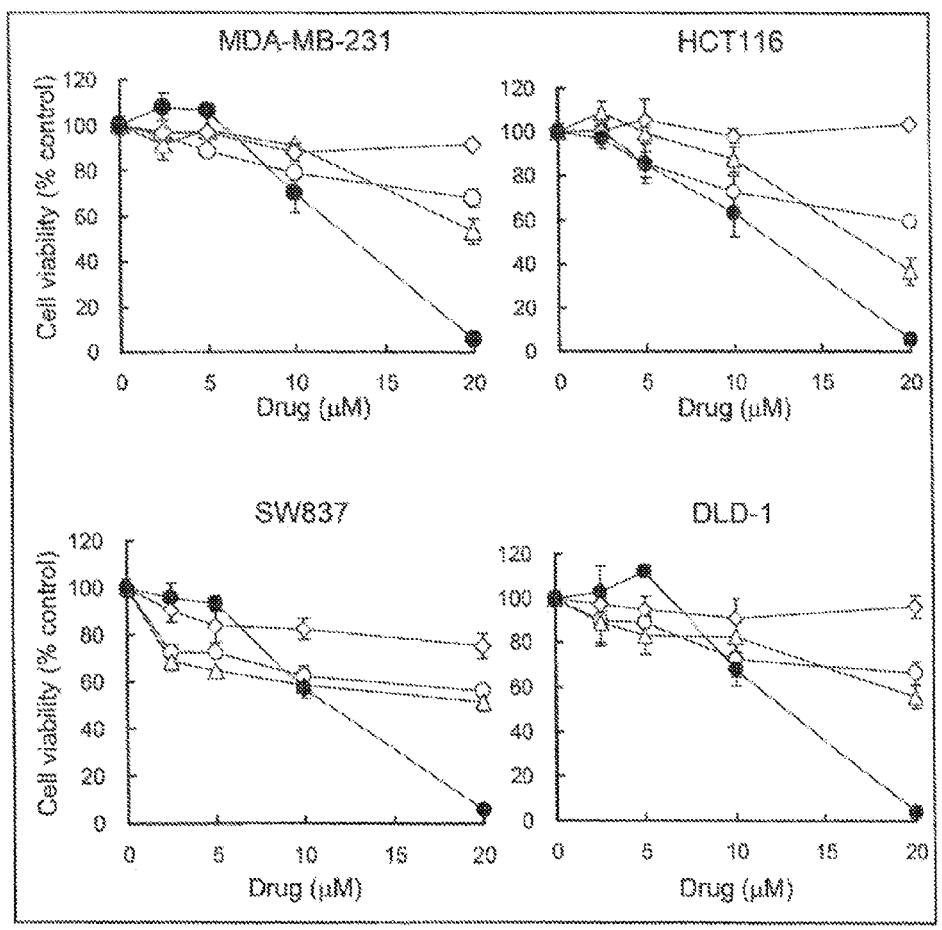
FIG. 1G shows that the treatment of EB-lytic chimeric peptide results in sufficient cytotoxic activity to TKI-resistant cancer cell lines having k-ras mutation. Four types of mutated k-ras cancer cell lines (MDA-MB-231) were cultured with various concentrations of TKI (erlotinib (white circle), gefitinib (white triangle) and PD153035 (white rhomboid); 0 to 20 μM) or EB-lytic chimeric peptide (black circle; 0 to 20 μM) for 72 hours, and cytotoxic activity was assessed using WST-8 reagent. The vertical axis shows cell viability (%) with respect to control, and the horizontal axis shows concentration (μM) of TKI and EB-lytic. The assay was repeated three times, and the results are represented as mean of the triplicate measurements ±SD (bar).

The k-ras mutated cancer cell lines (MDA-MB-231, HCT116, SW837 and DLD-1) were resistant to erlotinib, gefitinib and PD153035, but the treatment with EB-lytic chimeric peptide exhibited sufficient cytotoxic activity to the TKI-resistant cancer cell lines with k-ras mutations (FIG. 1G)

Thus, the EB-lytic chimeric peptide revealed to exhibit cytotoxic activity specific for k-ras mutated cancer cell lines.

(The Degree of Enhancement of Cytotoxic Activity Induced by the EB-lytic Chimeric Peptide Depends on Expression Levels of EGFR on the Cell Surface)

Figure 2A:
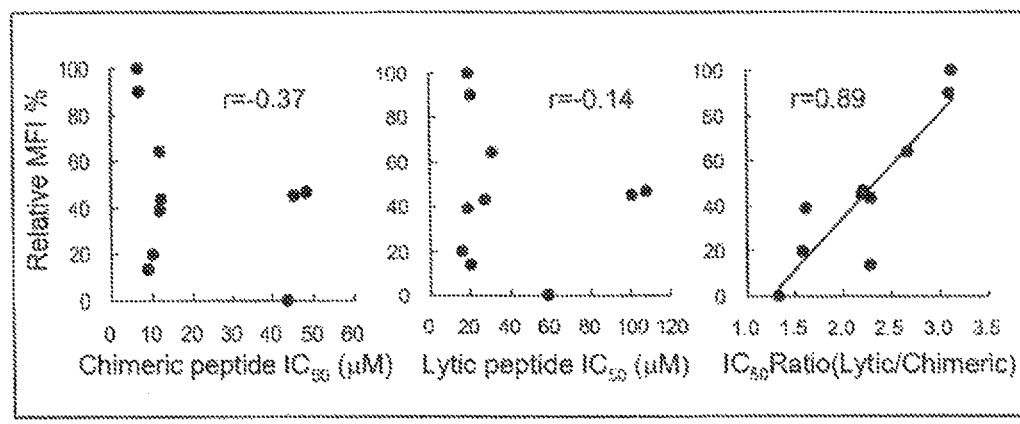
FIG. 2A shows that enhancement of cell-killing effect by EB-lytic chimeric peptide depends on expression of EGFR on a cell surface. Correlation with relative mean fluorescence intensity of EGFR antibody binding of $IC_{50}$ for EB-lytic chimeric peptide (left), $IC_{50}$ for lytic peptide (center), or $IC_{50}$ ratio of lytic peptide with respect to EB-lytic chimeric peptide (right) in seven cancer cell lines and three normal cell lines.

The inventors next examined whether or not the increase in cytotoxicity of the EB-lytic chimeric peptide correlated with the expression levels of EGFR on the cell surface. The expression levels of EGFR for seven cancer cell lines and three normal cell lines were assessed by flow cytometry using an FITC-conjugated anti-EGFR polyclonal antibody. As shown in FIG. 2A and Table 1, the expression levels of EGFR did not correlate with $IC_{50}$ of the EB-lytic chimeric peptide or lytic peptide (r=−0.37 for the chimeric peptide (FIG. 2A, left) and r=−0.14 for the lytic peptide (FIG. 2A, center)) However, the expression levels of EGFR sufficiently correlated with $IC_{50}$ ratio of the lytic peptide to the EB-lytic chimeric peptide, suggesting that the degree of enhancement of cytotoxic activity by the EB-lytic chimeric peptide as compared with that by the lytic peptide alone depends on the expression levels of EGFR on the cell surface (r=0.89; FIG. 2A, right)

Figure 2B:
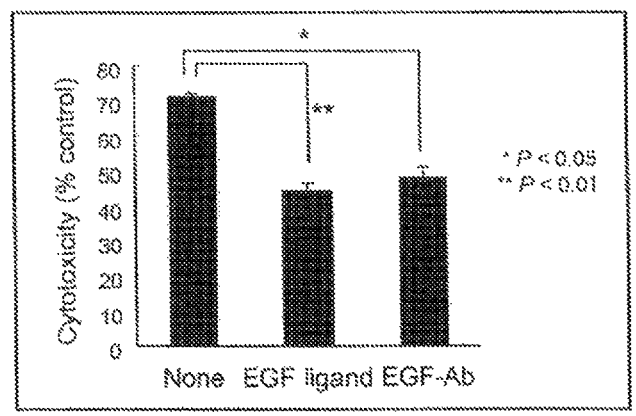
FIG. 2B shows that cell-killing effect of EB-lytic chimeric peptide to BxPC-3 cells can be inhibited by addition of EGFR antibody or recombinant EGF protein. Inhibition of cell-killing effect of EB-lytic chimeric peptide to BxPC-3 cells was evaluated by addition of a polyclonal anti-EGFR antibody or recombinant EGF protein one hour prior to exposure to the peptide. *P<0.05, **P<0.01.

To further confirm the specificity of EB-lytic chimeric peptide to EGFR, anti-EGFR polyclonal antibody (Ab) or recombinant human EGF were added to the BxPC-3 culture, one hour prior to the exposure to the EB-lytic chimeric peptide to assess the cytotoxic activity to cells. As shown in FIG. 2B, both EGF protein and EGFR-Ab were capable of blocking the cytotoxicity of EB-lytic chimeric peptide, demonstrating 27% inhibition by EGF ligand and 23% inhibition by EGFR-Ab. These results suggest that the binding of EB-lytic chimeric peptide to cells depends on the expression levels of EGFR on the cell surface.

(Interaction Profile for Binding of the EB-lytic Chimeric Peptide to EGFR Protein and Cell Surface Membrane Proteins)

Figure 3A:
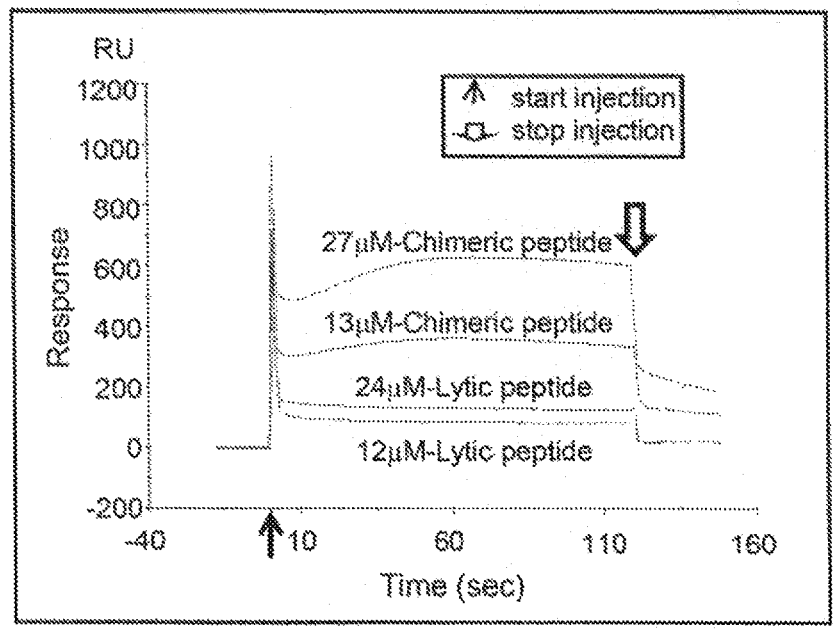
FIG. 3A shows binding properties of EB-lytic chimeric peptide and lytic peptide to EGFR protein. Samples of serially diluted EB-lytic chimeric peptide (27 μM to 13 μM) or lytic peptide (24 μM to 12 μM) were analyzed on sensor surfaces.
Figure 3B:
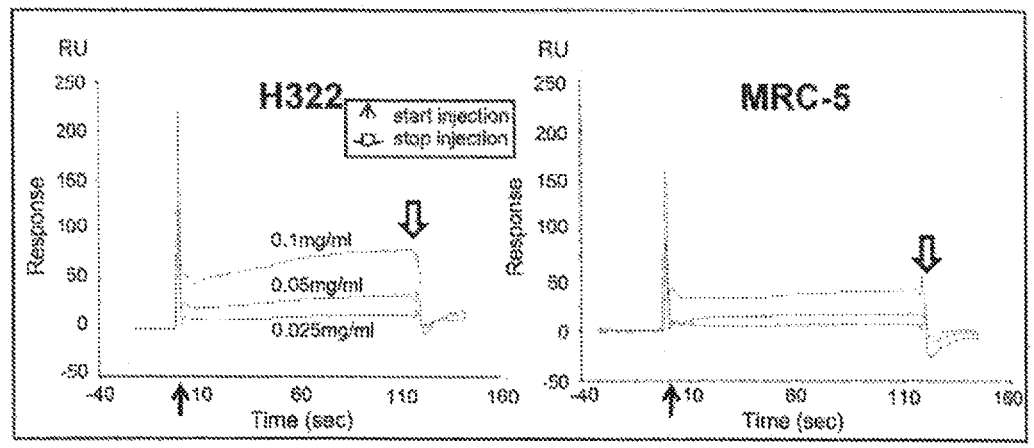
FIG. 3B shows interaction profile for binding of lytic peptide alone to cell surface membrane proteins extracted from H322 or MRC-5 cells. Samples of serially diluted membrane proteins (0.1 mg/ml to 0.025 mg/ml) were analyzed on sensor surfaces.
Figure 3C:
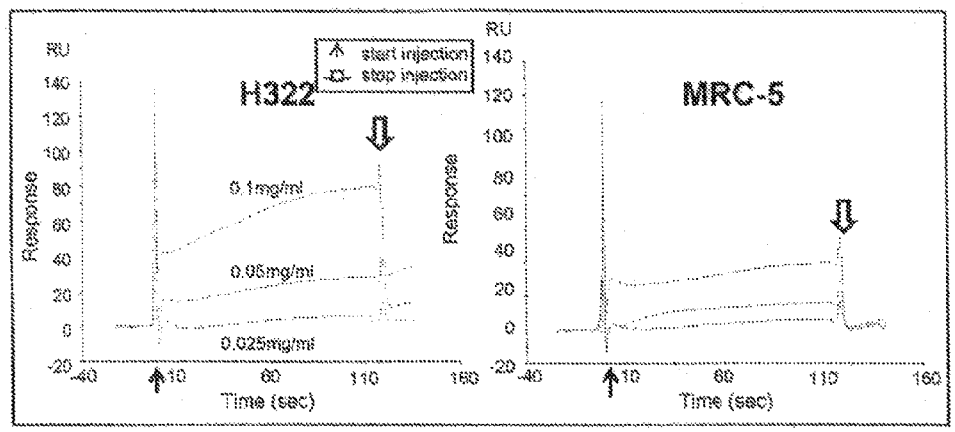
FIG. 3C shows interaction profile for binding of EB-lytic chimeric peptide to cell surface membrane proteins extracted from H322 or MRC-5 cells. Samples of serially diluted membrane proteins (0.1 mg/ml to 0.025 mg/ml) were analyzed on sensor surfaces.
Figure 3D:
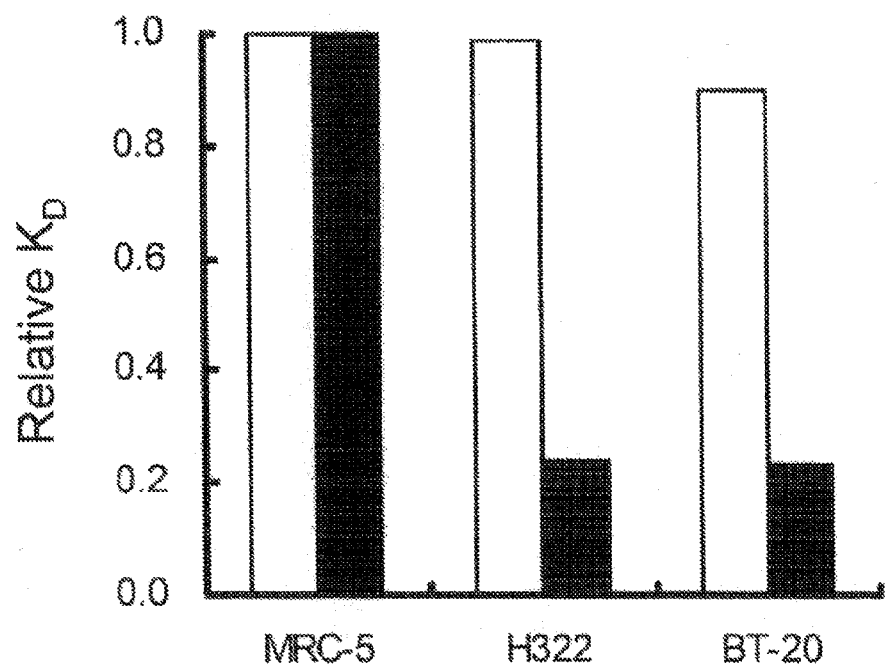
FIG. 3D shows relative $K_D$ values of EB-lytic chimeric peptide (black columns) or lytic peptide alone (white columns) to cell surface membrane proteins extracted from H322, BT-20 or MRC-5 cells.

To understand the binding property of peptides to EGFR, EGFR protein was immobilized on sensor chips and interaction profile with EB-lytic chimeric peptide or lytic peptide alone was analyzed using BIACORE. As shown in FIG. 3A, the resonance signal intensity increased according to the concentrations of EB-lytic chimeric peptide, indicating that the amount of EB-lytic chimeric peptide bound to EGFR protein is proportional to the increase in the concentrations of EB-lytic chimeric peptide. In contrast, the resonance signal intensity by lytic peptide alone minimally increased according to the concentrations. The $K_D$ value for EB-lytic chimeric peptide binding to EGFR protein was $2.6\times10^{-5}$ (M). Next, to understand the binding property of peptides to cells, either EB-lytic chimeric peptide or lytic peptide alone was immobilized on sensor chips, and interaction profile with cell surface membrane proteins extracted from H322, BT-20, or MRC-5 was analyzed using BIACORE. As shown in FIGS. 3B and 3C, the resonance signal intensity increased according to the concentrations of cell membrane proteins, indicating that the amount of cell membrane proteins bound to the peptide is proportional to the increase in the concentrations of cell membrane proteins. Interaction of cell membrane proteins to lytic peptide alone demonstrated similar binding constants in each cell line with increased level of the peptide. On the other hand, binding constants of EB-lytic chimeric peptide to H322 or BT-20 cancer cell membrane proteins were 4.2-fold (H322) or 4.4-fold (BT-20) stronger than lytic peptide alone (FIGS. 3B, 3C and 3D). In contrast, binding constant to MRC-5 normal cell membrane proteins did not vary significantly as compared to lytic peptide alone (FIG. 3D). These results were consistent with the data obtained from WST assays (FIG. 1), indicating that the cytotoxic activity of EB-lytic chimeric peptide correlated well with the affinity to the cell membranes.

(EB-lytic Chimeric Peptide Induces Rapid Killing of Cancer Cells)

Figure 4A:
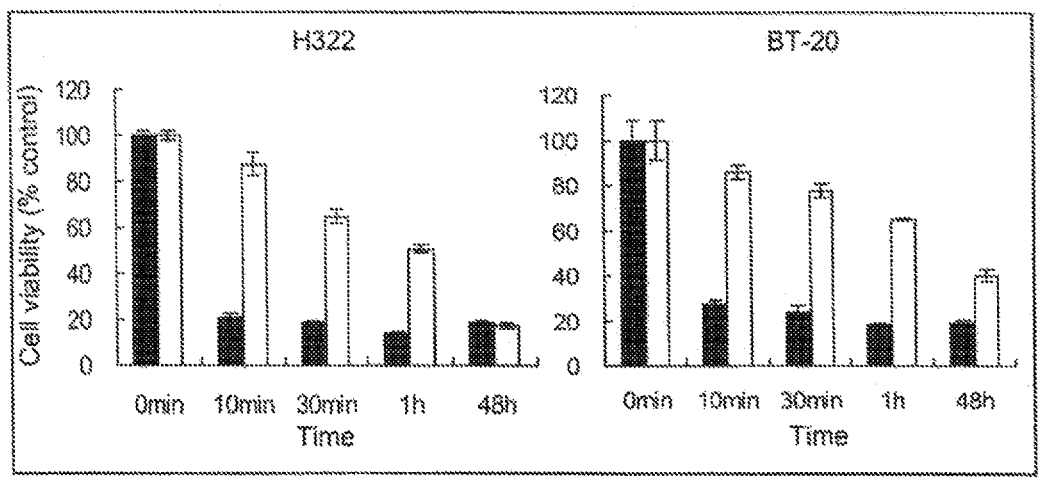
FIG. 4A shows that EB-lytic chimeric peptide induces rapid killing of cancer cells. H322 and BT-20 cells were treated with EB-lytic chimeric (black columns) or lytic peptide (white columns) for 10 minutes, 30 minutes, one hour or 48 hours, and then the medium containing peptides was replaced with a fresh medium, and culturing was further performed for 48 hours. The cells were analyzed for cell viability using WST-8.
Figure 4B:
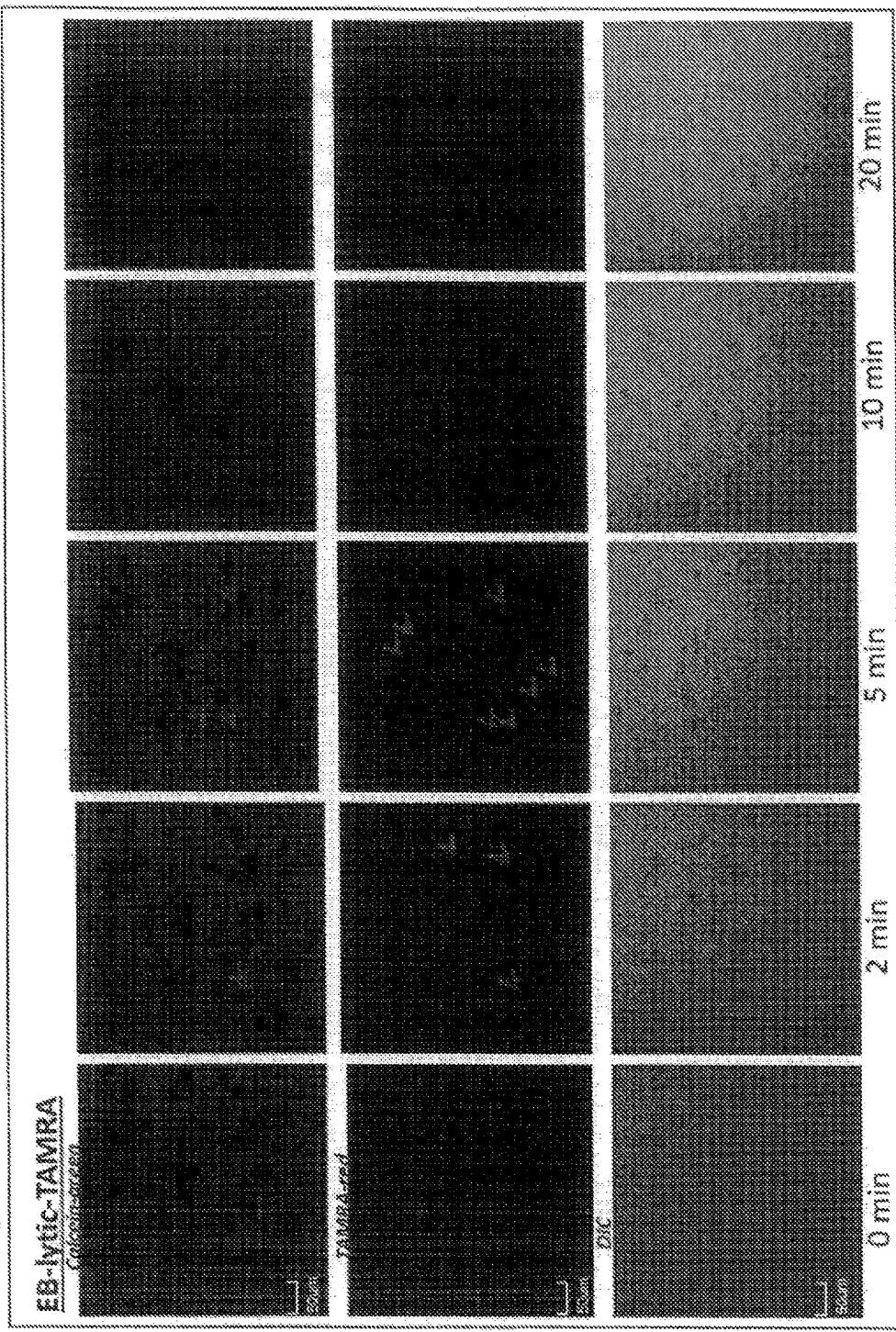
FIG. 4B shows permeabilization of cell membranes by EB-lytic chimeric peptide in MDA-MB-231 breast cancer cells. Cells ($3 \times 10^4$ cells/ml) in calcein solution for 0 minute, two minutes, five minutes, 10 minutes and 20 minutes after addition of EB-lytic peptide-TAMRA at a final concentration of 10 μM. Arrows and arrowheads indicate permeated cells and peptides which permeated a membrane, respectively.
Figure 4D:
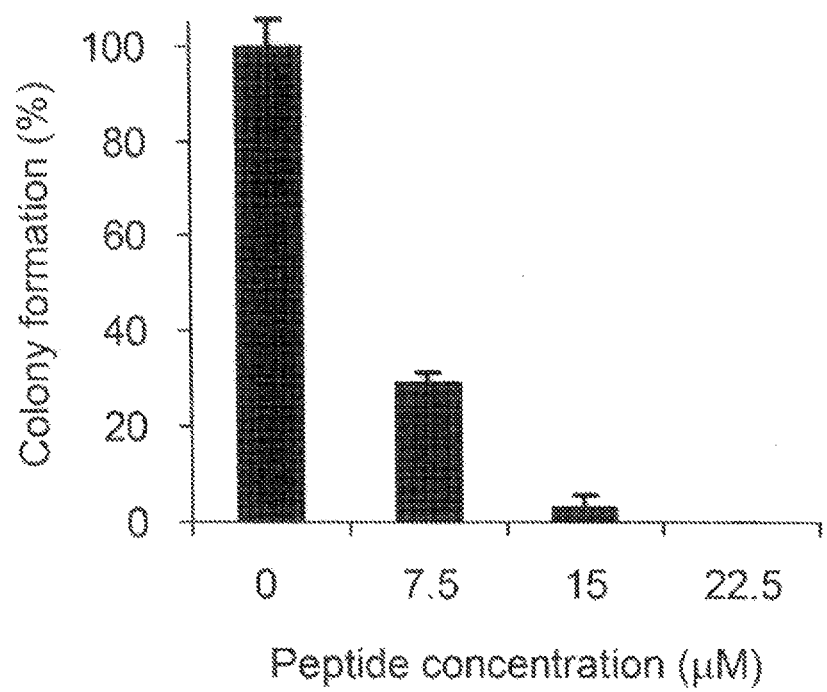
FIG. 4D shows inhibition of cellular growth by EB-lytic chimeric peptide. H322 cells were cultured for 10 days in a medium containing various concentrations (0 to 22.5 μM) of EB-lytic chimeric peptide. After staining with crystal violet, colonies composed of at least 50 cells were scored, and the results are represented as percentage relative to untreated cells, based on the number of colonies. Untreated cells formed 117±10 colonies. Data are means of duplicate measurements; bars show SD.

To assess the appropriate time duration of EB-chimeric peptide to kill cancer cells, H322 or BT-20 cells were treated with either EB-chimeric peptide or lytic peptide alone for 10 minutes, 30 minutes, one hour, or 48 hours. As shown in FIG. 4, treatment of H322 or BT-20 cells with lytic peptide alone resulted in loss of viability in the time-dependent manner. In contrast, a mere 10-minute exposure of H322 or BT-20 cells to EB-chimeric peptide (10 μM) sufficiently killed cancer cells, and more than 70% of cell-killing effect was exhibited. Confocal microscope analysis also demonstrated that this chimeric peptide penetrates the cell membrane to make the pore on the cancer cell surface. The influx of calcein-labeled medium to cytosol of cancer cells was observed within 20 minutes (FIG. 43). However, this rapid penetration was not observed in the case of lytic peptide alone (FIG. 4C). These results suggest that EB-chimeric peptide kills cancer cells quite rapidly as compared to lytic peptide alone. In vitro colony-forming assay also demonstrated that this chimeric peptide inhibits the cell growth of H322 cancer cells in concentration-dependent manner (FIG. 4D).

(EB-chimeric Peptide Induces Caspase Activation and Annexin V-positive Expression in Cancer Cells)

Figure 5:
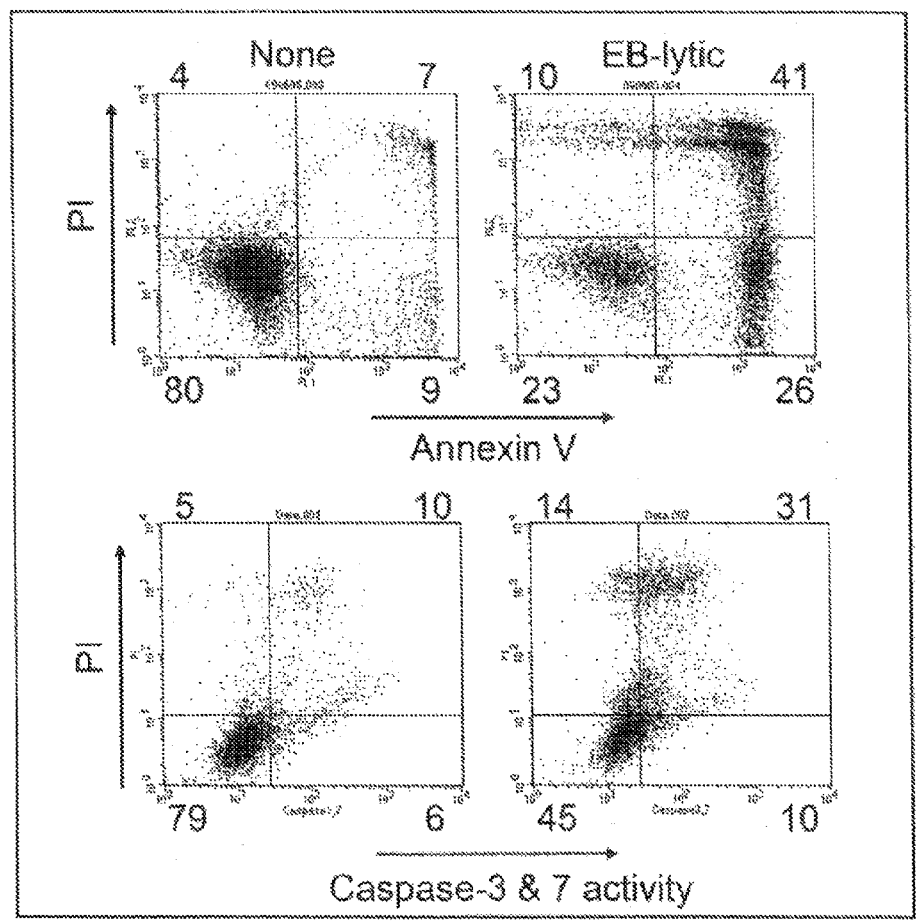
FIG. 5 shows that EB-lytic chimeric peptide induces caspase activation and Annexin V-positive expression in cancer cells. BT-20 cells incubated with EB-lytic chimeric peptide (5 μM) were analyzed after two hours by dual-color flow cytometry for Annexin V labeling (upper panel) or caspase activity by DEVDase activity (lower panel) in the green channel, and for PI staining in the red channel. The value indicates the percentage of cells in each quadrant.

To investigate the cell death mechanism of action caused by EB-chimeric peptide, an Annexin V assay and a caspase assay using multiparametric flow cytometry analysis were performed. As shown in FIG. 5A two hour-exposure of EB-lytic chimeric peptide (5 μM) to BT-20 breast cancer cells induced caspase activation and Annexin V-positive expression. From these results, EB-lytic chimeric peptide disintegrated the plasma membrane of cancer cells, and thus it appears that the chimeric peptide induced cell death of the cancer cells by an apoptotic mechanism.

(In vitro Inhibition of H322 Cancer Cell Growth)

Figure 6:
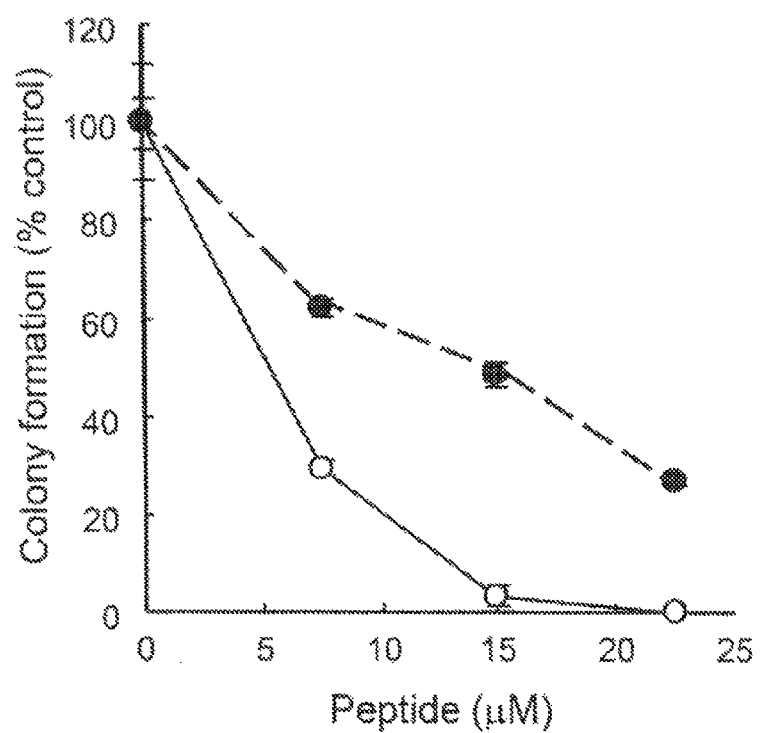
FIG. 6 shows in vitro cellular growth inhibition of H322 lung cancer cells. H322 cells were cultured in a medium containing various concentrations (0 to 22.5 μM) of EB-chimeric peptide or lytic peptide alone for 10 days. After staining with crystal violet, colonies composed of at least 50 cells were scored, and the results are represented as percentage of the number of colonies (100%, untreated cells). Untreated cells formed 117±10 colonies. Data are means of duplicate measurements; bars show SD.

To further confirm the cytotoxic activity of EB-lytic chimeric peptide to H322 cancer cells, colony-forming assay was performed (Kawakami K, Kawakami M, Leland P, Puri R K. Internalization property of interleukin-4 receptor alpha chain increases cytotoxic effect of interleukin-4 receptor-targeted cytotoxin in cancer cells. Olin Cancer Res 2002; 8:258-66; Kawakami K, Joshi B H, Puri R K. Sensitization of cancer cells to interleukin 13-pseudomonas exotoxin-induced cell death by gene transfer of interleukin 13 receptor alpha chain. Hum Gene Ther 2000; 11:1829-35). As shown in FIG. 6, although H322 cells were sensitive to lytic peptide alone ($IC_{50}$, 14.2 μM), the cells showed at least two times higher sensitivity to the chimeric peptide ($IC_{50}$<7.5 μM). The IC$_{50}$ values of two peptides by colony-forming assay correlate well with the IC$_{50}$ values determined by WST assay.

TABLE 1

Cytotoxicity of peptides to various cell lines and EGFR expression

| | IC$_{50}$ (µM) | | | Relative MFI* |
|---|---|---|---|---|
| Cell lines | Lytic peptide alone mean ± SD | EB-lytic peptide mean ± SD | IC$_{50}$ Ratio Lytic/ EB-lytic | (anti-EGFR antibody, %) mean ± SD |
| Cancer cells | | | | |
| H322 | 21 ± 3.2 | 6.8 ± 0.5 | 3.1 | 90 ± 23 |
| BT-20 | 20 ± 2.9 | 6.5 ± 0.7 | 3.1 | 100 |
| U251 | 20 ± 2.5 | 12 ± 2.0 | 1.6 | 39 ± 5.6 |
| H460 | 20 ± 1.6 | 8.9 ± 1.6 | 2.3 | 13 ± 3.6 |
| BxPC-3 | 32 ± 1.6 | 12 ± 0.9 | 2.7 | 64 ± 17 |
| SU.86.86 | 28 ± 0.5 | 12 ± 2.3 | 2.3 | 43 ± 4.6 |
| LNCaP | 16 ± 2.5 | 10 ± 1.3 | 1.6 | 20 ± 7.0 |
| Normal cells | | | | |
| WI-38 | 100 ± 3.1 | 46 ± 2.7 | 2.2 | 45 ± 4.6 |
| MRC-5 | 110 ± 8.1 | 49 ± 5.8 | 2.3 | 47 ± 13 |
| HEK293 | 58 ± 0.3 | 44 ± 2.8 | 1.3 | 0 |

*The relative MFI (mean fluorescence intensity) is the extent of binding of the FITC-conjugated anti-EGFR polyclonal antibody to cells, where the mean MFI values for BT-20 and HEK293 cells are set at 100% and 0%, respectively.

[Discussion]

In this study, the inventors linked two functional domains of amino acids to produce a novel chimeric peptide termed "peptidetoxin" of the present invention, which was designed as a bifunctional peptide binding to EGFR to lyse the plasma membrane for the targeting of EGFR-overexpressing cancer cells. The inventors found that the EB-lytic chimeric peptide kills cancer cells more rapidly and efficiently when compared with lytic peptide alone. On the other hand, the inventors found that normal cells are not very sensitive to both peptides.

The inventors propose a mechanism of action of EB-lytic chimeric peptide in cancer killing as follows. First, EB portion of the chimeric peptide binds EGFR on the cell surface, followed by binding of the lytic moiety of the chimeric peptide and disintegration of the cell membrane more rapidly than free lytic peptide. EB peptide bound specifically and efficiently to EGFR with a dissociation constant of 22 nM (Li Z, Zhao R, Wu X, et al. Identification and characterization of a novel peptide ligand of epidermal growth factor receptor for targeted delivery of therapeutics. FASEB J 2005; 19:1978-85). Therefore, it was suggested that the affinity of EB-EGFR interaction is greater than the affinity of the lytic peptide and cell membrane.

Similar to the lytic peptide, mitochondriotoxic and proapoptotic peptide has polycationic sequence (KLAKLAK)$_2$ (SEQ ID NO: 4), invades into endocytic compartment by a peptide having membrane-permeable sequence without disintegration of the cell membrane, and induces mitochondrial damage (Ellerby H M, Arap W, Ellerby L M, et al. Anti-cancer activity of targeted pro-apoptotic peptides. Nat Med 1999; 5:1032-8). A cell membrane-lytic peptide invades in the cell after disintegration of the cell membrane, induces mitochondrial damage and activation of caspase, and triggers apoptosis. On the other hand, Pseudomonas exotoxin-based immunotoxins (interleukin-13-pseudomonas exotoxin (IL13-PE38QQR) (SEQ ID NO: 6)) induce apoptosis partially, and mere 10-30% of head and neck cancer cells undergo apoptotic cell death (Kawakami M, Kawakami K, Puri R K. Apoptotic pathways of cell death induced by an interleukin-13 receptor-targeted recombinant cytotoxin in head and neck cancer cells. Cancer Immunol Immunother 2002; 50:691-700). Cancer cells treated with this hybrid peptide are Annexin V- and caspase 3, 7-positive when assayed by flow cytometry. Furthermore, this peptide also induced rapid cancer cell death. Thus, this targeted chimeric peptide has an advantage of inducing cancer cell death rapidly as compared to bacterial toxin-based immunotoxin, and may be capable of inducing bystander action or natural immunity at the treatment site in vivo.

Generally, peptides are relatively easily inactivated by serum components in human body (Papo N, Braunstein A, Eshhar Z, Shai Y. Suppression of human prostate tumor growth in mice by a cytoLytic D-, L-amino acid peptide: membrane lysis, increased necrosis, and inhibition of prostate-specific antigen secretion. Cancer Res 2004; 64:5779-86). It has been shown that diastereomeric peptides are relatively free from inactivation in serum, and lytic diastereomeric peptide administrated either intratumorally or intravenously reduces the tumor growth of animal models of human prostate cancer without rapid degradation of the peptide in blood (Papo N, Braunstein A, Eshhar Z, Shai Y. Suppression of human prostate tumor growth in mice by a cytoLytic D-, L-amino acid peptide: membrane lysis, increased necrosis, and inhibition of prostate-specific antigen secretion. Cancer Res 2004; 64:5779-86). Other type of peptide-based drug reported recently, which binds to Hsp90 in the cancer cell to destabilize its client proteins, also inhibits human breast cancer cell growth in mice with intravenous injection in mice at the concentration of 50 mg/kg (Plescia, J. et al., Rational design of shepherdin, a novel anticancer agent. Cancer Cell 7, 457-468 (2005)). In this study, it was found that the intravenous administration of EB-lytic peptide newly designed by the inventors reduced the tumor growth at a lower concentration as compared to other peptide drug candidates, suggesting the high potential of this novel chimeric peptide as a novel and useful tool for cancer therapy. Although EB-lytic chimeric peptide may be resistant to the inactivation in blood flow, as a method for increasing more the efficacy of the peptide in in vivo use, it is believed that use in combination with other material or topical administration will be effective. For example, it has been shown that atelocollagen, calf dermis type I collagen highly purified by pepsin treatment, is a fascinating drug delivery system (DDS) for protein drug and siRNA (Fujioka K, Maeda M, Hojo T, Sano A. Protein release from collagen matrices. Adv Drug Deliv Rev 1998; 31:247-66; Takeshita F, Minakuchi Y, Nagahara S, et al. Efficient delivery of small interfering RNA to bone-metastatic tumors by using atelocollagen in vivo. Proc Natl Acad Sci USA 2005; 102:12177-82). It has been reported that protein drugs administered topically together with atelocollagen are continuously released from the injected site over a long period of time (Fujioka K, Maeda M, Hojo T, Sano A. Protein release from collagen matrices. Adv Drug Deliv Rev 1998; 31:247-66). Thus, it is believed that atelocollagen is sufficiently worthy of tests in combination with the peptidetoxin of the inventors in in vivo model of human cancers. Currently, these possibilities are under investigation in the laboratory of the inventors.

Immunotoxin is composed of a protein toxin having killing moiety and a targeting moiety linked thereto for selectivity for cancer cells, such as a ligand or an antibody. Immunotoxins can be classified into two categories which are chemical conjugates as first-generation immunotoxins and recombinant protein as second-generation immunotoxins (Reiter Y, Pastan I. Recombinant Fv immunotoxins and Fv fragments as novel agents for cancer therapy and diagnosis. Trens Biotechnol 1998; 16:513-520). The conventional immunotoxins usually show hurdles in clinical use (for example, immunogenicity, undesirable toxicity, difficulty in production, limited halflife and production of neutralizing antibody in a body) (Kreitman R J. Immunotoxins for Targeted Cancer Therapy. AAPS J 2006; 8:E532-51; Li Z, Yu T, Zhao P, Ma J. Immunotoxins and Cancer Therapy. Cell Mol Immunol 2005; 2:106-112; Posey J A, Khazaeli M B, Bookman M A, et al., A phase I trial of the single-chain immunotoxin SGN-10 (BR96sFv-PE40) in patients with advanced solid tumors. Clin Cancer Res 2002; 8:3092-3029). However, because peptides can be synthesized chemically, production of peptides can be performed with affordable cost as compared to protein drugs. In addition, various combinations of candidate peptides for targeting and toxic moieties can be generally tested easily in preclinical settings. For example, a toxic moiety having tumoricidal activity, such as mitochondriotoxin (Ellerby H M, Arap W, Ellerby L M, et al. Anti-cancer activity of targeted pro-apoptotic peptides. Nat Med 1999; 5:1032-8) or antibiotics-like derivative peptides (Kim S, Kim S S, Bang Y J, Kim S J, Lee B J. In vitro activities of native and designed peptide antibiotics against drug sensitive and resistant tumor cell lines. Peptides 2003; 24:945-953), can be utilized. As a targeting moiety, interleukin-11 (Zurita A J, Troncoso P, Cardo-Vila M, Logothetis C J, Pasqualini R, Arap W. Combinatorial screenings in patients: the Interleukin-11 receptor α as a candidate target in the progression of human prostate cancer. Cancer Res 2004; 64:435-439) and prostate-specific membrane antigen (PSMA; Rege K, Patel S J, Megeed Z, Yarmush M L. Amphipathic peptide-based fusion peptides and immunoconjugates for the targeted ablation of prostate cancer cells. Cancer Res 2007; 67:6368-6375), in addition to EGFR, can be targeted. However, an explosive portion peptide needs stronger cell-killing activity like plant or bacterial toxin, and must be widely exploited together with a warhead peptide for targeting on cancer cells.

In conclusion, peptidetoxin provided by the present invention, that targets unique protein on the cancer cells is a new possible tool for the anticancer target therapy. The inventors propose the concept of this chimeric peptide, peptidetoxin, as a concept of immunotoxin of next generation. The research and development of peptidetoxins will enable in future an individualized treatment of cancer according to the individual profile, i.e. treatment with a chimeric peptide which is targeted specifically for resected tumor from patients. Ultimately, this strategy may be useful for the treatment of not only cancer but also other diseases.

Example 2

Exhaustive Analysis of EGF-receptor Binding Peptides

In the present Example, experiments for determining whether or not it is possible to use EGF receptor-binding peptide analogs (having the amino acid sequence $X_1X_2X_3X_4X_{56}X_7X_8X_9X_{10}X_{11}X_{12}$ (SEQ ID NO: 8), wherein:

$X_1$ is Y, or an amino acid similar thereto which is S, H or F;
$X_2$ is H, or an amino acid similar thereto which is R or K;
$X_3$ is W, or an amino acid similar thereto which is Y, F or H;
$X_4$ is Y, or an amino acid similar thereto which is S, H or F;
$X_5$ is G, or an amino acid similar thereto which is A, V, I or L;
$X_6$ is Y, or an amino acid similar thereto which is S, H or F;
$X_7$ is T, or an amino acid similar thereto which is S, H or F;
$X_8$ is P, or an amino acid similar thereto which is hydroxyl proline;
$X_9$ is Q, or an amino acid similar thereto which is N;
$X_{10}$ is N, or an amino acid similar thereto which is S, H or F;
$X_{11}$ is V, or an amino acid similar thereto which is G, A, L or I; and
$X_{12}$ is I, or an amino acid similar thereto which is G, A, V or L.

Except for difference in peptide sequence, all protocols is in accordance with Example 1.

(Protocol)

Among the aforementioned mutated peptides, first, paying attention to the second H which has charge, K- and R-mutants were chemically synthesized. As described in Example 1, using BIACORE, binding affinity with recombinant human EGFR was evaluated by comparison with that of wild-type EGFR-binding peptide. Only for what had higher effect in the results, chimeric peptide with the cancer cell membrane-lytic sequence was synthesized, and cell-killing effect to human lung cancer cell line H322 was compared between wile-type EGFR-binding chimeric peptide and the cancer cell membrane-lytic alone.

(Results)

Figure 7A:
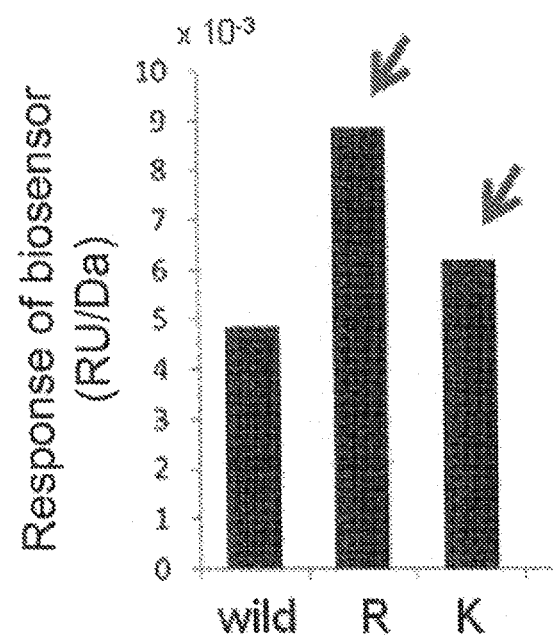
FIG. 7A shows the results of binding affinity BIACORE analysis for EGFR-binding sequence mutant peptide and recombinant human EGFR. Mutants were chemically synthesized by changing the second H having charge in the wild-type EGFR-binding peptide sequence into K or R, and binding affinity with EGFR was assessed using enhancement of biosensor response of BIACORE as an indicator.
Figure 7B:
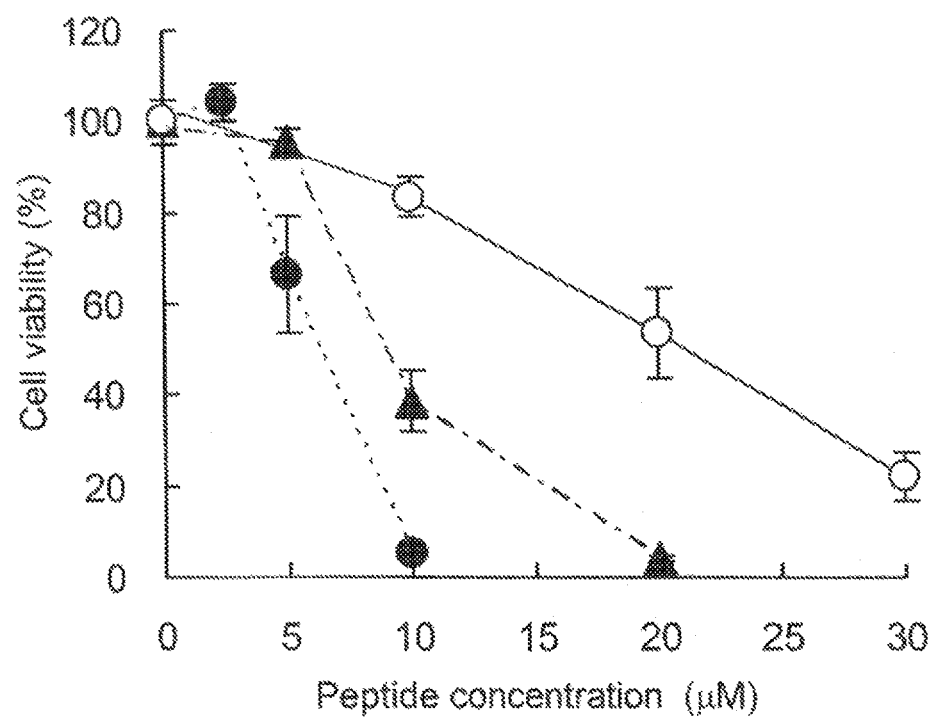
FIG. 7B shows the results of comparison of cell-killing effect between R-mutant peptide which had high binding affinity with EGFR and the cancer cell membrane-lytic peptide alone. Human lung cancer cell line H322 was cultured with serially diluted concentrations (0 to 30 μM) of two peptides for 72 hours, and cell-killing effect was assessed using WST-8 reagent. These results are represented as mean of triplicate measurements ±SD (bar), and the assay was repeated three times. Triangle, EB-chimeric peptide; black circle: R-mutant EB-chimeric peptide; white circle, membrane-lytic peptide.

The results are shown in FIG. 7. In comparison with the wild-type peptide, for K-substituted peptide, some enhancement of biosensor response was observed, and for R-substituted peptide, response of two fold of wild-type was observed (FIG. 7A). The cell-killing effect to H322 was enhanced more for the R-substituted chimeric peptide (black circle) than for wild-type EGFR-binding chimeric peptide (triangle) (FIG. 78).

Example 3

Combination of Cancer Cell Membrane-Lytic Sequence (Only L-Amino Acid) and IL-4 Receptor (IL4R)-Targeted Sequence as a Cancer Cell-Targeted Sequence In the present Example, it was investigated whether or not the same effect as in Example 1, such as enhancement of cell-killing effect, was observed using a chimeric peptide formed by combining the cancer cell membrane-lytic sequence of KLLLKLLKKLLKLLKKK (all amino acids are L-amino acids; LyticL; SEQ ID NO: 27) and IL4R-targeted sequence. The chimeric peptide sequence is as follows:

```
IL4-LyticL:
                                    (SEQ ID NO: 18)
KQLIRFLKRLDRNGGGKLLLKLLKKLLKLLKKK.
```

(Protocol)

Based on the results of binding three-dimensional structure analysis of IL4R and IL-4, partial peptide sequence which is important for binding (KQLIRFLKRLDRN (SEQ ID NO: 26)) was designed and chemically synthesized. By BIACORE analysis, binding affinity with human recombinant IL4R protein was assessed. The aforementioned chimeric peptide was synthesized, and in vitro cell-killing effect to human breast cancer cell line MDA-MB-231 and human pancreatic cancer cell line BxPC-3 was assessed.

(Results)

Figure 8A:
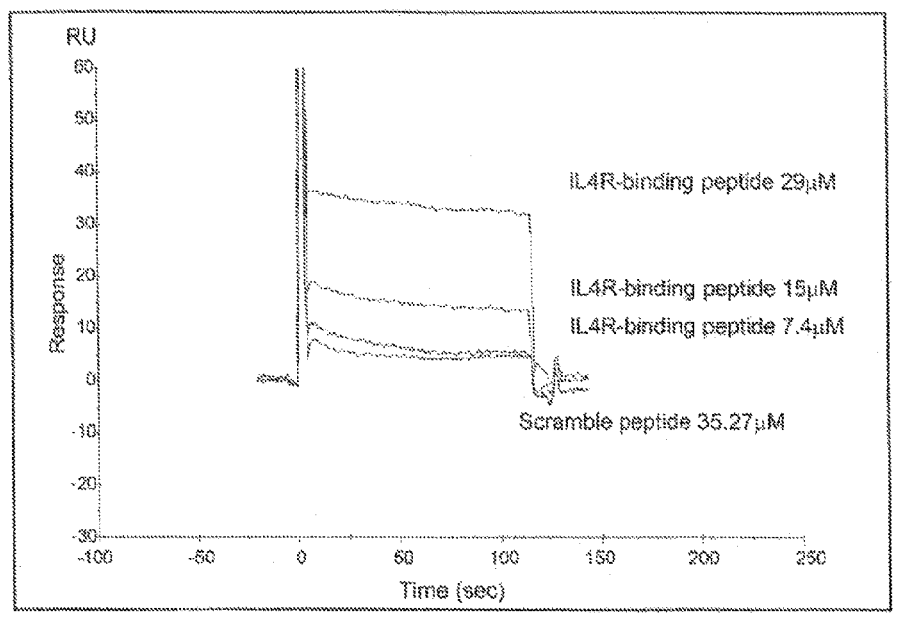
FIG. 8A shows binding properties of IL4R-binding peptide and scramble sequence peptide to recombinant human IL4R. Samples of serially diluted IL4R-binding peptide (29 μM to 7.4 μM) were analyzed on sensor surfaces.
Figure 8B:
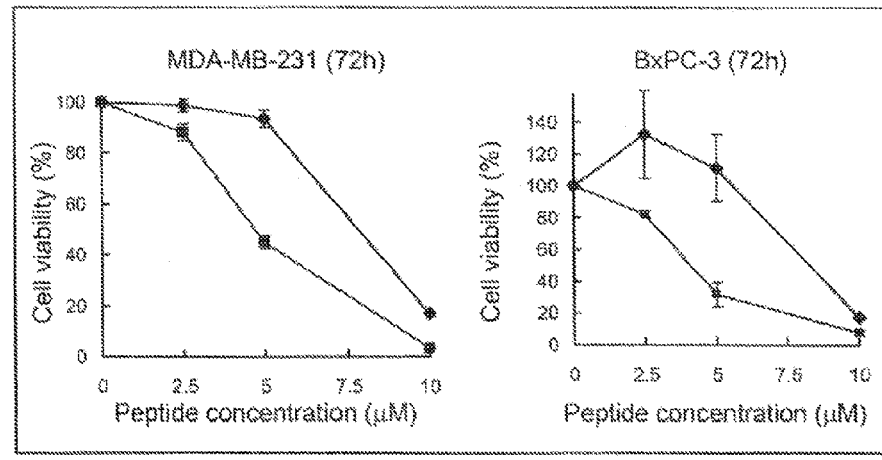
FIG. 8B shows the results of comparison of cell-killing effect between IL4R-targeted cancer cell membrane-lytic chimeric peptide (IL4-LyticL; quadrangle) and the cancer cell membrane-lytic peptide alone (LyticL; rhomboid). Human breast cancer cell line MDA-MB-231 (left) and human pancreatic cancer cell line BxPC-3 (right) were cultured with serially diluted concentrations (0 to 10 μM) of two peptides for 72 hours, and cell-killing effect was assessed using WST-8 reagent. The assay was repeated three times, and the results are represented as mean of triplicate measurements ±SD (bar).
Figure 8C:
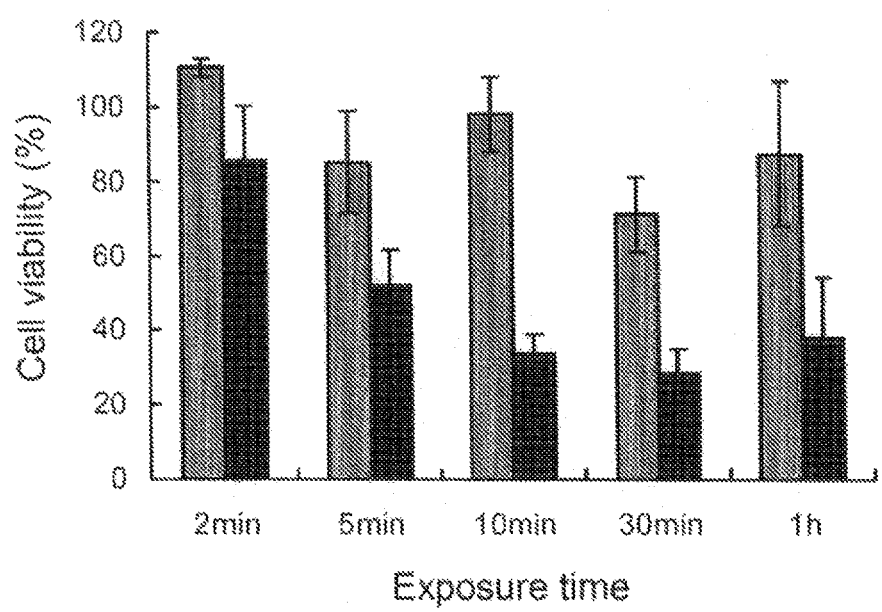
FIG. 8C shows that IL4R-targeted cancer cell membrane-lytic chimeric peptide (IL4-LyticL) induces rapid killing of cancer cells. BxPC-3 cells were treated with 10 μM of IL4-LyticL (black columns) or LyticL (gray columns) for two minutes, five minutes, 10 minutes, 30 minutes or one hour, and then the medium containing peptides was replaced with a fresh medium and culturing was further performed for 48 hours. The cells were analyzed for cell viability using WST-8.

The results are shown in FIG. 8. For IL4R-binding peptide sequence (KQLIRFLKRLDRN (SEQ ID NO: 26)), binding affinity with human recombinant IL4R protein was observed by BIACORE analysis (FIG. 8A). For IL4R-targeted cancer cell membrane-lytic chimeric peptide (IL4-LyticL), in both of the two cancer cell lines, cell-killing effect was enhanced as compared to the cancer cell membrane-lytic peptide alone (LyticL) (FIG. 8B). It was demonstrated that as a result of chimerization, contact for 10 minutes sufficiently induces the cancer cells (BxPC-3) to cell death (FIG. 8C).

Example 4

Combination of Cancer Cell Membrane-Lytic Sequence (Only L-Amino Acid) and IL-13 Receptor (IL13R)-Targeted Sequence as a Cancer Cell-Targeted Sequence In the present Example, it was investigated whether or not the same effect as in Example 1, such as enhancement of cell-killing effect, was observed using a chimeric peptide formed by combining the cancer cell membrane-lytic sequence of KLLLKLLKKLLKLLKKK (all amino acids are L-amino acids; LyticL; SEQ ID NO: 27) and IL13R-targeted sequence. The chimeric peptide sequence is as follows:

```
IL13-LyticL:
                                      (SEQ ID NO: 19)
KDLLLHLKKLFREGQFNGGGKLLLKLLKKLLKLLKKK.
```

Figure 9A:
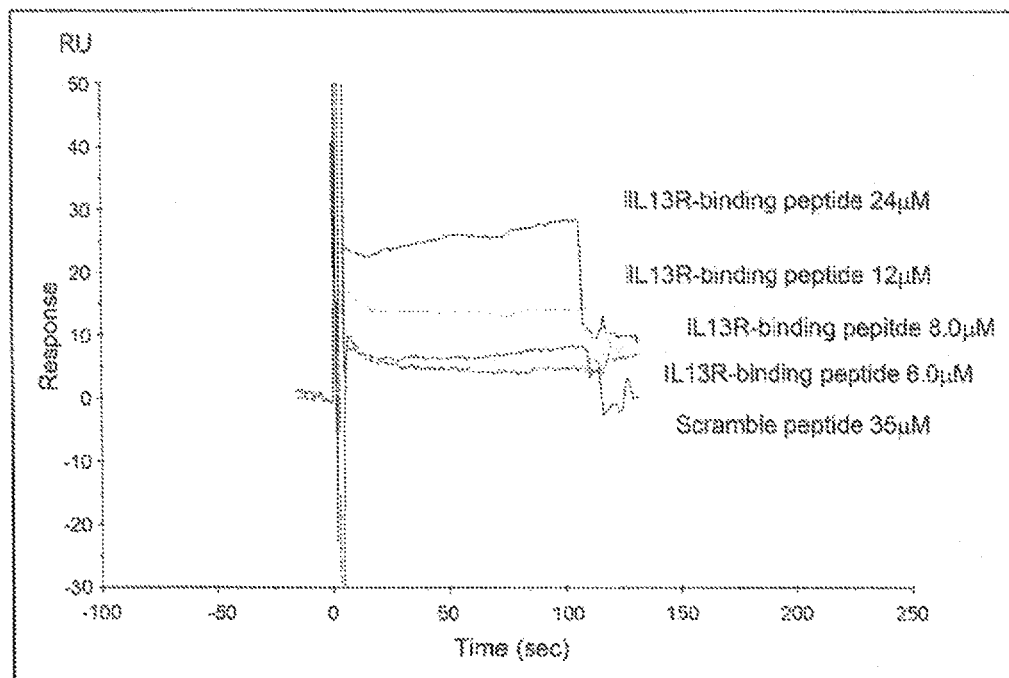
FIG. 9A shows binding properties of IL13R-binding peptide and scramble sequence peptide to recombinant human IL13R. Samples of serially diluted IL13R-binding peptide (24 μM to 6.0 μM) were analyzed on sensor surfaces.
Figure 9B:
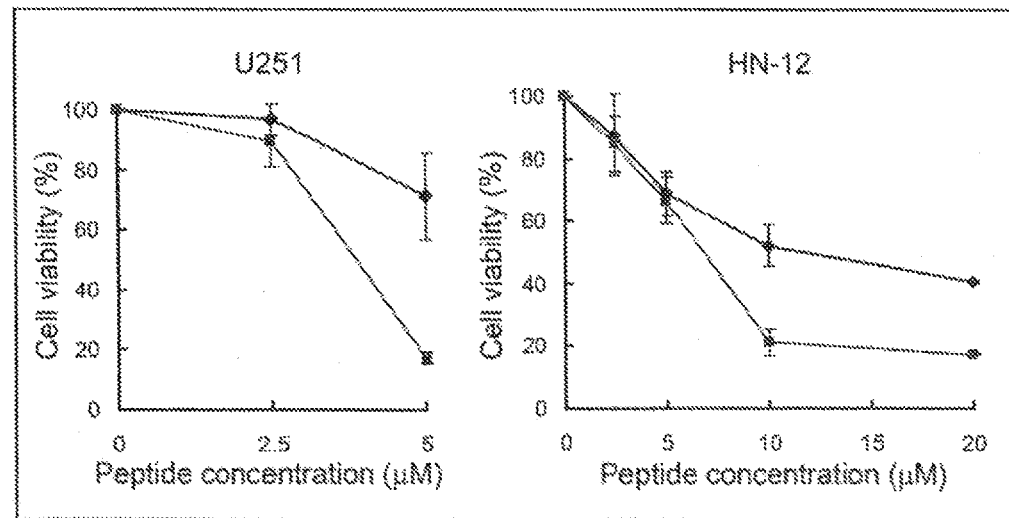
FIG. 9B shows the results of comparison of cell-killing effect between IL13R-targeted cancer cell membrane-lytic chimeric peptide (IL13-LyticL) and the cancer cell membrane-lytic peptide alone (LyticL). Human brain tumor cell line U251 (left) and human head and neck cancer cell line HN-12 (right) were cultured with serially diluted concentrations (0 to 20 μM) of two peptides for 72 hours, and cell-killing effect was assessed using WST-8 reagent. The assay was repeated three times, and the results are represented as mean of triplicate measurements ±SD (bar) Rhomboid, LyticL; quadrangle, IL13-LyticL.
Figure 9C:
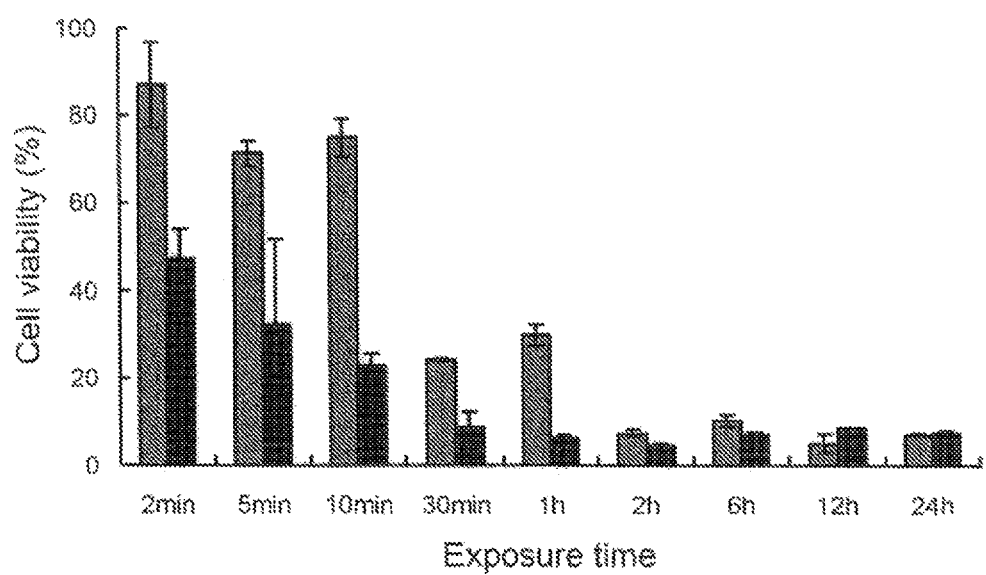
FIG. 9C shows that IL13R-targeted cancer cell membrane-lytic chimeric peptide (IL13-LyticL) induces rapid killing of cancer cells. U251 cells were treated with 10 μM of IL13-LyticL (black columns) or LyticL (gray columns) for two minutes, five minutes, 10 minutes, 30 minutes, or one hour to 24 hours, and then the medium containing peptides was replaced with a fresh medium and culturing was further performed for 48 hours. The cells were analyzed for cell viability using WST-8.

(Protocol)
Based on the results of binding three-dimensional structure analysis of IL13R and IL-13, partial peptide sequence which is important for binding (KDLLLHLKKLFREGQFN (SEQ ID NO: 28)) was designed and chemically synthesized. By BIACORE analysis, binding affinity with human recombinant IL13R protein was assessed. The aforementioned chimeric peptide was synthesized, and in vitro cell-killing effect to human brain tumor cell line U251 and human head and neck cancer cell line HN-12 was assessed.
(Results)
The results are shown in FIG. 9. For IL13R-binding peptide sequence (KDLLLHLKKLFREGQFN (SEQ ID NO: 28)), binding affinity with human recombinant IL13R protein was observed by BIACORE analysis (FIG. 9A). For IL13R-targeted cancer cell membrane-lytic chimeric peptide (IL13-LyticL), in both of the two cancer cell lines, cell-killing effect was enhanced as compared to the cancer cell membrane-lytic peptide alone (LyticL) (FIG. 9B). It was demonstrated that as a result of chimerization, contact for 10 minutes sufficiently induces the cancer cells (U251) to cell death (FIG. 9C).

Example 5

Combination of Cancer Cell Membrane-Lytic Sequence (Only L-Amino Acid) and Neuropilin-1 (NRP1)-Targeted Sequence as a Cancer Cell-Targeted Sequence In the present Example, it was investigated whether or not the same effect as in Example 1, such as enhancement of cell-killing effect, was observed using a chimeric peptide formed by combining the cancer cell membrane-lytic sequence of KLLLKLLKKLLKLLKKK (all amino acids are L-amino acids; LyticL; SEQ ID NO: 27) and NRP1-targeted sequence. The chimeric peptide sequence is as follows:

```
Sema3A-LyticL:
                                      (SEQ ID NO: 20)
NYQWVPYQGRVPYPRGGGKLLLKLLKKLLKLLKKK.
```

Figure 10A:
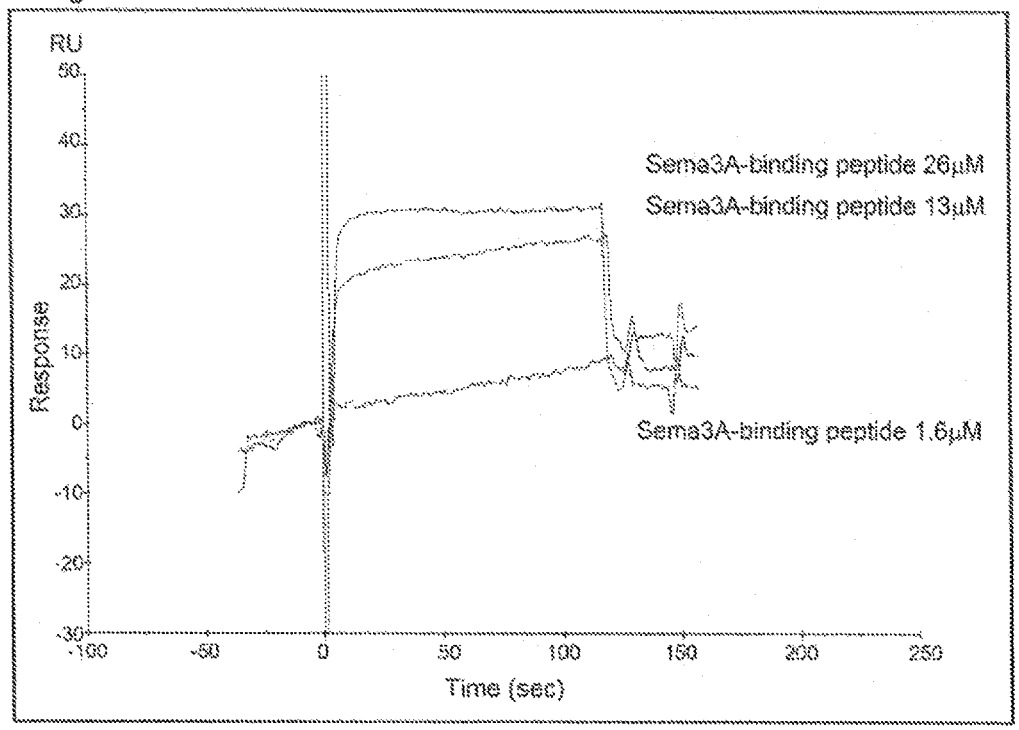
FIG. 10A shows binding properties of neuropilin-1 (NRP1)-binding peptide and scramble sequence peptide to recombinant human NRP1. Samples of serially diluted NRP1-binding peptide (24 μM to 6.0 μM) were analyzed on sensor surfaces.
Figure 10B:
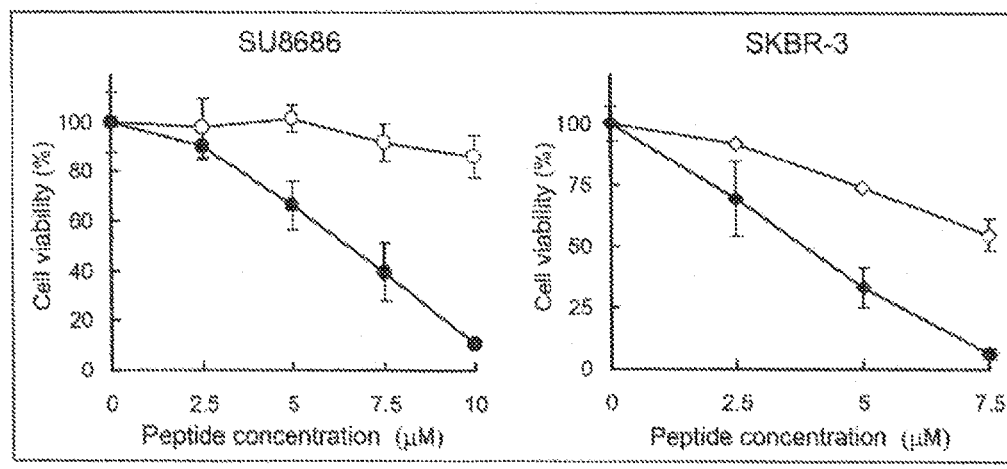
FIG. 10B shows the results of comparison of cell-killing effect between NRP1-targeted cancer cell membrane-lytic chimeric peptide (Sema3A-LyticL; black circle) and the cancer cell membrane-lytic peptide alone (LyticL; white circle). Human pancreatic cancer cell line SU8686 (left) and human breast cancer cell line SKBR-3 (right) were cultured with serially diluted concentrations (0 to 10 μM) of two peptides for 72 hours, and a cell-killing effect was assessed using WST-8 reagent. The assay was repeated three times, and the results are represented as mean of triplicate measurements ±SD (bar).

(Protocol)
Based on the results of binding three-dimensional structure analysis of NRP1 and a Sema3A, a ligand thereof, partial peptide sequence which is important for binding (NYQWVPYQGRVPYPR(SEQ ID NO: 29)) was designed and chemically synthesized. By BIACORE analysis, binding affinity with human recombinant NRP1 protein was assessed. The aforementioned chimeric peptide was synthesized, and in vitro cell-killing effect to human pancreatic cancer cell line SU86.86 and human breast cancer cell line SKBR3 was assessed.
(Results)
The results are shown in FIG. 10. For NRP1-binding peptide sequence (NYQWVPYQGRVPYPR (SEQ ID NO: 29)), binding affinity with human recombinant NRP1 protein was observed by BIACORE analysis (FIG. 10A). For NRP1-targeted cancer cell membrane-lytic chimeric peptide (Sema3A-LyticL), in both of the two cancer cell lines, cell-killing effect was enhanced as compared to the cancer cell membrane-lytic peptide alone (LyticL) (FIG. 10B).

Example 6

Combination of Cell Membrane-Lytic and Nucleic Acid-Binding Sequence and EGFR-Targeted Sequence as a Cancer Cell-Targeted Sequence In the present Example, it was investigated whether or not the same effect as in Example 1, such as enhancement of cell-killing effect, was observed using a chimeric peptide formed by combining cell membrane-lytic and nucleic acid-binding sequence (RLLRRLLRRLLRK (SEQ ID NO: 13); hereinafter, abbreviated as buf) and EGFR-targeted sequence. The chimeric peptide sequence is as follows:

```
EGFbuf:
                                      (SEQ ID NO: 21)
YHWYGYTPQNVIGGGGGRLLRRLLRRLLRK.
```

Figure 11A:
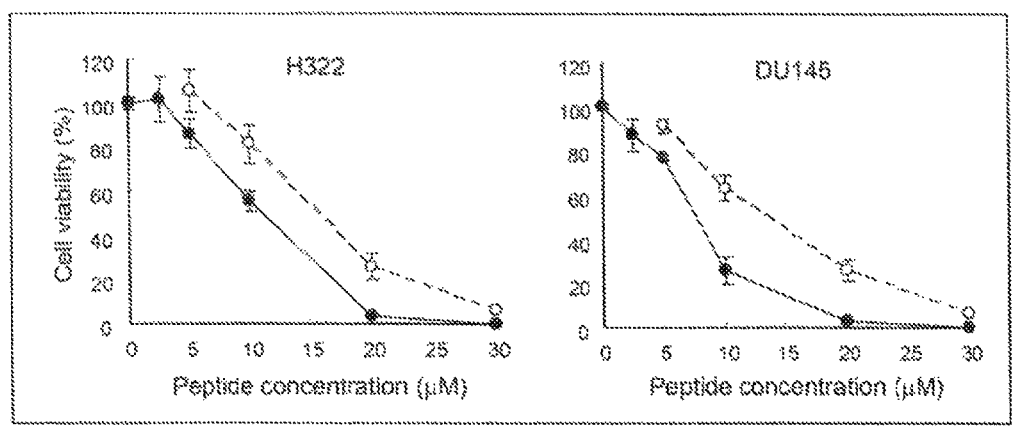
FIG. 11A shows the results of comparison of cell-killing effect between cell membrane-lytic and nucleic acid-binding sequence (buf; white circle) and EGFR-targeted chimeric peptide thereof (EGFbuf; black circle). Human lung cancer cell line H322 (left) and human prostate cancer cell line DU145 (right) were cultured with serially diluted concentrations (0 to 30 μM) of two peptides for 72 hours, and cell-killing effect was assessed using WST-8 reagent. The results are represented as mean of triplicate measurements ±SD (bar).
Figure 11B:
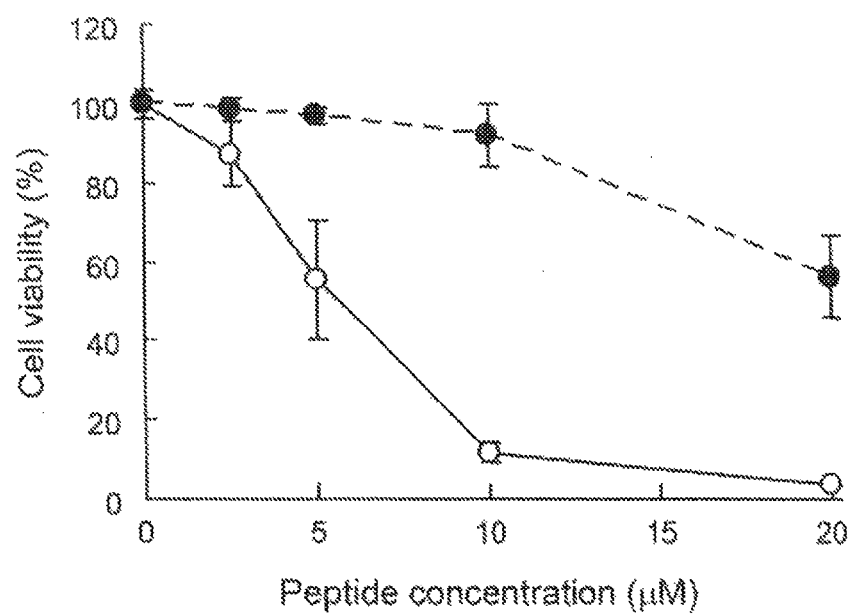
FIG. 11B shows the results of comparison of cell-killing effect of the EGFR-targeted chimeric peptide (EGFbuf) to lung cancer cell line H322 (white circle) and lung normal cell line MRC-5 (black circle). The two cells were cultured with serially diluted concentrations (0 to 20 μM) of EGFbuf peptide for 72 hours, and cell-killing effect was assessed using WST-8 reagent. The results are represented as mean of triplicate measurements ±SD (bar).

(Protocol)
The aforementioned chimeric peptide (EGFbuf) and explosive portion peptide alone (buf) were synthesized, and in vitro cell-killing effect to human lung cancer cell line H323, human prostate cancer cell line DU145 and human lung normal cell line MRC-5 was assessed.
(Results)
The results are shown in FIG. 11. For EGFR-targeted chimeric peptide (EGFbuf), in both of the two cancer cell lines, cell-killing effect was enhanced as compared to the cancer cell membrane-lytic peptide alone (buf) (FIG. 11A). Furthermore, when cell-killing effects of EGFbuf to lung cancer cell line H322 and lung normal cell line MRC-5 were compared, cell-killing sensitiveness to cancer cells was high (FIG. 11B).

Example 7

Combination of Cancer Cell Membrane-lytic Sequence (L-,D-Mixed Amino Acid Composition) and Three Binding Sequences to a Receptor with High Expression in Cancer Cells In the present Example, it was investigated whether or not the same effect as in Example 1, such as enhancement of cell-killing effect, was observed using a chimeric peptide formed by combining cell membrane-lytic sequence (KL LLKLLKKLLKLLKKK (underlined letters represent D-amino acids, and the others are L-amino acids; SEQ ID NO: 1)) and three binding sequences to a receptor with high expression in cancer cells (her2, VEGF receptor, Transferrin receptor). The chimeric peptide sequences are as follows (underlined letters represent D-amino acids, and the others are L-amino acids):

```
HER2-Lytic:
                                    (SEQ ID NO: 15)
YCDGFYACYMDVGGGKLLLKLLKKLLKLLKKK VEGFR-Lytic:
                                    (SEQ ID NO: 16)
WHSDMEWWYLLGGGGKLLLKLLKKLLKLLKKK TfR-Lytic:
                                    (SEQ ID NO: 17)
THRPPMWSPVWPGGGKLLLKLLKKLLKLLKKK.
```

(Protocol)

By searching documents, the aforementioned three receptor-binding peptide sequences were found, and chimeric peptides with a cancer cell membrane-lytic sequence (KLLLK LLKKLLKLLKKK; the underlined letters represent D-amino acids; hereinafter, abbreviated as Lytic; SEQ ID NO: 1) were designed and chemically synthesized. The aforementioned chimeric peptides were synthesized, and in vitro cell-killing effect to human lung cancer cell line H322 and human lung normal cell line MRC-5 was assessed.

(Results)

Figure 12A:
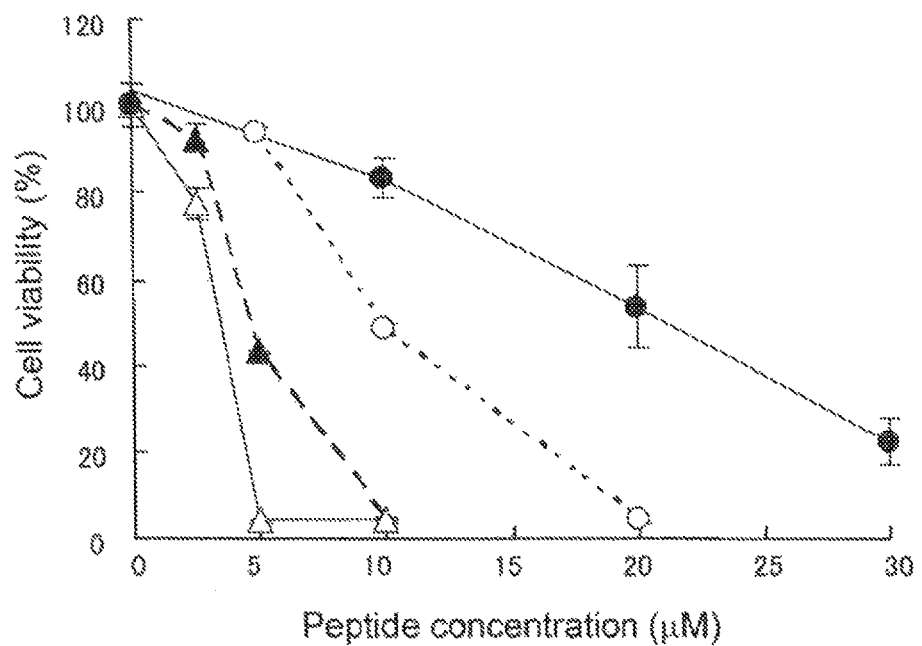
FIGS. 12A and 12B show the results of comparison of cell-killing effect of targeted chimeric peptide by cancer cell membrane-lytitc sequence (D,L-mix; the same sequence as in Example 1) alone and three sequences binding to a receptor with high expression in cancer cells (her2, VEGF receptor, Transferrin receptor). Human lung cancer cell line H322 (FIG. 12A) or human lung normal cell line MRC-5 (FIG. 12B) were cultured with serially diluted concentrations (0 to 80 μM) of the four peptides for 72 hours, and cell-killing effect was assessed using WST-8 reagent. The assay was repeated three times, and the results are represented as mean of triplicate measurements ±SD (bar). Black triangle: TfR-Lytic; white circle: Her2-Lytic; white triangle: VEGFR1-Lytic; black circle: Lytic.
Figure 12B:
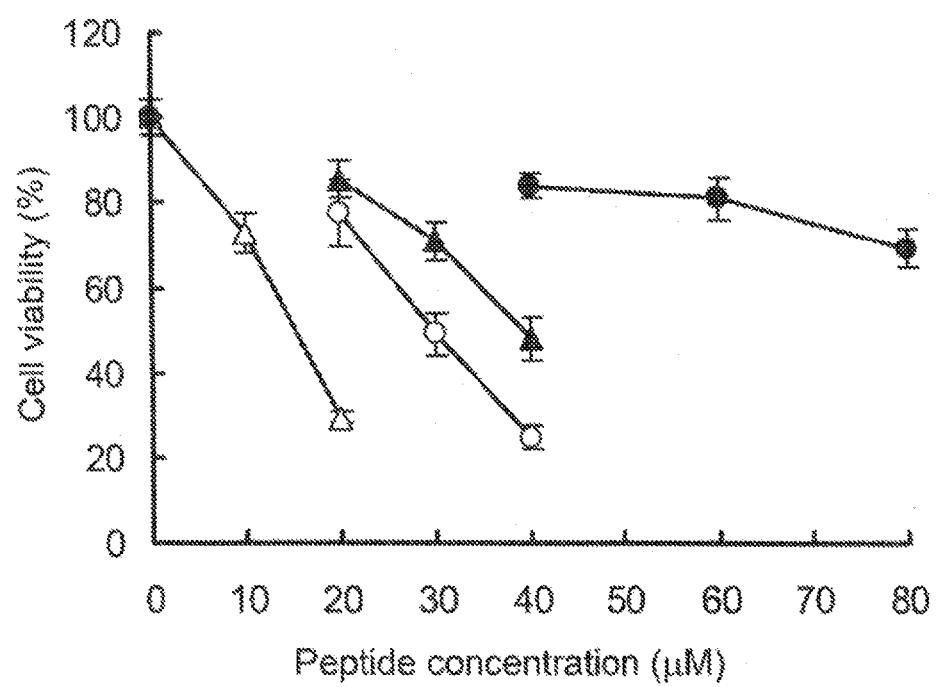

The results are shown in FIG. 12. For any of the three anticancer targeted cell membrane-lytic chimeric peptides, in human lung cancer cell line H322, the cell-killing effect was enhanced as compared to Lytic peptide alone (FIG. 12A). Furthermore, in vitro cell-killing effect to human lung normal cell line MRC-5 was milder as compared to that of the two cancer cell lines (FIG. 12B).

Example 8

Tests of Other Receptor Peptides with High Expression in Cancer Cells

In the present Example, it is investigated whether or not other receptor peptides with high expression in cancer cells can be used.

The peptides to be used are as follows. Except for difference in peptide sequence, all protocols are in accordance with Example 1.

(Cancer Cell Growth System Receptor)

Fibroblast growth factor receptor (FGFR): MQLPLAT (SEQ ID NO: 5) or AAVALLPAVLLALLAP (SEQ ID NO: 6)

(Angiogenesis System Receptor)

Human epidermal growth factor receptor type 2 (HER2): LLGPYELWELSH(SEQ ID NO: 52), ALVRYKD-PLFVWGFL (SEQ ID NO: 53), KCCYSL (SEQ ID NO: 54), WTGWCLNPEESTWGFCTGSF (SEQ ID NO: 55) or DTD-MCWWWSREFGWECAGAG (SEQ ID NO: 56)

Neuropilin 1 (NRP1)/vascular endothelial growth factor receptor 2 (VEGFR2): ATWLPPR (SEQ ID NO: 36)

Vascular endothelial growth factor receptor 1 (VEGFR1/Flt1):

VEPNCDIHVMWEWECFERL-NH2 (SEQ ID NO: 32) or GGNECDAIRMWEWECFERL (SEQ ID NO: 33)

Ephrin B1 (EphB1): EWLS (SEQ ID NO: 37)

Ephrin B2 (EphB2): SNEW (SEQ ID NO: 38)

(Cytokine/chemokine Receptors)

interleukin-11 receptor (IL11R): CGRRAGGSC (cyclic) (SEQ ID NO: 22)

(Other Receptors with High Expression in Cancer Cells)

glucose regulatory protein 78 (GRP78): WDLAWMFR-LPVG (SEQ ID NO: 39), CTVALPGGYVRVC (cyclic) (SEQ ID NO: 40) or YPHIDSLGHWRR (SEQ ID NO: 58)

(Cancer Antigen Surface Protein)

prostate-specific membrane antigen (PSMA): CQKHH-NYLC (SEQ ID NO: 35)

(Results)

Similar to the case of using EGFR, by BIACORE analysis, binding affinity specific for each receptor can be confirmed, and it can be expected that chimeric peptide of each binding sequence and a cancer cell membrane-lytic sequence has enhanced cell-killing effect as compared to cancer cell membrane-lytic peptide alone.

Example 9

Therapy Using Anticancer Targeted Chimeric Peptide (Peptidetoxin)

Using the chimeric peptide produced in Example 1, therapeutic effect was confirmed. An anticancer targeted chimeric peptide (peptidetoxin) was designed, which is formed by binding a warhead portion peptide which binds to a molecule such as a receptor with high expression in a cancer cell and an explosive portion peptide which exhibits strong cell-killing effect to the cancer cell. Antitumor effect in cancer-bearing animal models was studied.

(Protocol)

To 5-weeks-old female nude mice balb/c-nu/nu, human pancreatic cancer cell line BxPC-3 ($5 \times 10^6$ cells/150 µl phosphate buffer) was injected subcutaneously. From day 5 after the transplantation, the EB-lytic chimeric peptide was intratumorally administered three times per week for three weeks at 0 mg/kg, 0.3 mg/kg, 1 mg/kg (50 µl phosphate buffer/mouse). The tumor diameters were measured over time using an electronic caliper, and the tumor volume ($mm^3$) was calculated as longer diameter×shorter diameter×shorter diameter×0.5.

(Results)

The results are shown in FIG. 13.

In the group administered with phosphate buffer, increase of the tumor was observed over time, but in the group administered with the EB-lytic chimeric peptide, both in the group administered with 0.3 mg/kg and 1 mg/kg, dilatation of the tumors was inhibited significantly. The dose of 0.3 mg/kg is a very small amount, and sufficient antitumor effect is expected also in human. This result reveals that such a peptide has a considerably strong effect as compared with conventional arts, although peptides have been believed to be easily decomposed in a body and to have a weak effect. Stabilization by peptide chemical modification or the like or combination with DDS or the like further increases stability in the body, and enhancement of the drug effect can also be expected.

Considering the results of the present Example, theoretical explanation that the results are data which demonstrate that the chimeric peptide is actual anticancer agent for human. That is, using the data shown in FIG. 13, it is understood by those skilled in the art that the data can be "regarded equivalent" to data in human. Since the cancer cell lines transplanted were derived from human and many anticancer agents clinically used underwent similar research process, this is regarded as a theory established in the art. Thus, from the results of the present Example, it is understood that the chimeric peptide of the present invention can be affirmed as an "anticancer agent" for human.

Example 10

Antitumor Effect by Intravenous Administration of EB-lytic

Figure 14:
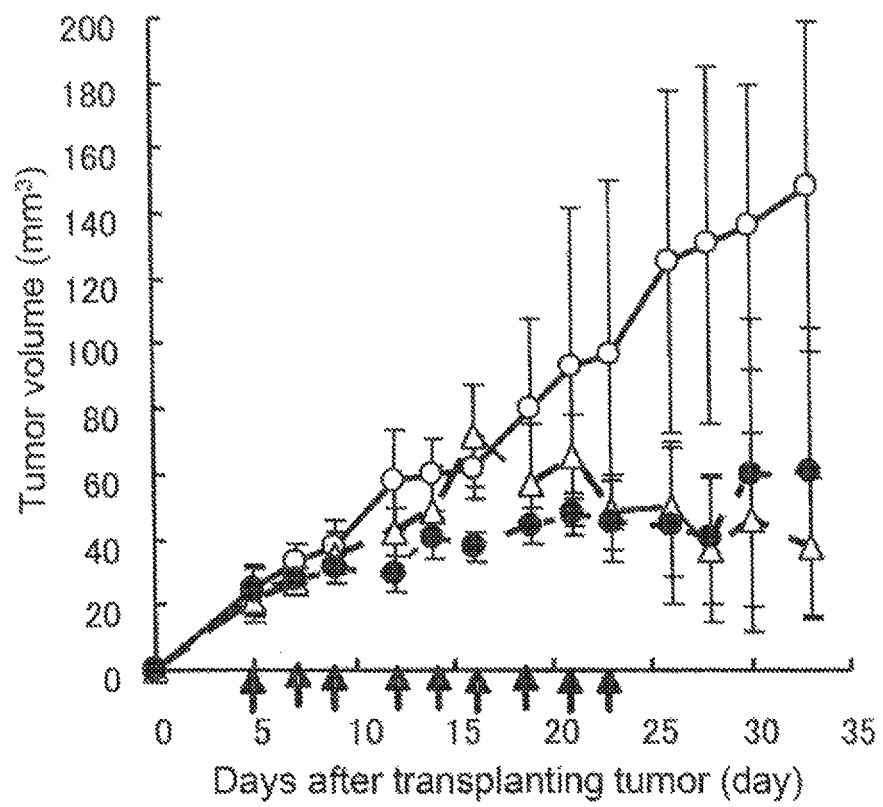
FIG. 14 shows antitumor effect of systemic administration of the same EB-lytic chimeric peptide as in Example 1 in mouse models bearing human pancreatic cancer cell line BxPC-3. Human pancreatic cancer cell line BxPC-3 was subcutaneously transplanted to nude mice. From day 5 after the transplantation, the peptide was intravenously administered three times per week for three weeks. The results are represented as mean of three mice of each group ±SD (bar). White circle is a group administered with saline, white triangle is a group administered with 1 mg/kg of the EB-lytic chimeric peptide, and black circle is a group administered with 5 mg/kg of the EB-lytic chimeric peptide.
Figure 15A:
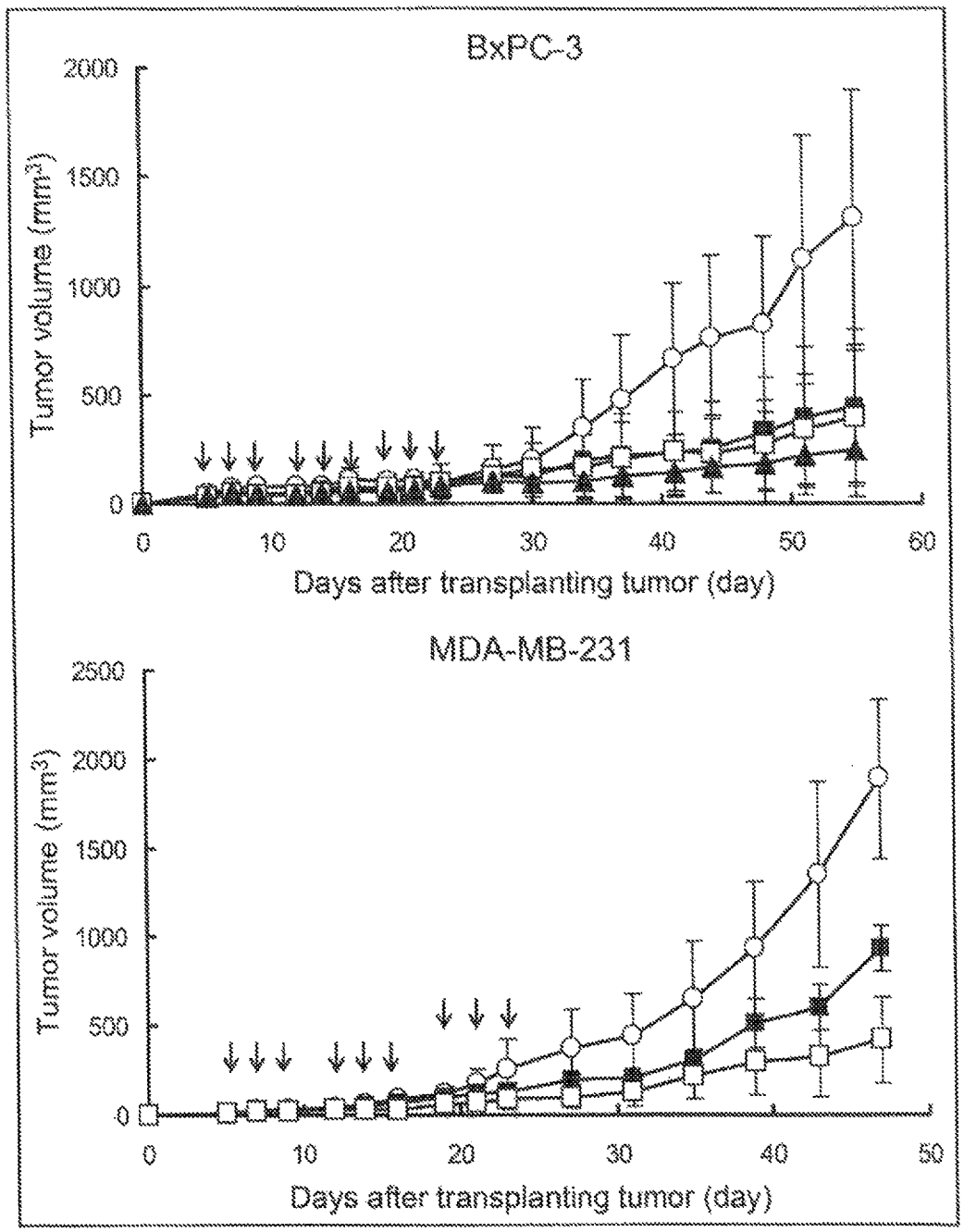
FIG. 15A shows antitumor effect of the same EB-lytic chimeric peptide as in Example 1 in mouse models bearing human pancreatic cancer cell line BxPC-3 (upper) and mouse models bearing human breast cancer cell line MDA-MB-231 (lower). BxPC-3 pancreatic cancer cells or breast cancer cells were subcutaneously transplanted to athymic nude mice. As shown by the arrow, from day 5, saline (control (white circle)) or EB-lytic peptide (2 mg/kg (black quadrangle), 5 mg/kg (white quadrangle) or 10 mg/kg (black triangle)) was intravenously administered. Each group is formed by six animals (n=6), and the experiment was repeated two times. The results are represented as mean±SD.
Figure 15B:
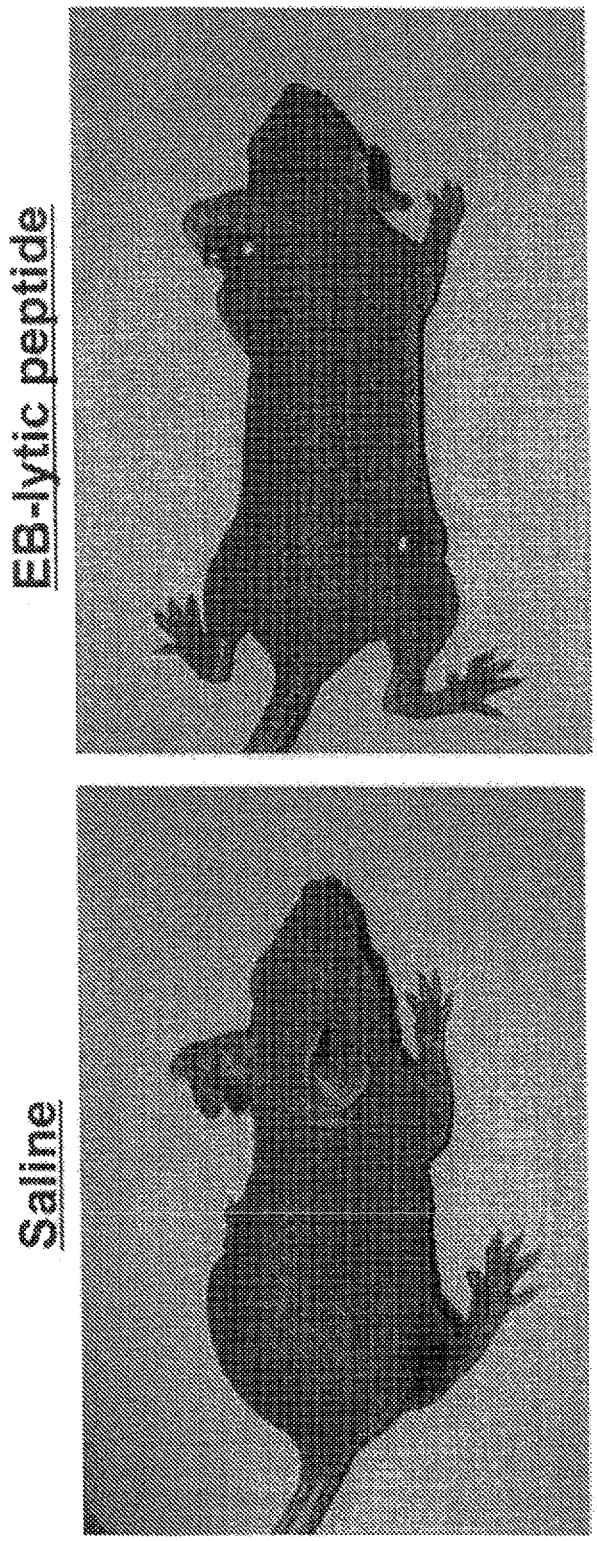
FIG. 15B shows reduction of MDA-MB-231 tumor in the athymic nude mice after the intravenous treatment. MDA-MB-231 cells were dorsally transplanted to the mice. After engrafting, the mice were treated by intravenous injection of saline (left panel) or EB-lytic peptide (right panel). Arrow indicates location of tumor.

In the same manner as described in the previous section, therapeutic effect was confirmed using the chimeric peptide produced in Example 1. In the present Example, antitumor effect by systemic administration was examined.
(Protocol)
To 5-week-old female nude mice balb/c-nu/nu, human pancreatic cancer cell line BxPC-3 ($5 \times 10^6$ cells/150 µl phosphate buffer) was injected subcutaneously. From day 5 after the transplantation, the EB-lytic (EB-Lytic) chimeric peptide was intravenously administered three times per week for three weeks at 0 (control), 1 and 5 mg/kg, or as an experimental system separate from such, at 0, 2, 5 and 10 mg/kg (50 µl phosphate buffer/mouse). The tumor diameters were measured over time using an electronic caliper, and the tumor volume (mm$^3$) was calculated as longer diameter×shorter diameter×shorter diameter×0.5.
(Results)
The results are shown in FIG. 14 and upper portion of FIG. 15A. As apparent from the above description, FIGS. 14 and 15A respectively show results of independent experimental systems.

For the group administered with phosphate buffer, increase of tumor was observed over time, but for the group administered with EB-lytic chimeric peptide, both 1 and 5 mg/kg, dilatation of tumor was significantly inhibited. The dose of 1 mg/kg is a very small amount in systemic administration, and a sufficient antitumor effect is expected also in humans. Furthermore, tumor volumes at day 55 in the groups administered with 2, 5 and 10 mg/kg were, as compared to the tumor volume of the control group treated with saline (1310 mm$^3$), 34% (440 mm$^3$, $P<0.05$), 30% (399 mm$^3$, $P<0.05$) and 19% (244 mm$^3$, $P<0.01$), respectively. Such results revealed that the peptide is very strongly effective as compared to conventional arts, although so far a peptide has been immediately decomposed in a body and had a weak effect and it has been believed systemic administration of a peptide is very difficult. By stabilization by peptide chemical modification or the like, combination with DDS or the like, and the like, stability in body is further increased, and enhancement of drug effect can also be expected.

Example 11

Therapeutic Method

In the present Example, application to actual therapy is investigated.

Here, stabilization of kinetics in a body, together with discussion of stabilization of kinetics in body, release control and the like using DDS (Drug Delivery System), antitumor effect in cancer-bearing animal models is studied.
(DDS)
The EB-lytic chimeric peptide was mixed with atelocollagen, and using gelled preparation for topical administration, inhibition of decomposition and release-controlling effect are studied. Furthermore, for systemic administration, formulation for exhibiting an effect of inhibiting peptide decomposition without gelling is studied. For such study, free profile analysis from atelocollagen mixture of the peptide in vitro is performed and the optimal percentage of atelocollagen content is determined.
(Antitumor Effect in Cancer-Bearing Animal Models)
A gelled mixture for topical administration (EB-lytic chimeric peptide and atelocollagen) is intratumorally administered to nude mouse cancer-bearing models to assess antitumor effect, in the same manner as in Example 9. Furthermore, the mixture for systemic administration is intravenously administered to assess antitumor effect in the same manner. For both administration methods, tests for setting usage and dose are conducted.

By conducting such experiments, it can be expected that intratumoral administration of the gelled mixture formulation of EB-lytic chimeric peptide and atelocollagen results in sufficient antitumor effect due to inhibition of peptide decomposition and release-controlling effect, even if the number of administrations is reduced. For intravenous administration of a non-gelled mixture for systemic administration, higher antitumor effect as compared to peptide alone is expected.

Example 12

In vivo Test for Setting Dose

Using the chimeric peptide produced in Example 1, dose setting is studied.
(Protocol)
To 5-weeks-old female nude mice balb/c-nu/nu, human pancreatic cancer cell line BxPC-3 ($5 \times 10^6$ cells/150₁11 phosphate buffer) was injected subcutaneously. From day 5 after the transplantation, the EB-lytic chimeric peptide is intravenously administered three times per week for three weeks at 0 mg/kg, 0.5 mg/kg, 1 mg/kg, 2 mg/kg or 5 mg/kg (50 µl phosphate buffer/mouse). The tumor diameters are measured over time using an electronic caliper, and the tumor volume (mm$^3$) is calculated as longer diameter×shorter diameter×shorter diameter×0.5.

Example 13

In vivo Test for Setting Usage

Using the chimeric peptide produced in Example 1, usage setting is studied.
(Protocol)
To 5-weeks-old female nude mice balb/c-nu/nu, human pancreatic cancer cell line BxPC-3 ($5 \times 10^6$ cells/150 µl phosphate buffer) is injected subcutaneously. From day 5 after the transplantation, the EB-lytic chimeric peptide is intravenously administered three times per week for three weeks or five times per week for one week at 1 mg/kg (50 µl phosphate buffer/mouse). The tumor diameters are measured over time using an electronic caliper, and the tumor volume (mm$^3$) is calculated as longer diameter×shorter diameter×shorter diameter×0.5.

Example 14

Tests in Other Cancer Cells

Using the chimeric peptide produced in Example 1, antitumor effect in other type of cancer was studied.
(Protocol)
To 5-weeks-old female nude mice balb/c-nu/nu, human breast cancer cell line MDA-MB-231 or human prostate cancer cell line DU145 ($5 \times 10^6$ cells/150 µl phosphate buffer) was injected subcutaneously. From day 5 after the transplantation, the EB-lytic chimeric peptide is intravenously administered three times per week for three weeks at 0.5 mg/kg (50 µl phosphate buffer/mouse). The tumor diameters are measured over time using an electronic caliper, and the tumor volume (mm$^3$) is calculated as longer diameter×shorter diameter× shorter diameter×0.5.

(Breast Cancer Cell Line MDA-MB-231)

To assess antitumor effect of EB-lytic chimeric peptide inhuman cancer xenograft model, in vivo antitumor activity of the EB-lytic chimeric peptide in tumor xenograft was studied. Breast cancer cell line MDA-MB-231 (5×10$^6$ cells/ 150 µl phosphate buffer) was subcutaneously injected to the flank region of 7- to 9-weeks-old female nude mice balb/c-nu/nu (body weight: 17-21 g). At the time point when the tumor reached to the volume of 20 to 60 mm$^3$, the animals were randomly divided into three groups, which were intravenously administered (50 µl/injection) with saline (control) or EB-lytic peptide (2 mg/kg or 5 mg/kg) three times per week for three weeks (nine administrations in total). The tumor diameters were measured over time using an electronic caliper, and the tumor volume (mm$^3$) was calculated as longer diameter×shorter diameter×shorter diameter×0.5. At the time of termination of the treatment, the mice were killed and the tumors were extracted. After staining with hematoxyline, histological test was conducted using optical microscope. All values are represented as mean±SD, and statistical analysis was performed by one-way ANOVA and Dunnet test. Differences were considered to be significant at $P<0.05$.

Figure 15C:
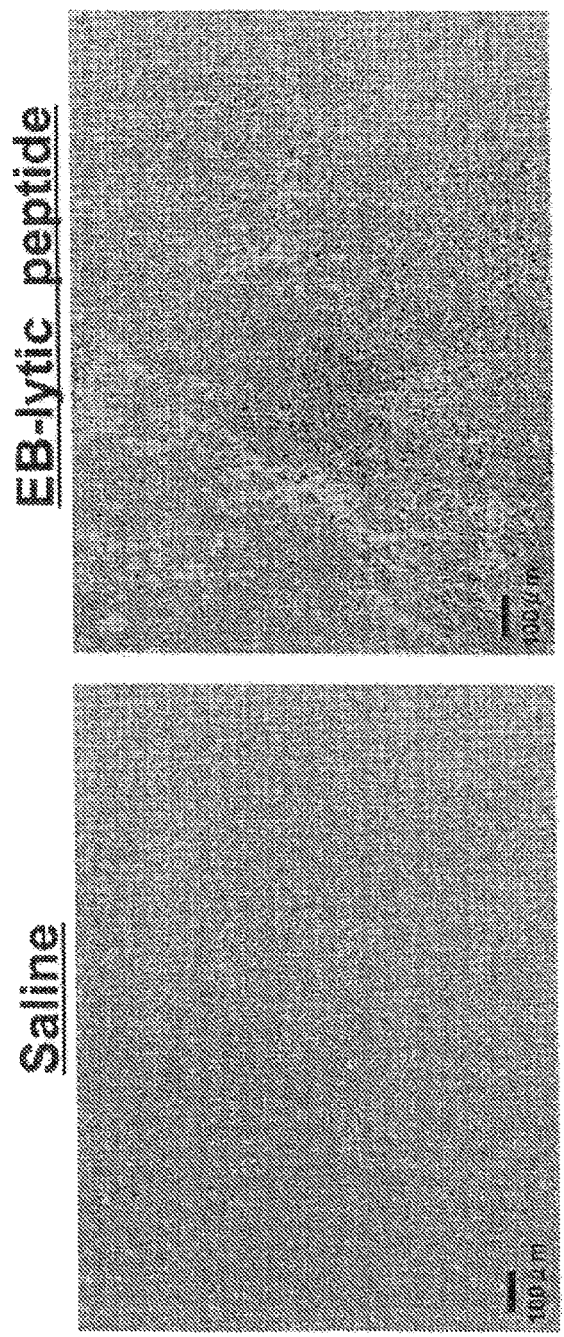
FIG. 15C shows histological test for MDA-MB-231 tumor after the treatment with the same EB-lytic chimeric peptide as in Example 1. Formalin-fixed and paraffin-embedded tumor sections from the animals treated with saline (left panel) or EB-lytic chimeric peptide (right panel) were stained with hematoxylin, and analyzed with optical microscope.

The control group exhibited gradual tumor growth to reach 1885 mm$^3$ at day 48. On the other hand, administration of the EB-lytic peptide (2 mg/kg, 5 mg/kg or 10 mg/kg, intravenous administration of three times per week) significantly inhibited tumor growth (FIGS. 15A (lower portion) and 15B). Day 48, mean tumor volume was 933 mm$^3$ in the group administered with 2 mg/kg, and 419 mm$^3$ in the group administered with 5 mg/kg ($P<0.01$ as compared with the mice of the control group). As shown in FIG. 15C, the number of tumor cells drastically reduced in the mice treated with the EB-lytic peptide (FIG. 15C, right panel). These results indicate that the newly designed EB-lytic hybrid peptide successfully induces tumor death.

Example 15

EB(H2R)-Lytic Chimeric Peptide

In the present Example, activity of EB(H2R)-Lytic chimeric peptide was investigated.

Figure 16A:
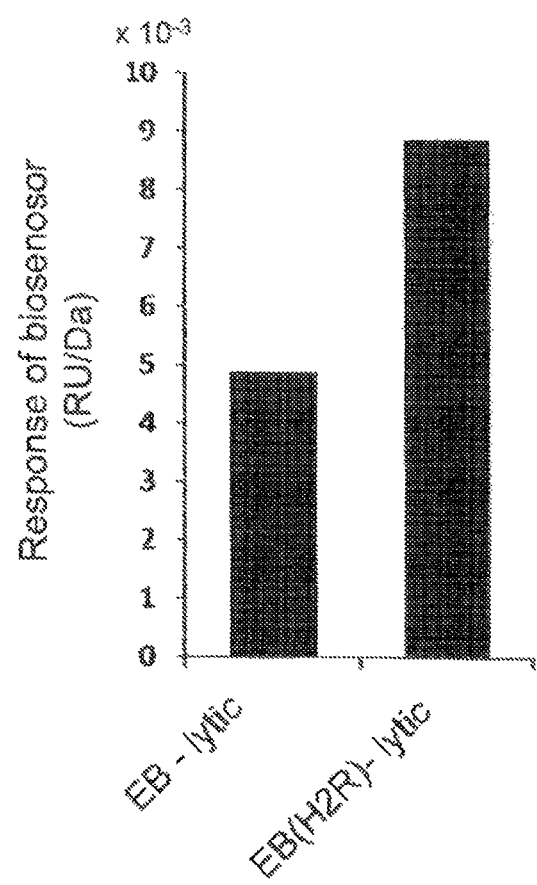
FIG. 16A shows binding analysis using BIACORE system.
Figure 16B:
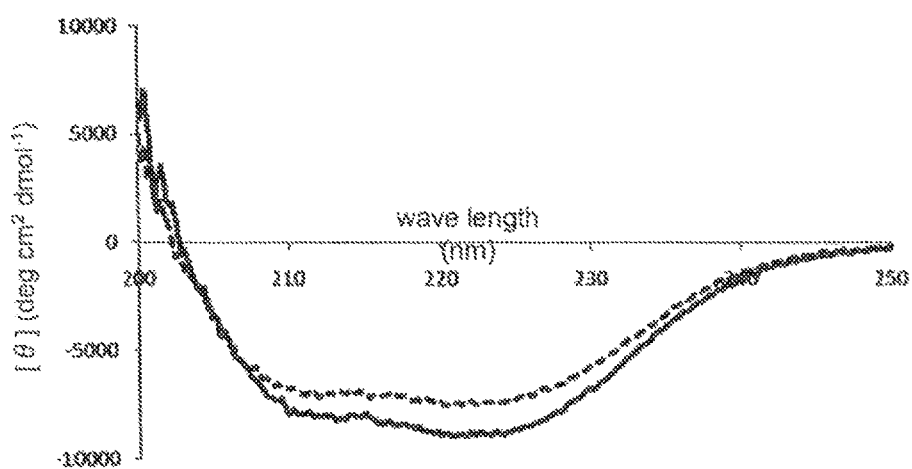
FIG. 16B shows secondary structure analysis for EB-lytic peptide (dotted line) and EB(H2R)-lytic peptide (solid line) using CD spectrum. The peptide concentrations were 50 µM.

For wild-type EB-Lytic (YHWYGYTPQNVIGGGKL LLKLLKKLLKLLKKK; SEQ ID NO: 2; underlines represent D-amino acids) and mutated EB (H2R)-Lytic (YRW-YGYTPQNVIGGGKLLLKLLKKLLKLLKKK; SEQ ID NO: 43; underlined letters represent D-amino acids), comparison of binding affinity was performed by BIACORE system. The results are shown in FIG. 16A. Furthermore, using CD spectrum, secondary structure analysis was performed for EB-lytic peptide and EB(H2R)-lytic peptide. The results are shown in FIG. 16B. The peptide concentrations were 50 µM. Except for differences in peptide sequence, the protocol is in accordance with Example 1.

(Cell Viability Assay)

Figure 16C:
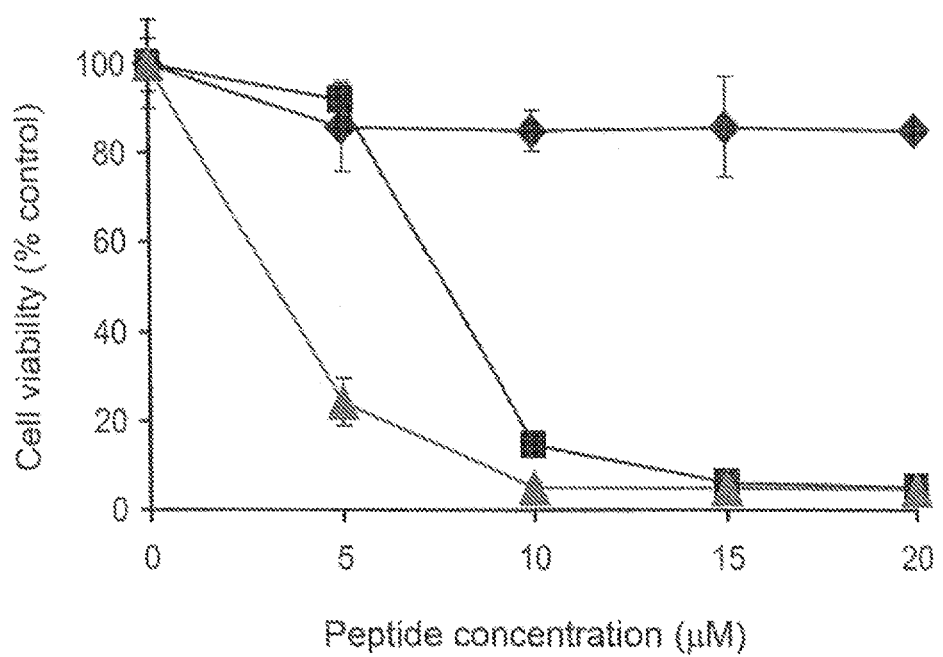
FIG. 16C shows cytotoxicity of the lytic peptide (rhomboid), EB-lytic peptide (quadrangle) and EB(H2R)-lytic peptide (triangle) in BT20 cells.

Using lytic peptide, wild-type EB-lytic peptide and EB(H2R)-lytic peptide, comparison of cytotoxicity to BT20 cells was performed. A total of 3×10$^3$ cells per well were seeded in 96-well plates, cultured for 24 hours in a medium containing 10% FBS, and incubated with increasing concentrations of peptide in 100 µl for 48 to 72 hours at 37° C. Cell viability was measured with WST-8 solution (Cell Count Reagent SF; Nakalai Tesque). The results are shown in FIG. 16C.

(EB(H2R)-Lytic Enhances Cytotoxic Activity to Cancer Cells)

Figure 17B:
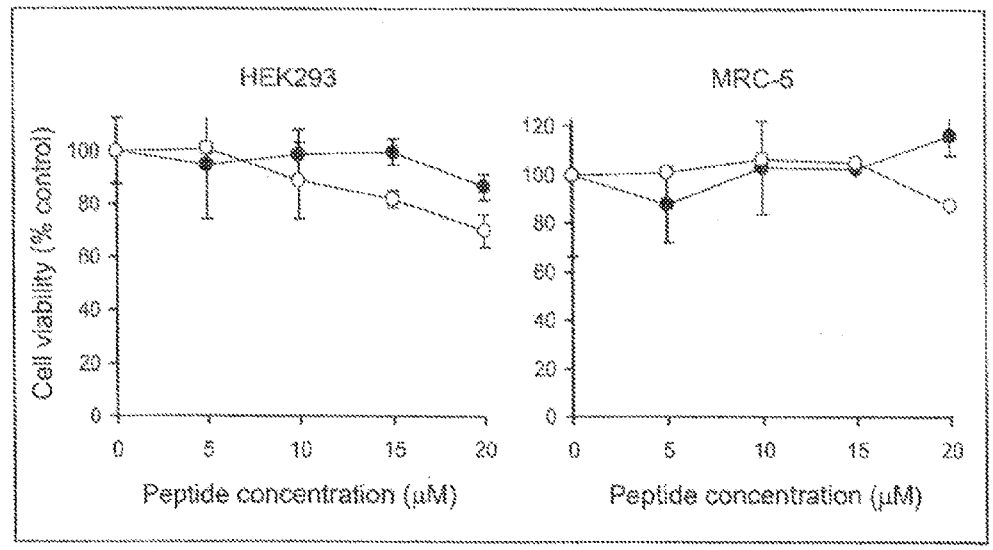
FIG. 17B shows cytotoxicity of EB(H2R)-lytic chimeric peptide or EB-lytic peptide in various human normal cell lines. Normal cell lines MRC-5 and HEK293 were cultured with various concentrations (0 to 20 µM) of the aforementioned peptides, cytotoxic activity was assessed, and cytotoxicity assay was performed as described above. White circle, EB(H2R)-lytic peptide; black circle, EB-lytic peptide.

Cancer cell lines H322, BT-20, U251, BxPC-3, SU86.86 and LNCaP were cultured with various concentrations (0 to 20 µM) of EB-lytic chimeric peptide or EB(H2R)-lytic chimeric peptide for 72 hours, and cytotoxic activity was assessed using WST-8 reagent. The results are shown in FIG. 17A. Furthermore, normal cell lines MRC-5 and HEK293 were cultured with various concentrations (0 to 20 µM) of the aforementioned peptides for 72 hours, cytotoxic activity was assessed, and cytotoxicity assay was conducted as described above. The results are shown in FIG. 17B. The results indicate that the newly designed lytic peptide is suitable for chimeric peptide for enhancing cytotoxic activity to cancer cells.

(EB(H2R)-Lytic Induces Rapid Killing of Cancer Cells)

Figure 18:
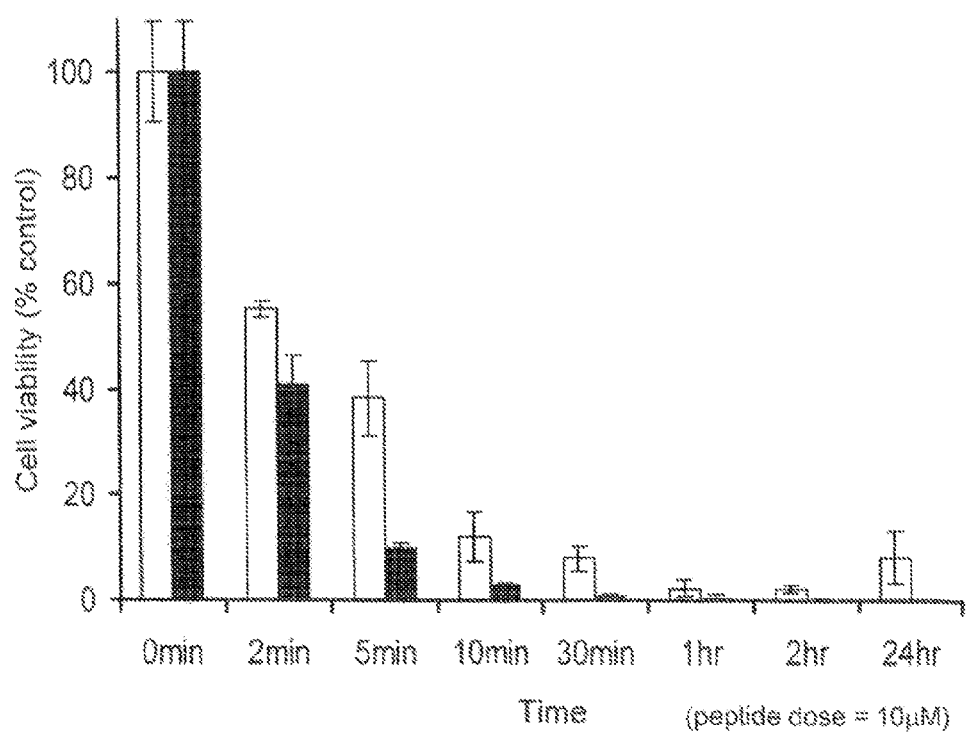
FIG. 18 shows that the EB-lytic chimeric peptide disintegrates the cell membrane to induce rapid killing of cancer cells. H322 cells were treated with 10 µM of EB-lytic chimeric peptide (white columns) or EB(H2R)-lytic chimeric peptide (black columns) for two minutes, five minutes, 10 minutes, 30 minutes, one hour, two hours or 24 hours, and then the medium containing peptides was replaced with a fresh medium. The cells were further cultured for 24 h. The cells were analyzed for cell viability using WST-8. The results are represented as mean±SD (bar).

H322 cells were treated with EB-lytic chimeric (white columns) or EB(H2R)-lytic chimeric peptide (black columns) for two minutes, five minutes, 10 minutes, 30 minutes, one hour, two hours or 24 hours, and then the medium containing peptides was replaced with a fresh medium. The cells were further cultured for 24 hours. The cells were analyzed for cell viability using WST-8. The results are shown in FIG. 18. The results indicate that the EB-lytic chimeric peptide permeates the plasma membrane and induces rapid killing of cancer cells.

The results are summarized in Table 2.

TABLE 2

Cytotoxicity of peptides to various cell lines and EGFR expression.

| | IC$_{50}$ (µM) | | IC$_{50}$ Ratio EB-lytic peptide/ EB(H2R)-lytic peptide | Relative MFI* (anti-EGFR antibody, %) mean ± SD |
|---|---|---|---|---|
| Cell lines | EB-lytic peptide mean | EB(H2R)-lytic peptide mean | | |
| Cancer cells | | | | |
| H322 | 6.8 | 3.2 | 2.1 | 90 ± 23 |
| BT-20 | 6.5 | 1.9 | 3.4 | 100 |
| U251 | 12 | 8.4 | 1.4 | 39 ± 5.6 |
| BxPC-3 | 12 | 6.6 | 1.8 | 64 ± 17 |
| SU.86.86 | 12 | 7.4 | 1.6 | 43 ± 4.6 |
| LNCaP | 10 | 4.8 | 2.1 | 20 ± 7.0 |
| Normal cells | | | | |
| MRC-5 | 49 | >20 | | 47 ± 13 |
| HEK293 | 44 | >20 | | 0 |

*The relative MFI (mean fluorescence intensity) is the extent of binding of the FITC-conjugated anti-EGFR polyclonal antibody to cells, where the mean MFI values for BT-20 and HEK293 cells are set at 100% and 0%, respectively.

(EB(H2R)-Lytic Disintegrates Cancer Cell Membrane More Efficiently than EB-Lytic)

Ability of disintegrating cancer cell membrane of EB(H2R)-Lytic and EB-Lytic was studied.

Calcein, a soluble fluorescence molecule, was added to H322 lung cancer cells in a glass-bottomed dish at a final concentration of 2 µM. Small aliquots of Lytic peptide alone, EB-Lytic or EB(H2R)-Lytic (15 µl) were directly added to the dish at a final concentration of 10 µM. At 0 minute, two minutes, five minutes, 10 minutes and 20 minutes after addition of peptide, using Olympus FV1000 confocal laser scanning microscope (Olympus), confocal images were taken. The images are shown in FIG. 19A.

Figure 19A:
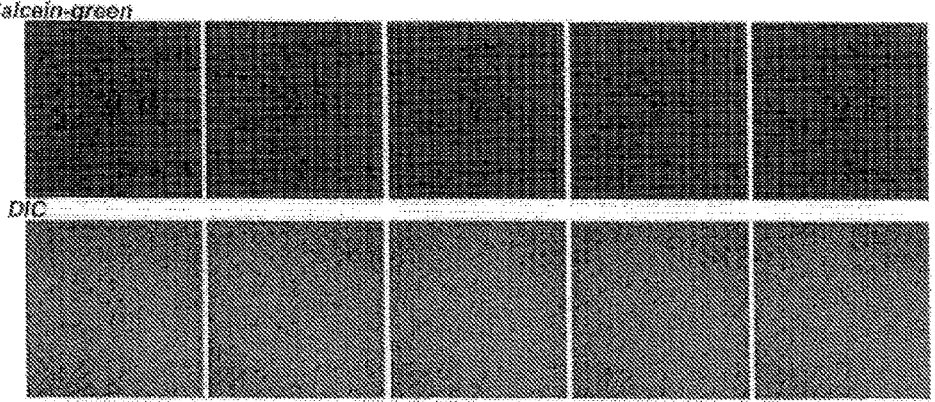
FIG. 19A shows permeation of cell membrane by Lytic peptide in H322 lung cancer cells. Confocal microscopic images of cells in calcein solution of 0 minute, two minutes, five minutes, 10 minutes and 20 minutes after addition of lytic peptide at final concentration of 10 µM are shown. From the top, images of Lytic peptide alone, EB-Lytic peptide and EB(H2R)-Lytic peptide are shown. These images indicate that the number of cells which became green (cells with the membrane disintegrated) for Lytic peptide alone did not change over time, whereas the number of cells which became green increased over time for EB-Lytic peptide and EB(H2R)-Lytic peptide and the number increases in shorter time for EB(H2R)-Lytic peptide than for EB-Lytic peptide.
Figure 19A:
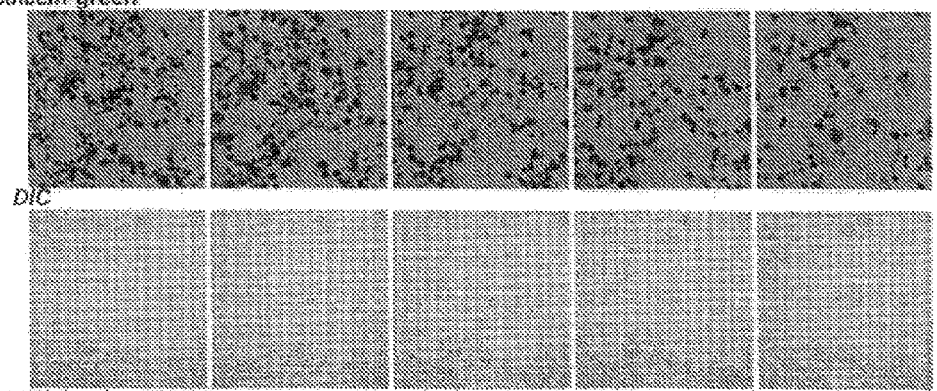
Figure 19A:
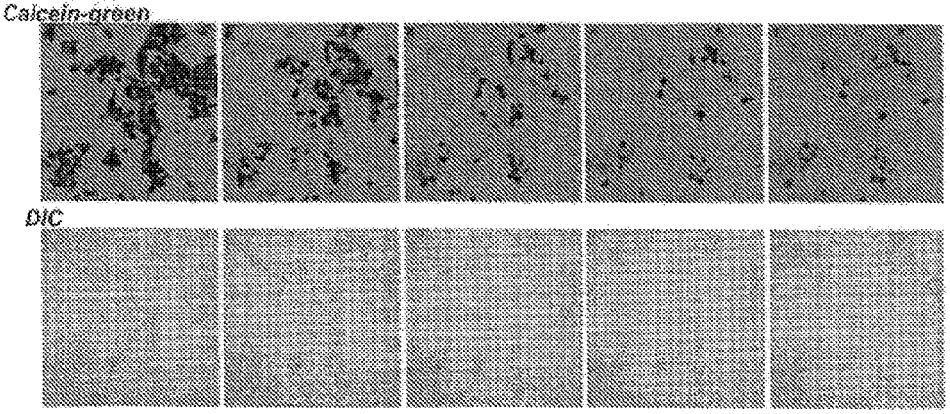

From the images shown in FIG. 19A, it is seen that for Lytic peptide alone (upper) the number of cells which became green (cells with the membrane disintegrated) did not change even after lapse of time while for EB-Lytic peptide (center) and EB(H2R)-Lytic peptide (lower) the number of cells which became green increased overtime and that the number increases in shorter time for EB(H2R)-Lytic peptide than for EB-Lytic peptide.

Figure 19B:
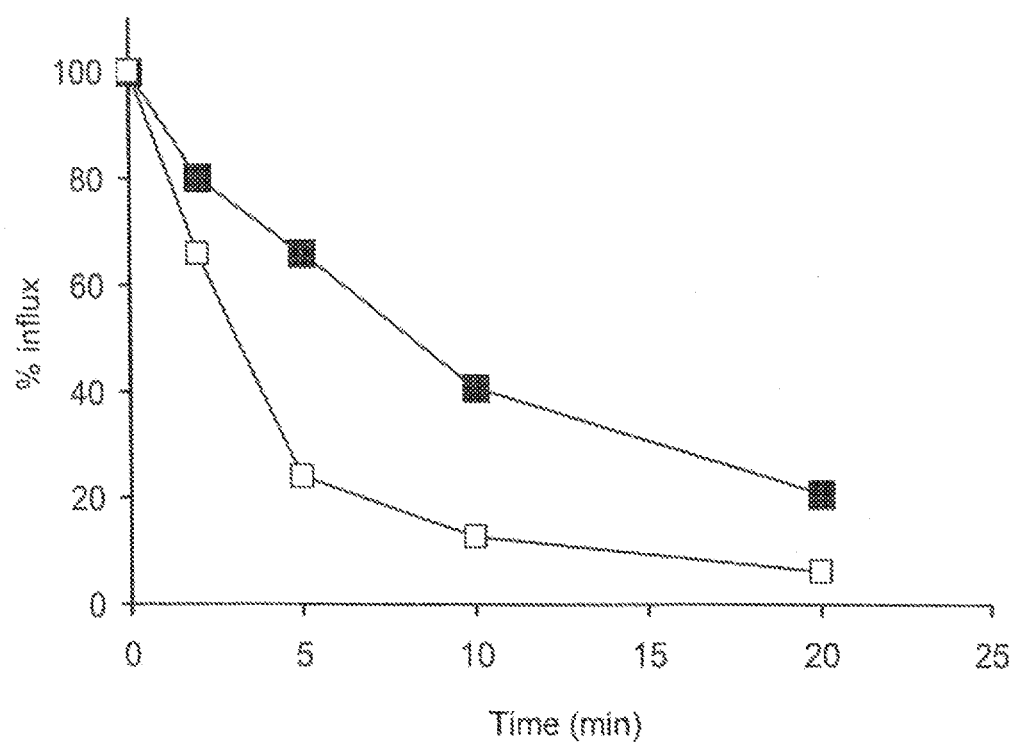
FIG. 19B shows a graph showing the percentage of influx of medium to the cells over time as calculated from the results of FIG. 19A. Also from this figure, it is seen that the percentage of influx of medium to the cells was more rapid for EB(H2R)-Lytic peptide (white quadrangle) than for EB-Lytic peptide (black quadrangle).

FIG. 19B is a graph showing percentage of influx of medium to the cells along lapse of time as calculated based on the results of FIG. 19A. This figure also indicates that the percentage of influx to the cells was more efficient for EB(H2R)-Lytic peptide than EB-Lytic peptide.

It is recognized that it revealed as a result of cell membrane permeation by calcein solution that EB(H2R)-Lytic is more efficient than EB-Lytic. Regarding FIGS. 19A and B, as negative control, the microscopic data for Lytic peptide alone in FIG. 19A can be employed. That is, it is difficult for this Lytic peptide alone to attain membrane-lytic ability. FIG. 19B is a graph of percentage of influx of calcein-containing medium. Thus, it is clearly seen that the membrane is clearly penetrated earlier for EB (2R)-Lytic.

(EB(H2R)-Lytic Induces Cell Death by an Apoptotic Mechanism in Cancer Cells More Strongly than EB-Lytic)

The ability of inducing Annexin V-positive expression in cancer cells by EB(H2R)-Lytic and EB-Lytic was studied.

In accordance with the method of Example 1, Annexin V assay and caspase assay were performed. Specifically, BT20 cells were treated for two hours at 37° C. with or without EB-Lytic or EB(H2R)-Lytic chimeric peptide at 5 µM. For determination of caspase activation or Annexin V-positive expression, peptide-treated cultures were simultaneously analyzed for caspase activity and propidium iodide (PI) staining using a carboxyfluorescein FLICA caspase-3&7 assay (Immunochemistry Technologies, Bloomington, Minn.), or, alternatively, for Annexin V labeling and PI staining by multiparametric flow cytometry. The results are shown in FIG. 20A (Annexin V) and FIG. 20B (caspase activity).

Regarding FIG. 20A, it is recognized that EB(H2R)-lytic is superior to EB-lytic in inducing Annexin V-positive expression. In BT-20 cells treated with respective peptides, the ratio of right half panel showing Annexin V-positive cells, and EB(H2R)-lytic induced Annexin V-positive expression more strongly.

Figure 20B:
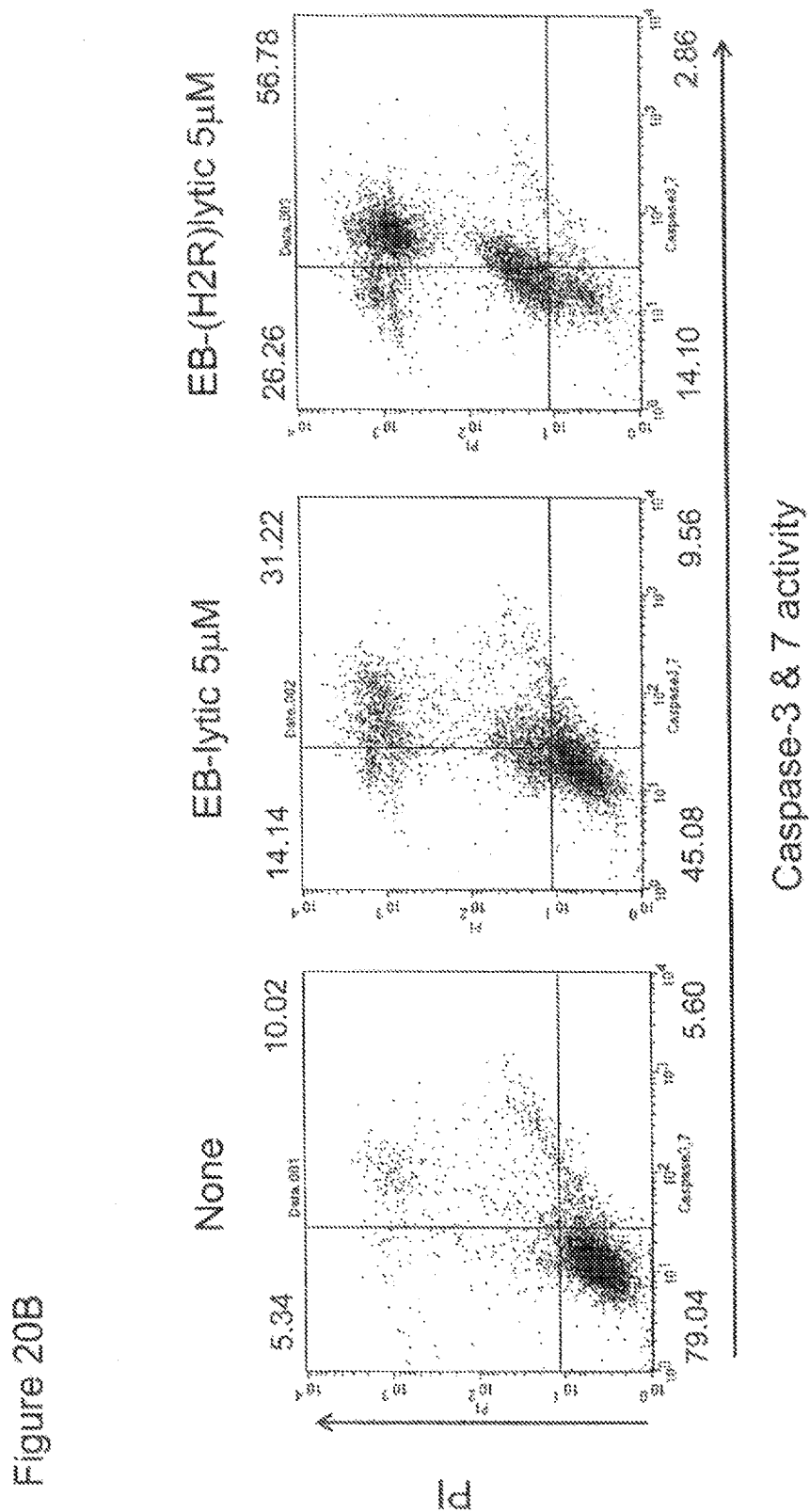
FIG. 20B shows that EB(H2R)-Lytic peptide induces caspase 3 & 7 activity more strongly than EB-Lytic peptide in cancer cells. Human breast cancer cell line BT20 cells were incubated with EB-Lytic peptide or EB(H2R)-Lytic peptide (5 µM of each) at 37° C. for two hours, and analyzed by calboxyfluorescein FLICA polycaspase assay for caspase 3 & 7 activity.

Furthermore, regarding FIG. 20B, it is recognized that induction of caspase activity of EB(H2R)-lytic is superior to EB-lytic. In BT-20 cells treated with the respective peptides, the ratio of the right half panel showing caspase 3,7-activated cells, and EB(H2R)-lytic induced caspase 3,7 activation more strongly.

From a viewpoint of an excellent anticancer agent, it is believed that causing suicide to avoid scattering therearound is much more advantageous than killing when side effects and other influences in vivo are taken into consideration. Regarding the hybrid peptide of the present invention, the killing mechanism hardly gives influence such as disorder to cells around a tumor in that the possibility of action is specific to cancer cells and the induction of apoptosis was suggested. Thus, the hybrid peptide of the present invention can be regarded excellent as a pharmaceutical. Furthermore, this evaluation system was employed due to its importance in accurate calculation of Annexin V-positive expression and caspase 3,7 activation which are important indicators of apoptosis.

Furthermore, in the present Example, it revealed that, when the peptide of the present invention was administered, live cells significantly decreased. Thus, it can also be proof that the peptide of the present invention selectively kills more cancer cells, regardless of whether or not it mediates an apoptotic mechanism.

Moreover, it can be recognized that the present Example demonstrated whether EB-lytic and EB(H2R)-lytic are excellent in cell-killing effect in view of degree and selectivity which cannot be achieved with conventional anticancer agents.

(Antitumor Effect of EB-Lytic Chimeric Peptide and EB(H2R)-Lytic Chimeric Peptide in Mouse Models Bearing Human Breast Cancer Cell Line MDA-MB-231)

In mouse models bearing human breast cancer cell line MDA-MB-231, antitumor effect of EB-Lytic chimeric peptide and EB(H2R)-Lytic chimeric peptide was studied.

Figure 21:
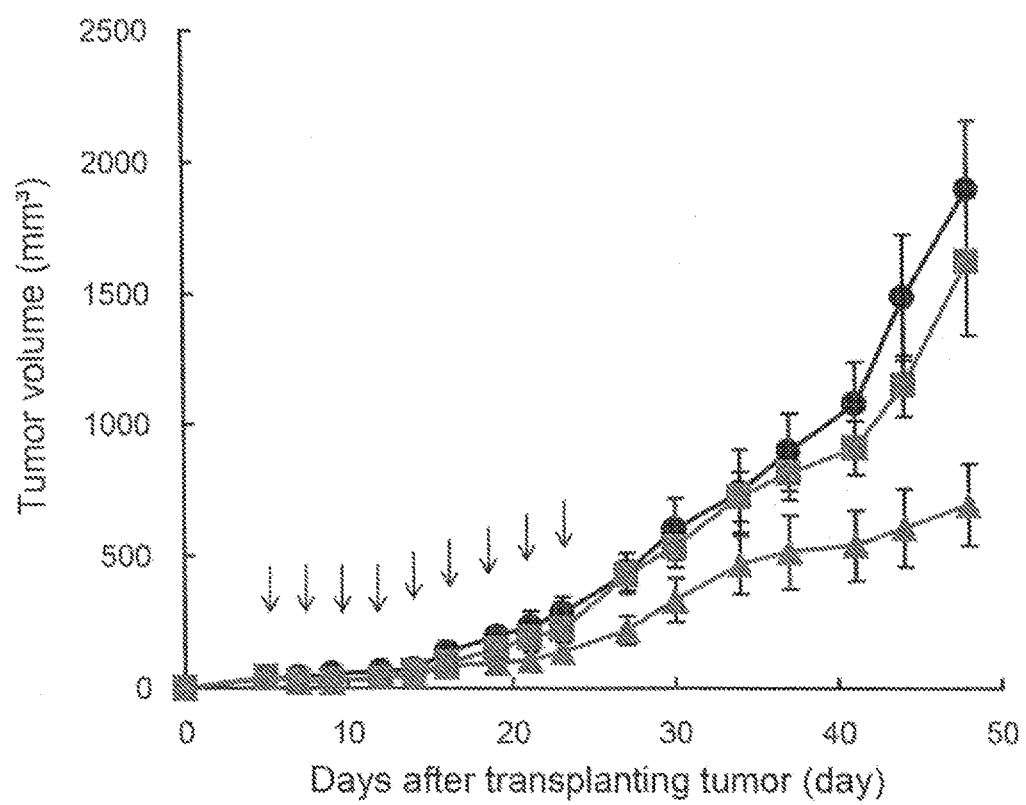
FIG. 21 shows antitumor effect of EB-Lytic peptide and EB(H2R)-Lytic chimeric peptide in mouse models bearing human breast cancer cell line MDA-MB-231. MDA-MB-231 breast cancer cells were subcutaneously transplanted to athymic nude mice, and as shown by arrow in the graph, from day 5 after the transplantation, saline (control: black circle), EB-Lytic peptide (1 mg/kg; quadrangle) or EB(H2R)-Lytic chimeric peptide (1 mg/kg; triangle) was intravenously injected. Each group was formed of six animals (n=6). The vertical axis shows a volume of tumor (mm$^3$) and the horizontal axis shows the number of days (day) after the transplantation of breast cancer cells. The data is represented as mean±SD. It is seen that the chimeric peptide in which the second position of EB peptide was changed from H into R (EB(H2R)-Lytic) has in vivo antitumor effect higher as compared to EB-Lytic chimeric peptide (EB-Lytic).

MDA-MB-231 breast cancer cells were subcutaneously transplanted to athymic nude mice. From day 5 after the transplantation, the animals were divided into three groups (n=6/group), and saline (control), EB-lytic peptide (1 mg/kg) or EB(H2R)-Lytic chimeric peptide (1 mg/kg) was intravenously injected. Results of measurement of tumor diameters over time are shown in FIG. 21.

As apparent from the figure, it is seen that the chimeric peptide in which the second H of the EB peptide has been changed from H into R (EB(H2R)-Lytic) has higher antitumor effect in vivo as compared to EB-Lytic chimeric peptide (EB-Lytic).

The results of FIG. 4 are results of comparison at a concentration of peptide of 1 mg/kg. Based on the results, it should be noted that EB(H2R)-lytic can attain sufficient antitumor effect even in systemic administration at 1 mg/kg. As apparent from other results, it is understood that administration of 5 mg/kg results in anticancer action of a considerable therapy level. Regarding administration of 1 mg/kg, EB(H2R)-lytic still attained sufficient effect. This should be regarded as just a surprising numerical value in view of the conventional state of art.

Specifically, EB(H2R)-Lytic exhibited sufficient antitumor effect even at a concentration of 1 mg/kg, and it is seen that EB(H2R)-Lytic is a very promising anticancer therapeutic drug.

Example 16

TfR-Lytic Chimeric Peptide

In the present Example, activity of TfR-Lytic chimeric peptide was investigated.

(EfR-Lytic Enhances Cytotoxic Activity to Cancer Cells)

Using TfR-Lytic chimeric peptide (THRPPMWSPVW-PGGGKLLLKLLKKLLKLLKKK; SEQ ID NO: 17; underlined letters represent D-amino acids), cytotoxic activity to cancer cells was studied.

Figure 22A:
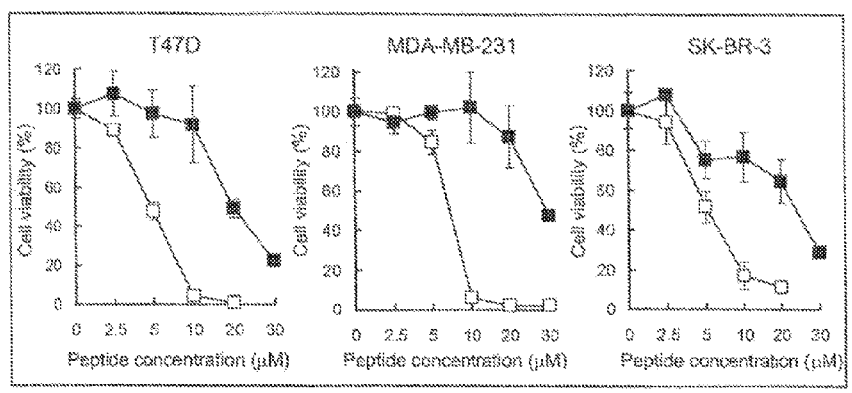
FIG. 22A shows that TfR-lytic peptide is suitable for chimeric peptide for enhancing cytotoxic activity to cancer cells. Cancer cell lines T47D, MDA-MB-231 and SKBR-3 were cultured with various concentrations (0 to 30 µM) of TfR-lytic chimeric peptide (white quadrangle) or lytic peptide (black quadrangle) for 72 hours, and cytotoxic activity was assessed with WST-8 reagent.
Figure 22B:
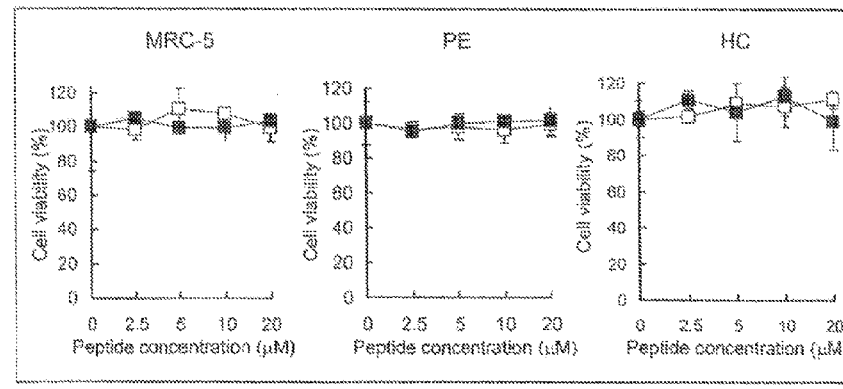
FIG. 22B shows cytotoxicity of TfR-lytic chimeric peptide in various normal cell lines. Normal cell lines MRC-5, PE and HC were cultured with various concentrations (0 to 100 µM) of the aforementioned peptides for 72 hours, and cytotoxic activity was assessed. The absolute value obtained from untreated cells was defined as 100%. Black quadrangle, TfR-lytic chimeric peptide; white quadrangle, lytic peptide.
Figure 23:
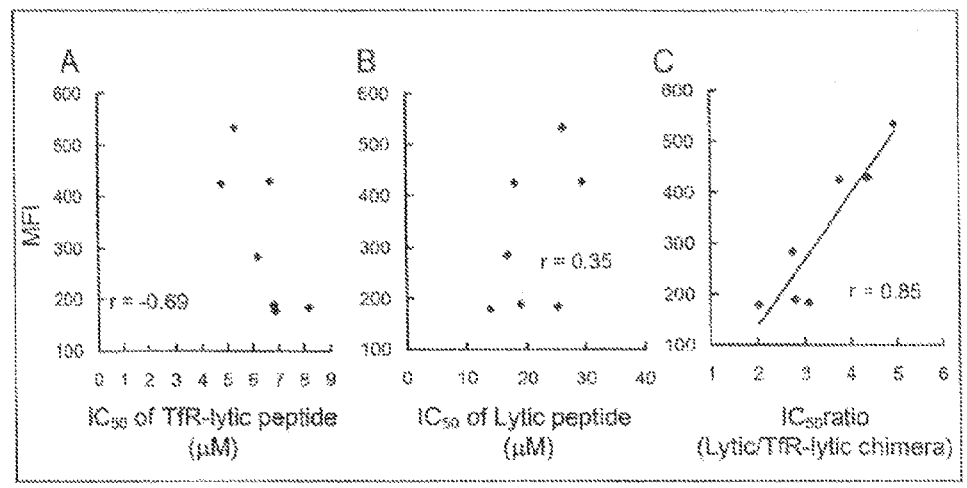
FIG. 23 shows correlation between $IC_{50}$ values related to enhancement of cytotoxicity by addition of TfR-lytic chimeric peptide. $IC_{50}$ of TfR-lytic chimeric peptide (A) and $IC_{50}$ of lytic peptide (B) or $IC_{50}$ ratio of lytic peptide/TfR-lytic chimeric peptide (C) and mean fluorescence intensity of TfR monoclonal antibody binding for seven cancer cell lines.

A total of $3\times10^3$ cells per well of cancer cell lines T47D, MDA-MB-231 and SKBR-3 were cultured with various concentrations (0 to 30 µM) of TfR-lytic chimeric peptide or lytic peptide for 72 hours, and cytotoxic activity was assessed using WST-8 reagent. The results are shown in FIG. 22A. Furthermore, normal cell lines MRC-5, PE and HC were cultured with various concentrations (0 to 100 µM) of the aforementioned peptides for 72 hours, and cytotoxic activity was assessed. The absolute value obtained from untreated cells was defined as 100%. The results are shown in FIG. 22B. Furthermore, regarding enhancement of cytotoxicity by addition of TfR-lytic chimeric peptide, $IC_{50}$ of TfR-lytic chimeric peptide and $IC_{50}$ of lytic peptide, or $IC_{50}$ ratio of lytic peptide/TfR-lytic chimeric peptide were studied. Correlation between $IC_{50}$ values was observed. These results indicate that TfR-lytic peptide is suitable for chimeric peptide for enhancing cytotoxic activity to cancer cells. The results are summarized in Table 3.

TABLE 3

Cytotoxicity of peptides to various cell lines and TfR expression.

| | $IC_{50}$ (μM) | | | |
|---|---|---|---|---|
| Cell lines | Lytic peptide alone Mean | TfR-lytic peptide Mean | $IC_{50}$ ratio Lytic/ TfR-lytic | MFI* Mean |
| Cancer cells | | | | |
| T47D | 18.2 | 4.8 | 3.8 | 425.7 |
| MDA-MB-231 | 29.5 | 6.7 | 4.4 | 428.7 |
| SK-BR-3 | 26.3 | 5.3 | 5.0 | 533.6 |
| LNCaP | 17.0 | 6.2 | 2.7 | 284.0 |
| U251 | 19.0 | 6.8 | 2.8 | 188.9 |
| SN-19 | 25.3 | 8.2 | 3.1 | 184.1 |
| COLO587 | 13.9 | 6.9 | 2.0 | 179.2 |
| Normal cells | | | | |
| MRC-5 | >20 | >20 | — | 64.6 |
| HC cell (hepatocyte cell) | >20 | >20 | — | 89.6 |
| PE cell (pancreatic epidermal) | >20 | >20 | — | 41.2 |

*The MFI (mean fluorescence intensity) is the extent of binding of the PE-conjugated anti-Transferrin receptor monoclonal antibody to cells.

(TfR-Lytic Induces Rapid Killing Specific for TfR-Expressing Cancer Cells)

Figure 24A:
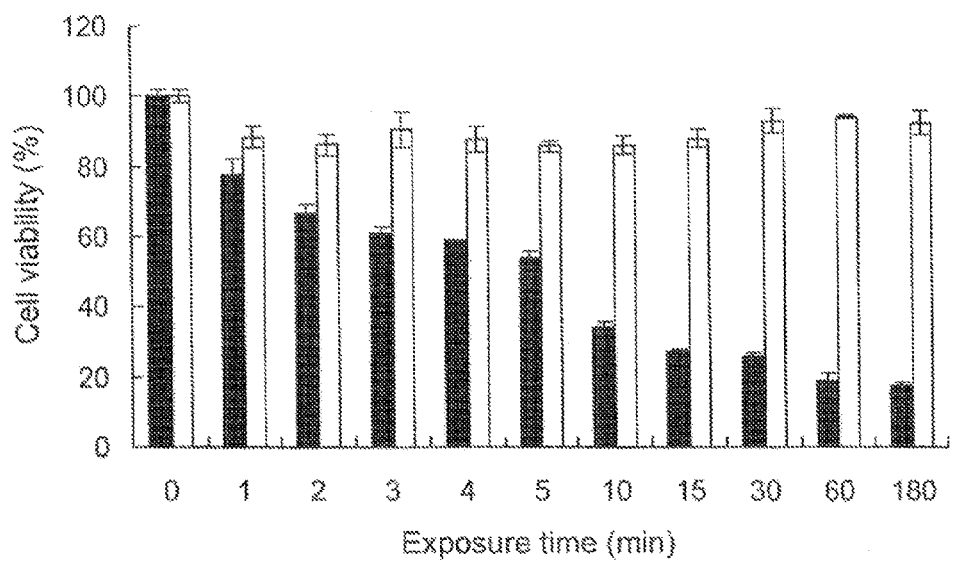
FIG. 24A shows that TfR-lytic peptide disintegrates the cell membrane to rapidly kill T47D cancer cells. T47D cells were exposed to TfR-lytic chimeric peptide (black columns) or lytic peptides (white columns) for various periods of time (1 to 180 minutes), and after exposure for a certain period of time, the medium was replaced with a fresh medium. The cells were finally cultured for 72 hours, and cell viability was analyzed using WST-8. The results are represented as mean±SD (bar).

It is indicated that TfR-lytic peptide permeates plasma membrane to rapidly kill T47D cancer cells. T47D cells were treated with TfR-lytic chimeric peptide (black columns) or lytic peptide (white columns) for various periods of time (1 to 180 minutes), and then the medium containing peptides was replaced with a fresh medium. The cells were further cultured for 72 hours. The cells were analyzed for cell viability using WST-8. The results are shown in FIG. 24A.

Figure 24B:
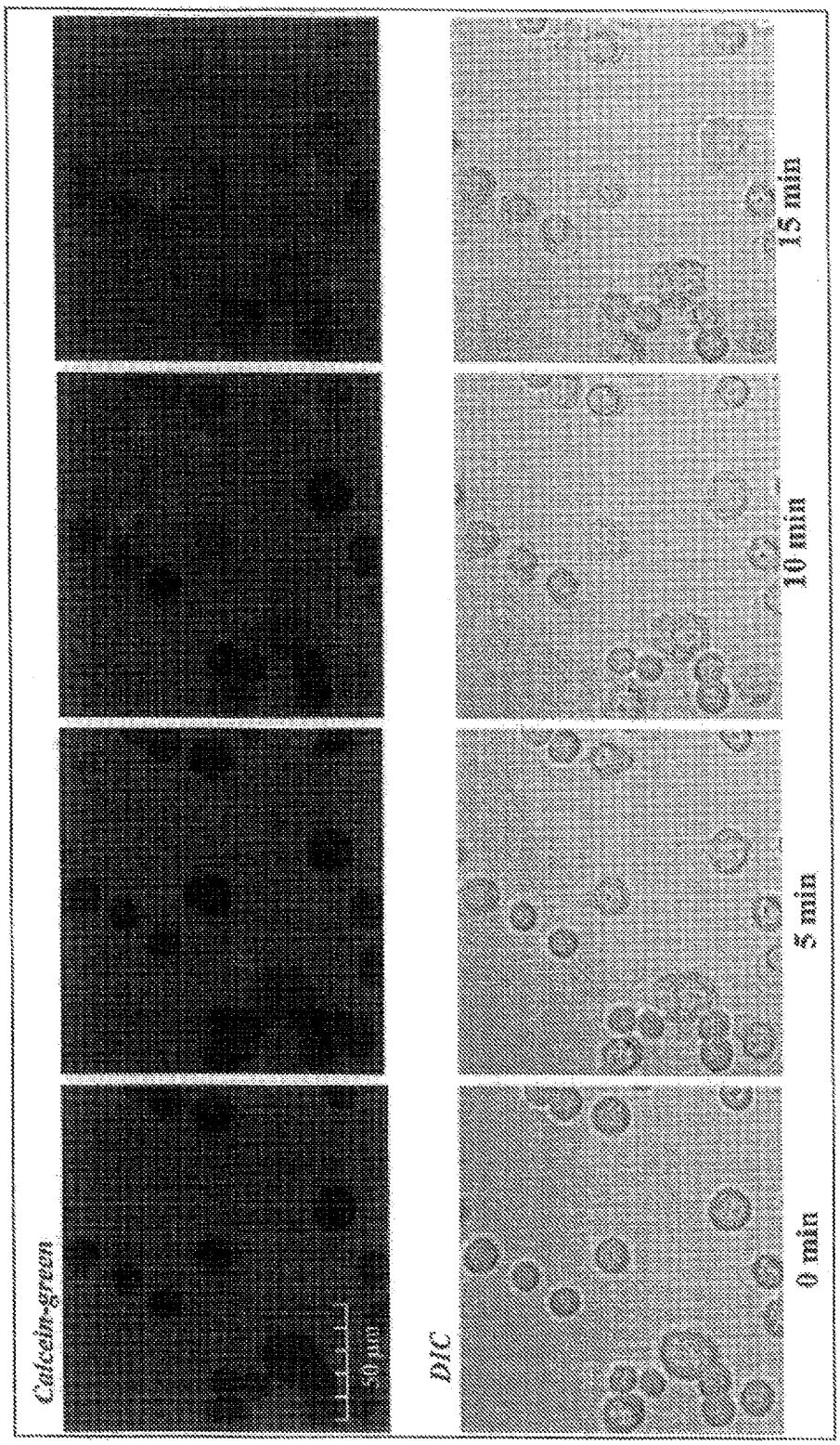
FIG. 24B shows permeabilization of membrane by TfR-lytic chimeric peptide in T47D breast cancer cells. Cells in calcein solution of 0 minute, five minutes, 10 minutes and 15 minutes after addition of TfR-lytic chimeric peptide at concentration of 10 µM are shown. Arrow shows permeated cells and peptide which permeated the membrane.

Furthermore, after addition of TfR-lytic chimeric peptide at concentration of 10 μM, the cells in calcein solution were observed after 0 minute, five minutes, 10 minutes and 15 minutes. In T47D breast cancer cells, TfR-lytic chimeric peptide which permeated the membrane was observed (FIG. 24B).

Figure 25A:
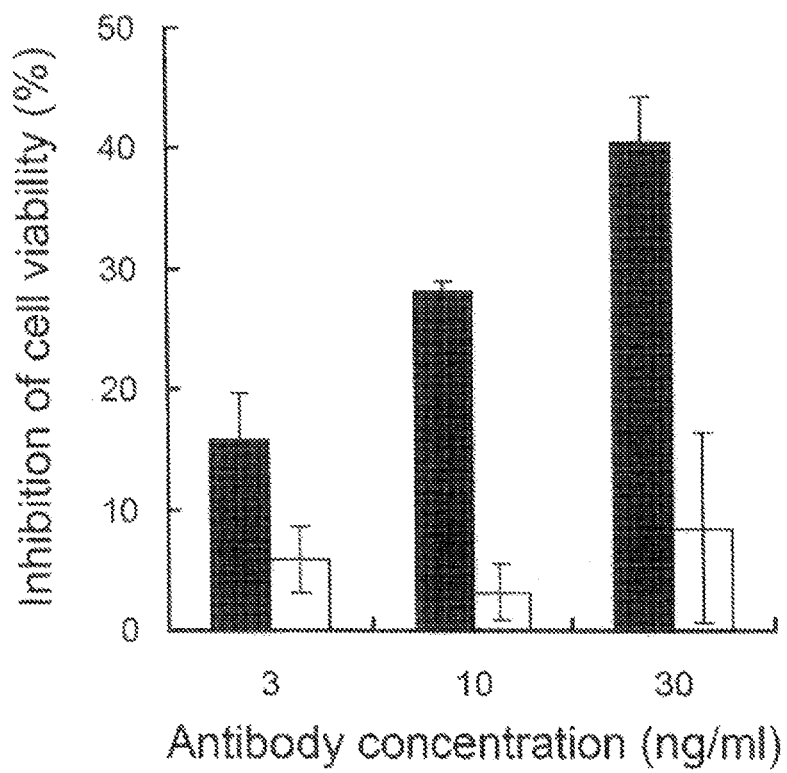
FIG. 25A shows inhibition of cell viability of cancer cell lines by TfR-lytic chimeric peptide. Before the treatment with peptide (5 µM), T47D cells were incubated with increasing concentration of anti-TfR monoclonal antibody (black columns) or nonspecific mouse IgG1 (isotype control; white columns) for three hours.

Moreover, before the treatment with peptide (5 μM), T47D cells were incubated with increasing concentration of anti-TfR monoclonal antibody or nonspecific mouse IgG1 (isotype control) for three hours, which demonstrated inhibition of cell viability by TfR-lytic chimeric peptide (FIG. 25A).

(Cytotoxicity of siRNA or Scramble Sequence (sc) RNA to Cancer Cell Lines)

T47D and MDA-MB-231 cells were transfected with siRNA or scRNA, and four days after the transfection, the level of target gene in the cells was analyzed by flow cytometry analysis (data not shown). The inhibition ratio was assessed using WST-8 reagent. The assay was repeated three times, and the results are represented as mean of triplicate measurements ±SD (bar). The results are shown in FIG. 25B.

(Possibility of TfR-lytic Chimeric Peptide to Induce Cell Death Via an Apoptotic Mechanism in Cancer Cells)

Figure 26A:
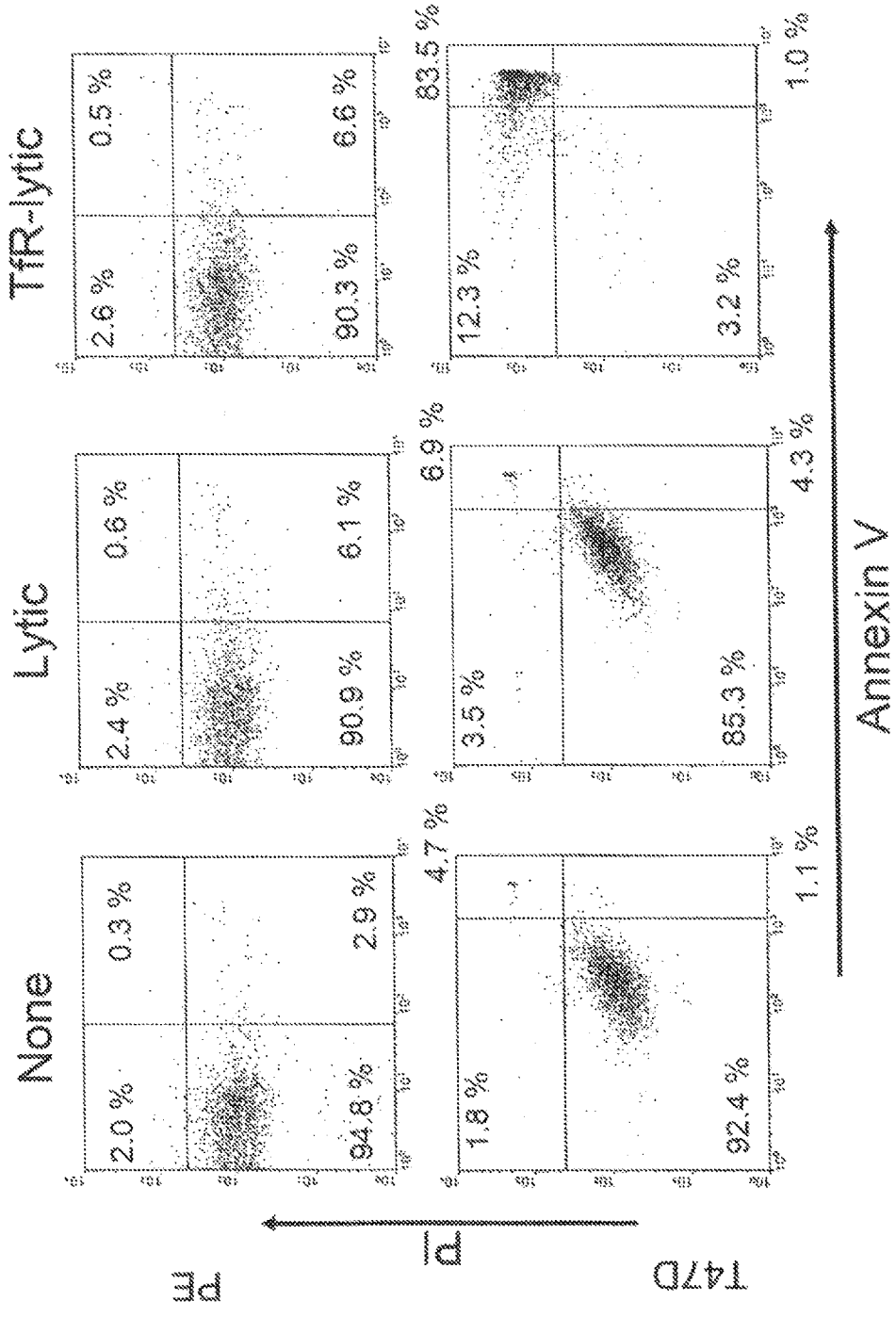
FIG. 26A shows that TfR-lytic chimeric peptide induced Annexin V-positive expression in cancer cells. T47D cells and PE cells were incubated with TfR-lytic chimeric peptide (10 µM) and lytic peptide (10 µM). After two hours, dual-color flow cytometry analysis was performed for Annexin V-positive in the green channel, and for propidium iodide staining in the red channel.
Figure 26B:
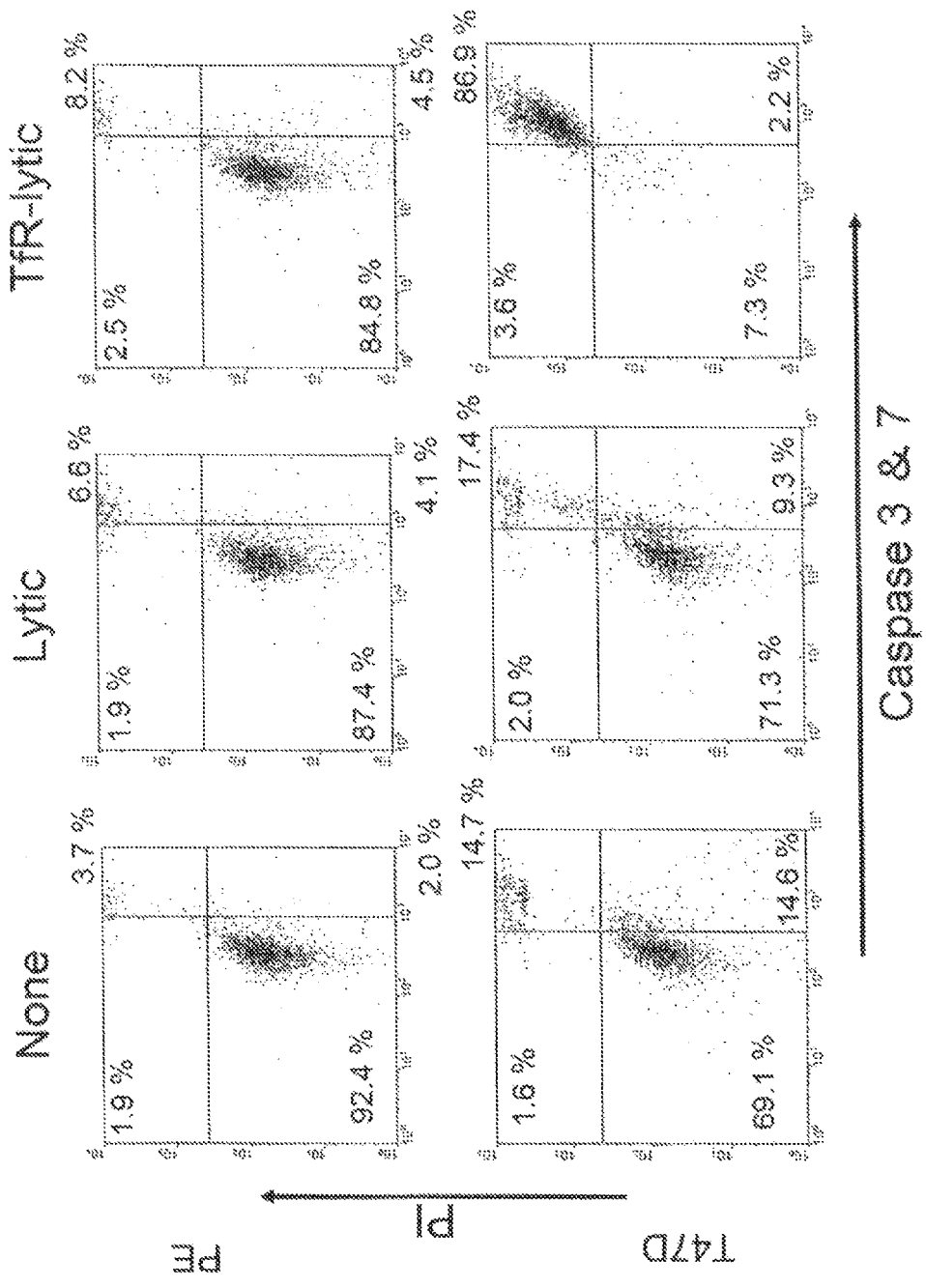
FIG. 26B shows that TfR-lytic chimeric peptide induced caspase activation in cancer cells. T47D cells and PE cells were incubated with TfR-lytic chimeric peptide (10 µM) and lytic peptide (10 µM). After two hours, dual-color flow cytometry analysis was performed for caspase 3 & 7 activity in the green channel, and for propidium iodide staining in the red channel.

T47D and PE cells were incubated with TfR-lytic chimeric peptide (10 μM) and lytic peptide (10 μM) for two hours. Annexin V (FIG. 26A) and caspase 3,7 activity (FIG. 26B) were detected in the green channel, and propidium iodide staining was detected in the red channel, and flow cytometry analysis was performed. In T47D cells treated with TfR-lytic chimeric peptide, the ratio of the right half panel showing Annexin V-positive cells and caspase 3,7-activated cells increased. On the other hand, in normal cells PE, even with treatment with TfR-lytic chimeric peptide, the percentage of Annexin V-positive cells and caspase 3,7-activated cells did not increase. It was suggested that TfR-lytic chimeric peptide induces cancer cell death by an apoptotic mechanism in a cancer cell-selective manner.

(Comparison of Action of Various Lytic Peptides to Induction of Cell Death by an Apoptotic Mechanism in Cancer Cell Lines)

Figure 26C:
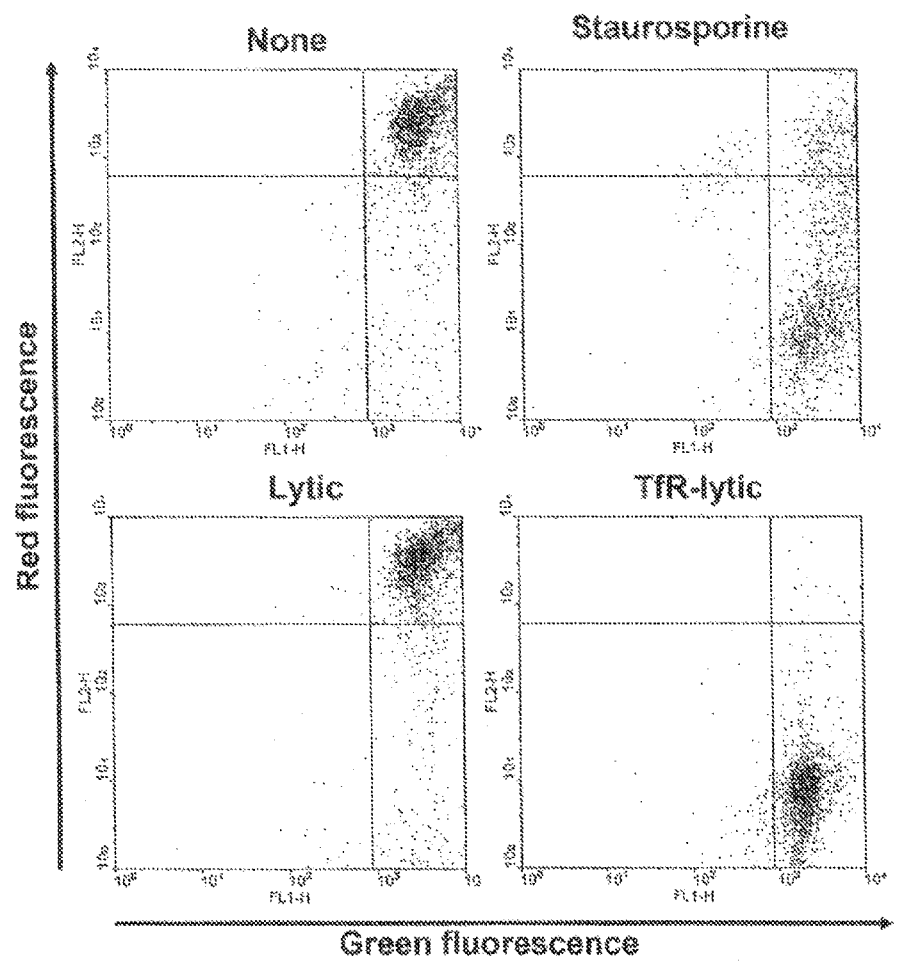
FIG. 26C shows comparison of action of various lytic peptides in cancer cell lines. T47D cells labeled with mitochondrial transmembrane potential-dependent fluorochrome JC-1 were untreated (untreated: upper left panel) or treated with Staurosporine (control mitochondrial membrane potential: upper right panel), lytic peptide (lower left panel) or TfR-lytic chimeric peptide (lower right panel). After two hours, by flow cytometry, distinctive ratio in changes in red fluorescence or green fluorescence indicating transmembrane potential was analyzed.

T47D cells labeled with mitochondrial transmembrane potential-dependent fluorochrome JC-1 were untreated (untreated: upper left panel) or treated with Staurosporine (control mitochondrial membrane potential: upper right panel), lytic peptide (lower left panel) or TfR-lytic chimeric peptide (lower right panel). After two hours, by flow cytometry, distinctive ratio in changes in red fluorescence or green fluorescence indicating transmembrane potential was analyzed. The results are shown in FIG. 26C.

Figure 26D:
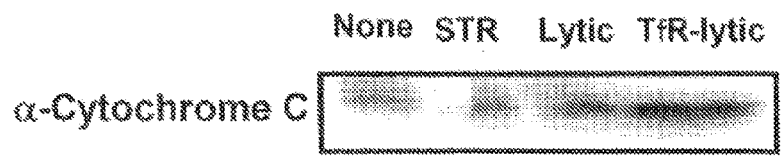
FIG. 26D shows Western blot analysis for release of cytochrome c in cells treated with various lytic peptides. T47D cells were incubated with Staurosporine, TfR-lytic chimeric peptide (10 µM) and lytic peptide (10 µM). After two hours, cytoplasm extract was isolated, and by Western blot analysis using an antibody to cytochrome c, release of cytochrome c was investigated.

Furthermore, T47D cells were incubated with Staurosporine, TfR-lytic chimeric peptide (10 μM) and lytic peptide (10 μM). After two hours, cytoplasm extract was isolated, and by Western blot analysis using an antibody to cytochrome c, release of cytochrome c was investigated. The results of the Western blot analysis are shown in FIG. 26D.

(In vivo Antitumor Activity of TfR-lytic Chimeric Peptide)

Figure 27A:
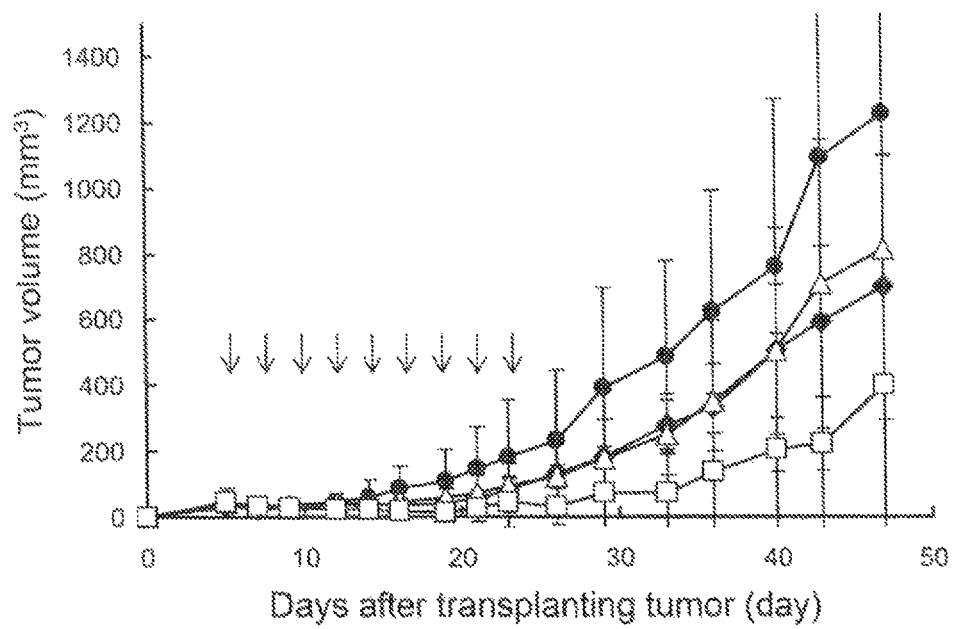
FIG. 27A shows in vivo antitumor activity of TfR-lytic chimeric peptide (intratumoral injection) MDA-MB-231 breast cancer cells were subcutaneously transplanted to athymic nude mice. As shown by arrow, from day 5, saline (control (black circle)) or TfR-lytic peptide (0.3 mg/kg (black rhomboid), 1 mg/kg (white triangle) or 3 mg/kg (white quadrangle)) was intratumorally injected. Each group was formed by three animals (n=3). The data is represented as mean±SD.

MDA-MB-231 breast cancer cells were subcutaneously transplanted to athymic nude mice. As shown by arrow, from day 5, saline (control) or TfR-lytic peptide (0.3 mg/kg, 1 mg/kg or 3 mg/kg) was intratumorally injected. Each group was formed by three animals (n=3). The results of measurement of tumor diameters over time are shown in FIG. 27A.

Figure 27B:
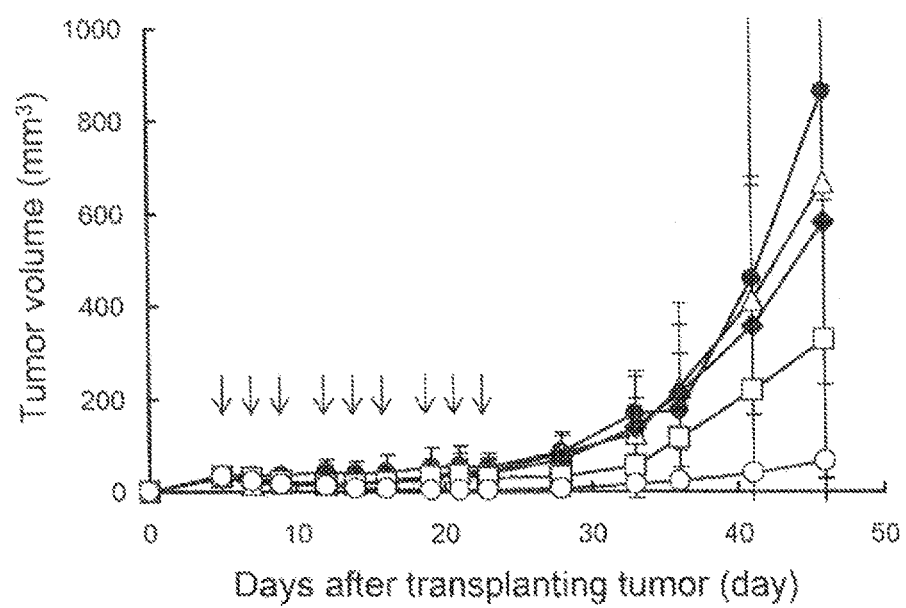
FIG. 27B shows in vivo antitumor activity of TfR-lytic chimeric peptide (intravenous injection). MDA-MB-231 cells were subcutaneously transplanted to athymic nude mice. As shown by arrow, from day 5, saline (control (black circle)) or TfR-lytic peptide (0.5 mg/kg (white triangle), 1 mg/kg (black rhomboid), 2 mg/kg (white quadrangle) or 5 mg/kg (white circle)) was intravenously injected. Each group was formed by three animals (n=3). The data is represented as mean±SD.
Figure 28:
FIGS. 28A-B shows three-dimensional composite structure of interleukin-4 (IL4) and interleukin-4 receptor a helix (IL-4Ra).
Figure 28:
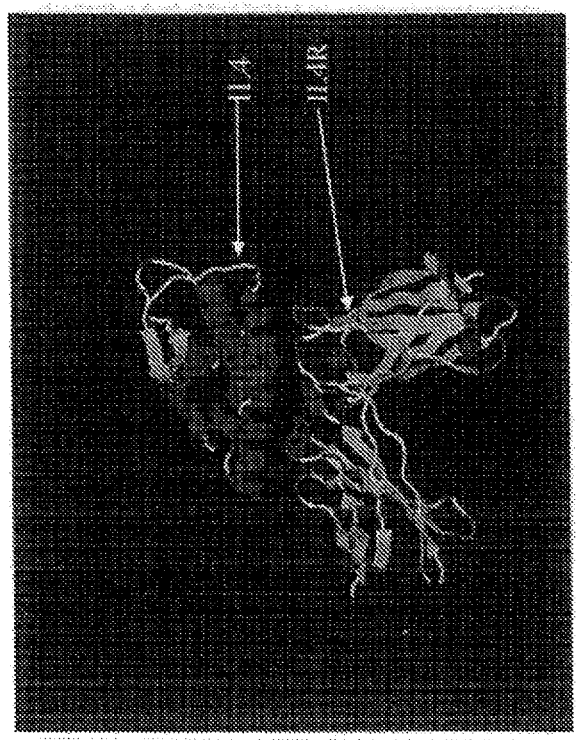

Furthermore, to the athymic nude mice which were subcutaneously transplanted with MDA-MB-231 breast cancer cells in the same manner, as shown by arrow, from day 5, saline (control) or TfR-lytic peptide (0 mg/kg, 0.5 mg/kg, 1 mg/kg, 2 mg/kg or 5 mg/kg) was intravenously injected. Each group was formed by three animals (n=3). The results of measurement of tumor diameters over time are shown in FIG. 27B.

In vivo antitumor activity of TfR-lytic chimeric peptide was observed.

Example 17

IL4-Lytic Chimeric Peptide

In the present Example, activity of IL4-Lytic chimeric peptide was investigated.

(IL4-Lytic (L,D) Exhibits Selective Toxicity to Cancer Cells)

Using IL4-Lytic L formed only of L amino acids (KQLIR-FLKRLDRNGGGKLLLKLLKKLLKLLKKK; SEQ ID NO: 18) and D,L-mixed IL4-Lytic (D,L) (KQLIR-FLKRLDRNGGGKL<u>L</u>LKL<u>L</u>KKL<u>L</u>K<u>L</u>LKKK; SEQ ID NO: 44; underlined letters represent D-amino acids), cytotoxic activity to cancer cells was studied.

Figure 29:
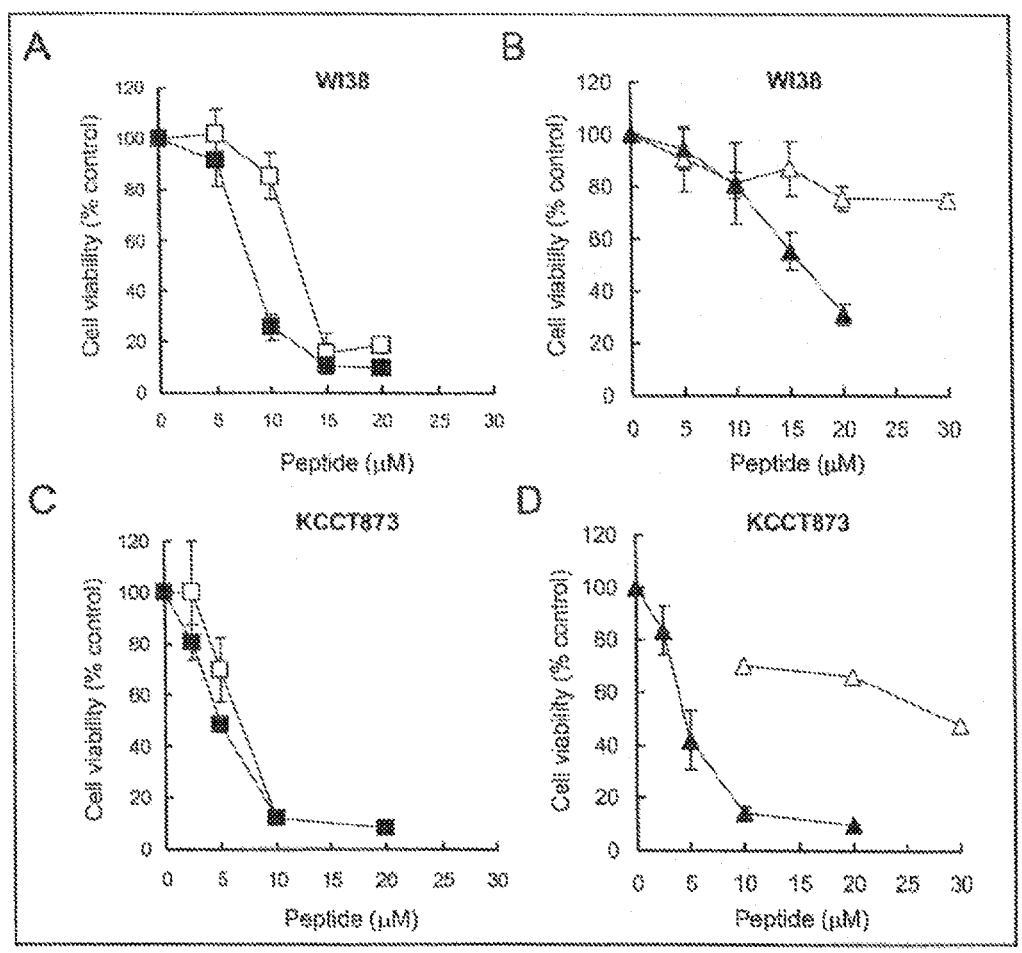
FIGS. 29A-D shows selective toxicity of the designed chimeric peptide conjugated to L, D-lytic peptide [IL4-Lytic (L,D)] between normal cells and cancer cells. Normal cell line WI-38 (FIGS. 29A and 29B) and cancer cell line KCCT873 (FIGS. 29C and 29D) were cultured with various concentrations (0 to 30 µM) of IL4-lytic (L) chimeric peptide, lytic (L) peptide, IL-4-lytic (L,D) chimeric peptide or lytic (L,D) peptide for 72 hours. Cytotoxic activity was assessed using WST-8 reagent. White quadrangle, lytic (L) peptide; black quadrangle, IL4-lytic (L) peptide; white triangle, lytic (L,D) peptide; black triangle, IL4-lytic (L,D) peptide.

A total of $3\times10^3$ cells per well of normal cell line WI-38 (A, B) and cancer cell line KCCT873 (C,D) were seeded in 96-well plates, cultured in a medium containing 10% FBS for 24 hours, and incubated with increasing concentrations (0 to 30 μM) of IL4-lytic (L) chimeric peptide, lytic (L) peptide, IL-4-lytic (L,D) chimeric peptide or lytic (L,D) peptide in 100 μl for 72 hours at 37° C. Cell viability was measured with WST-8 solution (Cell Count Reagent SF; Nakalai Tesque). The results are shown in FIG. 29 and Table 4.

TABLE 4

Cytotoxicity of peptides to various cell lines.

| | IC$_{50}$ (µM) | | | |
|---|---|---|---|---|
| Cell lines | lytic (L) Mean ± SD | IL4-lytic (L) Mean ± SD | lytic (L, D) Mean ± SD | IL4-lytic (L, D) Mean ± SD |
| Normal cells | | | | |
| PE | 20> | 20> | 20> | 20> |
| HEK293T | 11.3 ± 1.1 | 7.2 ± 0.7 | 58 ± 0.3 | 14.2 ± 1.3 |
| WI-38 | 14.4 ± 1.3 | 9.8 ± 0.8 | 100 ± 3.1 | 16.1 ± 0.5 |
| Cancer cells | | | | |
| BxPC-3 | 6.7 ± 0.4 | 3.2 ± 0.4 | 37.1 ± 0.7 | 6.8 ± 0.3 |
| MDA-MB-231 | 8.1 ± 0.4 | 5.6 ± 0.5 | 27.1 ± 1.5 | 5.7 ± 0.4 |
| A172 | 7.4 ± 0.3 | 3.8 ± 1.1 | 30.5 ± 0.9 | 6.8 ± 0.4 |
| KCCT873 | 7.6 ± 0.8 | 4.6 ± 0.1 | 27.7 ± 1.4 | 5.9 ± 0.6 |
| U251 | 6.5 ± 1.1 | 3.7 ± 0.1 | 17.2 ± 2.5 | 6.6 ± 0.4 |

From these results, it is recognized that use of D,L-mixed sequence was therapeutically preferred in comparison with use of a sequence consisting only of L-amino acids. It was also confirmed that selectivity between cancer cells and normal cells was also retained.

(Detection of IL-4Ra Expression on Cell Surface of Cancer Cell Lines)

Figure 30:
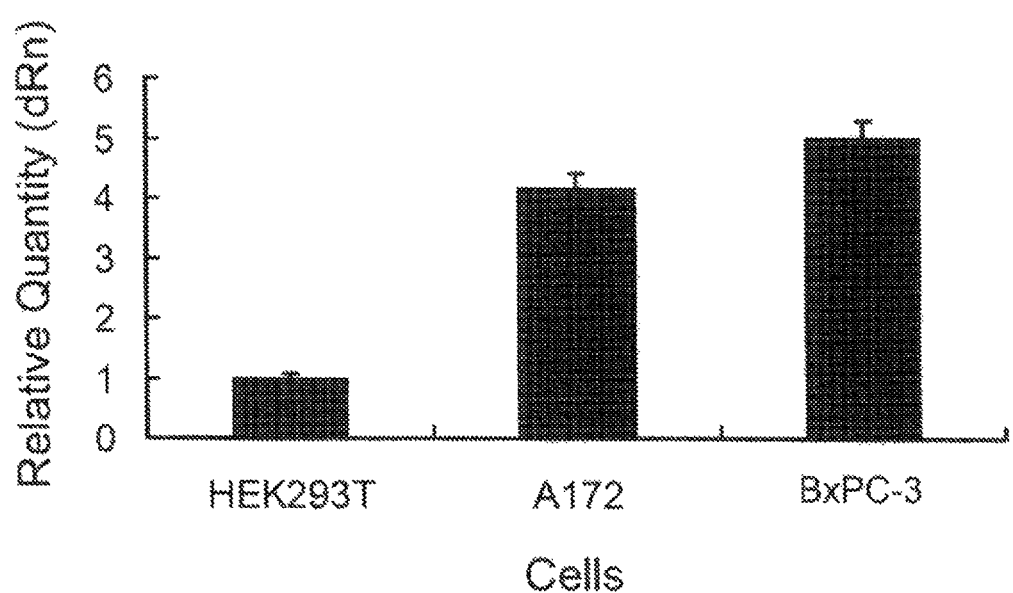
FIG. 30 shows detection of IL-4Ra expression on cell surface of cancer cell lines. Total RNA from A172, BxPC-3 and normal cell line HEK293 were reverse-transcribed to cDNA, and then detection was performed by quantitative PCR using IL-4Ra-specific primer. Glyceraldehyde-3-phosphate dehydrogenase (GAPDH) was used as an internal standard.

Total RNA from A172, BxPC-3 and normal cell line HEK293 were reverse-transcribed to cDNA, and then detection was performed by quantitative PCR using IL-4Ra-specific primer. Glyceraldehyde-3-phosphate dehydrogenase (GAPDH) was used as an internal standard. The results are shown in FIG. 30.

(IL4-Lytic (L,D) Chimeric Peptide Rapidly Kills Cancer Cells)

Figure 31:
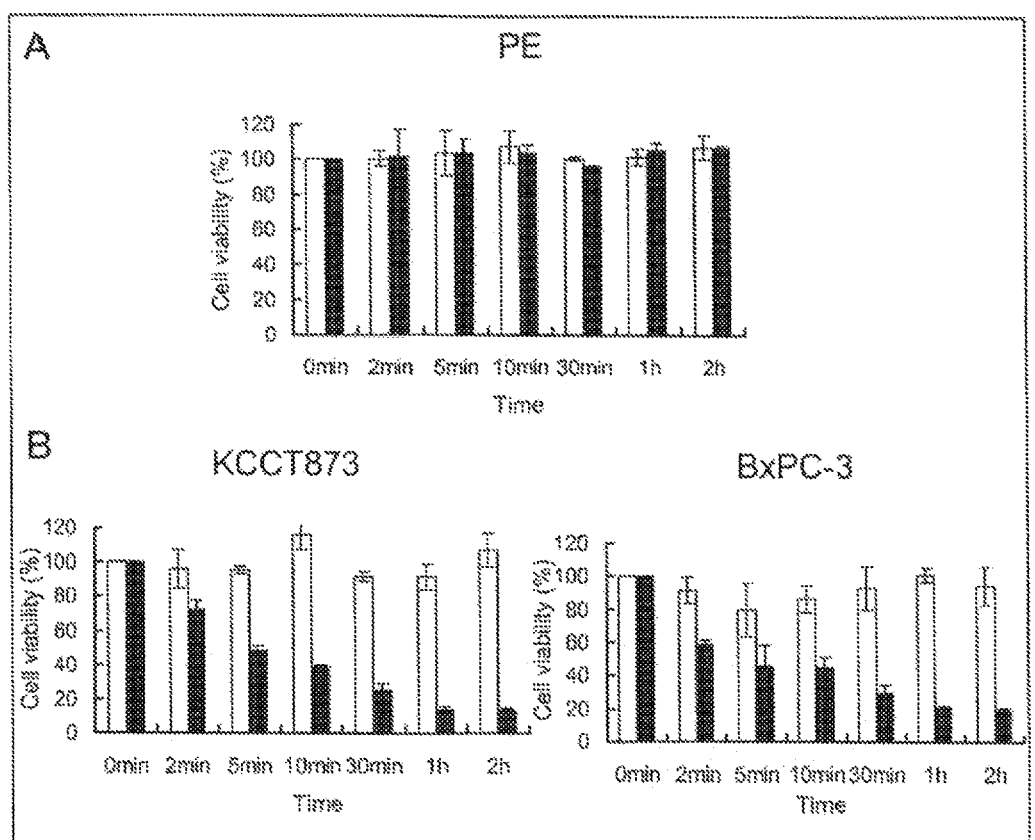
FIGS. 31A-B shows that IL4-Lytic (L,D) chimeric peptide rapidly kills cancer cells. PE cells (FIG. 31A), KCCT873 cells and BxPC-3 cells (FIG. 31B) were treated with IL4-lytic (L,D) chimeric peptide (black columns) or lytic (L,D) peptide (white columns) for two minutes, five minutes, 10 minutes, 30 minutes, one hour or two hours. The medium containing peptides was replaced with a fresh medium, and the cells were further cultured for 72 hours. Cell viability was determined using WST-8 reagent. The results are represented as mean±SD (bar).

PE cells (A), KCCT873 cells and BxPC-3 cells (B) were treated with IL4-lytic (L,D) chimeric peptide (black columns) or lytic (L,D) peptide (white columns) for two minutes, five minutes, 10 minutes, 30 minutes, one hour or two hours. The medium containing peptides was replaced with a fresh medium, and the cells were further cultured for 72 hours. Cell viability was determined using WST-8 reagent. The results are shown in FIG. 31.

(Possibility that Cancer Cell Death by IL4-Lytic (L,D) Chimeric Peptide Mediates an Apoptotic Mechanism)

Figure 32:
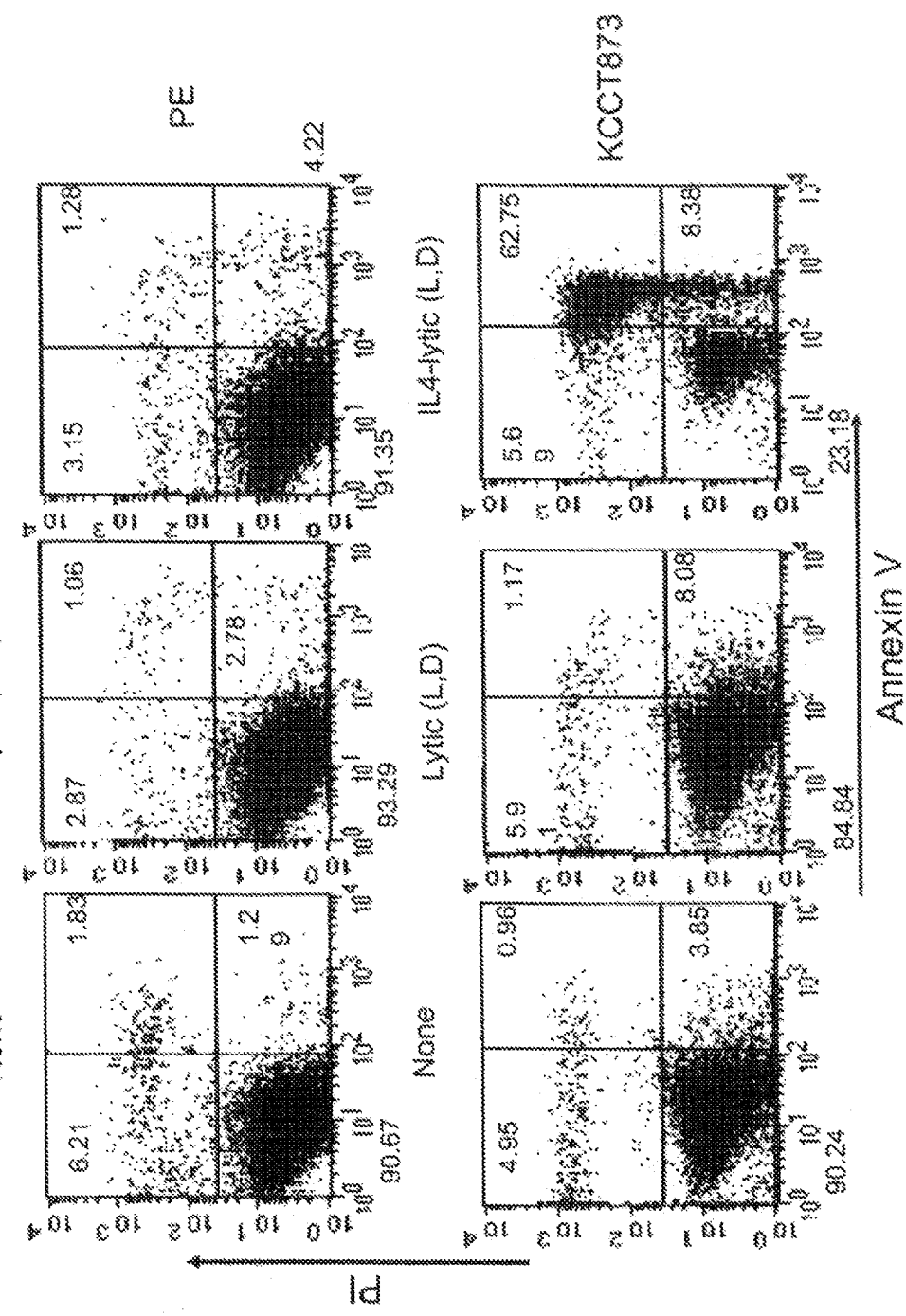
FIG. 32 shows that IL4-Lytic (L,D) chimeric peptide induces Annexin V-positive expression of cancer cells. PE cells which are normal cells (upper) and KCCT873 cells which are cancer cells (lower) were incubated with IL4-lytic (L,D) chimeric peptide or lytic (L,D) peptide (10 µM) for two hours. Subsequently, dual-color flow cytometry analysis was performed for Annexin V labeling in green channel and PI staining in red channel. Percentage of cells in each quadrant is shown.

PE cells which are normal cells and KCCT873 cells which are cancer cells were incubated with IL4-lytic (L,D) chimeric peptide or lytic (L,D) peptide (10 µM) for two hours. Subsequently, dual-color flow cytometry analysis was performed for Annexin V labeling in green channel and PI staining in red channel. The results are shown in FIG. 32. The values indicate percentage of cells in each quadrant is indicated.

(In vivo Antitumor Activity of IR4-Lytic (L,D) Chimeric Peptide)

Figure 33A:
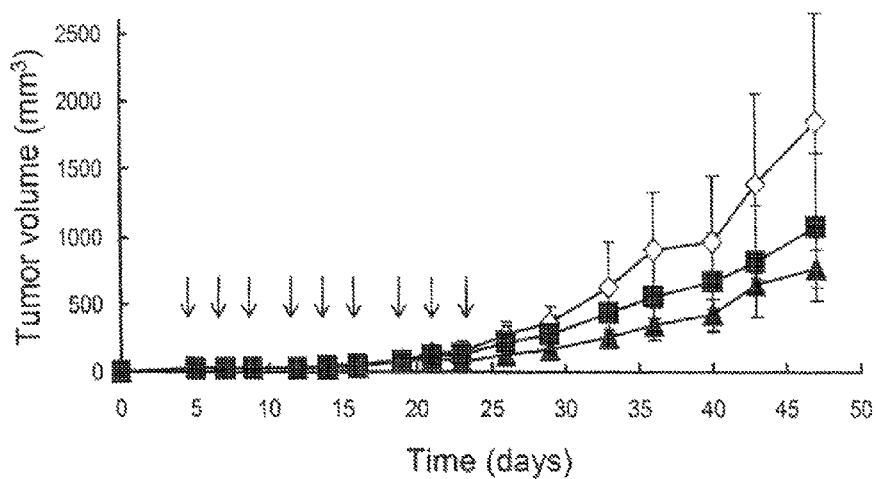
FIG. 33A shows in vivo antitumor activity of IL4-Lytic (L,D) chimeric peptide (intratumoral injection). MDA-MB-231 breast cancer cells were subcutaneously transplanted to athymic nude mice. As shown by arrow, from day 5, saline (NaCl; control (white rhomboid)) or IL4-lytic (L,D) peptide (0.5 mg/kg (black quadrangle) or 2 mg/kg (black triangle)) was intratumorally injected. Each group was formed by three animals (n=3).

MDA-MB-231 breast cancer cells were subcutaneously transplanted to athymic nude mice. As shown by arrow, from day 5, saline (control) or IL4-lytic (L,D) peptide (0.5 mg/kg or 2 mg/kg) was intratumorally injected. Each group was formed by three animals (n=3). The results of measurement of tumor diameters over time are shown in FIG. 33A.

Figure 33B:
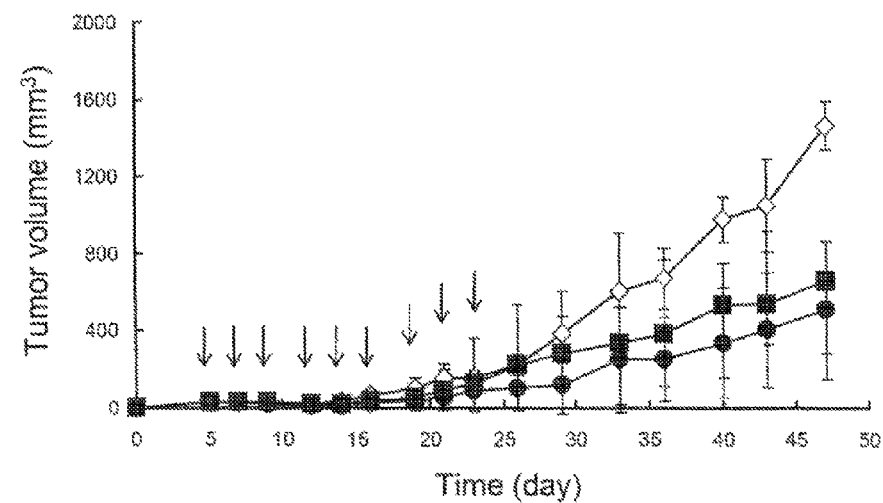
FIG. 33B shows in vivo antitumor activity of IL4-lytic (L,D) chimeric peptide (intravenous injection). MDA-MB-231 breast cancer cells were subcutaneously transplanted to athymic nude mice. As shown by arrow, from day 5, saline (control (white rhomboid)) or IL4-lytic (L,D) peptide (2 mg/kg (black quadrangle) or 5 mg/kg (black circle)) was intravenously injected. Each group was formed by three animals (n=3). The data is represented as mean±SD (bar).

Furthermore, to the athymic nude mice which were subcutaneously transplanted with MDA-MB-231 breast cancer cells in the same manner, as shown by arrow, from day 5, saline (control) or IL4-lytic (L,D) peptide (2 mg/kg or 5 mg/kg) was intravenously injected. Each group was formed by three animals (n=3). The results of measurement of tumor diameters over time are shown in FIG. 33B.

Example 18

Sema3A-nLytic Chimeric Peptide

In the present Example, activity of Sema3A-nLytic chimeric peptide was investigated.

(Cytotoxic Activity of Sema3A-nLytic to Various Cell Lines)

Using newly designed nLytic peptide (LLKLLKKLLKKL LKL; SEQ ID NO: 45; underlined letters represent D-amino acids), Sema3A(aa363-377)-nLytic peptide (NYQWVPYQGRVPYPRGGLLKLLKKLLKKLLKL; SEQ ID NO: 46; underlined letters represent D-amino acids) and Sema3A(aa371-377)-nLytic peptide (D,L) (GRVPYPRGGLLKLLKKLLKKLLKL; SEQ ID NO: 47; underlined letters represent fl-amino acids), cytotoxic activity to cancer cells was studied.

A total of 3×10³ cells per well of pancreas cell line were seeded in 96-well plates, cultured for 24 hours in a medium containing 10% FBS, and incubated with increasing concentrations (0 to 50 µM) of Sema3A-nLytic peptide or nLytic peptide alone in 100 µl for 48 hours at 37° C. Cell viability was measured with WST-8 solution (Cell Count Reagent SF; Nakalai Tesque). The results are shown in FIG. 34A and Table 5.

TABLE 5

Cytotoxic activity of Sema3A-nLytic on pancreatic cell lines.

| | IC$_{50}$ (µM) | | |
|---|---|---|---|
| Cell lines | nLytic alone | Sema3A(aa363-377)-nLytic | Sema3A(aa371-377)-nLytic |
| Cancer cells | | | |
| BxPC-3 | 38.5* | 12.5 | 14.7 |
| CFPAC-1 | 22.6 | 10.6 | 9.2 |
| Panc-1 | 28.2 | 13.1 | 14.1 |
| SU8686 | 19.5 | 7.9 | 8.0 |
| Normal cells | | | |
| Pancreatic epithelium | >50 | >50 | >50 |

*IC$_{50}$, the concentration of peptide at which 50% inhibition of cell viability is observed compared to untreated cells.

(Cytotoxic Activity of Sema3A-nLytic to Breast Cancer Cell Lines)

Figure 34B:
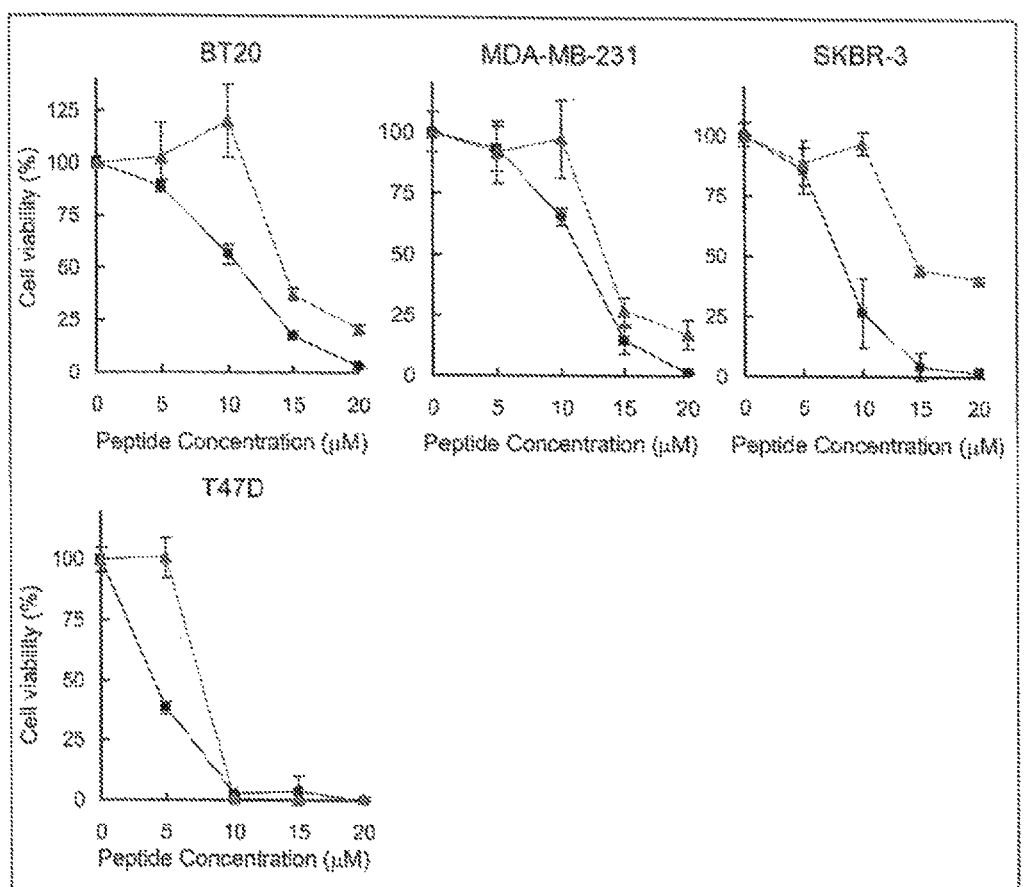
FIG. 34B shows cytotoxic activity of Sema3A-nLytic for various cell lines. Breast cancer cells were cultured with various concentrations (0 to 20 μM) of Sema3A-nLytic (371-377) or Sema3A-nLytic (363-377) for 48 hours, and cytotoxic activity was assessed using WST-8 reagent. The assay was repeated three times, and the results are represented as means of triplicate measurements ±SD (bar). Quadrangle, Sema3A-nLytic (363-377) peptide; triangle, Sema3A-nLytic (371-377) peptide.

Breast cancer cells were cultured with various concentrations (0 to 20 µM) of Sema3A (371-377)-nLytic or Sema3A (363-377)-nLytic for 48 hours, and cytotoxic activity was assessed with WST-8 reagent. The results are shown in FIG. 34B and Table 6.

TABLE 6

Cytotoxic activity of Sema3A-nLytic on breast cancer cell lines.

| | IC$_{50}$ (µM) | | |
|---|---|---|---|
| Cell lines | nLytic alone | Sema3A(aa363-377)-nLytic | Sema3A(aa371-377)-nLytic |
| BT20 | 38.0 | 10.9 | 11.4 |
| MDA-MB-231 | 29.6 | 11.5 | 8.1 |
| SKBR-3 | | 8.0 | 14.5 |
| T47D | 12.5 | 4.1 | 3.7 |

*IC$_{50}$, the concentration of peptide at which 50% inhibition of cell viability is observed compared to untreated cells.

In normal cells, as shown in Table 5, IC$_{50}$ is a numerical value of >50, and the effect was attained at lower concentrations in the cancer cells shown in Table 6. In view of this, it is believed that there is selectivity between normal cells and cancer cells.

(Cytotoxic Activity of Sema3A-nLytic to Various Cell Lines)

Figure 34C:
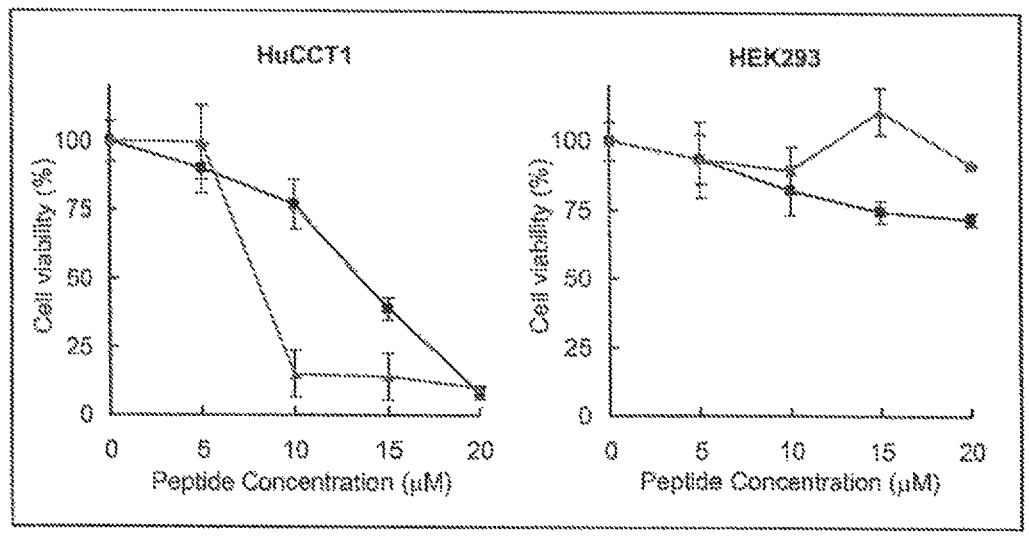
FIG. 34C shows cytotoxic activity of Sema3A-nLytic for various cell lines. Two cells (left: HuCCT1; right: HEK293) were cultured with various concentrations (0 to 20 μM) of Sema3A-nLytic (363-377) or Sema3A-nLytic (371-377) for 48 hours, and cytotoxic activity was assessed using WST-8 reagent. The assay was repeated three times, and the results are represented as mean of triplicate measurements ±SD (bar). Quadrangle, Sema3A-nLytic (363-377) peptide; triangle, Sema3A-nLytic (371-377) peptide.

Various cells were cultured with various concentrations (0 to 20 µM) of Sema3A-nLytic (363-377) or Sema3A-nLytic (371-377) for 48 hours, and cytotoxic activity was assessed with WST-8 reagent. The assay was repeated three times, and the results are represented as mean of triplicate measurements ±SD (bar). The results are shown in FIG. 34C and Table 7.

TABLE 7

Cytotoxic activity of Sema3A-nLytic on various cell lines.

| | IC$_{50}$ (µM) | |
|---|---|---|
| Cell lines | Sema3A(aa363-377)-nLytic | Sema3A(aa371-377)-nLytic |
| Cancer cells | | |
| HuCCT-1 | 13.6 | 7.9 |
| Normal cells | | |
| HEK293T | >20 | >20 |

*IC$_{50}$, the concentration of peptide at which 50% inhibition of cell viability is observed compared to untreated cells.

Figure 35:
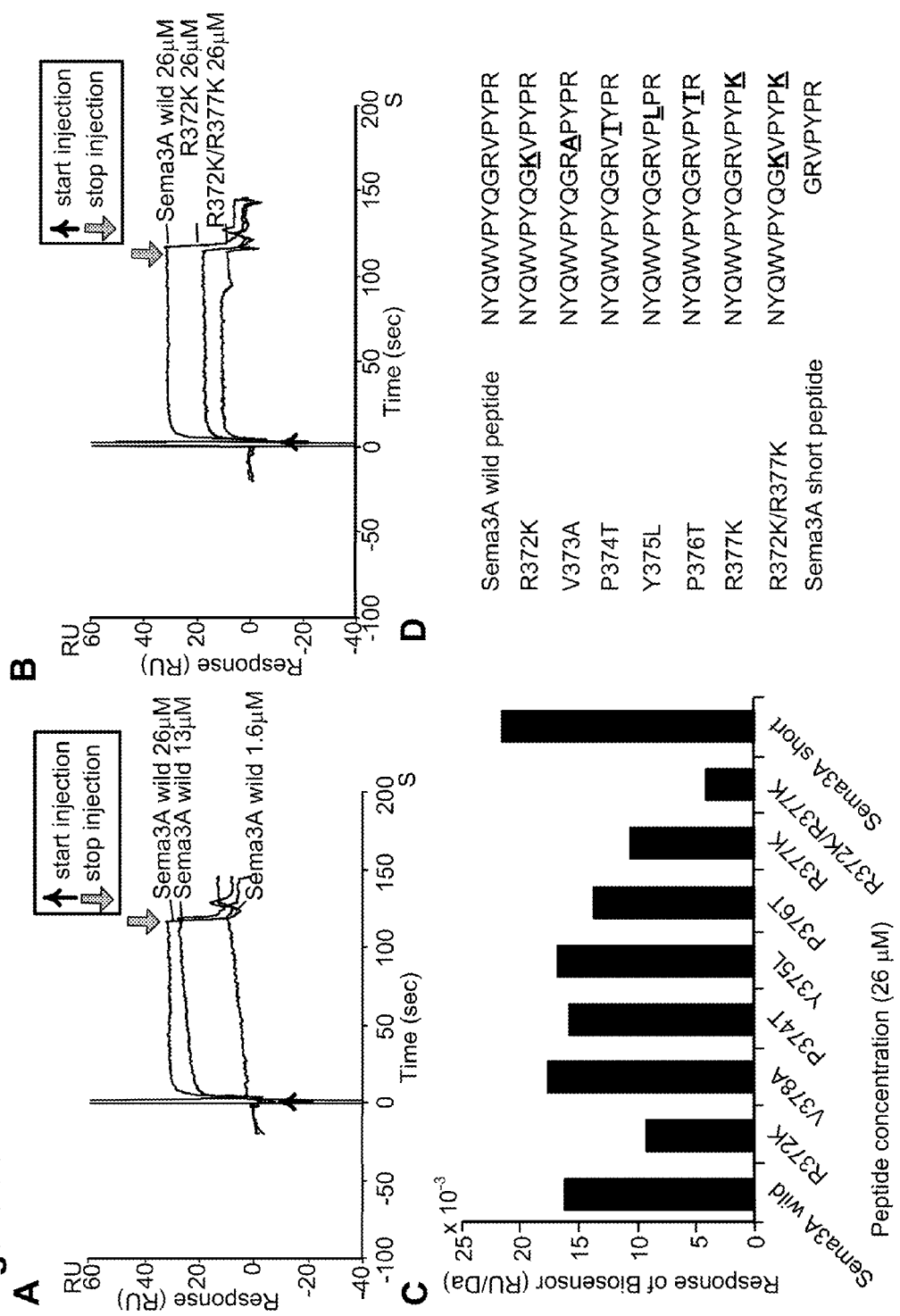
FIGS. 35A-D shows analysis of interaction with neuropilin-1 (NRP1) of wild-type and some mutated peptides of Sema3A using BIACORE.

Furthermore, using BIACORE, wild-type peptide and some mutated peptides of Sema3A were analyzed for interaction with neuropilin-1 (NRP-1). The results are shown in FIG. 35. (A) Binding of wild-type Sema3A peptide to NRP-1 protein. Serially diluted various concentrations (1.6 µM, 13 µM, 26 µM) of wild-type Sema3A peptide samples were analyzed on parallel sensor surface. (B) Binding of wild-type peptide and mutated peptides of Sema3A (R372K and R372K/R377K) to NRP-1 protein. Various serially diluted wild-type Sema3A peptide samples (26 µM) were analyzed on parallel sensor surface. (C) Outline of binding ability of various Sema3A peptides to NRP-1 protein. (D) Peptide sequence of wild-type peptide and mutated peptides of Sema3A.

(Expression of Neuropilin-1 in Pancreatic Cancer Cell Line and Breast Cancer Cell Line)

Figure 36:
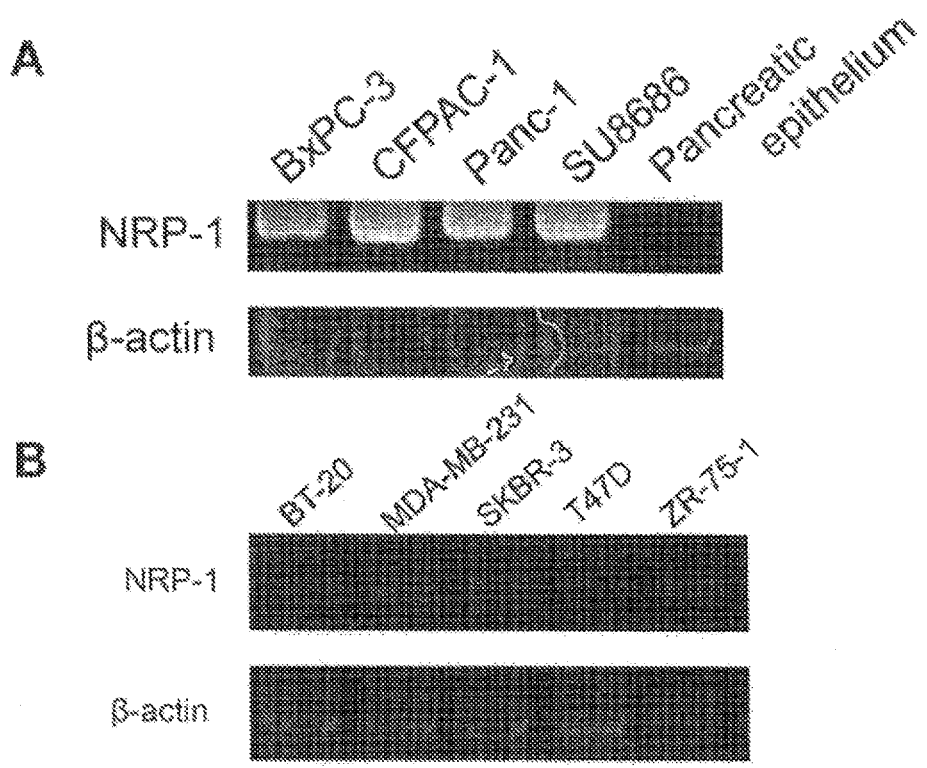
FIGS. 36A-B shows expression of NRP1 in pancreatic cancer cell lines and breast cancer cell lines.

Expression of neuropilin in some pancreatic cancer cell lines (BxPC-3, CFPAC-1, Panc-1 and SU8686) and pancreatic epithelial cells and breast cancer cells (BT-20, MDA-MB-231, SKBR-3 and T47D) was estimated by RT-PCR analysis. In all RT-PCR analyses, β-actin was used as positive control. The results are shown in FIG. 36.

(Possibility that Cancer Cell Death by Sema3A-Lytic Mediates an Apoptotic Mechanism)

Figure 37:
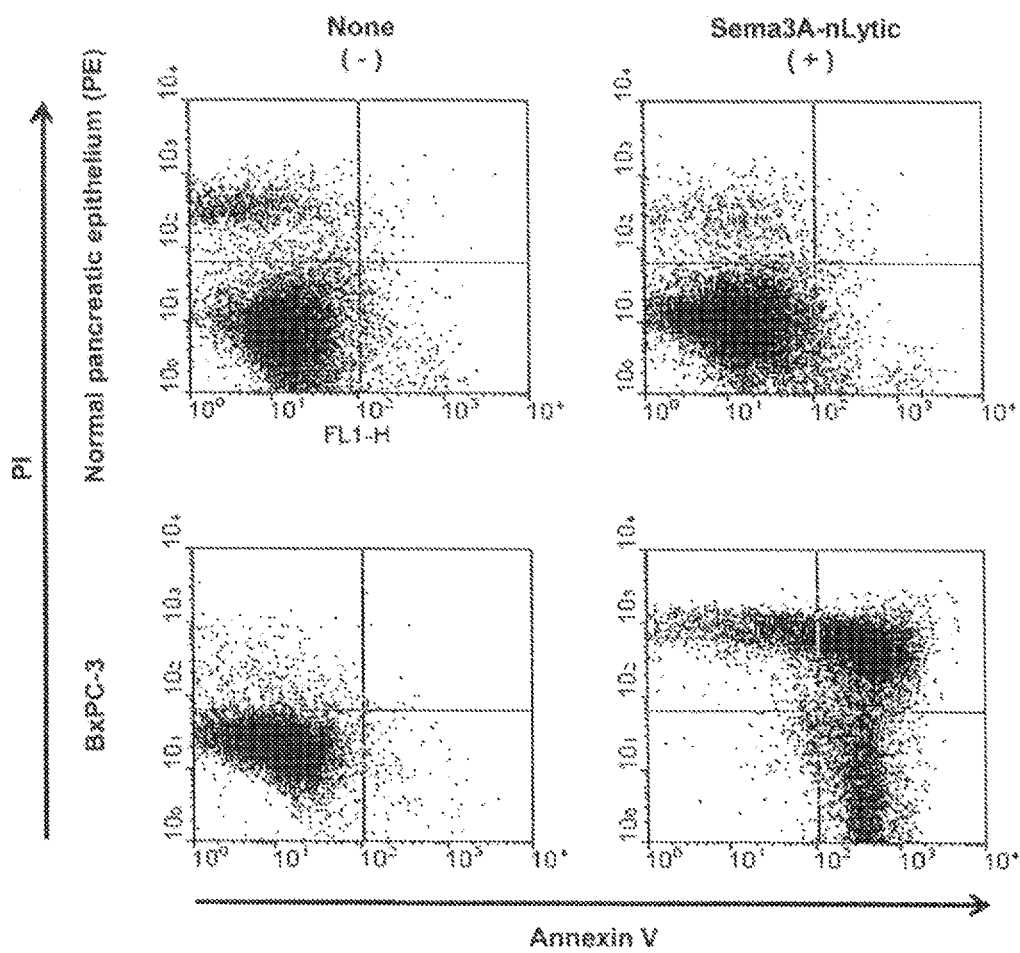
FIG. 37 shows that Sema3A-nLytic induces Annexin V-positive expression in cancer cells. PE cells (upper pannel) and BxPC-3 cell (lower panel) were incubated with Sema3A-nLytic peptide (5 μM) at 37° C. for three hours, and after six hours, analyzed for Annexin V labeling by dual-color flow cytometry.

PE cells (upper panel) and BxPC-3 cells (lower panel) were incubated with Sema3A-Lytic peptide (5 µM) for three hours at 37° C., and after six hours analyzed for Annexin V labeling by dual-color flow cytometry. The results are shown in FIG. 37. As apparent from the figure, in BxPC-3 cells treated with Sema3A-nLytic, the ratio of the right half the panel which shows Annexin V-positive cells increased. On the other hand, in normal cells PE, the percentage of Annexin V-positive dead cells did not increase even with treatment with Sema3A-nLytic. It was suggested that Sema3A-nLytic induces cancer cell death by an apoptotic mechanism in a cancer cell-selective manner.

Example 19

Sema3A-kLytic Chimeric Peptide

In the present Example, using newly designed kLytic peptide (KLLLKLLKKLLKLLKKK; underlined letters represent D-amino acids; SEQ ID NO: 49) and Sema3A(aa363-377)-kLytic peptide (NYQWVPYQGRVPYPRGGGKL LKLLKKLLKLLKKK; underlined letters represent D-amino acids; SEQ ID NO 50), cytotoxic activity to cancer cells was studied.

Figure 38A:
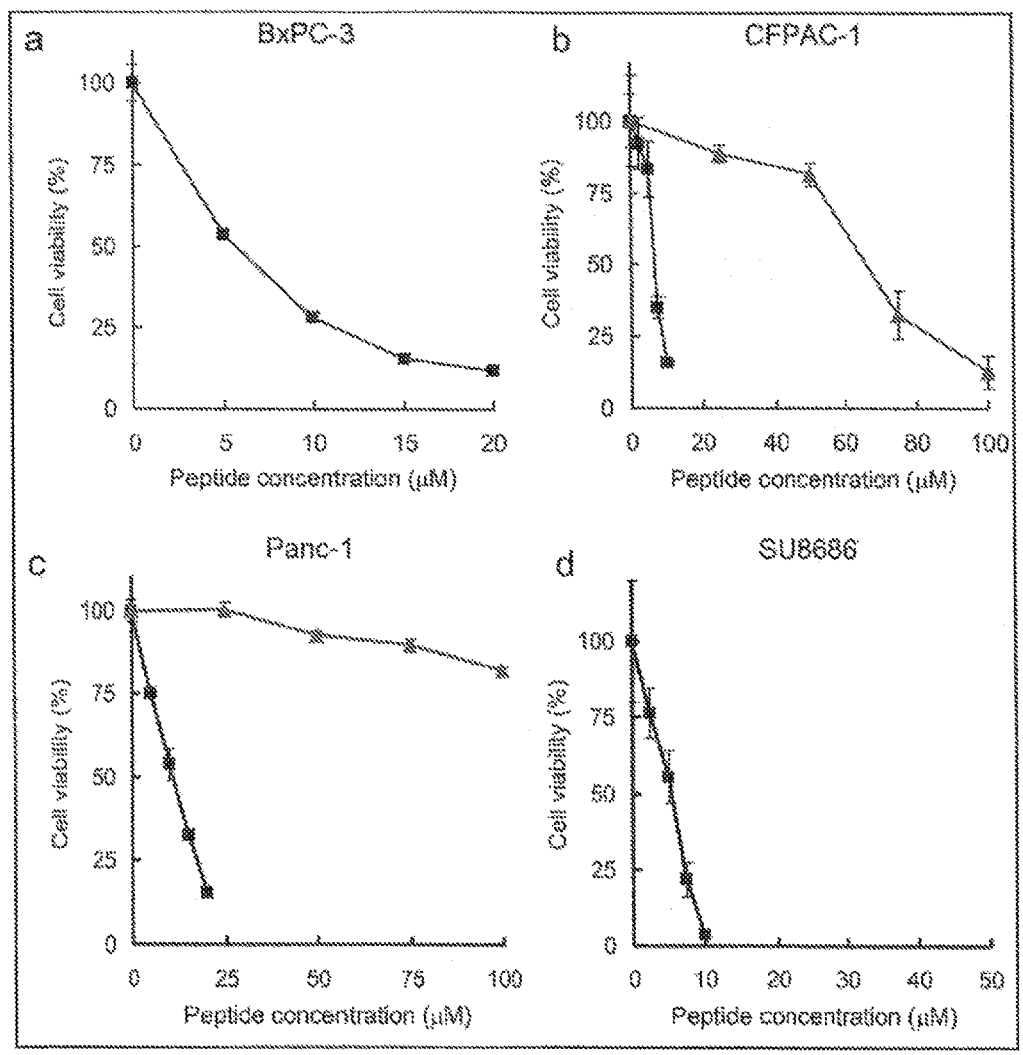
FIG. 38A shows a graph of cell-killing effect of Sema3A (aa363-377)-kLytic or kLytic alone to cancer cells. Four pancreatic cancer cell lines ((a) BxPC-3, (b) CFPAC-1, (c) Panc-1 and (d) SU8686) were cultured with various concentrations of Sema3A (aa363-377)-kLytic (quadrangle) or kLytic (triangle) for 48 hours, and cytotoxic activity was assessed using WST-8 reagent. The vertical axis shows cell viability (%) and the horizontal axis shows peptide concentration (μM).
Figure 38B:
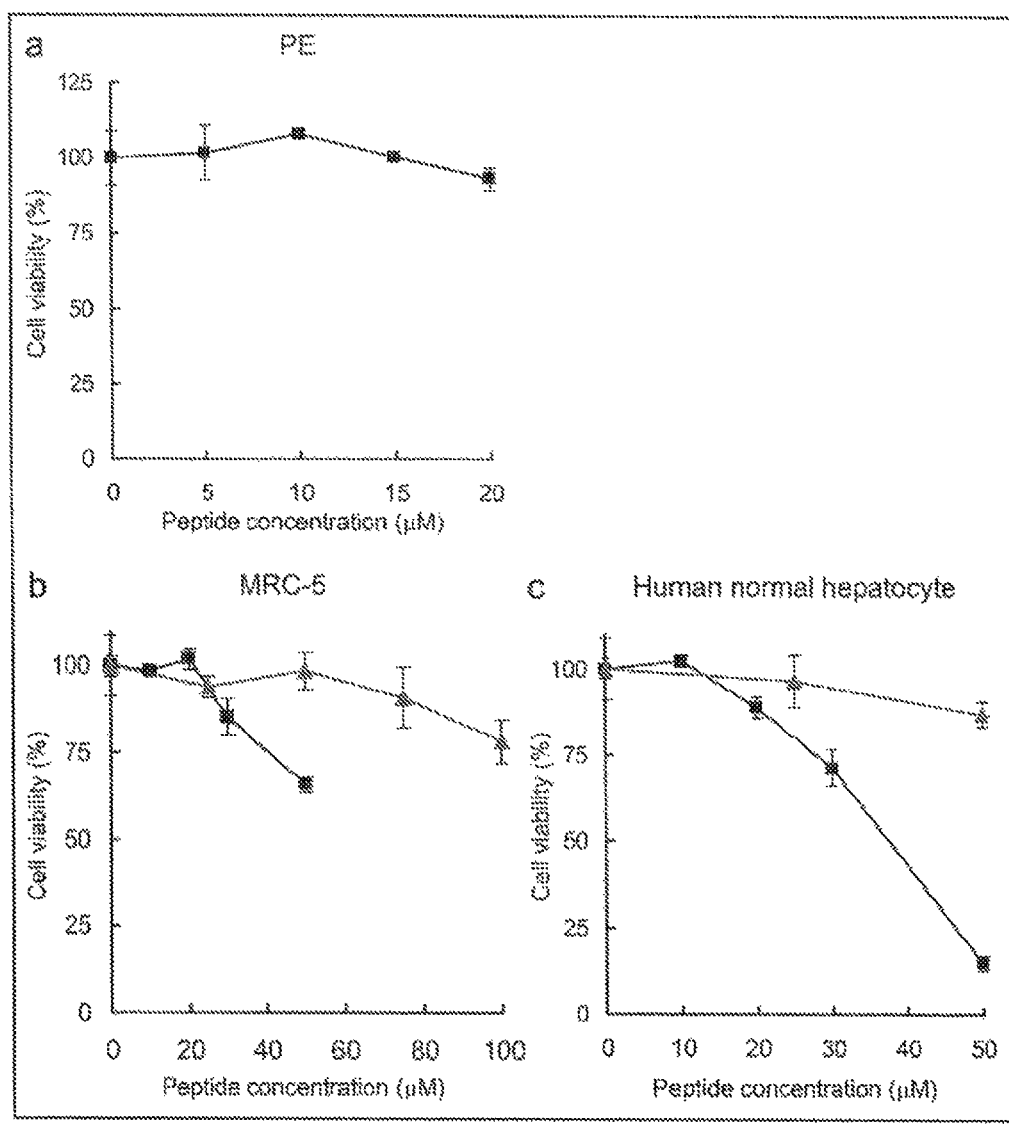
FIG. 38B shows a graph of cell-killing effect of kLytic (quadrangle) or Sema3A(aa363-377)-kLytic (triangle) to normal cells. Three normal cell lines ((a) PE, (b) MRC-5 and (c) human normal hepatocyte) were cultured with various concentrations of Sema3A(aa363-377)-kLytic or kLytic for 48 hours, and cytotoxic activity was assessed using WST-8 reagent. The vertical axis shows cell viability (%) and the horizontal axis shows peptide concentration (μM).

A total of 3×10$^3$ cells per well of pancreas cell line were seeded in 96-well plates, cultured for 24 hours in a medium containing 10% FBS, and incubated with increasing concentrations (0 to 50 µM) of Sema3A-kLytic (aa366-377) peptide or kLytic peptide alone in 100 µl for 48 hours at 37° C. Cell viability was measured with WST-8 solution (Cell Count Reagent SF; Nakalai Tesque). The results are shown in FIG. 38 and Table 8.

TABLE 8

Cytotoxic activity of Sema3A-kLytic on pancreatic cancer cells and normal cells.

| | IC$_{50}$ (µM) | |
|---|---|---|
| Cell lines | Sema3A(aa363-377)-kLytic | kLytic |
| Cancer cells | | |
| BxPC-3 | 5.7 ± 2.3 | 32 ± 1.6 |
| CFPAC-1 | 6.7 ± 0.1 | 67 ± 0.9 |
| Panc-1 | 13 ± 2.7 | 100< |
| SU8686 | 5.2 ± 0.4 | 28 ± 0.5 |
| Normal cells | | |
| Pancreatic epidermal cell | 20< | |
| MRC-5 | 50< | 100< |
| Human normal hepatocyte cell | 37.5 | 50< |

*IC$_{50}$, the concentration of peptide at which 50% inhibition of cell viability is observed compared to untreated cells.

In view that the effect was attained at lower concentrations in cancer cells as shown in Table 8, it is believed that there is selectivity between normal cells and cancer cells.

(Expression of Neurolilin-1 in Pancreatic Cancer Cell Lines)

Expression of neuropilin-1 in some pancreatic cancer cell lines (BxPC-3, Panc-1, SU8686 and CFPAC-1) and pancreatic epithelial cells was estimated by RT-PCR analysis. In all RT-PCR analyses, GAPDH was used as positive control. The results are shown in FIG. 39A.

Furthermore, for each cell, using real-time PCR, expression of neuropilin-1 was determined. For all controls, analysis was performed using GAPDH. The results are shown in FIG. 39B.

Figure 39A:
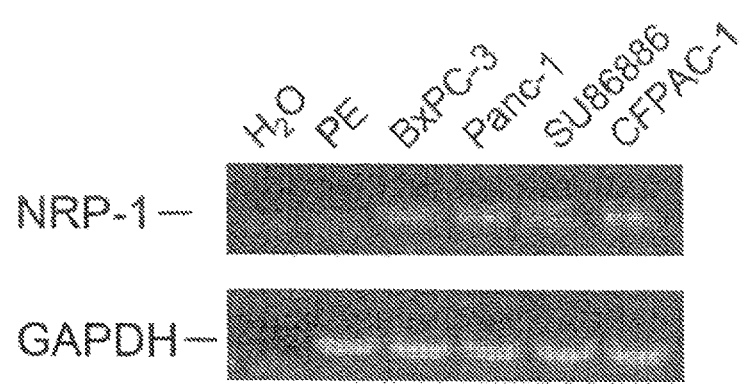
FIG. 39A shows expression of neuropilin-1 in some pancreatic cancer cell lines (BxPC-3, Panc-1, SU8686 and CFPAC-1) and pancreatic epithelial cells as estimated by RT-PCR analysis. For all RT-PCR analyses, GAPDH was used as positive control.
Figure 39B:
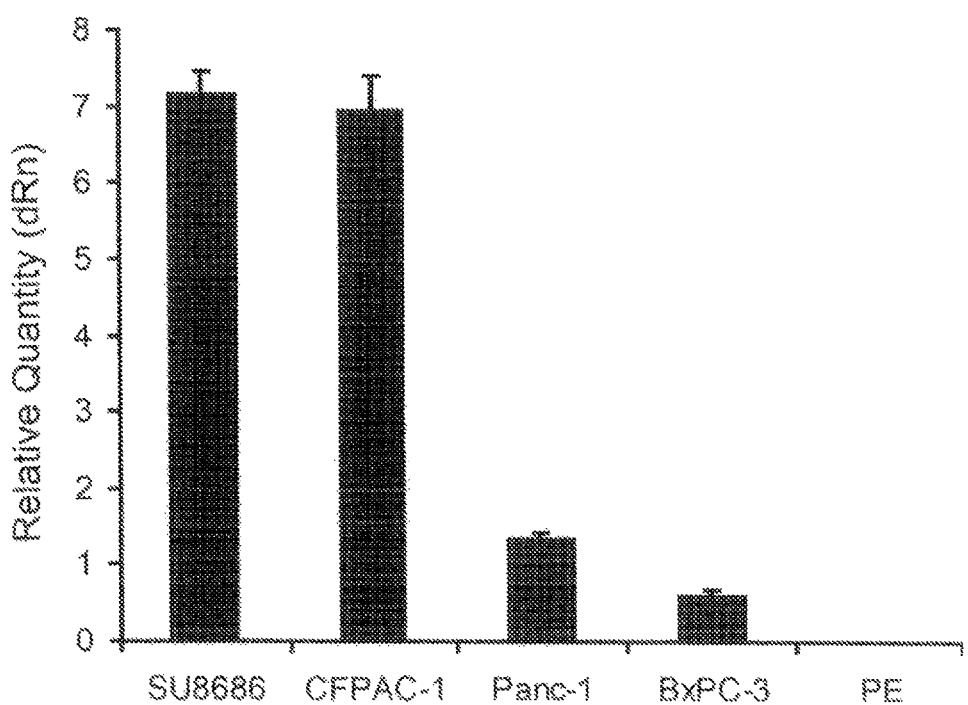
FIG. 39B shows determination of expression of neuropilin-1 by real-time PCR. For each of the cells shown in the graph of FIG. 39A, expression of neuropilin-1 was determined using real-time PCR. All controls were analyzed using GAPDH.

As apparent from FIGS. 39A and 39B, in SU8686 and CFPAC-1, expression level of NRP-1 was high. In these cell lines, cell-killing effect of Sema3A (366-377)-kLytic peptide was excellent, and thus anticancer effect by a hybrid peptide targeted for NRP-1 can be expected.

(Possibility that Cancer Cell Death by Sema3A (363-377)-kLytic Mediates an Apoptotic Mechanism)

It was studied whether or not Sema3A (363-377)-kLytic peptide induces Annexin V-positive expression in human pancreatic cancer cell line SU8686 which highly expresses NRP-1.

Figure 40:
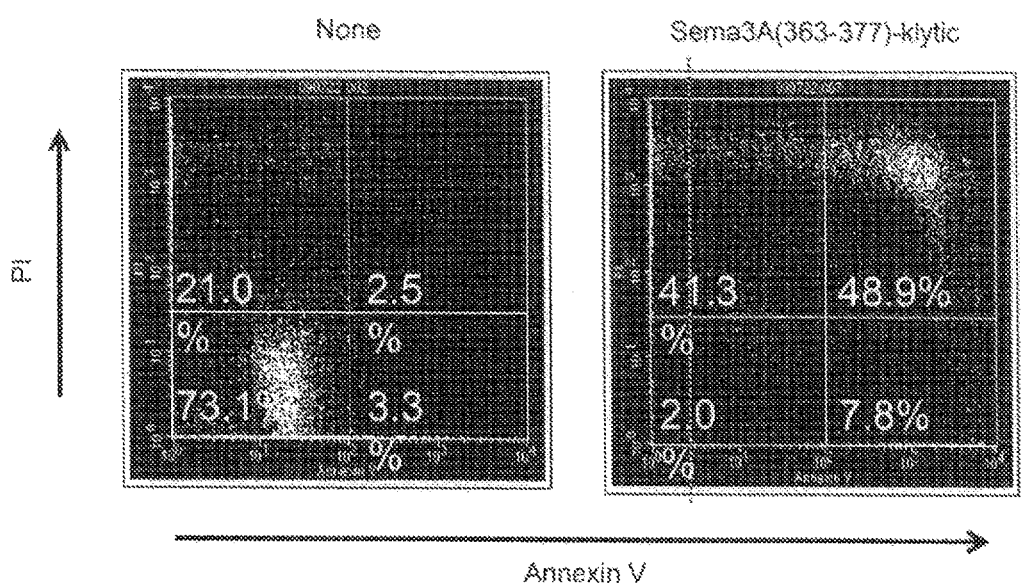
FIG. 40 shows the results of incubating human pancreatic cancer cell line SU8686 with Sema3A(363-377)-kLytic peptide (10 μM) at 37° C. for three hours and performing dual-color flow cytometry analysis for Annexin V labeling. These results indicate that Sema3A(363-377)-kLytic also induces Annexin V-positive expression to cancer cells.

SU8686 cells were incubated with Sema3A (363-377)-kLytic peptide (10 µM) for three hours at 37° C., and were analyzed for Annexin V labeling by dual-color flow cytometry. The results are shown in FIG. 40. As apparent from the figure, in SU8686 cells treated with Sema3A (363-377)-kLytic, the ratio of the right half panel which shows Annexin V-positive dead cells increased. It was suggested that Sema3A (363-377)-kLytic also induces cell death of cancer cells by an apoptotic mechanism.

Specifically, from these results, anticancer tumor equivalent to that of EB(H2R)-Lytic can be also expected for Sema3A(363-377)-kLytic peptide in vivo.
(In vivo Anticancer Action of (Sema3A(363-377)-kLytic Peptide)
(Protocol)

Human pancreatic cancer cell line BxPC-3 ($5 \times 10^6$ cells/150 µl phosphate buffer) is subcutaneously injected to female 5-week-old nude mice balb/c-nu/nu. From day 5 after the transplantation, Sema3A(363-377)-kLytic peptide is intravenously administered three times per week for three weeks, at 0, 0.5, 1, 2 or 5 mg/kg/50 µl phosphate buffer per mouse. The tumor diameters are measured with electronic caliper over time and the tumor volume ($mm^3$) is calculated as longer diameter×shorter diameter×shorter diameter×0.5.

Example 20

VEGFR2-Lytic Peptide

Using VEGFR2-lytic peptide ATWLPPRGGGKLLLKLL KKLLKLLKKK (underlined letters represent D-amino acids; SEQ ID NO: 51), cytotoxic activity to cancer cells was studied.

Figure 41:
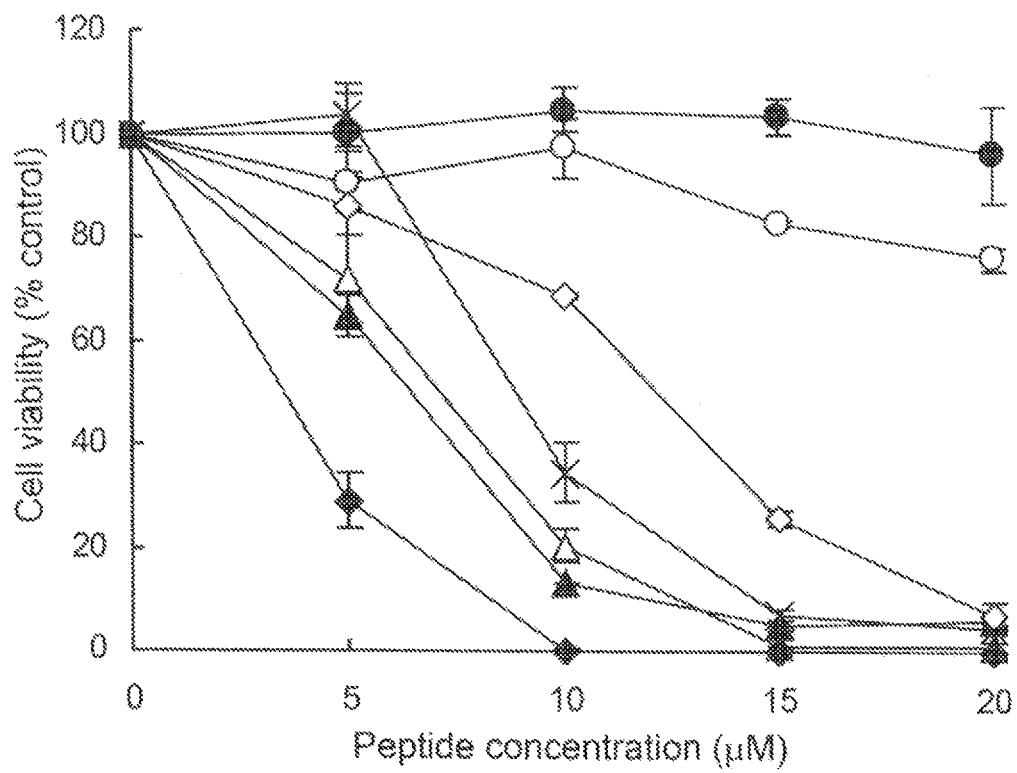
FIG. 41 shows cytotoxic activity of VEGFR2-lytic peptide to cancer cells and normal cells. Five cancer cell lines (OE19 (white triangle), T47D (black triangle), Bxpc3 (white rhomboid), U937 (black rhomboid) and LNCaP (x)) and two normal cell lines (HEK293 (white circle) and MRC-5 (black circle)) were cultured with various concentrations (0 to 20 μM) of VEGFR2-lytic peptide for 72 hours, and cytotoxic activity was assessed using WST-8 reagent. The vertical axis shows cell viability (%) and the horizontal axis shows peptide concentration (μM). The assay was repeated three times, and the results are represented as mean of triplicate measurements ±SD (bar). It is seen that VEGFR2-lytic peptide has cytotoxic activity specific for cancer cells.

A total of $3 \times 10^3$ cells per well of five cancer cell lines (OE19, T47D, BxPC-3, U937 and LNCaP) and two normal cell lines (HEK293 and MRC-5) were seeded in 96-well plates, cultured for 24 hours in a medium containing 10% FBS, and cultured with increasing concentration (0 to 20 µM) of VEGFR2-lytic peptide in 100 µl for 72 hours. Cytotoxic activity was assessed with WST-8 reagent (Cell Count Reagent SF; Nakalai Tesque). The results are shown in Table 9 and FIG. 41.

TABLE 9

Cytotoxic activity of VEGFR2-Lytic on various cancer cells and normal cells.

| Cell lines | $IC_{50}$ (µM) VEGFR2-Lytic |
|---|---|
| Cancer cells | |
| OE19 | 7.1 |
| T47D | 6.4 |
| BxPC-3 | 12.2 |
| U937 | 3.5 |
| LNCaP | 8.9 |
| Normal cells | |
| HEK293 | >20 |
| MRC-5 | >20 |

*$IC_{50}$, the concentration of peptide at which 50% inhibition of cell viability is observed compared to untreated cells.

As shown in the table, the effect was attained at lower concentration in cancer cells. In view of this, it is believed that there is selectivity between normal cells and cancer cells.
(In vivo Anticancer Action of VEGFR2-Lytic Peptide)
(Protocol)

Human pancreatic cancer cell line BxPC-3 ($5 \times 10^6$ cells/150 µl phosphate buffer) is subcutaneously injected to female 5-week-old nude mice balb/c-nu/nu. From day 5 after the transplantation, VEGFR2-Lytic peptide is intravenously administered three times per week for three weeks, at 0, 0.5, 1, 2 or 5 mg/kg/50 µl phosphate buffer per mouse. The tumor diameters are measured with electronic caliper over time and the tumor volume ($mm^3$) is calculated as longer diameter×shorter diameter×shorter diameter×0.5.

Example 21

Test for Stability of Peptide

Stability of the chimeric peptides produced in Example 1 is studied.
(Protocol)

The peptidetoxins are stored for a short or long period at −20° C., 4° C. and 25° C. in saline or serum. Based on quantitative analysis by HPLC and cell-killing effect to cultured cancer cells and the like, chemical and biological activities are assessed.

Example 22

A Method of Screening a Pharmaceutical/Anticancer Agent Using an Amino Acid Sequence Targeting Both EGFR in Cancer Cells with High EGFR Expression and the Cancer Cell Membrane of the Cancer Cells In the present Example, a method of screening a pharmaceutical/anticancer agent using an amino acid sequence targeting both EGFR in cancer cells with high EGFR expression and the cancer cell membrane is demonstrated.
(Protocol)

Cell membrane samples of cancer cells with high EGFR expression (human lung cancer cell line H322 or the like) are prepared, and BIACORE analysis is performed as follows. A test drug to be screened needs to be biotinated.

Surface plasmon resonance (SPR) experiments are performed with a BIACORE biosensor system 3000 (BIACORE Inc., Uppsala, Sweden). About 5000 RU of streptavidin (Sigma) is immobilized on the surface of CM5 sensor chips via N-hydroxysuccinimide and N-ethyl-N'-(dimethylaminopropyl) carbodiimide activation chemistry, and then 2000-3000 RU of biotin-conjugated test drug, such as peptide, are injected over the streptavidin-immobilized sensor chip. As a control of nonspecific binding, the unreacted carboxymethyl groups of a sensor chip without immobilized streptavidin are blocked with ethanolamine. As an analyte, cell surface proteins which are prepared using the Mem-PER eukaryotic membrane protein extraction reagent kit (Pierce) are injected over the flow-cell in the flow rate of 20 µl/min. at 25° C. In order to prevent nonspecific binding during the assay, BBS buffer (0.01 M HEPES, 0.15 M NaCl, 0.005% Tween 20, 3 mM EDTA [pH 7.4]) is used as running buffer. All protein concentrations used in these experiments are determined by the Bradford method (Bradford M M. A rapid and sensitive method for the quantitation of microgram quantities of protein utilizing the principle of protein-dye binding. Anal Biochem 1976; 72:248-54). Data analysis is performed using BIA evaluation ver.3.2 software (BIACORE)
(Results)

The membrane samples of cancer cells with high EGFR expression are reacted with the sensor chip immobilized with the test drug.

In the case of test drug which bind to both EGFR and cancer cell membrane, higher response is exhibited, and the test drug can be screened.

As described above, the present invention has been illustrated by way of preferred embodiments of the invention, but the invention should not be interpreted to be limited to these embodiments. It is understood that the scope of the present invention should be interpreted only based on the claims. It is understood that those skilled in the art can carry out the equivalent scope from the specific preferred embodiments based on the description of the invention and common general knowledge. It is understood that the contents of the patent, patent applications and documents quoted herein should be incorporated herein as a reference for the specification so that the contents per se are equivalent to be specifically described herein.

INDUSTRIAL APPLICABILITY

The present invention provides an anticancer agent with side effects alleviated.

[Sequence Listing Free Text]

SEQ ID NO: 1: amino acid sequence of a cancer cell membrane-lytic peptide
KLLLKLLKKLLKLLKKK (underlined letters represent D-amino acids)

SEQ ID NO: 2: amino acid sequence of EB (EGFR-binding)-cancer cell membrane-lytic chimeric peptide
YHWYGYTPQNVIGGGKLLLKLLKKLLKLLKKK (underlined letters represent D-amino acids)

SEQ ID NO: 3: amino acid sequence of recombinant human EGF receptor (rhEGFR) NP_005219 (among 1210AA, remaining 1186AA except for the underlined. N-terminal 24AA)

SEQ ID NO: 4: polycathionic amino acid sequence of mitochondriotoxic peptide and apoptosis-inducing peptide KLAKLAKKLAKLAK SEQ ID NO: 5: amino acid sequence of fibroblast growth factor receptor (FGFR)-binding peptide: MQLPLAT SEQ ID NO: 6: amino acid sequence of fibroblast growth factor receptor (FGFR)-binding peptide: AAVALLPAVLLALLAP SEQ ID NO: 7: amino acid sequence which is EGF receptor-binding peptide: YHWYGYTPQNVI SEQ ID NO: 8: amino acid sequence which is EGF receptor-binding peptide: $X_1X_2X_3X_4X_5X_6X_7X_8X_9X_{10}X_{11}X_{12}$

SEQ ID NO: 9: YRWYGYTPQNVI

SEQ ID NO: 10: YKWYGYTPQNVI

SEQ ID NO: 11: FLKLLKKLAAKLF

SEQ ID NO: 12: RLLRRLLRRLLRRLLRRLLR

SEQ ID NO: 13: RLLRRLLRRLLRK

SEQ ID NO: 14: EB(H2R)-Lytic: YRWYGYTPQNVIGGGKLLLKLLKKLLKLLKKK

SEQ ID NO: 15: HER2-Lytic: YCDGFYACYMDVGGGKLLLKLLKKLLKLLKKK (underlined letters represent D-amino acids and the remaining are L-amino acids)

SEQ ID NO: 16: VEGFR1-Lytic: WHSDMEWWYLLGGGGKLLLKLLKKLLKLLKKK (underlined letters represent D-amino acids and the remaining are L-amino acids)

SEQ ID NO: 17: TfR-Lytic: THRPPMWSPVWPGGGKLLLKLLKKLLKLLKKK (underlined letters represent D-amino acids and the remaining are L-amino acids)

SEQ ID NO: 18: IL4-LyticL: KQLIRFLKRLDRNGGGKLLLKLLKKLLKLLKKK

SEQ ID NO: 19: IL13-LyticL: KDLLLHLKKLFREGQFNGGGKLLLKLLKKLLKLKKK

SEQ ID NO: 20: Sema3A-LyticL<binding to human neuropilin-1>:
NYQWVPYQGRVPYPRGGGKLLLKLLKKLLKLLKKK SEQ ID NO: 21: EGFbuf: YHWYGYTPQNVIGGGGGRLLRRLLRRLLRK SEQ ID NO: 22: amino acid sequence of interleukin-11 receptor (IL11R)-binding peptide: CGRRAGGSC (cyclic)

SEQ ID NO: 23: cell-permeable peptide TA sequence: YGRKKRRQRRR

SEQ ID NO: 24: cell-permeable peptide R11 sequence: RRRRRRRRRRR

SEQ ID NO: 25: cytotoxic peptide: RQIKIQFQNRRMKWKKKAYARIGNSYFK

SEQ ID NO: 26: IL4R-binding peptide sequence: KQLIRFLKRLDRN

SEQ ID NO: 27: LyticL: KLLLKLLKKLLKLLKKK (L-amino acids alone)

SEQ ID NO: 28: IL13R-binding peptide sequence: KDLLLHLKKLFREGQFN

SEQ ID NO: 29: sequence necessary for binding to neuropilin receptor-binding peptide (sequence important for binding to ligand Sema3A): NYQWVPYQGRVPYPR SEQ ID NO: 30: human epidermal growth factor receptor 2 (HER2)-binding peptide sequence: YCDGFYACYMDV SEQ ID NO: 31: amino acid sequence of vascular epithelial growth factor receptor 1 (VEGFR1)-binding peptide: WHSDMEWWYLLG SEQ ID NO: 32: amino acid sequence of vascular epithelial growth factor receptor 1 (VEGFR1)-binding peptide: VEPNCDIHVMWEWECFERL SEQ ID NO: 33: amino acid sequence of vascular epithelial growth factor receptor (VEGFR)-binding peptide: GGNECDAIRMWEWECFERL SEQ ID NO: 34: amino acid sequence of transferrin receptor (TfR)-binding peptide: THRPPMWSPVWP SEQ ID NO: 35: amino acid sequence of prostate-specific membrane antigen (PSMA)-binding peptide: CQKHHNYLC SEQ ID NO: 36: amino acid sequence of neuropilin-1 (NRP1)/vascular endothelial growth factor receptor 2 (VEGFR2) binding peptide: ATWLPPR SEQ ID NO: 37: amino acid sequence of ephrin B1(EphB1)-binding peptide: EWLS SEQ ID NO: 38: amino acid sequence ephrin 52 (EphB2) binding peptide: SNEW SEQ ID NO: 39: amino acid sequence of binding peptide of glucose regulation protein 78(GRP78): WDLAWMFRLPVG SEQ ID NO: 40: amino acid sequence of glucose regulation protein 78 (GRP78) binding peptide: CTVALPGGYVRVC (cyclic)

SEQ ID NO: 41: original Lytic peptide: LKLLKKLLKKLLKLL-NH$_2$ (underlined letters represent D-amino acids and the remaining are L-amino acids)

SEQ ID NO: 42: EB-original Lytic: YHWYGYTPQNVIGGG LKLLKKLLKKLLKLL-NH$_2$ (underlined letters represent D-amino acids and the remaining are L-amino acids)

SEQ ID NO: 43: EB(H2R)-Lytic: YRWYGYTPQNVIGGG KLLLKLLKKLLKLLKKK (underlined letters represent D-amino acids and the remaining are L-amino acids)

SEQ ID NO: 44: IL4-Lytic(D,L): KQLIRFLKRLDRNGGG KLLLKLLKKLLKLLKKK (underlined letters represent D-amino acids and the remaining are L-amino acids)

SEQ ID NO: 45: nLytic: LLKLLKKLLKKLLKL (underlined letters represent D-amino acids and the remaining are L-amino acids)

SEQ ID NO: 46: Sema3A(aa363-377)-nLytic: NYQWVPYQGRVPYPRGGLLKLLKKLLKKLLKL (underlined letters represent D-amino acids and the remaining are L-amino acids)

SEQ ID NO: 47: Sema3A(aa371-377)-nLytic: GRVPYPRGGLLKLLKKLLKKLLKL (underlined letters represent D-amino acids and the remaining are L-amino acids)

SEQ ID NO: 48: KLLLKLLKKLLKLLKKK (wherein each amino acid is independently L-, D-, or D,L-mixed amino acid)

SEQ ID NO: 49: kLytic peptide: KL<u>L</u>LKL<u>L</u>KK<u>LL</u>KL<u>L</u>KKK (underlined letters represent D-amino acids and the remaining are L-amino acids)

SEQ ID NO: 50: Sema3A(363-377)-kLytic peptide: NYQWVPYQGRVPYPRGGGKL<u>L</u>LK<u>L</u>LKK<u>L</u>LK<u>L</u>LKKK (underlined letters represent D-amino acids and the remaining are L-amino acids)

SEQ ID NO: 51: VEGFR2-lytic peptide: ATWLPPRGGGKL<u>L</u>LK<u>L</u>LKK<u>L</u>LK<u>L</u>LKKK (underlined letters represent D-amino acids and the remaining are L-amino acids)

SEQ ID NO: 52: human epidermal growth factor receptor type 2 (HER2)-binding peptide sequence: LLGPYELWELSH SEQ ID NO: 53: human epidermal growth factor receptor type 2 (HER2)-binding peptide sequence: ALVRYKDPLFVWGFL SEQ ID NO: 54: human epidermal growth factor receptor type 2 (HER2)-binding peptide sequence: KCCYSL SEQ ID NO: 55: human epidermal growth factor receptor type 2 (HER2)-binding peptide sequence: WTGWCLNPEESTWGFCTGSF SEQ ID NO: 56: human epidermal growth factor receptor type 2 (HER2)-binding peptide sequence: DTDMCWWWSREFGWECAGAG SEQ ID NO: 57: amino acid sequence of Tat [human immunodeficiency virus 1] (NP_057853): MEPVDPRLEPWKHPGSQPKT ACTNCYCKKC CFHCQVCFIT KALGISYGRK KRRQRRRAHQ NSQTHQASLS KQPTSQPRGD PTGPKE

---

The invention claimed is:

1. A chimeric peptide comprising a receptor-binding peptide and a cytotoxic peptide, wherein the receptor-binding peptide is a Transferrin Receptor (TfR)-binding peptide comprising the amino acid sequence set forth in SEQ ID NO: 34, and wherein the cytotoxic peptide is a cell membrane-lytic peptide comprising a 10- to 20-amino acid sequence consisting only of K and L wherein the amino acids are L- D- or a mixture of D- and L- amino acids.

2. The chimeric peptide according to claim 1, wherein the cell membrane-lytic peptide is the amino acid sequence set forth in SEQ ID NO: 48, and the amino acids are L-, D- or a mixture of D- and L- amino acids.

3. The chimeric peptide according to claim 1, wherein the cytotoxic peptide is the amino acid sequence set forth in SEQ ID NO: 1.

4. The chimeric peptide according to claim 1, further comprising a spacer peptide.

5. The chimeric peptide according to claim 4, wherein the spacer peptide is a sequence of at least one amino acid in length and wherein the spacer peptide is a sequence in which up to 5 of glycine residues, proline residues, or a mixture thereof are linked.

6. The chimeric peptide according to claim 4, wherein the spacer peptide is GGG.

7. The chimeric peptide according to claim 1 comprising the amino acid sequence set forth in SEQ ID NO: 17.

8. A pharmaceutical composition comprising the chimeric peptide according to claim 1.

9. An anticancer agent comprising the chimeric peptide according to claim 1.

10. A nucleic acid encoding the chimeric peptide according to claim 1.

11. A vector comprising a nucleic acid which encodes the chimeric peptide according to claim 1.

12. An isolated host cell comprising a nucleic acid which encodes the chimeric peptide according to claim 1.

13. A method of treating cancer which overexpress TfR comprising the step of administering the chimeric peptide of claim 1.

* * * * *

UNITED STATES PATENT AND TRADEMARK OFFICE
CERTIFICATE OF CORRECTION

PATENT NO.         : 8,940,862 B2
APPLICATION NO.    : 13/857752
DATED              : January 27, 2015
INVENTOR(S)        : Koji Kawakami et al.

Page 1 of 1

It is certified that error appears in the above-identified patent and that said Letters Patent is hereby corrected as shown below:

In the Claims

Column 103, Line 37:
"only of K and L wherein the amino acids are L- D- or a" should read, --only of K and L wherein the amino acids are L-, D- or a--.

Signed and Sealed this
Tenth Day of May, 2016

Michelle K. Lee
*Director of the United States Patent and Trademark Office*

SEQUENCE LISTING

```
<160> NUMBER OF SEQ ID NOS: 67

<210> SEQ ID NO 1
<211> LENGTH: 17
<212> TYPE: PRT
<213> ORGANISM: artificial sequence
<220> FEATURE:
<223> OTHER INFORMATION: cell membrane lytic peptide; position 3, 6, 8,
      9 and 13 are D-amino acids.

<400> SEQUENCE: 1

Lys Leu Leu Leu Lys Leu Leu Lys Lys Leu Leu Lys Leu Leu Lys Lys
1               5                   10                  15

Lys

<210> SEQ ID NO 2
<211> LENGTH: 32
<212> TYPE: PRT
<213> ORGANISM: artificial sequence
<220> FEATURE:
<223> OTHER INFORMATION: EB-lytic chimeric peptide; position 18, 21, 23,
      24 and 28 are D-amino acids.

<400> SEQUENCE: 2

Tyr His Trp Tyr Gly Tyr Thr Pro Gln Asn Val Ile Gly Gly Gly Lys
1               5                   10                  15

Leu Leu Leu Lys Leu Leu Lys Lys Leu Leu Lys Leu Leu Lys Lys Lys
                20                  25                  30

<210> SEQ ID NO 3
<211> LENGTH: 1186
<212> TYPE: PRT
<213> ORGANISM: artificial sequence
<220> FEATURE:
<223> OTHER INFORMATION: rhEGFR

<400> SEQUENCE: 3

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
```

```
               65                  70                  75                  80
          Gln Ile Ile Arg Gly Asn Met Tyr Tyr Glu Asn Ser Tyr Ala Leu Ala
                              85                  90                  95
          Val Leu Ser Asn Tyr Asp Ala Asn Lys Thr Gly Leu Lys Glu Leu Pro
                         100                 105                 110
          Met Arg Asn Leu Gln Glu Ile Leu His Gly Ala Val Arg Phe Ser Asn
                    115                 120                 125
          Asn Pro Ala Leu Cys Asn Val Glu Ser Ile Gln Trp Arg Asp Ile Val
          130                 135                 140
          Ser Ser Asp Phe Leu Ser Asn Met Ser Met Asp Phe Gln Asn His Leu
          145                 150                 155                 160
          Gly Ser Cys Gln Lys Cys Asp Pro Ser Cys Pro Asn Gly Ser Cys Trp
                         165                 170                 175
          Gly Ala Gly Glu Glu Asn Cys Gln Lys Leu Thr Lys Ile Ile Cys Ala
                         180                 185                 190
          Gln Gln Cys Ser Gly Arg Cys Arg Gly Lys Ser Pro Ser Asp Cys Cys
                    195                 200                 205
          His Asn Gln Cys Ala Ala Gly Cys Thr Gly Pro Arg Glu Ser Asp Cys
                    210                 215                 220
          Leu Val Cys Arg Lys Phe Arg Asp Glu Ala Thr Cys Lys Asp Thr Cys
          225                 230                 235                 240
          Pro Pro Leu Met Leu Tyr Asn Pro Thr Thr Tyr Gln Met Asp Val Asn
                         245                 250                 255
          Pro Glu Gly Lys Tyr Ser Phe Gly Ala Thr Cys Val Lys Lys Cys Pro
                         260                 265                 270
          Arg Asn Tyr Val Val Thr Asp His Gly Ser Cys Val Arg Ala Cys Gly
                    275                 280                 285
          Ala Asp Ser Tyr Glu Met Glu Glu Asp Gly Val Arg Lys Cys Lys Lys
                    290                 295                 300
          Cys Glu Gly Pro Cys Arg Lys Val Cys Asn Gly Ile Gly Ile Gly Glu
          305                 310                 315                 320
          Phe Lys Asp Ser Leu Ser Ile Asn Ala Thr Asn Ile Lys His Phe Lys
                         325                 330                 335
          Asn Cys Thr Ser Ile Ser Gly Asp Leu His Ile Leu Pro Val Ala Phe
                         340                 345                 350
          Arg Gly Asp Ser Phe Thr His Thr Pro Pro Leu Asp Pro Gln Glu Leu
                    355                 360                 365
          Asp Ile Leu Lys Thr Val Lys Glu Ile Thr Gly Phe Leu Leu Ile Gln
          370                 375                 380
          Ala Trp Pro Glu Asn Arg Thr Asp Leu His Ala Phe Glu Asn Leu Glu
          385                 390                 395                 400
          Ile Ile Arg Gly Arg Thr Lys Gln His Gly Gln Phe Ser Leu Ala Val
                         405                 410                 415
          Val Ser Leu Asn Ile Thr Ser Leu Gly Leu Arg Ser Leu Lys Glu Ile
                         420                 425                 430
          Ser Asp Gly Asp Val Ile Ile Ser Gly Asn Lys Asn Leu Cys Tyr Ala
                    435                 440                 445
          Asn Thr Ile Asn Trp Lys Lys Leu Phe Gly Thr Ser Gly Gln Lys Thr
                    450                 455                 460
          Lys Ile Ile Ser Asn Arg Gly Glu Asn Ser Cys Lys Ala Thr Gly Gln
          465                 470                 475                 480
          Val Cys His Ala Leu Cys Ser Pro Glu Gly Cys Trp Gly Pro Glu Pro
                         485                 490                 495
```

-continued

```
Arg Asp Cys Val Ser Cys Arg Asn Val Ser Arg Gly Arg Glu Cys Val
            500                 505                 510
Asp Lys Cys Asn Leu Leu Glu Gly Glu Pro Arg Glu Phe Val Glu Asn
            515                 520                 525
Ser Glu Cys Ile Gln Cys His Pro Glu Cys Leu Pro Gln Ala Met Asn
            530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
            565                 570                 575
Gly Glu Asn Asn Thr Leu Val Trp Lys Tyr Ala Asp Ala Gly His Val
            580                 585                 590
Cys His Leu Cys His Pro Asn Cys Thr Tyr Gly Cys Thr Gly Pro Gly
            595                 600                 605
Leu Glu Gly Cys Pro Thr Asn Gly Pro Lys Ile Pro Ser Ile Ala Thr
            610                 615                 620
Gly Met Val Gly Ala Leu Leu Leu Leu Val Val Ala Leu Gly Ile
625                 630                 635                 640
Gly Leu Phe Met Arg Arg Arg His Ile Val Arg Lys Arg Thr Leu Arg
            645                 650                 655
Arg Leu Leu Gln Glu Arg Glu Leu Val Glu Pro Leu Thr Pro Ser Gly
            660                 665                 670
Glu Ala Pro Asn Gln Ala Leu Leu Arg Ile Leu Lys Glu Thr Glu Phe
            675                 680                 685
Lys Lys Ile Lys Val Leu Gly Ser Gly Ala Phe Gly Thr Val Tyr Lys
            690                 695                 700
Gly Leu Trp Ile Pro Glu Gly Glu Lys Val Lys Ile Pro Val Ala Ile
705                 710                 715                 720
Lys Glu Leu Arg Glu Ala Thr Ser Pro Lys Ala Asn Lys Glu Ile Leu
            725                 730                 735
Asp Glu Ala Tyr Val Met Ala Ser Val Asp Asn Pro His Val Cys Arg
            740                 745                 750
Leu Leu Gly Ile Cys Leu Thr Ser Thr Val Gln Leu Ile Thr Gln Leu
            755                 760                 765
Met Pro Phe Gly Cys Leu Leu Asp Tyr Val Arg Glu His Lys Asp Asn
            770                 775                 780
Ile Gly Ser Gln Tyr Leu Leu Asn Trp Cys Val Gln Ile Ala Lys Gly
785                 790                 795                 800
Met Asn Tyr Leu Glu Asp Arg Arg Leu Val His Arg Asp Leu Ala Ala
            805                 810                 815
Arg Asn Val Leu Val Lys Thr Pro Gln His Val Lys Ile Thr Asp Phe
            820                 825                 830
Gly Leu Ala Lys Leu Leu Gly Ala Glu Glu Lys Glu Tyr His Ala Glu
            835                 840                 845
Gly Gly Lys Val Pro Ile Lys Trp Met Ala Leu Glu Ser Ile Leu His
            850                 855                 860
Arg Ile Tyr Thr His Gln Ser Asp Val Trp Ser Tyr Gly Val Thr Val
865                 870                 875                 880
Trp Glu Leu Met Thr Phe Gly Ser Lys Pro Tyr Asp Gly Ile Pro Ala
            885                 890                 895
Ser Glu Ile Ser Ser Ile Leu Glu Lys Gly Glu Arg Leu Pro Gln Pro
            900                 905                 910
```

```
Pro Ile Cys Thr Ile Asp Val Tyr Met Ile Met Val Lys Cys Trp Met
            915                 920                 925
Ile Asp Ala Asp Ser Arg Pro Lys Phe Arg Glu Leu Ile Ile Glu Phe
930                 935                 940
Ser Lys Met Ala Arg Asp Pro Gln Arg Tyr Leu Val Ile Gln Gly Asp
945                 950                 955                 960
Glu Arg Met His Leu Pro Ser Pro Thr Asp Ser Asn Phe Tyr Arg Ala
            965                 970                 975
Leu Met Asp Glu Glu Asp Met Asp Asp Val Val Asp Ala Asp Glu Tyr
            980                 985                 990
Leu Ile Pro Gln Gln Gly Phe Phe Ser Ser Pro Ser Thr Ser Arg Thr
            995                 1000                1005
Pro Leu Leu Ser Ser Leu Ser Ala Thr Ser Asn Asn Ser Thr Val
    1010                1015                1020
Ala Cys Ile Asp Arg Asn Gly Leu Gln Ser Cys Pro Ile Lys Glu
    1025                1030                1035
Asp Ser Phe Leu Gln Arg Tyr Ser Ser Asp Pro Thr Gly Ala Leu
    1040                1045                1050
Thr Glu Asp Ser Ile Asp Asp Thr Phe Leu Pro Val Pro Glu Tyr
    1055                1060                1065
Ile Asn Gln Ser Val Pro Lys Arg Pro Ala Gly Ser Val Gln Asn
    1070                1075                1080
Pro Val Tyr His Asn Gln Pro Leu Asn Pro Ala Pro Ser Arg Asp
    1085                1090                1095
Pro His Tyr Gln Asp Pro His Ser Thr Ala Val Gly Asn Pro Glu
    1100                1105                1110
Tyr Leu Asn Thr Val Gln Pro Thr Cys Val Asn Ser Thr Phe Asp
    1115                1120                1125
Ser Pro Ala His Trp Ala Gln Lys Gly Ser His Gln Ile Ser Leu
    1130                1135                1140
Asp Asn Pro Asp Tyr Gln Gln Asp Phe Phe Pro Lys Glu Ala Lys
    1145                1150                1155
Pro Asn Gly Ile Phe Lys Gly Ser Thr Ala Glu Asn Ala Glu Tyr
    1160                1165                1170
Leu Arg Val Ala Pro Gln Ser Ser Glu Phe Ile Gly Ala
    1175                1180                1185

<210> SEQ ID NO 4
<211> LENGTH: 14
<212> TYPE: PRT
<213> ORGANISM: artificial sequence
<220> FEATURE:
<223> OTHER INFORMATION: polycationic sequence

<400> SEQUENCE: 4

Lys Leu Ala Lys Leu Ala Lys Lys Leu Ala Lys Leu Ala Lys
1               5                   10

<210> SEQ ID NO 5
<211> LENGTH: 7
<212> TYPE: PRT
<213> ORGANISM: artificial sequence
<220> FEATURE:
<223> OTHER INFORMATION: FGFR binding peptide

<400> SEQUENCE: 5

Met Gln Leu Pro Leu Ala Thr
1               5
```

```
<210> SEQ ID NO 6
<211> LENGTH: 16
<212> TYPE: PRT
<213> ORGANISM: artificial sequence
<220> FEATURE:
<223> OTHER INFORMATION: FGFR binding peptide

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 12
<212> TYPE: PRT
<213> ORGANISM: artificial sequence
<220> FEATURE:
<223> OTHER INFORMATION: EGFR binding peptide

<400> SEQUENCE: 7

Tyr His Trp Tyr Gly Tyr Thr Pro Gln Asn Val Ile
1               5                   10

<210> SEQ ID NO 8
<211> LENGTH: 12
<212> TYPE: PRT
<213> ORGANISM: artificial sequence
<220> FEATURE:
<223> OTHER INFORMATION: EGFR binding peptide analog
<220> FEATURE:
<221> NAME/KEY: misc_feature
<222> LOCATION: (1)..(1)
<223> OTHER INFORMATION: Xaa corresponds to X1 which may be Tyr, Ser,
      His, or Phe
<220> FEATURE:
<221> NAME/KEY: misc_feature
<222> LOCATION: (2)..(2)
<223> OTHER INFORMATION: Xaa corresponds to X2 which may be His, Arg, or
      Lys
<220> FEATURE:
<221> NAME/KEY: misc_feature
<222> LOCATION: (3)..(3)
<223> OTHER INFORMATION: Xaa corresponds to X3 which may be Trp, Tyr,
      Phe, or His
<220> FEATURE:
<221> NAME/KEY: misc_feature
<222> LOCATION: (4)..(4)
<223> OTHER INFORMATION: Xaa corresponds to X4 which may be Tyr, Ser,
      His, or Phe
<220> FEATURE:
<221> NAME/KEY: misc_feature
<222> LOCATION: (5)..(5)
<223> OTHER INFORMATION: Xaa corresponds to X5 which may be Gly, Ala,
      Val, Ile, or Leu
<220> FEATURE:
<221> NAME/KEY: misc_feature
<222> LOCATION: (6)..(6)
<223> OTHER INFORMATION: Xaa corresponds to X6 which may be Tyr, Ser,
      His, or Phe
<220> FEATURE:
<221> NAME/KEY: misc_feature
<222> LOCATION: (7)..(7)
<223> OTHER INFORMATION: Xaa corresponds to X7 which may be Thr, Ser,
      His, or Phe
<220> FEATURE:
<221> NAME/KEY: misc_feature
<222> LOCATION: (8)..(8)
<223> OTHER INFORMATION: Xaa corresponds to X8 which may be Pro or
      hydroxyproline
<220> FEATURE:
<221> NAME/KEY: misc_feature
<222> LOCATION: (9)..(9)
<223> OTHER INFORMATION: Xaa corresponds to X9 which may be Gln or Asn
<220> FEATURE:
```

-continued

```
<221> NAME/KEY: misc_feature
<222> LOCATION: (10)..(10)
<223> OTHER INFORMATION: Xaa corresponds to X10 which may be Asn, Ser,
      His, or Phe
<220> FEATURE:
<221> NAME/KEY: misc_feature
<222> LOCATION: (11)..(11)
<223> OTHER INFORMATION: Xaa corresponds to X11 which may be Val, Gly,
      Ala, Leu, or Ile
<220> FEATURE:
<221> NAME/KEY: misc_feature
<222> LOCATION: (12)..(12)
<223> OTHER INFORMATION: Xaa corresponds to X12 which may be Ile, Gly,
      Ala, Val, or Leu

<400> SEQUENCE: 8

Xaa Xaa Xaa Xaa Xaa Xaa Xaa Xaa Xaa Xaa Xaa Xaa
1               5                   10

<210> SEQ ID NO 9
<211> LENGTH: 12
<212> TYPE: PRT
<213> ORGANISM: artificial sequence
<220> FEATURE:
<223> OTHER INFORMATION: EGFR binding peptide

<400> SEQUENCE: 9

Tyr Arg Trp Tyr Gly Tyr Thr Pro Gln Asn Val Ile
1               5                   10

<210> SEQ ID NO 10
<211> LENGTH: 12
<212> TYPE: PRT
<213> ORGANISM: artificial sequence
<220> FEATURE:
<223> OTHER INFORMATION: EGFR binding peptide

<400> SEQUENCE: 10

Tyr Lys Trp Tyr Gly Tyr Thr Pro Gln Asn Val Ile
1               5                   10

<210> SEQ ID NO 11
<211> LENGTH: 13
<212> TYPE: PRT
<213> ORGANISM: artificial sequence
<220> FEATURE:
<223> OTHER INFORMATION: cell membrane potential destabilizing peptide

<400> SEQUENCE: 11

Phe Leu Lys Leu Leu Lys Lys Leu Ala Ala Lys Leu Phe
1               5                   10

<210> SEQ ID NO 12
<211> LENGTH: 20
<212> TYPE: PRT
<213> ORGANISM: artificial sequence
<220> FEATURE:
<223> OTHER INFORMATION: cell membrane lytic/nucleic acid binding
      peptide

<400> SEQUENCE: 12

Arg Leu Leu Arg Arg Leu Leu Arg Arg Leu Leu Arg Arg Leu Leu Arg
1               5                   10                  15

Arg Leu Leu Arg
            20

<210> SEQ ID NO 13
<211> LENGTH: 13
```

```
<212> TYPE: PRT
<213> ORGANISM: artificial sequence
<220> FEATURE:
<223> OTHER INFORMATION: cell membrane lytic/nucleic acid binding
      peptide

<400> SEQUENCE: 13

Arg Leu Leu Arg Arg Leu Leu Arg Arg Leu Leu Arg Lys
1               5                   10

<210> SEQ ID NO 14
<211> LENGTH: 32
<212> TYPE: PRT
<213> ORGANISM: artificial sequence
<220> FEATURE:
<223> OTHER INFORMATION: EB(H2R)-lytic chimeric peptide; position 18,
      21, 23, 24 and 28 are D-amino acids.

<400> SEQUENCE: 14

Tyr Arg Trp Tyr Gly Tyr Thr Pro Gln Asn Val Ile Gly Gly Gly Lys
1               5                   10                  15

Leu Leu Leu Lys Leu Leu Lys Lys Leu Lys Leu Leu Lys Lys
            20                  25                  30

<210> SEQ ID NO 15
<211> LENGTH: 32
<212> TYPE: PRT
<213> ORGANISM: artificial sequence
<220> FEATURE:
<223> OTHER INFORMATION: HER2-lytic chimeric peptide; position 18, 21,
      23, 24 and 28 are D-amino acids.

<400> SEQUENCE: 15

Tyr Cys Asp Gly Phe Tyr Ala Cys Tyr Met Asp Val Gly Gly Gly Lys
1               5                   10                  15

Leu Leu Leu Lys Leu Leu Lys Lys Leu Leu Lys Leu Leu Lys Lys
            20                  25                  30

<210> SEQ ID NO 16
<211> LENGTH: 32
<212> TYPE: PRT
<213> ORGANISM: artificial sequence
<220> FEATURE:
<223> OTHER INFORMATION: VEGFR1-lytic chimeric peptide; position 18, 21,
      23, 24 and 28 are D-amino acids.

<400> SEQUENCE: 16

Trp His Ser Asp Met Glu Trp Trp Tyr Leu Leu Gly Gly Gly Gly Lys
1               5                   10                  15

Leu Leu Leu Lys Leu Leu Lys Lys Leu Leu Lys Leu Leu Lys Lys
            20                  25                  30

<210> SEQ ID NO 17
<211> LENGTH: 32
<212> TYPE: PRT
<213> ORGANISM: artificial sequence
<220> FEATURE:
<223> OTHER INFORMATION: TfR-lytic chimeric peptide; position 18, 21,
      23, 24 and 28 are D-amino acids.

<400> SEQUENCE: 17

Thr His Arg Pro Pro Met Trp Ser Pro Val Trp Pro Gly Gly Gly Lys
1               5                   10                  15

Leu Leu Leu Lys Leu Leu Lys Lys Leu Leu Lys Leu Leu Lys Lys
            20                  25                  30
```

<210> SEQ ID NO 18
<211> LENGTH: 33
<212> TYPE: PRT
<213> ORGANISM: artificial sequence
<220> FEATURE:
<223> OTHER INFORMATION: IL4-lyticL chimeric peptide

<400> SEQUENCE: 18

Lys Gln Leu Ile Arg Phe Leu Lys Arg Leu Asp Arg Asn Gly Gly
1               5                   10                  15

Lys Leu Leu Leu Lys Leu Leu Lys Leu Leu Lys Leu Leu Lys Lys
            20                  25                  30

Lys

<210> SEQ ID NO 19
<211> LENGTH: 37
<212> TYPE: PRT
<213> ORGANISM: artificial sequence
<220> FEATURE:
<223> OTHER INFORMATION: IL13-lyticL chimeric peptide

<400> SEQUENCE: 19

Lys Asp Leu Leu Leu His Leu Lys Lys Leu Phe Arg Glu Gly Gln Phe
1               5                   10                  15

Asn Gly Gly Gly Lys Leu Leu Leu Lys Leu Leu Lys Lys Leu Leu Lys
            20                  25                  30

Leu Leu Lys Lys Lys
        35

<210> SEQ ID NO 20
<211> LENGTH: 35
<212> TYPE: PRT
<213> ORGANISM: artificial sequence
<220> FEATURE:
<223> OTHER INFORMATION: Sema3A-lyticL chimeric peptide

<400> SEQUENCE: 20

Asn Tyr Gln Trp Val Pro Tyr Gln Gly Arg Val Pro Tyr Pro Arg Gly
1               5                   10                  15

Gly Gly Lys Leu Leu Lys Leu Leu Lys Lys Leu Leu Lys Leu Leu
            20                  25                  30

Lys Lys Lys
        35

<210> SEQ ID NO 21
<211> LENGTH: 30
<212> TYPE: PRT
<213> ORGANISM: artificial sequence
<220> FEATURE:
<223> OTHER INFORMATION: EGFbuf sequence

<400> SEQUENCE: 21

Tyr His Trp Tyr Gly Tyr Thr Pro Gln Asn Val Ile Gly Gly Gly
1               5                   10                  15

Gly Arg Leu Leu Arg Arg Leu Leu Arg Arg Leu Leu Arg Lys
            20                  25                  30

<210> SEQ ID NO 22
<211> LENGTH: 9
<212> TYPE: PRT
<213> ORGANISM: artificial sequence
<220> FEATURE:
<223> OTHER INFORMATION: IL11R binding peptide (cyclic peptide)

<400> SEQUENCE: 22

Cys Gly Arg Arg Ala Gly Gly Ser Cys
1               5

<210> SEQ ID NO 23
<211> LENGTH: 11
<212> TYPE: PRT
<213> ORGANISM: artificial sequence
<220> FEATURE:
<223> OTHER INFORMATION: TAT sequence

<400> SEQUENCE: 23

Tyr Gly Arg Lys Lys Arg Arg Gln Arg Arg Arg
1               5                   10

<210> SEQ ID NO 24
<211> LENGTH: 11
<212> TYPE: PRT
<213> ORGANISM: artificial sequence
<220> FEATURE:
<223> OTHER INFORMATION: R11 sequence

<400> SEQUENCE: 24

Arg Arg Arg Arg Arg Arg Arg Arg Arg Arg Arg
1               5                   10

<210> SEQ ID NO 25
<211> LENGTH: 28
<212> TYPE: PRT
<213> ORGANISM: artificial sequence
<220> FEATURE:
<223> OTHER INFORMATION: cytotoxic peptide

<400> SEQUENCE: 25

Arg Gln Ile Lys Ile Gln Phe Gln Asn Arg Arg Met Lys Trp Lys Lys
1               5                   10                  15

Lys Ala Tyr Ala Arg Ile Gly Asn Ser Tyr Phe Lys
            20                  25

<210> SEQ ID NO 26
<211> LENGTH: 13
<212> TYPE: PRT
<213> ORGANISM: artificial sequence
<220> FEATURE:
<223> OTHER INFORMATION: IL4R binding peptide

<400> SEQUENCE: 26

Lys Gln Leu Ile Arg Phe Leu Lys Arg Leu Asp Arg Asn
1               5                   10

<210> SEQ ID NO 27
<211> LENGTH: 17
<212> TYPE: PRT
<213> ORGANISM: artificial sequence
<220> FEATURE:
<223> OTHER INFORMATION: cencer cell membrane lytic sequence; all amino
      acids are L-amino acids

<400> SEQUENCE: 27

Lys Leu Leu Leu Lys Leu Leu Lys Lys Leu Leu Lys Leu Leu Lys Lys
1               5                   10                  15

Lys

<210> SEQ ID NO 28

```
<211> LENGTH: 17
<212> TYPE: PRT
<213> ORGANISM: artificial sequence
<220> FEATURE:
<223> OTHER INFORMATION: IL13R binding peptide

<400> SEQUENCE: 28

Lys Asp Leu Leu Leu His Leu Lys Lys Leu Phe Arg Glu Gly Gln Phe
1               5                   10                  15

Asn

<210> SEQ ID NO 29
<211> LENGTH: 15
<212> TYPE: PRT
<213> ORGANISM: artificial sequence
<220> FEATURE:
<223> OTHER INFORMATION: NRP1 binding peptide

<400> SEQUENCE: 29

Asn Tyr Gln Trp Val Pro Tyr Gln Gly Arg Val Pro Tyr Pro Arg
1               5                   10                  15

<210> SEQ ID NO 30
<211> LENGTH: 12
<212> TYPE: PRT
<213> ORGANISM: artificial sequence
<220> FEATURE:
<223> OTHER INFORMATION: HER2 binding peptide

<400> SEQUENCE: 30

Tyr Cys Asp Gly Phe Tyr Ala Cys Tyr Met Asp Val
1               5                   10

<210> SEQ ID NO 31
<211> LENGTH: 12
<212> TYPE: PRT
<213> ORGANISM: artificial sequence
<220> FEATURE:
<223> OTHER INFORMATION: VEGFR1 binding pepitde

<400> SEQUENCE: 31

Trp His Ser Asp Met Glu Trp Trp Tyr Leu Leu Gly
1               5                   10

<210> SEQ ID NO 32
<211> LENGTH: 19
<212> TYPE: PRT
<213> ORGANISM: artificial sequence
<220> FEATURE:
<223> OTHER INFORMATION: VEGFR1 binding peptide; -CONH2 is existing at
      C-terminal.

<400> SEQUENCE: 32

Val Glu Pro Asn Cys Asp Ile His Val Met Trp Glu Trp Glu Cys Phe
1               5                   10                  15

Glu Arg Leu

<210> SEQ ID NO 33
<211> LENGTH: 19
<212> TYPE: PRT
<213> ORGANISM: artificial sequence
<220> FEATURE:
<223> OTHER INFORMATION: VEGFR1 binding peptide

<400> SEQUENCE: 33

Gly Gly Asn Glu Cys Asp Ala Ile Arg Met Trp Glu Trp Glu Cys Phe
```

Glu Arg Leu

<210> SEQ ID NO 34
<211> LENGTH: 12
<212> TYPE: PRT
<213> ORGANISM: artificial sequence
<220> FEATURE:
<223> OTHER INFORMATION: Transferrin Receptor(TfR) binding peptide

<400> SEQUENCE: 34

Thr His Arg Pro Pro Met Trp Ser Pro Val Trp Pro
1               5                   10

<210> SEQ ID NO 35
<211> LENGTH: 9
<212> TYPE: PRT
<213> ORGANISM: artificial sequence
<220> FEATURE:
<223> OTHER INFORMATION: PSMA binding peptide

<400> SEQUENCE: 35

Cys Gln Lys His His Asn Tyr Leu Cys
1               5

<210> SEQ ID NO 36
<211> LENGTH: 7
<212> TYPE: PRT
<213> ORGANISM: artificial sequence
<220> FEATURE:
<223> OTHER INFORMATION: NRP1/VEGFR2 binding peptide

<400> SEQUENCE: 36

Ala Thr Trp Leu Pro Pro Arg
1               5

<210> SEQ ID NO 37
<211> LENGTH: 4
<212> TYPE: PRT
<213> ORGANISM: artificial sequence
<220> FEATURE:
<223> OTHER INFORMATION: EphB1R binding peptide

<400> SEQUENCE: 37

Glu Trp Leu Ser
1

<210> SEQ ID NO 38
<211> LENGTH: 4
<212> TYPE: PRT
<213> ORGANISM: artificial sequence
<220> FEATURE:
<223> OTHER INFORMATION: EphB2R binding peptide

<400> SEQUENCE: 38

Ser Asn Glu Trp
1

<210> SEQ ID NO 39
<211> LENGTH: 12
<212> TYPE: PRT
<213> ORGANISM: artificial sequence
<220> FEATURE:
<223> OTHER INFORMATION: GRP78 binding peptide

<400> SEQUENCE: 39

```
Trp Asp Leu Ala Trp Met Phe Arg Leu Pro Val Gly
1               5                   10
```

<210> SEQ ID NO 40
<211> LENGTH: 13
<212> TYPE: PRT
<213> ORGANISM: artificial sequence
<220> FEATURE:
<223> OTHER INFORMATION: GRP78 binding pepitde (cyclic peptide)

<400> SEQUENCE: 40

```
Cys Thr Val Ala Leu Pro Gly Gly Tyr Val Arg Val Cys
1               5                   10
```

<210> SEQ ID NO 41
<211> LENGTH: 15
<212> TYPE: PRT
<213> ORGANISM: artificial sequence
<220> FEATURE:
<223> OTHER INFORMATION: original lytic peptide; position 3, 6, 8, 9 and
      13 are D-amino acids, and -CONH2 is existing at C-terminal.

<400> SEQUENCE: 41

```
Leu Lys Leu Leu Lys Lys Leu Leu Lys Lys Leu Leu Lys Leu Leu
1               5                   10                  15
```

<210> SEQ ID NO 42
<211> LENGTH: 30
<212> TYPE: PRT
<213> ORGANISM: artificial sequence
<220> FEATURE:
<223> OTHER INFORMATION: EB-original Lytic peptide; position 18, 21, 23,
      24 and 28 are D-amino acids, and -CONH2 is existing at C-terminal.

<400> SEQUENCE: 42

```
Tyr His Trp Tyr Gly Tyr Thr Pro Gln Asn Val Ile Gly Gly Gly Leu
1               5                   10                  15

Lys Leu Leu Lys Lys Leu Leu Lys Lys Leu Leu Lys Leu Leu
            20                  25                  30
```

<210> SEQ ID NO 43
<211> LENGTH: 32
<212> TYPE: PRT
<213> ORGANISM: artificial sequence
<220> FEATURE:
<223> OTHER INFORMATION: EB(H2R)-Lytic peptide; position 18, 21, 23, 24
      and 28 are D-amino acids.

<400> SEQUENCE: 43

```
Tyr Arg Trp Tyr Gly Tyr Thr Pro Gln Asn Val Ile Gly Gly Gly Lys
1               5                   10                  15

Leu Leu Leu Lys Leu Leu Lys Lys Leu Leu Lys Leu Leu Lys Lys Lys
            20                  25                  30
```

<210> SEQ ID NO 44
<211> LENGTH: 33
<212> TYPE: PRT
<213> ORGANISM: artificial sequence
<220> FEATURE:
<223> OTHER INFORMATION: IL4-Lytic(D,L) peptide; position 19, 22, 24, 25
      and 29 are D-amino acids.

<400> SEQUENCE: 44

```
Lys Gln Leu Ile Arg Phe Leu Lys Arg Leu Asp Arg Asn Gly Gly Gly
1               5                   10                  15

Lys Leu Leu Leu Lys Leu Leu Lys Lys Leu Leu Lys Leu Leu Lys Lys
```

```
                    20                  25                  30
Lys

<210> SEQ ID NO 45
<211> LENGTH: 15
<212> TYPE: PRT
<213> ORGANISM: artificial sequence
<220> FEATURE:
<223> OTHER INFORMATION: nLytic peptide; position 3, 7, 8 and 13 are
      D-amino acids.

<400> SEQUENCE: 45

Leu Leu Lys Leu Leu Lys Lys Leu Leu Lys Lys Leu Leu Lys Leu
1               5                   10                  15

<210> SEQ ID NO 46
<211> LENGTH: 32
<212> TYPE: PRT
<213> ORGANISM: artificial sequence
<220> FEATURE:
<223> OTHER INFORMATION: Sema3A(aa363-377)-nLytic peptide; position 20,
      24, 25 and 30 are D-amino acids.

<400> SEQUENCE: 46

Asn Tyr Gln Trp Val Pro Tyr Gln Gly Arg Val Pro Tyr Pro Arg Gly
1               5                   10                  15

Gly Leu Leu Lys Leu Leu Lys Lys Leu Leu Lys Lys Leu Leu Lys Leu
                20                  25                  30

<210> SEQ ID NO 47
<211> LENGTH: 24
<212> TYPE: PRT
<213> ORGANISM: artificial sequence
<220> FEATURE:
<223> OTHER INFORMATION: Sema3A(aa371-377)-nLytic; position 12, 16, 17
      and 22 are D-amino acids.

<400> SEQUENCE: 47

Gly Arg Val Pro Tyr Pro Arg Gly Gly Leu Leu Lys Leu Leu Lys Lys
1               5                   10                  15

Leu Leu Lys Lys Leu Leu Lys Leu
                20

<210> SEQ ID NO 48
<211> LENGTH: 17
<212> TYPE: PRT
<213> ORGANISM: artificial sequence
<220> FEATURE:
<223> OTHER INFORMATION: cell membrane lytic peptide

<400> SEQUENCE: 48

Lys Leu Leu Leu Lys Leu Leu Lys Lys Leu Leu Lys Leu Leu Lys Lys
1               5                   10                  15

Lys

<210> SEQ ID NO 49
<211> LENGTH: 17
<212> TYPE: PRT
<213> ORGANISM: artificial sequence
<220> FEATURE:
<223> OTHER INFORMATION: kLytic peptide; position 3, 6, 8, 9 and 13 are
      D-amino acids.

<400> SEQUENCE: 49

Lys Leu Leu Leu Lys Leu Leu Lys Lys Leu Leu Lys Leu Leu Lys Lys
```

```
1               5                   10                  15
Lys

<210> SEQ ID NO 50
<211> LENGTH: 35
<212> TYPE: PRT
<213> ORGANISM: artificial sequence
<220> FEATURE:
<223> OTHER INFORMATION: Sema3A(363-377)-kLytic peptide; position 21,
      24, 26, 27 and 31 are D-amino acids.

<400> SEQUENCE: 50

Asn Tyr Gln Trp Val Pro Tyr Gln Gly Arg Val Pro Tyr Pro Arg Gly
1               5                   10                  15

Gly Gly Lys Leu Leu Leu Lys Leu Leu Lys Lys Leu Leu Lys Leu Leu
            20                  25                  30

Lys Lys Lys
        35

<210> SEQ ID NO 51
<211> LENGTH: 27
<212> TYPE: PRT
<213> ORGANISM: artificial sequence
<220> FEATURE:
<223> OTHER INFORMATION: VEGFR2-Lytic peptide; position 13, 16, 18, 19
      and 23 are D-amino acids.

<400> SEQUENCE: 51

Ala Thr Trp Leu Pro Pro Arg Gly Gly Gly Lys Leu Leu Leu Lys Leu
1               5                   10                  15

Leu Lys Lys Leu Leu Lys Leu Leu Lys Lys Lys
            20                  25

<210> SEQ ID NO 52
<211> LENGTH: 12
<212> TYPE: PRT
<213> ORGANISM: artificial sequence
<220> FEATURE:
<223> OTHER INFORMATION: HER2 binding peptide

<400> SEQUENCE: 52

Leu Leu Gly Pro Tyr Glu Leu Trp Glu Leu Ser His
1               5                   10

<210> SEQ ID NO 53
<211> LENGTH: 15
<212> TYPE: PRT
<213> ORGANISM: artificial sequence
<220> FEATURE:
<223> OTHER INFORMATION: HER2 binding peptide

<400> SEQUENCE: 53

Ala Leu Val Arg Tyr Lys Asp Pro Leu Phe Val Trp Gly Phe Leu
1               5                   10                  15

<210> SEQ ID NO 54
<211> LENGTH: 6
<212> TYPE: PRT
<213> ORGANISM: artificial sequence
<220> FEATURE:
<223> OTHER INFORMATION: HER2 binding peptide

<400> SEQUENCE: 54

Lys Cys Cys Tyr Ser Leu
1               5
```

<210> SEQ ID NO 55
<211> LENGTH: 20
<212> TYPE: PRT
<213> ORGANISM: artificial sequence
<220> FEATURE:
<223> OTHER INFORMATION: HER2 binding peptide

<400> SEQUENCE: 55

Trp Thr Gly Trp Cys Leu Asn Pro Glu Glu Ser Thr Trp Gly Phe Cys
1               5                   10                  15

Thr Gly Ser Phe
            20

<210> SEQ ID NO 56
<211> LENGTH: 20
<212> TYPE: PRT
<213> ORGANISM: artificial sequence
<220> FEATURE:
<223> OTHER INFORMATION: HER2 binding peptide

<400> SEQUENCE: 56

Asp Thr Asp Met Cys Trp Trp Ser Arg Glu Phe Gly Trp Glu Cys
1               5                   10                  15

Ala Gly Ala Gly
            20

<210> SEQ ID NO 57
<211> LENGTH: 86
<212> TYPE: PRT
<213> ORGANISM: Human immunodeficiency virus 1

<400> SEQUENCE: 57

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85

<210> SEQ ID NO 58
<211> LENGTH: 16
<212> TYPE: PRT
<213> ORGANISM: artificial sequence
<220> FEATURE:
<223> OTHER INFORMATION: Antp sequence

<400> SEQUENCE: 58

Arg Gln Ile Lys Ile Gln Phe Gln Asn Arg Arg Met Lys Trp Lys Lys
1               5                   10                  15

<210> SEQ ID NO 59
<211> LENGTH: 12
<212> TYPE: PRT
<213> ORGANISM: artificial sequence
<220> FEATURE:
<223> OTHER INFORMATION: Hsp90 TPR binding peptide

```
<400> SEQUENCE: 59

Lys Ala Tyr Ala Arg Ile Gly Asn Ser Tyr Phe Lys
1               5                   10

<210> SEQ ID NO 60
<211> LENGTH: 15
<212> TYPE: PRT
<213> ORGANISM: artificial sequence
<220> FEATURE:
<223> OTHER INFORMATION: Sema3A mutated peptide (R372K)

<400> SEQUENCE: 60

Asn Tyr Gln Trp Val Pro Tyr Gln Gly Lys Val Pro Tyr Pro Arg
1               5                   10                  15

<210> SEQ ID NO 61
<211> LENGTH: 15
<212> TYPE: PRT
<213> ORGANISM: artificial sequence
<220> FEATURE:
<223> OTHER INFORMATION: Sema3A mutated peptide (V373A)

<400> SEQUENCE: 61

Asn Tyr Gln Trp Val Pro Tyr Gln Gly Arg Ala Pro Tyr Pro Arg
1               5                   10                  15

<210> SEQ ID NO 62
<211> LENGTH: 15
<212> TYPE: PRT
<213> ORGANISM: artificial sequence
<220> FEATURE:
<223> OTHER INFORMATION: Sema3A mutated peptide (P374T)

<400> SEQUENCE: 62

Asn Tyr Gln Trp Val Pro Tyr Gln Gly Arg Val Thr Tyr Pro Arg
1               5                   10                  15

<210> SEQ ID NO 63
<211> LENGTH: 15
<212> TYPE: PRT
<213> ORGANISM: artificial sequence
<220> FEATURE:
<223> OTHER INFORMATION: Sema3A mutated peptide (Y375L)

<400> SEQUENCE: 63

Asn Tyr Gln Trp Val Pro Tyr Gln Gly Arg Val Pro Leu Pro Arg
1               5                   10                  15

<210> SEQ ID NO 64
<211> LENGTH: 15
<212> TYPE: PRT
<213> ORGANISM: artificial sequence
<220> FEATURE:
<223> OTHER INFORMATION: Sema3A mutated peptide (P376T)

<400> SEQUENCE: 64

Asn Tyr Gln Trp Val Pro Tyr Gln Gly Arg Val Pro Tyr Thr Arg
1               5                   10                  15

<210> SEQ ID NO 65
<211> LENGTH: 15
<212> TYPE: PRT
<213> ORGANISM: artificial sequence
<220> FEATURE:
<223> OTHER INFORMATION: Sema3A mutated peptide (R377K)
```

```
<400> SEQUENCE: 65

Asn Tyr Gln Trp Val Pro Tyr Gln Gly Arg Val Pro Tyr Pro Lys
1               5                   10                  15

<210> SEQ ID NO 66
<211> LENGTH: 15
<212> TYPE: PRT
<213> ORGANISM: artificial sequence
<220> FEATURE:
<223> OTHER INFORMATION: Sema3A mutated peptide (R372K/R377K)

<400> SEQUENCE: 66

Asn Tyr Gln Trp Val Pro Tyr Gln Gly Lys Val Pro Tyr Pro Lys
1               5                   10                  15

<210> SEQ ID NO 67
<211> LENGTH: 7
<212> TYPE: PRT
<213> ORGANISM: artificial sequence
<220> FEATURE:
<223> OTHER INFORMATION: Sema3A short peptide

<400> SEQUENCE: 67

Gly Arg Val Pro Tyr Pro Arg
1               5
```